US012440213B2

(12) United States Patent
Leimbach et al.

(10) Patent No.: US 12,440,213 B2
(45) Date of Patent: Oct. 14, 2025

(54) SURGICAL INSTRUMENT HAVING A POWER CONTROL CIRCUIT

(71) Applicant: Cilag GmbH International, Zug (CH)

(72) Inventors: Richard L. Leimbach, Cincinnati, OH (US); Richard F. Schwemberger, Cincinnati, OH (US); Brett E. Swensgard, West Chester, OH (US)

(73) Assignee: Cilag GmbH International, Zug (CH)

( * ) Notice: Subject to any disclaimer, the term of this patent is extended or adjusted under 35 U.S.C. 154(b) by 148 days.

(21) Appl. No.: 18/074,618

(22) Filed: Dec. 5, 2022

(65) Prior Publication Data

US 2023/0165584 A1 Jun. 1, 2023

Related U.S. Application Data

(63) Continuation of application No. 16/902,443, filed on Jun. 16, 2020, now Pat. No. 11,529,142, which is a (Continued)

(51) Int. Cl.

*A61B 17/072* (2006.01)
*A61B 17/068* (2006.01)

(Continued)

(52) U.S. Cl.

CPC ............ *A61B 17/10* (2013.01); *A61B 17/068* (2013.01); *A61B 17/07207* (2013.01);

(Continued)

(58) Field of Classification Search

CPC . A61B 17/10; A61B 17/068; A61B 17/07207; A61B 2017/00398;

(Continued)

(56) References Cited

U.S. PATENT DOCUMENTS

| | | | |
|---|---|---|---|
| 66,052 | A | 6/1867 | Smith |
| 662,587 | A | 11/1900 | Blake |

(Continued)

FOREIGN PATENT DOCUMENTS

| | | | |
|---|---|---|---|
| AU | 2012200594 A1 | 2/2012 | |
| AU | 2012203035 A1 | 6/2012 | |

(Continued)

OTHER PUBLICATIONS

ASTM procedure D2240-00, "Standard Test Method for Rubber Property-Durometer Hardness," (Published Aug. 2000).

(Continued)

*Primary Examiner* — Michelle Lopez

(74) *Attorney, Agent, or Firm* — Frost Brown Todd LLP

(57) ABSTRACT

Various embodiments are directed to a powered surgical instrument for cutting and fastening tissue. The instrument may comprise an end effector comprising a first jaw member and a second jaw member. The second jaw member may be coupled to move relative to the first jaw member from an open position, where the jaw members are apart from one another, to a closed position. The end effector may also comprise a firing bar positioned to fire by translating within the end effector when the first and second jaw members are in the closed position. Additionally, the surgical instrument may comprise a drive device, a clamping trigger and a control circuit. The drive device may be mechanically coupled to the firing bar. The clamping trigger may be mechanically coupled to the end effector such that actuation of the clamping trigger causes the second jaw member to pivot towards the first jaw member. The control circuit may comprise a firing switch, a clamp switch, a latching device and an end-of-stroke sensor. The firing switch may be configured to be in electrical communication with a power supply for powering the drive device and in electrical (Continued)

communication with the drive device. The clamp switch may be in mechanical communication with the clamping trigger. The latching device may be in electrical communication with the clamp switch, the power supply and the drive device. The end-of-stroke switch may be in electrical communication with the latching device. Additionally, the firing switch may be electrically connected to, upon actuation, connect the power supply to the drive device via a first connection comprising the latching device and the firing switch. Further, the end-of-stroke switch may be electrically connected to, upon sensing an end of a stroke of the firing bar, cause a change in a state of the latching device to break the first connection between the power supply and the drive device.

21 Claims, 43 Drawing Sheets

Related U.S. Application Data continuation of application No. 15/592,820, filed on May 11, 2017, now Pat. No. 10,695,062, which is a continuation of application No. 14/188,199, filed on Feb. 24, 2014, now Pat. No. 9,687,236, which is a continuation of application No. 12/896,381, filed on Oct. 1, 2010, now Pat. No. 8,695,866.

(51) Int. Cl.

| | |
|---|---|
| ***A61B 17/10*** | (2006.01) |
| ***H01M 10/42*** | (2006.01) |
| ***H02J 7/00*** | (2006.01) |
| *A61B 17/00* | (2006.01) |
| *A61B 17/29* | (2006.01) |

(52) U.S. Cl.

CPC .......... *H01M 10/42* (2013.01); *H02J 7/0068* (2013.01); *A61B 2017/00398* (2013.01); *A61B 2017/00734* (2013.01); *A61B 2017/07214* (2013.01); *A61B 2017/2923* (2013.01); *H01M 2200/103* (2013.01); *H01M 2220/30* (2013.01)

(58) Field of Classification Search

CPC .......... A61B 2017/00734; A61B 2017/07214; A61B 2017/2923; H02J 7/0068; H01M 2220/30

See application file for complete search history.

(56) References Cited

U.S. PATENT DOCUMENTS

| | | | |
|---|---|---|---|
| 670,748 | A | 3/1901 | Weddeler |
| 719,487 | A | 2/1903 | Minor |
| 804,229 | A | 11/1905 | Hutchinson |
| 903,739 | A | 11/1908 | Lesemann |
| 951,393 | A | 3/1910 | Hahn |
| 1,075,556 | A | 10/1913 | Fenoughty |
| 1,082,105 | A | 12/1913 | Anderson |
| 1,188,721 | A | 6/1916 | Bittner |
| 1,306,107 | A | 6/1919 | Elliott |
| 1,314,601 | A | 9/1919 | McCaskey |
| 1,466,128 | A | 8/1923 | Hallenbeck |
| 1,677,337 | A | 7/1928 | Grove |
| 1,794,907 | A | 3/1931 | Kelly |
| 1,849,427 | A | 3/1932 | Hook |
| 1,912,783 | A | 6/1933 | Meyer |
| 1,944,116 | A | 1/1934 | Stratman |
| 1,954,048 | A | 4/1934 | Jeffrey et al. |
| 2,028,635 | A | 1/1936 | Wappler |
| 2,037,727 | A | 4/1936 | La Chapelle |
| 2,120,951 | A | 6/1938 | Hodgman |
| 2,132,295 | A | 10/1938 | Hawkins |
| 2,161,632 | A | 6/1939 | Nattenheimer |
| D120,434 | S | 5/1940 | Gold |
| 2,211,117 | A | 8/1940 | Hess |
| 2,214,870 | A | 9/1940 | West |
| 2,224,108 | A | 12/1940 | Ridgway |
| 2,224,882 | A | 12/1940 | Peck |
| 2,256,295 | A | 9/1941 | Schmid |
| 2,318,379 | A | 5/1943 | Davis et al. |
| 2,329,440 | A | 9/1943 | La Place |
| 2,377,581 | A | 6/1945 | Shaffrey |
| 2,406,389 | A | 8/1946 | Lee |
| 2,420,552 | A | 5/1947 | Morrill |
| 2,441,096 | A | 5/1948 | Happe |
| 2,448,741 | A | 9/1948 | Scott et al. |
| 2,450,527 | A | 10/1948 | Smith |
| 2,491,872 | A | 12/1949 | Neuman |
| 2,507,872 | A | 5/1950 | Unsinger |
| 2,526,902 | A | 10/1950 | Rublee |
| 2,527,256 | A | 10/1950 | Jackson |
| 2,578,686 | A | 12/1951 | Fish |
| 2,638,901 | A | 5/1953 | Sugarbaker |
| 2,674,149 | A | 4/1954 | Benson |
| 2,701,489 | A | 2/1955 | Osborn |
| 2,711,461 | A | 6/1955 | Happe |
| 2,724,289 | A | 11/1955 | Wight |
| 2,742,955 | A | 4/1956 | Dominguez |
| 2,804,848 | A | 9/1957 | O'Farrell et al. |
| 2,808,482 | A | 10/1957 | Zanichkowsky et al. |
| 2,825,178 | A | 3/1958 | Hawkins |
| 2,853,074 | A | 9/1958 | Olson |
| 2,856,192 | A | 10/1958 | Schuster |
| 2,887,004 | A | 5/1959 | Stewart |
| 2,957,353 | A | 10/1960 | Lewis |
| 2,959,974 | A | 11/1960 | Emrick |
| 3,026,744 | A | 3/1962 | Rouse |
| 3,032,769 | A | 5/1962 | Palmer |
| 3,035,256 | A | 5/1962 | Egbert |
| 3,060,972 | A | 10/1962 | Sheldon |
| 3,075,062 | A | 1/1963 | Iaccarino |
| 3,078,465 | A | 2/1963 | Bobrov |
| 3,079,606 | A | 3/1963 | Bobrov et al. |
| 3,080,564 | A | 3/1963 | Strekopitov et al. |
| 3,166,072 | A | 1/1965 | Sullivan, Jr. |
| 3,180,236 | A | 4/1965 | Beckett |
| 3,196,869 | A | 7/1965 | Scholl |
| 3,204,731 | A | 9/1965 | Bent et al. |
| 3,252,643 | A | 5/1966 | Strekopytov et al. |
| 3,266,494 | A | 8/1966 | Brownrigg et al. |
| 3,269,630 | A | 8/1966 | Fleischer |
| 3,269,631 | A | 8/1966 | Takaro |
| 3,275,211 | A | 9/1966 | Hirsch et al. |
| 3,315,863 | A | 4/1967 | O'Dea |
| 3,317,103 | A | 5/1967 | Cullen et al. |
| 3,317,105 | A | 5/1967 | Astafjev et al. |
| 3,357,296 | A | 12/1967 | Lefever |
| 3,359,978 | A | 12/1967 | Smith, Jr. |
| 3,377,893 | A | 4/1968 | Shorb |
| 3,480,193 | A | 11/1969 | Ralston |
| 3,490,675 | A | 1/1970 | Green et al. |
| 3,494,533 | A | 2/1970 | Green et al. |
| 3,499,591 | A | 3/1970 | Green |
| 3,503,396 | A | 3/1970 | Pierie et al. |
| 3,509,629 | A | 5/1970 | Kidokoro |
| 3,551,987 | A | 1/1971 | Wilkinson |
| 3,568,675 | A | 3/1971 | Harvey |
| 3,572,159 | A | 3/1971 | Tschanz |
| 3,583,393 | A | 6/1971 | Takahashi |
| 3,589,589 | A | 6/1971 | Akopov |
| 3,598,943 | A | 8/1971 | Barrett |
| 3,604,561 | A | 9/1971 | Mallina et al. |
| 3,608,549 | A | 9/1971 | Merrill |
| 3,616,278 | A | 10/1971 | Jansen |
| 3,618,842 | A | 11/1971 | Bryan |
| 3,635,394 | A | 1/1972 | Natelson |
| 3,638,652 | A | 2/1972 | Kelley |
| 3,640,317 | A | 2/1972 | Panfili |
| 3,643,851 | A | 2/1972 | Green et al. |
| 3,650,453 | A | 3/1972 | Smith, Jr. |
| 3,661,339 | A | 5/1972 | Shimizu |

(56) References Cited

U.S. PATENT DOCUMENTS

| | | | |
|---|---|---|---|
| 3,661,666 | A | 5/1972 | Foster et al. |
| 3,662,939 | A | 5/1972 | Bryan |
| 3,685,250 | A | 8/1972 | Henry et al. |
| 3,688,966 | A | 9/1972 | Perkins et al. |
| 3,692,224 | A | 9/1972 | Astafiev et al. |
| 3,695,646 | A | 10/1972 | Mommsen |
| 3,709,221 | A | 1/1973 | Riely |
| 3,717,294 | A | 2/1973 | Green |
| 3,724,237 | A | 4/1973 | Wood |
| 3,726,755 | A | 4/1973 | Shannon |
| 3,727,904 | A | 4/1973 | Gabbey |
| 3,734,207 | A | 5/1973 | Fishbein |
| 3,740,994 | A | 6/1973 | De Carlo, Jr. |
| 3,744,495 | A | 7/1973 | Johnson |
| 3,746,002 | A | 7/1973 | Haller |
| 3,747,603 | A | 7/1973 | Adler |
| 3,747,692 | A | 7/1973 | Davidson |
| 3,751,902 | A | 8/1973 | Kingsbury et al. |
| 3,752,161 | A | 8/1973 | Bent |
| 3,797,494 | A | 3/1974 | Zaffaroni |
| 3,799,151 | A | 3/1974 | Fukaumi et al. |
| 3,808,452 | A | 4/1974 | Hutchinson |
| 3,815,476 | A | 6/1974 | Green et al. |
| 3,819,100 | A | 6/1974 | Noiles et al. |
| 3,821,919 | A | 7/1974 | Knohl |
| 3,822,818 | A | 7/1974 | Strekopytov et al. |
| 3,825,007 | A | 7/1974 | Rand |
| 3,826,978 | A | 7/1974 | Kelly |
| 3,836,171 | A | 9/1974 | Hayashi et al. |
| 3,837,555 | A | 9/1974 | Green |
| 3,841,474 | A | 10/1974 | Maier |
| 3,851,196 | A | 11/1974 | Hinds |
| 3,863,639 | A | 2/1975 | Kleaveland |
| 3,863,940 | A | 2/1975 | Cummings |
| 3,883,624 | A | 5/1975 | McKenzie et al. |
| 3,885,491 | A | 5/1975 | Curtis |
| 3,887,393 | A | 6/1975 | La Rue, Jr. |
| 3,892,228 | A | 7/1975 | Mitsui |
| 3,894,174 | A | 7/1975 | Cartun |
| 3,899,829 | A | 8/1975 | Storm et al. |
| 3,902,247 | A | 9/1975 | Fleer et al. |
| 3,940,844 | A | 3/1976 | Colby et al. |
| 3,944,163 | A | 3/1976 | Hayashi et al. |
| 3,950,686 | A | 4/1976 | Randall |
| 3,952,747 | A | 4/1976 | Kimmell, Jr. |
| 3,955,581 | A | 5/1976 | Spasiano et al. |
| 3,959,879 | A | 6/1976 | Sellers |
| RE28,932 | E | 8/1976 | Noiles et al. |
| 3,972,734 | A | 8/1976 | King |
| 3,973,179 | A | 8/1976 | Weber et al. |
| 3,981,051 | A | 9/1976 | Brumlik |
| 3,993,072 | A | 11/1976 | Zaffaroni |
| 3,999,110 | A | 12/1976 | Ramstrom et al. |
| 4,025,216 | A | 5/1977 | Hives |
| 4,027,746 | A | 6/1977 | Kine |
| 4,034,143 | A | 7/1977 | Sweet |
| 4,038,987 | A | 8/1977 | Komiya |
| 4,047,654 | A | 9/1977 | Alvarado |
| 4,054,108 | A | 10/1977 | Gill |
| 4,060,089 | A | 11/1977 | Noiles |
| 4,066,133 | A | 1/1978 | Voss |
| 4,085,337 | A | 4/1978 | Moeller |
| 4,100,820 | A | 7/1978 | Evett |
| 4,106,446 | A | 8/1978 | Yamada et al. |
| 4,106,620 | A | 8/1978 | Brimmer et al. |
| 4,108,211 | A | 8/1978 | Tanaka |
| 4,111,206 | A | 9/1978 | Vishnevsky et al. |
| 4,127,227 | A | 11/1978 | Green |
| 4,129,059 | A | 12/1978 | Van Eck |
| 4,132,146 | A | 1/1979 | Uhlig |
| 4,135,517 | A | 1/1979 | Reale |
| 4,149,461 | A | 4/1979 | Simeth |
| 4,154,122 | A | 5/1979 | Severin |
| 4,160,857 | A | 7/1979 | Nardella et al. |
| 4,169,476 | A | 10/1979 | Hiltebrandt |
| 4,169,990 | A | 10/1979 | Lerdman |
| 4,180,285 | A | 12/1979 | Reneau |
| 4,185,701 | A | 1/1980 | Boys |
| 4,190,042 | A | 2/1980 | Sinnreich |
| 4,198,734 | A | 4/1980 | Brumlik |
| 4,198,982 | A | 4/1980 | Fortner et al. |
| 4,203,444 | A | 5/1980 | Bonnell et al. |
| 4,207,898 | A | 6/1980 | Becht |
| 4,213,562 | A | 7/1980 | Garrett et al. |
| 4,226,242 | A | 10/1980 | Jarvik |
| 4,239,431 | A | 12/1980 | Davini |
| 4,241,861 | A | 12/1980 | Fleischer |
| 4,244,372 | A | 1/1981 | Kapitanov et al. |
| 4,250,436 | A | 2/1981 | Weissman |
| 4,250,817 | A | 2/1981 | Michel |
| 4,261,244 | A | 4/1981 | Becht et al. |
| 4,272,002 | A | 6/1981 | Moshofsky |
| 4,272,662 | A | 6/1981 | Simpson |
| 4,274,304 | A | 6/1981 | Curtiss |
| 4,274,398 | A | 6/1981 | Scott, Jr. |
| 4,275,813 | A | 6/1981 | Noiles |
| 4,278,091 | A | 7/1981 | Borzone |
| 4,282,573 | A | 8/1981 | Imai et al. |
| 4,289,131 | A | 9/1981 | Mueller |
| 4,289,133 | A | 9/1981 | Rothfuss |
| 4,290,542 | A | 9/1981 | Fedotov et al. |
| D261,356 | S | 10/1981 | Robinson |
| 4,293,604 | A | 10/1981 | Campbell |
| 4,296,654 | A | 10/1981 | Mercer |
| 4,296,881 | A | 10/1981 | Lee |
| 4,304,236 | A | 12/1981 | Conta et al. |
| 4,305,539 | A | 12/1981 | Korolkov et al. |
| 4,312,363 | A | 1/1982 | Rothfuss et al. |
| 4,312,685 | A | 1/1982 | Riedl |
| 4,317,451 | A | 3/1982 | Cerwin et al. |
| 4,319,576 | A | 3/1982 | Rothfuss |
| 4,321,002 | A | 3/1982 | Froehlich |
| 4,321,746 | A | 3/1982 | Grinage |
| 4,328,839 | A | 5/1982 | Lyons et al. |
| 4,331,277 | A | 5/1982 | Green |
| 4,340,331 | A | 7/1982 | Savino |
| 4,347,450 | A | 8/1982 | Colligan |
| 4,348,603 | A | 9/1982 | Huber |
| 4,349,028 | A | 9/1982 | Green |
| 4,350,151 | A | 9/1982 | Scott |
| 4,353,371 | A | 10/1982 | Cosman |
| 4,357,940 | A | 11/1982 | Muller |
| 4,361,057 | A | 11/1982 | Kochera |
| 4,366,544 | A | 12/1982 | Shima et al. |
| 4,369,013 | A | 1/1983 | Abildgaard et al. |
| 4,373,147 | A | 2/1983 | Carlson, Jr. |
| 4,376,380 | A | 3/1983 | Burgess |
| 4,379,457 | A | 4/1983 | Gravener et al. |
| 4,380,312 | A | 4/1983 | Landrus |
| 4,382,326 | A | 5/1983 | Rabuse |
| 4,383,634 | A | 5/1983 | Green |
| 4,389,963 | A | 6/1983 | Pearson |
| 4,393,728 | A | 7/1983 | Larson et al. |
| 4,394,613 | A | 7/1983 | Cole |
| 4,396,139 | A | 8/1983 | Hall et al. |
| 4,397,311 | A | 8/1983 | Kanshin et al. |
| 4,402,445 | A | 9/1983 | Green |
| 4,406,621 | A | 9/1983 | Bailey |
| 4,408,692 | A | 10/1983 | Sigel et al. |
| 4,409,057 | A | 10/1983 | Molenda et al. |
| 4,415,112 | A | 11/1983 | Green |
| 4,416,276 | A | 11/1983 | Newton et al. |
| 4,417,890 | A | 11/1983 | Dennehey et al. |
| 4,421,264 | A | 12/1983 | Arter et al. |
| 4,423,456 | A | 12/1983 | Zaidenweber |
| 4,425,915 | A | 1/1984 | Ivanov |
| 4,428,376 | A | 1/1984 | Mericle |
| 4,429,695 | A | 2/1984 | Green |
| 4,430,997 | A | 2/1984 | DiGiovanni et al. |
| 4,434,796 | A | 3/1984 | Karapetian et al. |
| 4,438,659 | A | 3/1984 | Desplats |
| 4,442,964 | A | 4/1984 | Becht |
| 4,448,194 | A | 5/1984 | DiGiovanni et al. |
| 4,451,743 | A | 5/1984 | Suzuki et al. |

(56) References Cited

U.S. PATENT DOCUMENTS 4,452,376 A 6/1984 Klieman et al.
4,454,887 A 6/1984 Kruger
4,459,519 A 7/1984 Erdman
4,461,305 A 7/1984 Cibley
4,467,805 A 8/1984 Fukuda
4,468,597 A 8/1984 Baumard et al.
4,469,481 A 9/1984 Kobayashi
4,470,414 A 9/1984 Imagawa et al.
4,471,780 A 9/1984 Menges et al.
4,471,781 A 9/1984 Di Giovanni et al.
4,473,077 A 9/1984 Noiles et al.
4,475,679 A 10/1984 Fleury, Jr.
4,476,864 A 10/1984 Tezel
4,478,220 A 10/1984 Di Giovanni et al.
4,480,641 A 11/1984 Failla et al.
4,481,458 A 11/1984 Lane
4,483,562 A 11/1984 Schoolman
4,485,816 A 12/1984 Krumme
4,485,817 A 12/1984 Swiggett
4,486,928 A 12/1984 Tucker et al.
4,488,523 A 12/1984 Shichman
4,489,875 A 12/1984 Crawford et al.
4,493,983 A 1/1985 Taggert
4,494,057 A 1/1985 Hotta
4,499,895 A 2/1985 Takayama
4,500,024 A 2/1985 DiGiovanni et al.
D278,081 S 3/1985 Green
4,503,842 A 3/1985 Takayama
4,505,272 A 3/1985 Utyamyshev et al.
4,505,273 A 3/1985 Braun et al.
4,505,414 A 3/1985 Filipi
4,506,671 A 3/1985 Green
4,512,038 A 4/1985 Alexander et al.
4,514,477 A 4/1985 Kobayashi
4,520,817 A 6/1985 Green
4,522,327 A 6/1985 Korthoff et al.
4,523,707 A 6/1985 Blake, III et al.
4,526,174 A 7/1985 Froehlich
4,527,724 A 7/1985 Chow et al.
4,530,357 A 7/1985 Pawloski et al.
4,530,453 A 7/1985 Green
4,531,522 A 7/1985 Bedi et al.
4,532,927 A 8/1985 Miksza, Jr.
4,540,202 A 9/1985 Amphoux et al.
4,548,202 A 10/1985 Duncan
4,556,058 A 12/1985 Green
4,560,915 A 12/1985 Soultanian
4,565,109 A 1/1986 Tsay
4,565,189 A 1/1986 Mabuchi
4,566,620 A 1/1986 Green et al.
4,569,346 A 2/1986 Poirier
4,569,469 A 2/1986 Mongeon et al.
4,571,213 A 2/1986 Ishimoto
4,573,468 A 3/1986 Conta et al.
4,573,469 A 3/1986 Golden et al.
4,573,622 A 3/1986 Green et al.
4,576,165 A 3/1986 Green et al.
4,576,167 A 3/1986 Noiles
4,580,712 A 4/1986 Green
4,585,153 A 4/1986 Failla et al.
4,586,501 A 5/1986 Claracq
4,586,502 A 5/1986 Bedi et al.
4,589,416 A 5/1986 Green
4,589,582 A 5/1986 Bilotti
4,589,870 A 5/1986 Citrin et al.
4,591,085 A 5/1986 Di Giovanni
RE32,214 E 7/1986 Schramm
4,597,753 A 7/1986 Turley
4,600,037 A 7/1986 Hatten
4,604,786 A 8/1986 Howie, Jr.
4,605,001 A 8/1986 Rothfuss et al.
4,605,004 A 8/1986 Di Giovanni et al.
4,606,343 A 8/1986 Conta et al.
4,607,636 A 8/1986 Kula et al.
4,607,638 A 8/1986 Crainich
4,608,980 A 9/1986 Aihara
4,608,981 A 9/1986 Rothfuss et al.
4,610,250 A 9/1986 Green
4,610,383 A 9/1986 Rothfuss et al.
4,612,933 A 9/1986 Brinkerhoff et al.
D286,180 S 10/1986 Korthoff
D286,442 S 10/1986 Korthoff et al.
4,617,893 A 10/1986 Donner et al.
4,617,914 A 10/1986 Ueda
4,617,935 A 10/1986 Cartmell et al.
4,619,262 A 10/1986 Taylor
4,619,391 A 10/1986 Sharkany et al.
4,624,401 A 11/1986 Gassner et al.
D287,278 S 12/1986 Spreckelmeier
4,628,459 A 12/1986 Shinohara et al.
4,628,636 A 12/1986 Folger
4,629,107 A 12/1986 Fedotov et al.
4,632,290 A 12/1986 Green et al.
4,633,861 A 1/1987 Chow et al.
4,633,874 A 1/1987 Chow et al.
4,634,419 A 1/1987 Kreizman et al.
4,635,638 A 1/1987 Weintraub et al.
4,641,076 A 2/1987 Linden
4,642,618 A 2/1987 Johnson et al.
4,642,738 A 2/1987 Meller
4,643,173 A 2/1987 Bell et al.
4,643,731 A 2/1987 Eckenhoff
4,646,722 A 3/1987 Silverstein et al.
4,646,745 A 3/1987 Noiles
4,651,734 A 3/1987 Doss et al.
4,652,820 A 3/1987 Maresca
4,654,028 A 3/1987 Suma
4,655,222 A 4/1987 Florez et al.
4,662,555 A 5/1987 Thornton
4,663,874 A 5/1987 Sano et al.
4,664,305 A 5/1987 Blake, III et al.
4,665,916 A 5/1987 Green
4,667,674 A 5/1987 Korthoff et al.
4,669,647 A 6/1987 Storace
4,671,278 A 6/1987 Chin
4,671,280 A 6/1987 Dorband et al.
4,671,445 A 6/1987 Barker et al.
4,672,964 A 6/1987 Dee et al.
4,675,944 A 6/1987 Wells
4,676,245 A 6/1987 Fukuda
4,679,460 A 7/1987 Yoshigai
4,679,719 A 7/1987 Kramer
4,684,051 A 8/1987 Akopov et al.
4,688,555 A 8/1987 Wardle
4,691,703 A 9/1987 Auth et al.
4,693,248 A 9/1987 Failla
4,698,579 A 10/1987 Richter et al.
4,700,703 A 10/1987 Resnick et al.
4,705,038 A 11/1987 Sjostrom et al.
4,708,141 A 11/1987 Inoue et al.
4,709,120 A 11/1987 Pearson
4,715,520 A 12/1987 Roehr, Jr. et al.
4,719,917 A 1/1988 Barrows et al.
4,721,099 A 1/1988 Chikama
4,722,340 A 2/1988 Takayama et al.
4,724,840 A 2/1988 McVay et al.
4,726,247 A 2/1988 Hormann
4,727,308 A 2/1988 Huljak et al.
4,728,020 A 3/1988 Green et al.
4,728,876 A 3/1988 Mongeon et al.
4,729,260 A 3/1988 Dudden
4,730,726 A 3/1988 Holzwarth
4,741,336 A 5/1988 Failla et al.
4,743,214 A 5/1988 Tai-Cheng
4,744,363 A 5/1988 Hasson
4,747,820 A 5/1988 Hornlein et al.
4,750,902 A 6/1988 Wuchinich et al.
4,752,024 A 6/1988 Green et al.
4,754,909 A 7/1988 Barker et al.
4,755,070 A 7/1988 Cerutti
4,761,326 A 8/1988 Barnes et al.
4,763,669 A 8/1988 Jaeger
4,767,044 A 8/1988 Green
D297,764 S 9/1988 Hunt et al.

(56) References Cited

U.S. PATENT DOCUMENTS

| | | | |
|---|---|---|---|
| 4,773,420 | A | 9/1988 | Green |
| 4,777,780 | A | 10/1988 | Holzwarth |
| 4,781,186 | A | 11/1988 | Simpson et al. |
| 4,784,137 | A | 11/1988 | Kulik et al. |
| 4,787,387 | A | 11/1988 | Burbank, III et al. |
| 4,788,485 | A | 11/1988 | Kawagishi et al. |
| D298,967 | S | 12/1988 | Hunt |
| 4,788,978 | A | 12/1988 | Strekopytov et al. |
| 4,790,225 | A | 12/1988 | Moody et al. |
| 4,790,314 | A | 12/1988 | Weaver |
| 4,805,617 | A | 2/1989 | Bedi et al. |
| 4,805,823 | A | 2/1989 | Rothfuss |
| 4,807,628 | A | 2/1989 | Peters et al. |
| 4,809,695 | A | 3/1989 | Gwathmey et al. |
| 4,815,460 | A | 3/1989 | Porat et al. |
| 4,817,643 | A | 4/1989 | Olson |
| 4,817,847 | A | 4/1989 | Redtenbacher et al. |
| 4,819,495 | A | 4/1989 | Hormann |
| 4,819,853 | A | 4/1989 | Green |
| 4,821,939 | A | 4/1989 | Green |
| 4,827,552 | A | 5/1989 | Bojar et al. |
| 4,827,911 | A | 5/1989 | Broadwin et al. |
| 4,828,542 | A | 5/1989 | Hermann |
| 4,828,944 | A | 5/1989 | Yabe et al. |
| 4,830,855 | A | 5/1989 | Stewart |
| 4,832,158 | A | 5/1989 | Farrar et al. |
| 4,833,937 | A | 5/1989 | Nagano |
| 4,834,096 | A | 5/1989 | Oh et al. |
| 4,834,720 | A | 5/1989 | Blinkhorn |
| 4,838,859 | A | 6/1989 | Strassmann |
| 4,844,068 | A | 7/1989 | Arata et al. |
| 4,848,637 | A | 7/1989 | Pruitt |
| 4,856,078 | A | 8/1989 | Konopka |
| 4,860,644 | A | 8/1989 | Kohl et al. |
| 4,862,891 | A | 9/1989 | Smith |
| 4,863,423 | A | 9/1989 | Wallace |
| 4,865,030 | A | 9/1989 | Polyak |
| 4,868,530 | A | 9/1989 | Ahs |
| 4,868,958 | A | 9/1989 | Suzuki et al. |
| 4,869,414 | A | 9/1989 | Green et al. |
| 4,869,415 | A | 9/1989 | Fox |
| 4,873,977 | A | 10/1989 | Avant et al. |
| 4,875,486 | A | 10/1989 | Rapoport et al. |
| 4,880,015 | A | 11/1989 | Nierman |
| 4,890,613 | A | 1/1990 | Golden et al. |
| 4,892,244 | A | 1/1990 | Fox et al. |
| 4,893,622 | A | 1/1990 | Green et al. |
| 4,894,051 | A | 1/1990 | Shiber |
| 4,896,584 | A | 1/1990 | Stoll et al. |
| 4,896,678 | A | 1/1990 | Ogawa |
| 4,900,303 | A | 2/1990 | Lemelson |
| 4,903,697 | A | 2/1990 | Resnick et al. |
| 4,909,789 | A | 3/1990 | Taguchi et al. |
| 4,915,100 | A | 4/1990 | Green |
| 4,919,679 | A | 4/1990 | Averill et al. |
| 4,921,479 | A | 5/1990 | Grayzel |
| 4,925,082 | A | 5/1990 | Kim |
| 4,928,699 | A | 5/1990 | Sasai |
| 4,930,503 | A | 6/1990 | Pruitt |
| 4,930,674 | A | 6/1990 | Barak |
| 4,931,047 | A | 6/1990 | Broadwin et al. |
| 4,931,737 | A | 6/1990 | Hishiki |
| 4,932,960 | A | 6/1990 | Green et al. |
| 4,933,800 | A | 6/1990 | Yang |
| 4,933,843 | A | 6/1990 | Scheller et al. |
| D309,350 | S | 7/1990 | Sutherland et al. |
| 4,938,408 | A | 7/1990 | Bedi et al. |
| 4,941,623 | A | 7/1990 | Pruitt |
| 4,943,182 | A | 7/1990 | Hoblingre |
| 4,944,443 | A | 7/1990 | Oddsen et al. |
| 4,946,067 | A | 8/1990 | Kelsall |
| 4,948,327 | A | 8/1990 | Crupi, Jr. |
| 4,949,707 | A | 8/1990 | LeVahn et al. |
| 4,949,927 | A | 8/1990 | Madocks et al. |
| 4,950,268 | A | 8/1990 | Rink |
| 4,951,860 | A | 8/1990 | Peters et al. |
| 4,951,861 | A | 8/1990 | Schulze et al. |
| 4,954,960 | A | 9/1990 | Lo et al. |
| 4,955,959 | A | 9/1990 | Tompkins et al. |
| 4,957,212 | A | 9/1990 | Duck et al. |
| 4,962,681 | A | 10/1990 | Yang |
| 4,962,877 | A | 10/1990 | Hervas |
| 4,964,559 | A | 10/1990 | Deniega et al. |
| 4,964,863 | A | 10/1990 | Kanshin et al. |
| 4,965,709 | A | 10/1990 | Ngo |
| 4,970,656 | A | 11/1990 | Lo et al. |
| 4,973,274 | A | 11/1990 | Hirukawa |
| 4,973,302 | A | 11/1990 | Armour et al. |
| 4,976,173 | A | 12/1990 | Yang |
| 4,978,049 | A | 12/1990 | Green |
| 4,978,333 | A | 12/1990 | Broadwin et al. |
| 4,979,952 | A | 12/1990 | Kubota et al. |
| 4,984,564 | A | 1/1991 | Yuen |
| 4,986,808 | A | 1/1991 | Broadwin et al. |
| 4,987,049 | A | 1/1991 | Komamura et al. |
| 4,988,334 | A | 1/1991 | Hornlein et al. |
| 4,995,877 | A | 2/1991 | Ams et al. |
| 4,995,959 | A | 2/1991 | Metzner |
| 4,996,975 | A | 3/1991 | Nakamura |
| 5,001,649 | A | 3/1991 | Lo et al. |
| 5,002,543 | A | 3/1991 | Bradshaw et al. |
| 5,002,553 | A | 3/1991 | Shiber |
| 5,005,754 | A | 4/1991 | Van Overloop |
| 5,009,222 | A | 4/1991 | Her |
| 5,009,661 | A | 4/1991 | Michelson |
| 5,012,411 | A | 4/1991 | Policastro et al. |
| 5,014,898 | A | 5/1991 | Heidrich |
| 5,014,899 | A | 5/1991 | Presty et al. |
| 5,015,227 | A | 5/1991 | Broadwin et al. |
| 5,018,515 | A | 5/1991 | Gilman |
| 5,018,657 | A | 5/1991 | Pedlick et al. |
| 5,019,077 | A | 5/1991 | De Bastiani et al. |
| 5,024,652 | A | 6/1991 | Dumenek et al. |
| 5,024,671 | A | 6/1991 | Tu et al. |
| 5,025,559 | A | 6/1991 | McCullough |
| 5,027,834 | A | 7/1991 | Pruitt |
| 5,030,226 | A | 7/1991 | Green et al. |
| 5,031,814 | A | 7/1991 | Tompkins et al. |
| 5,033,552 | A | 7/1991 | Hu |
| 5,035,040 | A | 7/1991 | Kerrigan et al. |
| 5,037,018 | A | 8/1991 | Matsuda et al. |
| 5,038,109 | A | 8/1991 | Goble et al. |
| 5,038,247 | A | 8/1991 | Kelley et al. |
| 5,040,715 | A | 8/1991 | Green et al. |
| 5,042,707 | A | 8/1991 | Taheri |
| 5,056,953 | A | 10/1991 | Marot et al. |
| 5,060,658 | A | 10/1991 | Dejter, Jr. et al. |
| 5,061,269 | A | 10/1991 | Muller |
| 5,062,491 | A | 11/1991 | Takeshima et al. |
| 5,062,563 | A | 11/1991 | Green et al. |
| 5,065,929 | A | 11/1991 | Schulze et al. |
| 5,071,052 | A | 12/1991 | Rodak et al. |
| 5,071,430 | A | 12/1991 | de Salis et al. |
| 5,074,454 | A | 12/1991 | Peters |
| 5,077,506 | A | 12/1991 | Krause |
| 5,079,006 | A | 1/1992 | Urquhart |
| 5,080,556 | A | 1/1992 | Carreno |
| 5,083,695 | A | 1/1992 | Foslien et al. |
| 5,084,057 | A | 1/1992 | Green et al. |
| 5,088,979 | A | 2/1992 | Filipi et al. |
| 5,088,997 | A | 2/1992 | Delahuerga et al. |
| 5,089,606 | A | 2/1992 | Cole et al. |
| 5,094,247 | A | 3/1992 | Hernandez et al. |
| 5,098,004 | A | 3/1992 | Kerrigan |
| 5,098,360 | A | 3/1992 | Hirota |
| 5,100,042 | A | 3/1992 | Gravener et al. |
| 5,100,420 | A | 3/1992 | Green et al. |
| 5,100,422 | A | 3/1992 | Berguer et al. |
| 5,104,025 | A | 4/1992 | Main et al. |
| 5,104,397 | A | 4/1992 | Vasconcelos et al. |
| 5,104,400 | A | 4/1992 | Berguer et al. |
| 5,106,008 | A | 4/1992 | Tompkins et al. |
| 5,108,368 | A | 4/1992 | Hammerslag et al. |
| 5,109,722 | A | 5/1992 | Hufnagle et al. |

(56) References Cited

U.S. PATENT DOCUMENTS

| | | | |
|---|---|---|---|
| 5,111,987 | A | 5/1992 | Moeinzadeh et al. |
| 5,116,349 | A | 5/1992 | Aranyi |
| D327,323 | S | 6/1992 | Hunt |
| 5,119,009 | A | 6/1992 | McCaleb et al. |
| 5,122,156 | A | 6/1992 | Granger et al. |
| 5,124,990 | A | 6/1992 | Williamson |
| 5,129,570 | A | 7/1992 | Schulze et al. |
| 5,137,198 | A | 8/1992 | Nobis et al. |
| 5,139,513 | A | 8/1992 | Segato |
| 5,141,144 | A | 8/1992 | Foslien et al. |
| 5,142,932 | A | 9/1992 | Moya et al. |
| 5,151,102 | A | 9/1992 | Kamiyama et al. |
| 5,155,941 | A | 10/1992 | Takahashi et al. |
| 5,156,151 | A | 10/1992 | Imran |
| 5,156,315 | A | 10/1992 | Green et al. |
| 5,156,609 | A | 10/1992 | Nakao et al. |
| 5,156,614 | A | 10/1992 | Green et al. |
| 5,158,222 | A | 10/1992 | Green et al. |
| 5,158,567 | A | 10/1992 | Green |
| D330,699 | S | 11/1992 | Gill |
| 5,163,598 | A | 11/1992 | Peters et al. |
| 5,163,842 | A | 11/1992 | Nonomura |
| 5,164,652 | A | 11/1992 | Johnson et al. |
| 5,168,605 | A | 12/1992 | Bartlett |
| 5,170,925 | A | 12/1992 | Madden et al. |
| 5,171,247 | A | 12/1992 | Hughett et al. |
| 5,171,249 | A | 12/1992 | Stefanchik et al. |
| 5,171,253 | A | 12/1992 | Klieman |
| 5,173,053 | A | 12/1992 | Swanson et al. |
| 5,173,133 | A | 12/1992 | Morin et al. |
| 5,176,677 | A | 1/1993 | Wuchinich |
| 5,176,688 | A | 1/1993 | Narayan et al. |
| 5,181,514 | A | 1/1993 | Solomon et al. |
| 5,187,422 | A | 2/1993 | Izenbaard et al. |
| 5,188,102 | A | 2/1993 | Idemoto et al. |
| 5,188,111 | A | 2/1993 | Yates et al. |
| 5,188,126 | A | 2/1993 | Fabian et al. |
| 5,190,517 | A | 3/1993 | Zieve et al. |
| 5,190,544 | A | 3/1993 | Chapman et al. |
| 5,190,560 | A | 3/1993 | Woods et al. |
| 5,190,657 | A | 3/1993 | Heagle et al. |
| 5,192,288 | A | 3/1993 | Thompson et al. |
| 5,193,731 | A | 3/1993 | Aranyi |
| 5,195,505 | A | 3/1993 | Josefsen |
| 5,195,968 | A | 3/1993 | Lundquist et al. |
| 5,197,648 | A | 3/1993 | Gingold |
| 5,197,649 | A | 3/1993 | Bessler et al. |
| 5,197,966 | A | 3/1993 | Sommerkamp |
| 5,197,970 | A | 3/1993 | Green et al. |
| 5,200,280 | A | 4/1993 | Karasa |
| 5,201,750 | A | 4/1993 | Hocherl et al. |
| 5,205,459 | A | 4/1993 | Brinkerhoff et al. |
| 5,207,672 | A | 5/1993 | Roth et al. |
| 5,207,697 | A | 5/1993 | Carusillo et al. |
| 5,209,747 | A | 5/1993 | Knoepfler |
| 5,209,756 | A | 5/1993 | Seedhom et al. |
| 5,211,649 | A | 5/1993 | Kohler et al. |
| 5,211,655 | A | 5/1993 | Hasson |
| 5,217,457 | A | 6/1993 | Delahuerga et al. |
| 5,217,478 | A | 6/1993 | Rexroth |
| 5,219,111 | A | 6/1993 | Bilotti et al. |
| 5,220,269 | A | 6/1993 | Chen et al. |
| 5,221,036 | A | 6/1993 | Takase |
| 5,221,281 | A | 6/1993 | Klicek |
| 5,222,945 | A | 6/1993 | Basnight |
| 5,222,963 | A | 6/1993 | Brinkerhoff et al. |
| 5,222,975 | A | 6/1993 | Crainich |
| 5,222,976 | A | 6/1993 | Yoon |
| 5,223,675 | A | 6/1993 | Taft |
| D338,729 | S | 8/1993 | Sprecklemeier et al. |
| 5,234,447 | A | 8/1993 | Kaster et al. |
| 5,236,269 | A | 8/1993 | Handy |
| 5,236,424 | A | 8/1993 | Imran |
| 5,236,440 | A | 8/1993 | Hlavacek |
| 5,236,629 | A | 8/1993 | Mahabadi et al. |
| 5,239,981 | A | 8/1993 | Anapliotis |
| 5,240,163 | A | 8/1993 | Stein et al. |
| 5,242,456 | A | 9/1993 | Nash et al. |
| 5,242,457 | A | 9/1993 | Akopov et al. |
| 5,244,462 | A | 9/1993 | Delahuerga et al. |
| 5,246,156 | A | 9/1993 | Rothfuss et al. |
| 5,246,443 | A | 9/1993 | Mai |
| 5,251,801 | A | 10/1993 | Ruckdeschel et al. |
| 5,253,793 | A | 10/1993 | Green et al. |
| 5,258,007 | A | 11/1993 | Spetzler et al. |
| 5,258,008 | A | 11/1993 | Wilk |
| 5,258,009 | A | 11/1993 | Conners |
| 5,258,010 | A | 11/1993 | Green et al. |
| 5,258,012 | A | 11/1993 | Luscombe et al. |
| 5,259,366 | A | 11/1993 | Reydel et al. |
| 5,259,835 | A | 11/1993 | Clark et al. |
| 5,260,637 | A | 11/1993 | Pizzi |
| 5,261,135 | A | 11/1993 | Mitchell |
| 5,261,877 | A | 11/1993 | Fine et al. |
| 5,261,922 | A | 11/1993 | Hood |
| 5,263,629 | A | 11/1993 | Trumbull et al. |
| 5,263,937 | A | 11/1993 | Shipp |
| 5,263,973 | A | 11/1993 | Cook |
| 5,264,218 | A | 11/1993 | Rogozinski |
| 5,268,622 | A | 12/1993 | Philipp |
| 5,269,794 | A | 12/1993 | Rexroth |
| 5,271,543 | A | 12/1993 | Grant et al. |
| 5,271,544 | A | 12/1993 | Fox et al. |
| RE34,519 | E | 1/1994 | Fox et al. |
| 5,275,322 | A | 1/1994 | Brinkerhoff et al. |
| 5,275,323 | A | 1/1994 | Schulze et al. |
| 5,275,608 | A | 1/1994 | Forman et al. |
| 5,279,416 | A | 1/1994 | Malec et al. |
| 5,281,216 | A | 1/1994 | Klicek |
| 5,281,400 | A | 1/1994 | Berry, Jr. |
| 5,282,806 | A | 2/1994 | Haber et al. |
| 5,282,826 | A | 2/1994 | Quadri |
| 5,282,829 | A | 2/1994 | Hermes |
| 5,284,128 | A | 2/1994 | Hart |
| 5,285,381 | A | 2/1994 | Iskarous et al. |
| 5,285,945 | A | 2/1994 | Brinkerhoff et al. |
| 5,286,253 | A | 2/1994 | Fucci |
| 5,289,963 | A | 3/1994 | McGarry et al. |
| 5,290,271 | A | 3/1994 | Jernberg |
| 5,290,310 | A | 3/1994 | Makower et al. |
| 5,291,133 | A | 3/1994 | Gokhale et al. |
| 5,292,053 | A | 3/1994 | Bilotti et al. |
| 5,293,024 | A | 3/1994 | Sugahara et al. |
| 5,297,714 | A | 3/1994 | Kramer |
| 5,300,087 | A | 4/1994 | Knoepfler |
| 5,302,148 | A | 4/1994 | Heinz |
| 5,303,606 | A | 4/1994 | Kokinda |
| 5,304,204 | A | 4/1994 | Bregen |
| D347,474 | S | 5/1994 | Olson |
| 5,307,976 | A | 5/1994 | Olson et al. |
| 5,308,353 | A | 5/1994 | Beurrier |
| 5,308,358 | A | 5/1994 | Bond et al. |
| 5,308,576 | A | 5/1994 | Green et al. |
| 5,309,387 | A | 5/1994 | Mori et al. |
| 5,309,927 | A | 5/1994 | Welch |
| 5,312,023 | A | 5/1994 | Green et al. |
| 5,312,024 | A | 5/1994 | Grant et al. |
| 5,312,329 | A | 5/1994 | Beaty et al. |
| 5,313,935 | A | 5/1994 | Kortenbach et al. |
| 5,313,967 | A | 5/1994 | Lieber et al. |
| 5,314,424 | A | 5/1994 | Nicholas |
| 5,314,445 | A | 5/1994 | Heidmueller Degwitz et al. |
| 5,314,466 | A | 5/1994 | Stern et al. |
| 5,318,221 | A | 6/1994 | Green et al. |
| 5,318,589 | A | 6/1994 | Lichtman |
| 5,320,627 | A | 6/1994 | Sorensen et al. |
| D348,930 | S | 7/1994 | Olson |
| 5,326,013 | A | 7/1994 | Green et al. |
| 5,329,923 | A | 7/1994 | Lundquist |
| 5,330,486 | A | 7/1994 | Wilk |
| 5,330,487 | A | 7/1994 | Thornton et al. |
| 5,330,502 | A | 7/1994 | Hassler et al. |
| 5,331,971 | A | 7/1994 | Bales et al. |
| 5,332,142 | A | 7/1994 | Robinson et al. |

(56) References Cited

U.S. PATENT DOCUMENTS

| | | | |
|---|---|---|---|
| 5,333,422 | A | 8/1994 | Warren et al. |
| 5,333,772 | A | 8/1994 | Rothfuss et al. |
| 5,333,773 | A | 8/1994 | Main et al. |
| 5,334,183 | A | 8/1994 | Wuchinich |
| 5,336,130 | A | 8/1994 | Ray |
| 5,336,229 | A | 8/1994 | Noda |
| 5,336,232 | A | 8/1994 | Green et al. |
| 5,338,317 | A | 8/1994 | Hasson et al. |
| 5,339,799 | A | 8/1994 | Kami et al. |
| 5,341,724 | A | 8/1994 | Vatel |
| 5,341,807 | A | 8/1994 | Nardella |
| 5,341,810 | A | 8/1994 | Dardel |
| 5,342,380 | A | 8/1994 | Hood |
| 5,342,381 | A | 8/1994 | Tidemand |
| 5,342,385 | A | 8/1994 | Norelli et al. |
| 5,342,395 | A | 8/1994 | Jarrett et al. |
| 5,342,396 | A | 8/1994 | Cook |
| 5,343,382 | A | 8/1994 | Hale et al. |
| 5,343,391 | A | 8/1994 | Mushabac |
| 5,344,059 | A | 9/1994 | Green et al. |
| 5,344,060 | A | 9/1994 | Gravener et al. |
| 5,344,454 | A | 9/1994 | Clarke et al. |
| 5,346,504 | A | 9/1994 | Ortiz et al. |
| 5,348,259 | A | 9/1994 | Blanco et al. |
| 5,350,104 | A | 9/1994 | Main et al. |
| 5,350,355 | A | 9/1994 | Sklar |
| 5,350,388 | A | 9/1994 | Epstein |
| 5,350,391 | A | 9/1994 | Iacovelli |
| 5,350,400 | A | 9/1994 | Esposito et al. |
| 5,352,229 | A | 10/1994 | Goble et al. |
| 5,352,235 | A | 10/1994 | Koros et al. |
| 5,352,238 | A | 10/1994 | Green et al. |
| 5,353,798 | A | 10/1994 | Sieben |
| 5,354,215 | A | 10/1994 | Viracola |
| 5,354,250 | A | 10/1994 | Christensen |
| 5,354,303 | A | 10/1994 | Spaeth et al. |
| 5,355,897 | A | 10/1994 | Pietrafitta et al. |
| 5,356,006 | A | 10/1994 | Alpern et al. |
| 5,356,064 | A | 10/1994 | Green et al. |
| 5,358,506 | A | 10/1994 | Green et al. |
| 5,358,510 | A | 10/1994 | Luscombe et al. |
| 5,359,231 | A | 10/1994 | Flowers et al. |
| D352,780 | S | 11/1994 | Glaeser et al. |
| 5,359,993 | A | 11/1994 | Slater et al. |
| 5,360,305 | A | 11/1994 | Kerrigan |
| 5,360,428 | A | 11/1994 | Hutchinson, Jr. |
| 5,361,902 | A | 11/1994 | Abidin et al. |
| 5,364,001 | A | 11/1994 | Bryan |
| 5,364,002 | A | 11/1994 | Green et al. |
| 5,364,003 | A | 11/1994 | Williamson, IV |
| 5,366,133 | A | 11/1994 | Geiste |
| 5,366,134 | A | 11/1994 | Green et al. |
| 5,366,479 | A | 11/1994 | McGarry et al. |
| 5,368,015 | A | 11/1994 | Wilk |
| 5,368,592 | A | 11/1994 | Stern et al. |
| 5,368,599 | A | 11/1994 | Hirsch et al. |
| 5,369,565 | A | 11/1994 | Chen et al. |
| 5,370,645 | A | 12/1994 | Klicek et al. |
| 5,372,124 | A | 12/1994 | Takayama et al. |
| 5,372,596 | A | 12/1994 | Klicek et al. |
| 5,372,602 | A | 12/1994 | Burke |
| 5,374,277 | A | 12/1994 | Hassler |
| 5,375,588 | A | 12/1994 | Yoon |
| 5,376,095 | A | 12/1994 | Ortiz |
| 5,379,933 | A | 1/1995 | Green et al. |
| 5,381,649 | A | 1/1995 | Webb |
| 5,381,782 | A | 1/1995 | DeLaRama et al. |
| 5,381,943 | A | 1/1995 | Allen et al. |
| 5,382,247 | A | 1/1995 | Cimino et al. |
| 5,383,460 | A | 1/1995 | Jang et al. |
| 5,383,738 | A | 1/1995 | Herbermann |
| 5,383,874 | A | 1/1995 | Jackson et al. |
| 5,383,880 | A | 1/1995 | Hooven |
| 5,383,881 | A | 1/1995 | Green et al. |
| 5,383,882 | A | 1/1995 | Buess et al. |
| 5,383,888 | A | 1/1995 | Zvenyatsky et al. |
| 5,383,895 | A | 1/1995 | Holmes et al. |
| 5,388,568 | A | 2/1995 | van der Heide |
| 5,389,072 | A | 2/1995 | Imran |
| 5,389,098 | A | 2/1995 | Tsuruta et al. |
| 5,389,102 | A | 2/1995 | Green et al. |
| 5,389,104 | A | 2/1995 | Hahnen et al. |
| 5,391,180 | A | 2/1995 | Tovey et al. |
| 5,392,979 | A | 2/1995 | Green et al. |
| 5,395,030 | A | 3/1995 | Kuramoto et al. |
| 5,395,033 | A | 3/1995 | Byrne et al. |
| 5,395,034 | A | 3/1995 | Allen et al. |
| 5,395,312 | A | 3/1995 | Desai |
| 5,395,384 | A | 3/1995 | Duthoit et al. |
| 5,397,046 | A | 3/1995 | Savage et al. |
| 5,397,324 | A | 3/1995 | Carroll et al. |
| 5,400,267 | A | 3/1995 | Denen et al. |
| 5,403,276 | A | 4/1995 | Schechter et al. |
| 5,403,312 | A | 4/1995 | Yates et al. |
| 5,404,106 | A | 4/1995 | Matsuda |
| 5,404,870 | A | 4/1995 | Brinkerhoff et al. |
| 5,404,960 | A | 4/1995 | Wada et al. |
| 5,405,072 | A | 4/1995 | Zlock et al. |
| 5,405,073 | A | 4/1995 | Porter |
| 5,405,344 | A | 4/1995 | Williamson et al. |
| 5,405,360 | A | 4/1995 | Tovey |
| 5,407,293 | A | 4/1995 | Crainich |
| 5,408,409 | A | 4/1995 | Glassman et al. |
| 5,409,498 | A | 4/1995 | Braddock et al. |
| 5,409,703 | A | 4/1995 | McAnalley et al. |
| D357,981 | S | 5/1995 | Green et al. |
| 5,411,481 | A | 5/1995 | Allen et al. |
| 5,411,508 | A | 5/1995 | Bessler et al. |
| 5,413,107 | A | 5/1995 | Oakley et al. |
| 5,413,267 | A | 5/1995 | Solyntjes et al. |
| 5,413,268 | A | 5/1995 | Green et al. |
| 5,413,272 | A | 5/1995 | Green et al. |
| 5,413,573 | A | 5/1995 | Koivukangas |
| 5,415,334 | A | 5/1995 | Williamson et al. |
| 5,415,335 | A | 5/1995 | Knodell, Jr. |
| 5,417,203 | A | 5/1995 | Tovey et al. |
| 5,417,361 | A | 5/1995 | Williamson, IV |
| 5,419,766 | A | 5/1995 | Chang et al. |
| 5,421,829 | A | 6/1995 | Olichney et al. |
| 5,422,567 | A | 6/1995 | Matsunaga |
| 5,423,471 | A | 6/1995 | Mastri et al. |
| 5,423,809 | A | 6/1995 | Klicek |
| 5,423,835 | A | 6/1995 | Green et al. |
| 5,425,355 | A | 6/1995 | Kulick |
| 5,425,745 | A | 6/1995 | Green et al. |
| 5,427,298 | A | 6/1995 | Tegtmeier |
| 5,431,322 | A | 7/1995 | Green et al. |
| 5,431,323 | A | 7/1995 | Smith et al. |
| 5,431,645 | A | 7/1995 | Smith et al. |
| 5,431,654 | A | 7/1995 | Nic |
| 5,431,666 | A | 7/1995 | Sauer et al. |
| 5,431,668 | A | 7/1995 | Burbank, III et al. |
| 5,433,721 | A | 7/1995 | Hooven et al. |
| 5,437,681 | A | 8/1995 | Meade et al. |
| 5,438,302 | A | 8/1995 | Goble |
| 5,438,997 | A | 8/1995 | Sieben et al. |
| 5,439,155 | A | 8/1995 | Viola |
| 5,439,156 | A | 8/1995 | Grant et al. |
| 5,439,479 | A | 8/1995 | Shichman et al. |
| 5,441,191 | A | 8/1995 | Linden |
| 5,441,193 | A | 8/1995 | Gravener |
| 5,441,483 | A | 8/1995 | Avitall |
| 5,441,494 | A | 8/1995 | Ortiz |
| 5,441,499 | A | 8/1995 | Fritzsch |
| 5,443,197 | A | 8/1995 | Malis et al. |
| 5,443,198 | A | 8/1995 | Viola et al. |
| 5,443,463 | A | 8/1995 | Stern et al. |
| 5,444,113 | A | 8/1995 | Sinclair et al. |
| 5,445,155 | A | 8/1995 | Sieben |
| 5,445,304 | A | 8/1995 | Plyley et al. |
| 5,445,604 | A | 8/1995 | Lang |
| 5,445,644 | A | 8/1995 | Pietrafitta et al. |
| 5,446,646 | A | 8/1995 | Miyazaki |
| 5,447,265 | A | 9/1995 | Vidal et al. |

(56) References Cited

U.S. PATENT DOCUMENTS

| | | | |
|---|---|---|---|
| 5,447,417 | A | 9/1995 | Kuhl et al. |
| 5,447,513 | A | 9/1995 | Davison et al. |
| 5,449,355 | A | 9/1995 | Rhum et al. |
| 5,449,365 | A | 9/1995 | Green et al. |
| 5,449,370 | A | 9/1995 | Vaitekunas |
| 5,452,836 | A | 9/1995 | Huitema et al. |
| 5,452,837 | A | 9/1995 | Williamson, IV et al. |
| 5,454,378 | A | 10/1995 | Palmer et al. |
| 5,454,822 | A | 10/1995 | Schob et al. |
| 5,454,824 | A | 10/1995 | Fontayne et al. |
| 5,454,827 | A | 10/1995 | Aust et al. |
| 5,456,401 | A | 10/1995 | Green et al. |
| 5,456,917 | A | 10/1995 | Wise et al. |
| 5,458,279 | A | 10/1995 | Plyley |
| 5,458,579 | A | 10/1995 | Chodorow et al. |
| 5,462,215 | A | 10/1995 | Viola et al. |
| 5,464,013 | A | 11/1995 | Lemelson |
| 5,464,144 | A | 11/1995 | Guy et al. |
| 5,464,300 | A | 11/1995 | Crainich |
| 5,465,819 | A | 11/1995 | Weilant et al. |
| 5,465,894 | A | 11/1995 | Clark et al. |
| 5,465,895 | A | 11/1995 | Knodel et al. |
| 5,465,896 | A | 11/1995 | Allen et al. |
| 5,466,020 | A | 11/1995 | Page et al. |
| 5,467,911 | A | 11/1995 | Tsuruta et al. |
| 5,468,253 | A | 11/1995 | Bezwada et al. |
| 5,470,006 | A | 11/1995 | Rodak |
| 5,470,007 | A | 11/1995 | Plyley et al. |
| 5,470,008 | A | 11/1995 | Rodak |
| 5,470,009 | A | 11/1995 | Rodak |
| 5,470,010 | A | 11/1995 | Rothfuss et al. |
| 5,471,129 | A | 11/1995 | Mann |
| 5,472,132 | A | 12/1995 | Savage et al. |
| 5,472,442 | A | 12/1995 | Klicek |
| 5,473,204 | A | 12/1995 | Temple |
| 5,474,057 | A | 12/1995 | Makower et al. |
| 5,474,223 | A | 12/1995 | Viola et al. |
| 5,474,566 | A | 12/1995 | Alesi et al. |
| 5,474,570 | A | 12/1995 | Kockerling et al. |
| 5,474,738 | A | 12/1995 | Nichols et al. |
| 5,476,206 | A | 12/1995 | Green et al. |
| 5,476,479 | A | 12/1995 | Green et al. |
| 5,476,481 | A | 12/1995 | Schondorf |
| 5,478,003 | A | 12/1995 | Green et al. |
| 5,478,308 | A | 12/1995 | Cartmell et al. |
| 5,478,354 | A | 12/1995 | Tovey et al. |
| 5,480,089 | A | 1/1996 | Blewett |
| 5,480,409 | A | 1/1996 | Riza |
| 5,482,197 | A | 1/1996 | Green et al. |
| 5,483,952 | A | 1/1996 | Aranyi |
| 5,484,095 | A | 1/1996 | Green et al. |
| 5,484,398 | A | 1/1996 | Stoddard |
| 5,484,451 | A | 1/1996 | Akopov et al. |
| 5,485,947 | A | 1/1996 | Olson et al. |
| 5,485,952 | A | 1/1996 | Fontayne |
| 5,487,377 | A | 1/1996 | Smith et al. |
| 5,487,499 | A | 1/1996 | Sorrentino et al. |
| 5,487,500 | A | 1/1996 | Knodel et al. |
| 5,489,058 | A | 2/1996 | Plyley et al. |
| 5,489,256 | A | 2/1996 | Adair |
| 5,489,290 | A | 2/1996 | Furnish |
| 5,490,819 | A | 2/1996 | Nicholas et al. |
| 5,492,671 | A | 2/1996 | Krafft |
| 5,496,312 | A | 3/1996 | Klicek |
| 5,496,317 | A | 3/1996 | Goble et al. |
| 5,497,933 | A | 3/1996 | DeFonzo et al. |
| 5,498,164 | A | 3/1996 | Ward et al. |
| 5,498,838 | A | 3/1996 | Furman |
| 5,501,654 | A | 3/1996 | Failla et al. |
| 5,503,320 | A | 4/1996 | Webster et al. |
| 5,503,635 | A | 4/1996 | Sauer et al. |
| 5,503,638 | A | 4/1996 | Cooper et al. |
| 5,505,363 | A | 4/1996 | Green et al. |
| 5,507,425 | A | 4/1996 | Ziglioli |
| 5,507,426 | A | 4/1996 | Young et al. |
| 5,507,773 | A | 4/1996 | Huitema et al. |
| 5,509,596 | A | 4/1996 | Green et al. |
| 5,509,916 | A | 4/1996 | Taylor |
| 5,509,918 | A | 4/1996 | Romano |
| 5,511,564 | A | 4/1996 | Wilk |
| 5,514,129 | A | 5/1996 | Smith |
| 5,514,149 | A | 5/1996 | Green et al. |
| 5,514,157 | A | 5/1996 | Nicholas et al. |
| 5,518,163 | A | 5/1996 | Hooven |
| 5,518,164 | A | 5/1996 | Hooven |
| 5,520,609 | A | 5/1996 | Moll et al. |
| 5,520,634 | A | 5/1996 | Fox et al. |
| 5,520,678 | A | 5/1996 | Heckele et al. |
| 5,520,700 | A | 5/1996 | Beyar et al. |
| 5,522,817 | A | 6/1996 | Sander et al. |
| 5,522,831 | A | 6/1996 | Sleister et al. |
| 5,527,264 | A | 6/1996 | Moll et al. |
| 5,527,320 | A | 6/1996 | Carruthers et al. |
| 5,529,235 | A | 6/1996 | Boiarski et al. |
| D372,086 | S | 7/1996 | Grasso et al. |
| 5,531,305 | A | 7/1996 | Roberts et al. |
| 5,531,744 | A | 7/1996 | Nardella et al. |
| 5,531,856 | A | 7/1996 | Moll et al. |
| 5,533,521 | A | 7/1996 | Granger |
| 5,533,581 | A | 7/1996 | Barth et al. |
| 5,533,661 | A | 7/1996 | Main et al. |
| 5,535,934 | A | 7/1996 | Boiarski et al. |
| 5,535,935 | A | 7/1996 | Vidal et al. |
| 5,535,937 | A | 7/1996 | Boiarski et al. |
| 5,540,375 | A | 7/1996 | Bolanos et al. |
| 5,540,705 | A | 7/1996 | Meade et al. |
| 5,541,376 | A | 7/1996 | Ladtkow et al. |
| 5,541,489 | A | 7/1996 | Dunstan |
| 5,542,594 | A | 8/1996 | McKean et al. |
| 5,542,945 | A | 8/1996 | Fritzsch |
| 5,542,949 | A | 8/1996 | Yoon |
| 5,543,119 | A | 8/1996 | Sutter et al. |
| 5,543,695 | A | 8/1996 | Culp et al. |
| 5,544,802 | A | 8/1996 | Crainich |
| 5,547,117 | A | 8/1996 | Hamblin et al. |
| 5,549,583 | A | 8/1996 | Sanford et al. |
| 5,549,621 | A | 8/1996 | Bessler et al. |
| 5,549,627 | A | 8/1996 | Kieturakis |
| 5,549,628 | A | 8/1996 | Cooper et al. |
| 5,549,637 | A | 8/1996 | Crainich |
| 5,551,622 | A | 9/1996 | Yoon |
| 5,553,624 | A | 9/1996 | Francese et al. |
| 5,553,675 | A | 9/1996 | Pitzen et al. |
| 5,553,765 | A | 9/1996 | Knodel et al. |
| 5,554,148 | A | 9/1996 | Aebischer et al. |
| 5,554,169 | A | 9/1996 | Green et al. |
| 5,556,020 | A | 9/1996 | Hou |
| 5,556,416 | A | 9/1996 | Clark et al. |
| 5,558,533 | A | 9/1996 | Hashizawa et al. |
| 5,558,665 | A | 9/1996 | Kieturakis |
| 5,558,671 | A | 9/1996 | Yates |
| 5,560,530 | A | 10/1996 | Bolanos et al. |
| 5,560,532 | A | 10/1996 | DeFonzo et al. |
| 5,561,881 | A | 10/1996 | Klinger et al. |
| 5,562,239 | A | 10/1996 | Boiarski et al. |
| 5,562,241 | A | 10/1996 | Knodel et al. |
| 5,562,682 | A | 10/1996 | Oberlin et al. |
| 5,562,690 | A | 10/1996 | Green et al. |
| 5,562,694 | A | 10/1996 | Sauer et al. |
| 5,562,701 | A | 10/1996 | Huitema et al. |
| 5,562,702 | A | 10/1996 | Huitema et al. |
| 5,563,481 | A | 10/1996 | Krause |
| 5,564,615 | A | 10/1996 | Bishop et al. |
| 5,569,161 | A | 10/1996 | Ebling et al. |
| 5,569,270 | A | 10/1996 | Weng |
| 5,569,284 | A | 10/1996 | Young et al. |
| 5,571,090 | A | 11/1996 | Sherts |
| 5,571,100 | A | 11/1996 | Goble et al. |
| 5,571,116 | A | 11/1996 | Bolanos et al. |
| 5,571,285 | A | 11/1996 | Chow et al. |
| 5,571,488 | A | 11/1996 | Beerstecher et al. |
| 5,573,169 | A | 11/1996 | Green et al. |
| 5,573,543 | A | 11/1996 | Akopov et al. |
| 5,574,431 | A | 11/1996 | McKeown et al. |

(56) References Cited

U.S. PATENT DOCUMENTS

| | | | |
|---|---|---|---|
| 5,575,054 | A | 11/1996 | Klinzing et al. |
| 5,575,789 | A | 11/1996 | Bell et al. |
| 5,575,799 | A | 11/1996 | Bolanos et al. |
| 5,575,803 | A | 11/1996 | Cooper et al. |
| 5,575,805 | A | 11/1996 | Li |
| 5,577,654 | A | 11/1996 | Bishop |
| 5,578,052 | A | 11/1996 | Koros et al. |
| 5,579,978 | A | 12/1996 | Green et al. |
| 5,580,067 | A | 12/1996 | Hamblin et al. |
| 5,582,611 | A | 12/1996 | Tsuruta et al. |
| 5,582,617 | A | 12/1996 | Klieman et al. |
| 5,582,907 | A | 12/1996 | Pall |
| 5,583,114 | A | 12/1996 | Barrows et al. |
| 5,584,425 | A | 12/1996 | Savage et al. |
| 5,586,711 | A | 12/1996 | Plyley et al. |
| 5,588,579 | A | 12/1996 | Schnut et al. |
| 5,588,580 | A | 12/1996 | Paul et al. |
| 5,588,581 | A | 12/1996 | Conlon et al. |
| 5,591,170 | A | 1/1997 | Spievack et al. |
| 5,591,187 | A | 1/1997 | Dekel |
| 5,597,107 | A | 1/1997 | Knodel et al. |
| 5,599,151 | A | 2/1997 | Daum et al. |
| 5,599,279 | A | 2/1997 | Slotman et al. |
| 5,599,344 | A | 2/1997 | Paterson |
| 5,599,350 | A | 2/1997 | Schulze et al. |
| 5,599,852 | A | 2/1997 | Scopelianos et al. |
| 5,601,224 | A | 2/1997 | Bishop et al. |
| 5,601,573 | A | 2/1997 | Fogelberg et al. |
| 5,601,604 | A | 2/1997 | Vincent |
| 5,602,449 | A | 2/1997 | Krause et al. |
| 5,603,443 | A | 2/1997 | Clark et al. |
| 5,605,272 | A | 2/1997 | Witt et al. |
| 5,605,273 | A | 2/1997 | Hamblin et al. |
| 5,607,094 | A | 3/1997 | Clark et al. |
| 5,607,095 | A | 3/1997 | Smith et al. |
| 5,607,303 | A | 3/1997 | Nakamura |
| 5,607,433 | A | 3/1997 | Polla et al. |
| 5,607,436 | A | 3/1997 | Pratt et al. |
| 5,607,450 | A | 3/1997 | Zvenyatsky et al. |
| 5,607,474 | A | 3/1997 | Athanasiou et al. |
| 5,609,285 | A | 3/1997 | Grant et al. |
| 5,609,601 | A | 3/1997 | Kolesa et al. |
| 5,611,709 | A | 3/1997 | McAnulty |
| 5,611,813 | A | 3/1997 | Lichtman |
| 5,613,499 | A | 3/1997 | Palmer et al. |
| 5,613,937 | A | 3/1997 | Garrison et al. |
| 5,613,966 | A | 3/1997 | Makower et al. |
| 5,614,887 | A | 3/1997 | Buchbinder |
| 5,615,820 | A | 4/1997 | Viola |
| 5,618,294 | A | 4/1997 | Aust et al. |
| 5,618,303 | A | 4/1997 | Marlow et al. |
| 5,618,307 | A | 4/1997 | Donlon et al. |
| 5,619,992 | A | 4/1997 | Guthrie et al. |
| 5,620,289 | A | 4/1997 | Curry |
| 5,620,326 | A | 4/1997 | Younker |
| 5,620,452 | A | 4/1997 | Yoon |
| 5,624,398 | A | 4/1997 | Smith et al. |
| 5,624,452 | A | 4/1997 | Yates |
| 5,626,587 | A | 5/1997 | Bishop et al. |
| 5,626,595 | A | 5/1997 | Sklar et al. |
| 5,626,979 | A | 5/1997 | Mitsui et al. |
| 5,628,446 | A | 5/1997 | Geiste et al. |
| 5,628,743 | A | 5/1997 | Cimino |
| 5,628,745 | A | 5/1997 | Bek |
| 5,630,539 | A | 5/1997 | Plyley et al. |
| 5,630,540 | A | 5/1997 | Blewett |
| 5,630,541 | A | 5/1997 | Williamson, IV et al. |
| 5,630,782 | A | 5/1997 | Adair |
| 5,631,973 | A | 5/1997 | Green |
| 5,632,432 | A | 5/1997 | Schulze et al. |
| 5,632,433 | A | 5/1997 | Grant et al. |
| 5,633,374 | A | 5/1997 | Humphrey et al. |
| 5,634,584 | A | 6/1997 | Okorocha et al. |
| 5,636,779 | A | 6/1997 | Palmer |
| 5,636,780 | A | 6/1997 | Green et al. |
| 5,637,110 | A | 6/1997 | Pennybacker et al. |
| 5,638,582 | A | 6/1997 | Klatt et al. |
| 5,639,008 | A | 6/1997 | Gallagher et al. |
| D381,077 | S | 7/1997 | Hunt |
| 5,643,291 | A | 7/1997 | Pier et al. |
| 5,643,293 | A | 7/1997 | Kogasaka et al. |
| 5,643,294 | A | 7/1997 | Tovey et al. |
| 5,643,319 | A | 7/1997 | Green et al. |
| 5,645,209 | A | 7/1997 | Green et al. |
| 5,647,526 | A | 7/1997 | Green et al. |
| 5,647,869 | A | 7/1997 | Goble et al. |
| 5,649,937 | A | 7/1997 | Bito et al. |
| 5,649,956 | A | 7/1997 | Jensen et al. |
| 5,651,491 | A | 7/1997 | Heaton et al. |
| 5,651,762 | A | 7/1997 | Bridges |
| 5,651,821 | A | 7/1997 | Uchida |
| 5,653,373 | A | 8/1997 | Green et al. |
| 5,653,374 | A | 8/1997 | Young et al. |
| 5,653,677 | A | 8/1997 | Okada et al. |
| 5,653,721 | A | 8/1997 | Knodel et al. |
| 5,653,748 | A | 8/1997 | Strecker |
| 5,655,698 | A | 8/1997 | Yoon |
| 5,656,917 | A | 8/1997 | Theobald |
| 5,657,417 | A | 8/1997 | Di Troia |
| 5,657,429 | A | 8/1997 | Wang et al. |
| 5,657,921 | A | 8/1997 | Young et al. |
| 5,658,238 | A | 8/1997 | Suzuki et al. |
| 5,658,281 | A | 8/1997 | Heard |
| 5,658,298 | A | 8/1997 | Vincent et al. |
| 5,658,300 | A | 8/1997 | Bito et al. |
| 5,658,307 | A | 8/1997 | Exconde |
| 5,662,258 | A | 9/1997 | Knodel et al. |
| 5,662,260 | A | 9/1997 | Yoon |
| 5,662,662 | A | 9/1997 | Bishop et al. |
| 5,662,667 | A | 9/1997 | Knodel |
| 5,664,404 | A | 9/1997 | Ivanov et al. |
| 5,665,085 | A | 9/1997 | Nardella |
| 5,667,517 | A | 9/1997 | Hooven |
| 5,667,526 | A | 9/1997 | Levin |
| 5,667,527 | A | 9/1997 | Cook |
| 5,667,864 | A | 9/1997 | Landoll |
| 5,669,544 | A | 9/1997 | Schulze et al. |
| 5,669,904 | A | 9/1997 | Platt, Jr. et al. |
| 5,669,907 | A | 9/1997 | Platt, Jr. et al. |
| 5,669,918 | A | 9/1997 | Balazs et al. |
| 5,672,945 | A | 9/1997 | Krause |
| 5,673,840 | A | 10/1997 | Schulze et al. |
| 5,673,841 | A | 10/1997 | Schulze et al. |
| 5,673,842 | A | 10/1997 | Bittner et al. |
| 5,674,184 | A | 10/1997 | Hassler, Jr. |
| 5,674,286 | A | 10/1997 | D'Alessio et al. |
| 5,678,748 | A | 10/1997 | Plyley et al. |
| 5,680,981 | A | 10/1997 | Mililli et al. |
| 5,680,982 | A | 10/1997 | Schulze et al. |
| 5,680,983 | A | 10/1997 | Plyley et al. |
| 5,681,341 | A | 10/1997 | Lunsford et al. |
| 5,683,349 | A | 11/1997 | Makower et al. |
| 5,685,474 | A | 11/1997 | Seeber |
| 5,686,090 | A | 11/1997 | Schilder et al. |
| 5,688,270 | A | 11/1997 | Yates et al. |
| 5,690,269 | A | 11/1997 | Bolanos et al. |
| 5,690,675 | A | 11/1997 | Sawyer et al. |
| 5,692,668 | A | 12/1997 | Schulze et al. |
| 5,693,020 | A | 12/1997 | Rauh |
| 5,693,042 | A | 12/1997 | Boiarski et al. |
| 5,693,051 | A | 12/1997 | Schulze et al. |
| 5,695,494 | A | 12/1997 | Becker |
| 5,695,502 | A | 12/1997 | Pier et al. |
| 5,695,504 | A | 12/1997 | Gifford, III et al. |
| 5,695,524 | A | 12/1997 | Kelley et al. |
| 5,697,542 | A | 12/1997 | Knodel et al. |
| 5,697,543 | A | 12/1997 | Burdorf |
| 5,697,909 | A | 12/1997 | Eggers et al. |
| 5,697,943 | A | 12/1997 | Sauer et al. |
| 5,700,265 | A | 12/1997 | Romano |
| 5,700,270 | A | 12/1997 | Peyser et al. |
| 5,700,276 | A | 12/1997 | Benecke |
| 5,702,387 | A | 12/1997 | Arts et al. |
| 5,702,408 | A | 12/1997 | Wales et al. |

(56) References Cited

U.S. PATENT DOCUMENTS

| | | | |
|---|---|---|---|
| 5,702,409 | A | 12/1997 | Rayburn et al. |
| 5,704,087 | A | 1/1998 | Strub |
| 5,704,534 | A | 1/1998 | Huitema et al. |
| 5,704,792 | A | 1/1998 | Sobhani |
| 5,706,997 | A | 1/1998 | Green et al. |
| 5,706,998 | A | 1/1998 | Plyley et al. |
| 5,707,392 | A | 1/1998 | Kortenbach |
| 5,709,334 | A | 1/1998 | Sorrentino et al. |
| 5,709,335 | A | 1/1998 | Heck |
| 5,709,680 | A | 1/1998 | Yates et al. |
| 5,709,706 | A | 1/1998 | Kienzle et al. |
| 5,711,472 | A | 1/1998 | Bryan |
| 5,711,960 | A | 1/1998 | Shikinami |
| 5,712,460 | A | 1/1998 | Carr et al. |
| 5,713,128 | A | 2/1998 | Schrenk et al. |
| 5,713,505 | A | 2/1998 | Huitema |
| 5,713,895 | A | 2/1998 | Lontine et al. |
| 5,713,896 | A | 2/1998 | Nardella |
| 5,713,920 | A | 2/1998 | Bezwada et al. |
| 5,715,604 | A | 2/1998 | Lanzoni |
| 5,715,836 | A | 2/1998 | Kliegis et al. |
| 5,715,987 | A | 2/1998 | Kelley et al. |
| 5,715,988 | A | 2/1998 | Palmer |
| 5,716,352 | A | 2/1998 | Viola et al. |
| 5,716,366 | A | 2/1998 | Yates |
| 5,718,359 | A | 2/1998 | Palmer et al. |
| 5,718,360 | A | 2/1998 | Green et al. |
| 5,718,548 | A | 2/1998 | Cotellessa |
| 5,718,714 | A | 2/1998 | Livneh |
| 5,720,744 | A | 2/1998 | Eggleston et al. |
| D393,067 | S | 3/1998 | Geary et al. |
| 5,724,025 | A | 3/1998 | Tavori |
| 5,725,536 | A | 3/1998 | Oberlin et al. |
| 5,725,554 | A | 3/1998 | Simon et al. |
| 5,728,110 | A | 3/1998 | Vidal et al. |
| 5,728,113 | A | 3/1998 | Sherts |
| 5,728,121 | A | 3/1998 | Bimbo et al. |
| 5,730,758 | A | 3/1998 | Allgeyer |
| 5,732,712 | A | 3/1998 | Adair |
| 5,732,821 | A | 3/1998 | Stone et al. |
| 5,732,871 | A | 3/1998 | Clark et al. |
| 5,732,872 | A | 3/1998 | Bolduc et al. |
| 5,733,308 | A | 3/1998 | Daugherty et al. |
| 5,735,445 | A | 4/1998 | Vidal et al. |
| 5,735,848 | A | 4/1998 | Yates et al. |
| 5,735,874 | A | 4/1998 | Measamer et al. |
| 5,736,271 | A | 4/1998 | Cisar et al. |
| 5,738,474 | A | 4/1998 | Blewett |
| 5,738,629 | A | 4/1998 | Moll et al. |
| 5,738,648 | A | 4/1998 | Lands et al. |
| 5,741,271 | A | 4/1998 | Nakao et al. |
| 5,743,456 | A | 4/1998 | Jones et al. |
| 5,746,770 | A | 5/1998 | Zeitels et al. |
| 5,747,953 | A | 5/1998 | Philipp |
| 5,749,889 | A | 5/1998 | Bacich et al. |
| 5,749,893 | A | 5/1998 | Vidal et al. |
| 5,749,896 | A | 5/1998 | Cook |
| 5,749,968 | A | 5/1998 | Melanson et al. |
| 5,752,644 | A | 5/1998 | Bolanos et al. |
| 5,752,965 | A | 5/1998 | Francis et al. |
| 5,752,970 | A | 5/1998 | Yoon |
| 5,752,973 | A | 5/1998 | Kieturakis |
| 5,755,717 | A | 5/1998 | Yates et al. |
| 5,755,726 | A | 5/1998 | Pratt et al. |
| 5,758,814 | A | 6/1998 | Gallagher et al. |
| 5,762,255 | A | 6/1998 | Chrisman et al. |
| 5,762,256 | A | 6/1998 | Mastri et al. |
| 5,762,458 | A | 6/1998 | Wang et al. |
| 5,765,565 | A | 6/1998 | Adair |
| 5,766,186 | A | 6/1998 | Faraz et al. |
| 5,766,188 | A | 6/1998 | Igaki |
| 5,766,205 | A | 6/1998 | Zvenyatsky et al. |
| 5,769,303 | A | 6/1998 | Knodel et al. |
| 5,769,640 | A | 6/1998 | Jacobus et al. |
| 5,769,748 | A | 6/1998 | Eyerly et al. |
| 5,769,791 | A | 6/1998 | Benaron et al. |
| 5,769,892 | A | 6/1998 | Kingwell |
| 5,772,099 | A | 6/1998 | Gravener |
| 5,772,379 | A | 6/1998 | Evensen |
| 5,772,578 | A | 6/1998 | Heimberger et al. |
| 5,772,659 | A | 6/1998 | Becker et al. |
| 5,773,991 | A | 6/1998 | Chen |
| 5,776,130 | A | 7/1998 | Buysse et al. |
| 5,778,939 | A | 7/1998 | Hok-Yin |
| 5,779,130 | A | 7/1998 | Alesi et al. |
| 5,779,131 | A | 7/1998 | Knodel et al. |
| 5,779,132 | A | 7/1998 | Knodel et al. |
| 5,782,396 | A | 7/1998 | Mastri et al. |
| 5,782,397 | A | 7/1998 | Koukline |
| 5,782,748 | A | 7/1998 | Palmer et al. |
| 5,782,749 | A | 7/1998 | Riza |
| 5,782,859 | A | 7/1998 | Nicholas et al. |
| 5,784,934 | A | 7/1998 | Izumisawa |
| 5,785,232 | A | 7/1998 | Vidal et al. |
| 5,785,647 | A | 7/1998 | Tompkins et al. |
| 5,787,897 | A | 8/1998 | Kieturakis |
| 5,791,231 | A | 8/1998 | Cohn et al. |
| 5,792,135 | A | 8/1998 | Madhani et al. |
| 5,792,162 | A | 8/1998 | Jolly et al. |
| 5,792,165 | A | 8/1998 | Klieman et al. |
| 5,792,573 | A | 8/1998 | Pitzen et al. |
| 5,794,834 | A | 8/1998 | Hamblin et al. |
| 5,796,188 | A | 8/1998 | Bays |
| 5,797,536 | A | 8/1998 | Smith et al. |
| 5,797,537 | A | 8/1998 | Oberlin et al. |
| 5,797,538 | A | 8/1998 | Heaton et al. |
| 5,797,637 | A | 8/1998 | Ervin |
| 5,797,900 | A | 8/1998 | Madhani et al. |
| 5,797,906 | A | 8/1998 | Rhum et al. |
| 5,797,927 | A | 8/1998 | Yoon |
| 5,797,941 | A | 8/1998 | Schulze et al. |
| 5,797,959 | A | 8/1998 | Castro et al. |
| 5,798,752 | A | 8/1998 | Buxton et al. |
| 5,799,857 | A | 9/1998 | Robertson et al. |
| 5,800,379 | A | 9/1998 | Edwards |
| 5,800,423 | A | 9/1998 | Jensen |
| 5,804,726 | A | 9/1998 | Geib et al. |
| 5,804,936 | A | 9/1998 | Brodsky et al. |
| 5,806,676 | A | 9/1998 | Wasgien |
| 5,807,241 | A | 9/1998 | Heimberger |
| 5,807,376 | A | 9/1998 | Viola et al. |
| 5,807,378 | A | 9/1998 | Jensen et al. |
| 5,807,393 | A | 9/1998 | Williamson, IV et al. |
| 5,809,441 | A | 9/1998 | McKee |
| 5,810,240 | A | 9/1998 | Robertson |
| 5,810,721 | A | 9/1998 | Mueller et al. |
| 5,810,811 | A | 9/1998 | Yates et al. |
| 5,810,846 | A | 9/1998 | Virnich et al. |
| 5,810,855 | A | 9/1998 | Rayburn et al. |
| 5,812,188 | A | 9/1998 | Adair |
| 5,813,813 | A | 9/1998 | Daum et al. |
| 5,814,055 | A | 9/1998 | Knodel et al. |
| 5,814,057 | A | 9/1998 | Oi et al. |
| 5,816,471 | A | 10/1998 | Plyley et al. |
| 5,817,084 | A | 10/1998 | Jensen |
| 5,817,091 | A | 10/1998 | Nardella et al. |
| 5,817,093 | A | 10/1998 | Williamson, IV et al. |
| 5,817,109 | A | 10/1998 | McGarry et al. |
| 5,817,119 | A | 10/1998 | Klieman et al. |
| 5,820,009 | A | 10/1998 | Melling et al. |
| 5,823,066 | A | 10/1998 | Huitema et al. |
| 5,824,333 | A | 10/1998 | Scopelianos et al. |
| 5,826,776 | A | 10/1998 | Schulze et al. |
| 5,827,271 | A | 10/1998 | Buysse et al. |
| 5,827,298 | A | 10/1998 | Hart et al. |
| 5,827,323 | A | 10/1998 | Klieman et al. |
| 5,829,662 | A | 11/1998 | Allen et al. |
| 5,830,598 | A | 11/1998 | Patterson |
| 5,833,690 | A | 11/1998 | Yates et al. |
| 5,833,695 | A | 11/1998 | Yoon |
| 5,833,696 | A | 11/1998 | Whitfield et al. |
| 5,836,503 | A | 11/1998 | Ehrenfels et al. |
| 5,836,960 | A | 11/1998 | Kolesa et al. |
| 5,839,369 | A | 11/1998 | Chatterjee et al. |

(56) References Cited

U.S. PATENT DOCUMENTS

| | | | |
|---|---|---|---|
| 5,839,639 | A | 11/1998 | Sauer et al. |
| 5,841,284 | A | 11/1998 | Takahashi |
| 5,843,021 | A | 12/1998 | Edwards et al. |
| 5,843,096 | A | 12/1998 | Igaki et al. |
| 5,843,097 | A | 12/1998 | Mayenberger et al. |
| 5,843,122 | A | 12/1998 | Riza |
| 5,843,132 | A | 12/1998 | Ilvento |
| 5,843,169 | A | 12/1998 | Taheri |
| 5,846,254 | A | 12/1998 | Schulze et al. |
| 5,847,566 | A | 12/1998 | Marritt et al. |
| 5,849,011 | A | 12/1998 | Jones et al. |
| 5,849,020 | A | 12/1998 | Long et al. |
| 5,849,023 | A | 12/1998 | Mericle |
| 5,851,179 | A | 12/1998 | Ritson et al. |
| 5,851,212 | A | 12/1998 | Zirps et al. |
| 5,853,366 | A | 12/1998 | Dowlatshahi |
| 5,855,311 | A | 1/1999 | Hamblin et al. |
| 5,855,583 | A | 1/1999 | Wang et al. |
| 5,860,581 | A | 1/1999 | Robertson et al. |
| 5,860,975 | A | 1/1999 | Goble et al. |
| 5,865,361 | A | 2/1999 | Milliman et al. |
| 5,865,638 | A | 2/1999 | Trafton |
| 5,868,361 | A | 2/1999 | Rinderer |
| 5,868,664 | A | 2/1999 | Speier et al. |
| 5,868,760 | A | 2/1999 | McGuckin, Jr. |
| 5,868,790 | A | 2/1999 | Vincent et al. |
| 5,871,135 | A | 2/1999 | Williamson IV et al. |
| 5,873,885 | A | 2/1999 | Weidenbenner |
| 5,876,401 | A | 3/1999 | Schulze et al. |
| 5,878,193 | A | 3/1999 | Wang et al. |
| 5,878,607 | A | 3/1999 | Nunes et al. |
| 5,878,937 | A | 3/1999 | Green et al. |
| 5,878,938 | A | 3/1999 | Bittner et al. |
| 5,881,777 | A | 3/1999 | Bassi et al. |
| 5,881,943 | A | 3/1999 | Heck et al. |
| 5,891,094 | A | 4/1999 | Masterson et al. |
| 5,891,160 | A | 4/1999 | Williamson, IV et al. |
| 5,891,558 | A | 4/1999 | Bell et al. |
| 5,893,506 | A | 4/1999 | Powell |
| 5,893,835 | A | 4/1999 | Witt et al. |
| 5,893,855 | A | 4/1999 | Jacobs |
| 5,893,863 | A | 4/1999 | Yoon |
| 5,893,878 | A | 4/1999 | Pierce |
| 5,894,979 | A | 4/1999 | Powell |
| 5,897,552 | A | 4/1999 | Edwards et al. |
| 5,897,562 | A | 4/1999 | Bolanos et al. |
| 5,899,824 | A | 5/1999 | Kurtz et al. |
| 5,899,914 | A | 5/1999 | Zirps et al. |
| 5,901,895 | A | 5/1999 | Heaton et al. |
| 5,902,312 | A | 5/1999 | Frater et al. |
| 5,903,117 | A | 5/1999 | Gregory |
| 5,904,647 | A | 5/1999 | Ouchi |
| 5,904,693 | A | 5/1999 | Dicesare et al. |
| 5,904,702 | A | 5/1999 | Ek et al. |
| 5,906,577 | A | 5/1999 | Beane et al. |
| 5,906,625 | A | 5/1999 | Bito et al. |
| 5,907,211 | A | 5/1999 | Hall et al. |
| 5,907,664 | A | 5/1999 | Wang et al. |
| 5,908,149 | A | 6/1999 | Welch et al. |
| 5,908,402 | A | 6/1999 | Blythe |
| 5,908,427 | A | 6/1999 | McKean et al. |
| 5,909,062 | A | 6/1999 | Krietzman |
| 5,911,353 | A | 6/1999 | Bolanos et al. |
| 5,915,616 | A | 6/1999 | Viola et al. |
| 5,916,225 | A | 6/1999 | Kugel |
| 5,918,791 | A | 7/1999 | Sorrentino et al. |
| 5,919,198 | A | 7/1999 | Graves, Jr. et al. |
| 5,921,956 | A | 7/1999 | Grinberg et al. |
| 5,922,001 | A | 7/1999 | Yoon |
| 5,922,003 | A | 7/1999 | Anctil et al. |
| 5,924,864 | A | 7/1999 | Loge et al. |
| 5,928,137 | A | 7/1999 | Green |
| 5,928,256 | A | 7/1999 | Riza |
| 5,931,847 | A | 8/1999 | Bittner et al. |
| 5,931,853 | A | 8/1999 | McEwen et al. |
| 5,937,951 | A | 8/1999 | Izuchukwu et al. |
| 5,938,667 | A | 8/1999 | Peyser et al. |
| 5,941,442 | A | 8/1999 | Geiste et al. |
| 5,941,890 | A | 8/1999 | Voegele et al. |
| 5,944,172 | A | 8/1999 | Hannula |
| 5,944,715 | A | 8/1999 | Goble et al. |
| 5,946,978 | A | 9/1999 | Yamashita |
| 5,947,984 | A | 9/1999 | Whipple |
| 5,947,996 | A | 9/1999 | Logeman |
| 5,948,030 | A | 9/1999 | Miller et al. |
| 5,948,429 | A | 9/1999 | Bell et al. |
| 5,951,301 | A | 9/1999 | Younker |
| 5,951,516 | A | 9/1999 | Bunyan |
| 5,951,552 | A | 9/1999 | Long et al. |
| 5,951,574 | A | 9/1999 | Stefanchik et al. |
| 5,951,575 | A | 9/1999 | Bolduc et al. |
| 5,951,581 | A | 9/1999 | Saadat et al. |
| 5,954,259 | A | 9/1999 | Viola et al. |
| 5,957,831 | A | 9/1999 | Adair |
| 5,964,394 | A | 10/1999 | Robertson |
| 5,964,774 | A | 10/1999 | McKean et al. |
| 5,966,126 | A | 10/1999 | Szabo |
| 5,971,916 | A | 10/1999 | Koren |
| 5,973,221 | A | 10/1999 | Collyer et al. |
| D416,089 | S | 11/1999 | Barton et al. |
| 5,976,122 | A | 11/1999 | Madhani et al. |
| 5,977,746 | A | 11/1999 | Hershberger et al. |
| 5,980,248 | A | 11/1999 | Kusakabe et al. |
| 5,980,569 | A | 11/1999 | Scirica |
| 5,984,949 | A | 11/1999 | Levin |
| 5,988,479 | A | 11/1999 | Palmer |
| 5,990,379 | A | 11/1999 | Gregory |
| 5,993,466 | A | 11/1999 | Yoon |
| 5,997,528 | A | 12/1999 | Bisch et al. |
| 5,997,552 | A | 12/1999 | Person et al. |
| 6,001,108 | A | 12/1999 | Wang et al. |
| 6,003,517 | A | 12/1999 | Sheffield et al. |
| 6,004,319 | A | 12/1999 | Goble et al. |
| 6,004,335 | A | 12/1999 | Vaitekunas et al. |
| 6,007,521 | A | 12/1999 | Bidwell et al. |
| 6,010,054 | A | 1/2000 | Johnson et al. |
| 6,010,513 | A | 1/2000 | Tormala et al. |
| 6,010,520 | A | 1/2000 | Pattison |
| 6,012,494 | A | 1/2000 | Balazs |
| 6,013,076 | A | 1/2000 | Goble et al. |
| 6,013,991 | A | 1/2000 | Philipp |
| 6,015,406 | A | 1/2000 | Goble et al. |
| 6,015,417 | A | 1/2000 | Reynolds, Jr. |
| 6,017,322 | A | 1/2000 | Snoke et al. |
| 6,017,354 | A | 1/2000 | Culp et al. |
| 6,017,356 | A | 1/2000 | Frederick et al. |
| 6,018,227 | A | 1/2000 | Kumar et al. |
| 6,019,745 | A | 2/2000 | Gray |
| 6,019,780 | A | 2/2000 | Lombardo et al. |
| 6,022,352 | A | 2/2000 | Vandewalle |
| 6,023,275 | A | 2/2000 | Horvitz et al. |
| 6,023,641 | A | 2/2000 | Thompson |
| 6,024,708 | A | 2/2000 | Bales et al. |
| 6,024,741 | A | 2/2000 | Williamson, IV et al. |
| 6,024,748 | A | 2/2000 | Manzo et al. |
| 6,024,750 | A | 2/2000 | Mastri et al. |
| 6,024,764 | A | 2/2000 | Schroeppel |
| 6,027,501 | A | 2/2000 | Goble et al. |
| 6,030,384 | A | 2/2000 | Nezhat |
| 6,032,849 | A | 3/2000 | Mastri et al. |
| 6,033,105 | A | 3/2000 | Barker et al. |
| 6,033,378 | A | 3/2000 | Lundquist et al. |
| 6,033,399 | A | 3/2000 | Gines |
| 6,033,427 | A | 3/2000 | Lee |
| 6,036,641 | A | 3/2000 | Taylor et al. |
| 6,036,667 | A | 3/2000 | Manna et al. |
| 6,037,724 | A | 3/2000 | Buss et al. |
| 6,037,927 | A | 3/2000 | Rosenberg |
| 6,039,126 | A | 3/2000 | Hsieh |
| 6,039,733 | A | 3/2000 | Buysse et al. |
| 6,039,734 | A | 3/2000 | Goble |
| 6,042,601 | A | 3/2000 | Smith |
| 6,042,607 | A | 3/2000 | Williamson, IV et al. |
| 6,043,626 | A | 3/2000 | Snyder et al. |

(56) References Cited

U.S. PATENT DOCUMENTS 6,045,560 A 4/2000 McKean et al.
6,047,861 A 4/2000 Vidal et al.
6,049,145 A 4/2000 Austin et al.
6,050,172 A 4/2000 Corves et al.
6,050,472 A 4/2000 Shibata
6,050,989 A 4/2000 Fox et al.
6,050,990 A 4/2000 Tankovich et al.
6,050,996 A 4/2000 Schmaltz et al.
6,053,390 A 4/2000 Green et al.
6,053,899 A 4/2000 Slanda et al.
6,053,922 A 4/2000 Krause et al.
6,054,142 A 4/2000 Li et al.
6,055,062 A 4/2000 Dina et al.
RE36,720 E 5/2000 Green et al.
6,056,735 A 5/2000 Okada et al.
6,056,746 A 5/2000 Goble et al.
6,059,806 A 5/2000 Hoegerle
6,062,360 A 5/2000 Shields
6,063,020 A 5/2000 Jones et al.
6,063,025 A 5/2000 Bridges et al.
6,063,050 A 5/2000 Manna et al.
6,063,095 A 5/2000 Wang et al.
6,063,097 A 5/2000 Oi et al.
6,063,098 A 5/2000 Houser et al.
6,065,679 A 5/2000 Levie et al.
6,065,919 A 5/2000 Peck
6,066,132 A 5/2000 Chen et al.
6,066,151 A 5/2000 Miyawaki et al.
6,068,627 A 5/2000 Orszulak et al.
6,071,233 A 6/2000 Ishikawa et al.
6,072,299 A 6/2000 Kurle et al.
6,074,386 A 6/2000 Goble et al.
6,074,401 A 6/2000 Gardiner et al.
6,075,441 A 6/2000 Maloney
6,077,280 A 6/2000 Fossum
6,077,286 A 6/2000 Cuschieri et al.
6,077,290 A 6/2000 Marini
6,079,606 A 6/2000 Milliman et al.
6,080,181 A 6/2000 Jensen et al.
6,082,577 A 7/2000 Coates et al.
6,083,191 A 7/2000 Rose
6,083,223 A 7/2000 Baker
6,083,234 A 7/2000 Nicholas et al.
6,083,242 A 7/2000 Cook
6,086,544 A 7/2000 Hibner et al.
6,086,600 A 7/2000 Kortenbach
6,090,106 A 7/2000 Goble et al.
6,090,123 A 7/2000 Culp et al.
6,093,186 A 7/2000 Goble
6,094,021 A 7/2000 Noro et al.
D429,252 S 8/2000 Haitani et al.
6,099,537 A 8/2000 Sugai et al.
6,099,551 A 8/2000 Gabbay
6,102,271 A 8/2000 Longo et al.
6,102,926 A 8/2000 Tartaglia et al.
6,104,162 A 8/2000 Sainsbury et al.
6,104,304 A 8/2000 Clark et al.
6,106,511 A 8/2000 Jensen
6,109,500 A 8/2000 Alli et al.
6,110,187 A 8/2000 Donlon
6,113,618 A 9/2000 Nic
6,117,148 A 9/2000 Ravo et al.
6,117,158 A 9/2000 Measamer et al.
6,119,913 A 9/2000 Adams et al.
6,120,433 A 9/2000 Mizuno et al.
6,120,462 A 9/2000 Hibner et al.
6,123,241 A 9/2000 Walter et al.
6,123,701 A 9/2000 Nezhat
H1904 H 10/2000 Yates et al.
RE36,923 E 10/2000 Hiroi et al.
6,126,058 A 10/2000 Adams et al.
6,126,359 A 10/2000 Dittrich et al.
6,126,670 A 10/2000 Walker et al.
6,131,789 A 10/2000 Schulze et al.
6,131,790 A 10/2000 Piraka
6,132,368 A 10/2000 Cooper
6,134,962 A 10/2000 Sugitani
6,139,546 A 10/2000 Koenig et al.
6,142,149 A 11/2000 Steen
6,142,933 A 11/2000 Longo et al.
6,147,135 A 11/2000 Yuan et al.
6,149,660 A 11/2000 Laufer et al.
6,151,323 A 11/2000 O'Connell et al.
6,152,935 A 11/2000 Kammerer et al.
6,155,473 A 12/2000 Tompkins et al.
6,156,056 A 12/2000 Kearns et al.
6,157,169 A 12/2000 Lee
6,159,146 A 12/2000 El Gazayerli
6,159,200 A 12/2000 Verdura et al.
6,159,224 A 12/2000 Yoon
6,162,208 A 12/2000 Hipps
6,162,220 A 12/2000 Nezhat
6,162,537 A 12/2000 Martin et al.
6,165,175 A 12/2000 Wampler et al.
6,165,184 A 12/2000 Verdura et al.
6,165,188 A 12/2000 Saadat et al.
6,167,185 A 12/2000 Smiley et al.
6,168,605 B1 1/2001 Measamer et al.
6,171,305 B1 1/2001 Sherman
6,171,316 B1 1/2001 Kovac et al.
6,171,330 B1 1/2001 Benchetrit
6,173,074 B1 1/2001 Russo
6,174,308 B1 1/2001 Goble et al.
6,174,309 B1 1/2001 Wrublewski et al.
6,174,318 B1 1/2001 Bates et al.
6,175,290 B1 1/2001 Forsythe et al.
6,179,195 B1 1/2001 Adams et al.
6,179,776 B1 1/2001 Adams et al.
6,181,105 B1 1/2001 Cutolo et al.
6,182,673 B1 2/2001 Kindermann et al.
6,185,356 B1 2/2001 Parker et al.
6,186,142 B1 2/2001 Schmidt et al.
6,186,957 B1 2/2001 Milam
6,187,003 B1 2/2001 Buysse et al.
6,190,386 B1 2/2001 Rydell
6,193,129 B1 2/2001 Bittner et al.
6,197,042 B1 3/2001 Ginn et al.
6,200,311 B1 3/2001 Danek et al.
6,200,330 B1 3/2001 Benderev et al.
6,202,914 B1 3/2001 Geiste et al.
6,206,894 B1 3/2001 Thompson et al.
6,206,897 B1 3/2001 Jamiolkowski et al.
6,206,903 B1 3/2001 Ramans
6,206,904 B1 3/2001 Ouchi
6,209,414 B1 4/2001 Uneme
6,210,403 B1 4/2001 Klicek
6,211,626 B1 4/2001 Lys et al.
6,213,999 B1 4/2001 Platt, Jr. et al.
6,214,028 B1 4/2001 Yoon et al.
6,220,368 B1 4/2001 Ark et al.
6,221,007 B1 4/2001 Green
6,221,023 B1 4/2001 Matsuba et al.
6,223,100 B1 4/2001 Green
6,223,835 B1 5/2001 Habedank et al.
6,224,617 B1 5/2001 Saadat et al.
6,228,080 B1 5/2001 Gines
6,228,081 B1 5/2001 Goble
6,228,083 B1 5/2001 Lands et al.
6,228,084 B1 5/2001 Kirwan, Jr.
6,228,089 B1 5/2001 Wahrburg
6,228,098 B1 5/2001 Kayan et al.
6,231,565 B1 5/2001 Tovey et al.
6,234,178 B1 5/2001 Goble et al.
6,235,036 B1 5/2001 Gardner et al.
6,237,604 B1 5/2001 Burnside et al.
6,238,384 B1 5/2001 Peer
6,241,139 B1 6/2001 Milliman et al.
6,241,140 B1 6/2001 Adams et al.
6,241,723 B1 6/2001 Heim et al.
6,245,084 B1 6/2001 Mark et al.
6,248,116 B1 6/2001 Chevillon et al.
6,248,117 B1 6/2001 Blatter
6,249,076 B1 6/2001 Madden et al.
6,249,105 B1 6/2001 Andrews et al.

(56) References Cited

U.S. PATENT DOCUMENTS

| | | | |
|---|---|---|---|
| 6,250,532 | B1 | 6/2001 | Green et al. |
| 6,251,485 | B1 | 6/2001 | Harris et al. |
| D445,745 | S | 7/2001 | Norman |
| 6,254,534 | B1 | 7/2001 | Butler et al. |
| 6,254,619 | B1 | 7/2001 | Garabet et al. |
| 6,254,642 | B1 | 7/2001 | Taylor |
| 6,258,107 | B1 | 7/2001 | Balazs et al. |
| 6,261,246 | B1 | 7/2001 | Pantages et al. |
| 6,261,286 | B1 | 7/2001 | Goble et al. |
| 6,261,679 | B1 | 7/2001 | Chen et al. |
| 6,264,086 | B1 | 7/2001 | McGuckin, Jr. |
| 6,264,087 | B1 | 7/2001 | Whitman |
| 6,264,617 | B1 | 7/2001 | Bales et al. |
| 6,269,997 | B1 | 8/2001 | Balazs et al. |
| 6,270,508 | B1 | 8/2001 | Klieman et al. |
| 6,270,916 | B1 | 8/2001 | Sink et al. |
| 6,273,252 | B1 | 8/2001 | Mitchell |
| 6,273,876 | B1 | 8/2001 | Klima et al. |
| 6,273,897 | B1 | 8/2001 | Dalessandro et al. |
| 6,277,114 | B1 | 8/2001 | Bullivant et al. |
| 6,280,407 | B1 | 8/2001 | Manna et al. |
| 6,283,981 | B1 | 9/2001 | Beaupre |
| 6,293,927 | B1 | 9/2001 | McGuckin, Jr. |
| 6,293,942 | B1 | 9/2001 | Goble et al. |
| 6,296,640 | B1 | 10/2001 | Wampler et al. |
| 6,302,311 | B1 | 10/2001 | Adams et al. |
| 6,302,743 | B1 | 10/2001 | Chiu et al. |
| 6,305,891 | B1 | 10/2001 | Burlingame |
| 6,306,134 | B1 | 10/2001 | Goble et al. |
| 6,306,149 | B1 | 10/2001 | Meade |
| 6,306,424 | B1 | 10/2001 | Vyakarnam et al. |
| 6,309,397 | B1 | 10/2001 | Julian et al. |
| 6,309,400 | B2 | 10/2001 | Beaupre |
| 6,309,403 | B1 | 10/2001 | Minor et al. |
| 6,312,435 | B1 | 11/2001 | Wallace et al. |
| 6,315,184 | B1 | 11/2001 | Whitman |
| 6,317,616 | B1 | 11/2001 | Glossop |
| 6,319,510 | B1 | 11/2001 | Yates |
| 6,320,123 | B1 | 11/2001 | Reimers |
| 6,322,494 | B1 | 11/2001 | Bullivant et al. |
| 6,324,339 | B1 | 11/2001 | Hudson et al. |
| 6,325,799 | B1 | 12/2001 | Goble |
| 6,325,805 | B1 | 12/2001 | Ogilvie et al. |
| 6,325,810 | B1 | 12/2001 | Hamilton et al. |
| 6,328,498 | B1 | 12/2001 | Mersch |
| 6,330,965 | B1 | 12/2001 | Milliman et al. |
| 6,331,181 | B1 | 12/2001 | Tierney et al. |
| 6,331,761 | B1 | 12/2001 | Kumar et al. |
| 6,333,029 | B1 | 12/2001 | Vyakarnam et al. |
| 6,334,860 | B1 | 1/2002 | Dorn |
| 6,334,861 | B1 | 1/2002 | Chandler et al. |
| 6,336,926 | B1 | 1/2002 | Goble |
| 6,338,737 | B1 | 1/2002 | Toledano |
| 6,338,738 | B1 | 1/2002 | Bellotti et al. |
| 6,343,731 | B1 | 2/2002 | Adams et al. |
| 6,346,077 | B1 | 2/2002 | Taylor et al. |
| 6,348,061 | B1 | 2/2002 | Whitman |
| 6,349,868 | B1 | 2/2002 | Mattingly et al. |
| D454,951 | S | 3/2002 | Bon |
| 6,352,503 | B1 | 3/2002 | Matsui et al. |
| 6,352,532 | B1 | 3/2002 | Kramer et al. |
| 6,355,699 | B1 | 3/2002 | Vyakarnam et al. |
| 6,356,072 | B1 | 3/2002 | Chass |
| 6,358,224 | B1 | 3/2002 | Tims et al. |
| 6,358,263 | B2 | 3/2002 | Mark et al. |
| 6,358,459 | B1 | 3/2002 | Ziegler et al. |
| 6,361,542 | B1 | 3/2002 | Dimitriu et al. |
| 6,364,828 | B1 | 4/2002 | Yeung et al. |
| 6,364,877 | B1 | 4/2002 | Goble et al. |
| 6,364,888 | B1 | 4/2002 | Niemeyer et al. |
| 6,366,441 | B1 | 4/2002 | Ozawa et al. |
| 6,370,981 | B2 | 4/2002 | Watarai |
| 6,371,114 | B1 | 4/2002 | Schmidt et al. |
| 6,373,152 | B1 | 4/2002 | Wang et al. |
| 6,377,011 | B1 | 4/2002 | Ben-Ur |
| 6,383,201 | B1 | 5/2002 | Dong |
| 6,387,092 | B1 | 5/2002 | Burnside et al. |
| 6,387,113 | B1 | 5/2002 | Hawkins et al. |
| 6,387,114 | B2 | 5/2002 | Adams |
| 6,391,038 | B2 | 5/2002 | Vargas et al. |
| 6,392,854 | B1 | 5/2002 | O'Gorman |
| 6,394,998 | B1 | 5/2002 | Wallace et al. |
| 6,398,779 | B1 | 6/2002 | Buysse et al. |
| 6,398,781 | B1 | 6/2002 | Goble et al. |
| 6,398,797 | B2 | 6/2002 | Bombard et al. |
| 6,402,766 | B2 | 6/2002 | Bowman et al. |
| 6,402,780 | B2 | 6/2002 | Williamson, IV et al. |
| 6,406,440 | B1 | 6/2002 | Stefanchik |
| 6,406,472 | B1 | 6/2002 | Jensen |
| 6,409,724 | B1 | 6/2002 | Penny et al. |
| H2037 | H | 7/2002 | Yates et al. |
| 6,412,639 | B1 | 7/2002 | Hickey |
| 6,413,274 | B1 | 7/2002 | Pedros |
| 6,415,542 | B1 | 7/2002 | Bates et al. |
| 6,416,486 | B1 | 7/2002 | Wampler |
| 6,416,509 | B1 | 7/2002 | Goble et al. |
| 6,419,695 | B1 | 7/2002 | Gabbay |
| 6,423,079 | B1 | 7/2002 | Blake, III |
| 6,424,885 | B1 | 7/2002 | Niemeyer et al. |
| RE37,814 | E | 8/2002 | Allgeyer |
| 6,428,070 | B1 | 8/2002 | Takanashi et al. |
| 6,428,487 | B1 | 8/2002 | Burdorff et al. |
| 6,429,611 | B1 | 8/2002 | Li |
| 6,430,298 | B1 | 8/2002 | Kettl et al. |
| 6,432,065 | B1 | 8/2002 | Burdorff et al. |
| 6,436,097 | B1 | 8/2002 | Nardella |
| 6,436,107 | B1 | 8/2002 | Wang et al. |
| 6,436,110 | B2 | 8/2002 | Bowman et al. |
| 6,436,115 | B1 | 8/2002 | Beaupre |
| 6,436,122 | B1 | 8/2002 | Frank et al. |
| 6,439,439 | B1 | 8/2002 | Rickard et al. |
| 6,439,446 | B1 | 8/2002 | Perry et al. |
| 6,440,146 | B2 | 8/2002 | Nicholas et al. |
| 6,441,577 | B2 | 8/2002 | Blumenkranz et al. |
| D462,758 | S | 9/2002 | Epstein et al. |
| 6,443,973 | B1 | 9/2002 | Whitman |
| 6,445,530 | B1 | 9/2002 | Baker |
| 6,447,518 | B1 | 9/2002 | Krause et al. |
| 6,447,523 | B1 | 9/2002 | Middleman et al. |
| 6,447,799 | B1 | 9/2002 | Ullman |
| 6,447,864 | B2 | 9/2002 | Johnson et al. |
| 6,450,391 | B1 | 9/2002 | Kayan et al. |
| 6,450,989 | B2 | 9/2002 | Dubrul et al. |
| 6,454,656 | B2 | 9/2002 | Brissette et al. |
| 6,454,781 | B1 | 9/2002 | Witt et al. |
| 6,457,338 | B1 | 10/2002 | Frenken |
| 6,457,625 | B1 | 10/2002 | Tormala et al. |
| 6,458,077 | B1 | 10/2002 | Boebel et al. |
| 6,458,142 | B1 | 10/2002 | Faller et al. |
| 6,458,147 | B1 | 10/2002 | Cruise et al. |
| 6,460,627 | B1 | 10/2002 | Below et al. |
| 6,463,824 | B1 | 10/2002 | Prell et al. |
| 6,468,275 | B1 | 10/2002 | Wampler et al. |
| 6,468,286 | B2 | 10/2002 | Mastri et al. |
| 6,471,106 | B1 | 10/2002 | Reining |
| 6,471,659 | B2 | 10/2002 | Eggers et al. |
| 6,478,210 | B2 | 11/2002 | Adams et al. |
| 6,482,063 | B1 | 11/2002 | Frigard |
| 6,482,200 | B2 | 11/2002 | Shippert |
| 6,482,217 | B1 | 11/2002 | Pintor et al. |
| 6,485,490 | B2 | 11/2002 | Wampler et al. |
| 6,485,503 | B2 | 11/2002 | Jacobs et al. |
| 6,485,667 | B1 | 11/2002 | Tan |
| 6,486,286 | B1 | 11/2002 | McGall et al. |
| 6,488,196 | B1 | 12/2002 | Fenton, Jr. |
| 6,488,197 | B1 | 12/2002 | Whitman |
| 6,488,659 | B1 | 12/2002 | Rosenman |
| 6,491,201 | B1 | 12/2002 | Whitman |
| 6,491,690 | B1 | 12/2002 | Goble et al. |
| 6,491,701 | B2 | 12/2002 | Tierney et al. |
| 6,491,702 | B2 | 12/2002 | Heilbrun et al. |
| 6,492,785 | B1 | 12/2002 | Kasten et al. |
| 6,494,882 | B1 | 12/2002 | Lebouitz et al. |
| 6,494,885 | B1 | 12/2002 | Dhindsa |

(56) References Cited

U.S. PATENT DOCUMENTS 6,494,888 B1 12/2002 Laufer et al.
6,494,896 B1 12/2002 D'Alessio et al.
6,498,480 B1 12/2002 Manara
6,500,176 B1 12/2002 Truckai et al.
6,500,189 B1 12/2002 Lang et al.
6,500,194 B2 12/2002 Benderev et al.
D468,749 S 1/2003 Friedman
6,503,139 B2 1/2003 Coral
6,503,257 B2 1/2003 Grant et al.
6,503,259 B2 1/2003 Huxel et al.
6,505,768 B2 1/2003 Whitman
6,506,197 B1 1/2003 Rollero et al.
6,506,399 B2 1/2003 Donovan
6,510,854 B2 1/2003 Goble
6,511,468 B1 1/2003 Cragg et al.
6,512,360 B1 1/2003 Goto et al.
6,514,252 B2 2/2003 Nezhat et al.
6,516,073 B1 2/2003 Schulz et al.
6,517,528 B1 2/2003 Pantages et al.
6,517,535 B2 2/2003 Edwards
6,517,565 B1 2/2003 Whitman et al.
6,517,566 B1 2/2003 Hovland et al.
6,520,971 B1 2/2003 Perry et al.
6,520,972 B2 2/2003 Peters
6,522,101 B2 2/2003 Malackowski
6,524,180 B1 2/2003 Simms et al.
6,525,499 B2 2/2003 Naganuma
D471,206 S 3/2003 Buzzard et al.
6,527,782 B2 3/2003 Hogg et al.
6,527,785 B2 3/2003 Sancoff et al.
6,530,942 B2 3/2003 Fogarty et al.
6,532,958 B1 3/2003 Buan et al.
6,533,157 B1 3/2003 Whitman
6,533,723 B1 3/2003 Lockery et al.
6,533,784 B2 3/2003 Truckai et al.
6,535,764 B2 3/2003 Imran et al.
6,539,297 B2 3/2003 Weiberle et al.
D473,239 S 4/2003 Cockerill
6,539,816 B2 4/2003 Kogiso et al.
6,540,737 B2 4/2003 Bacher et al.
6,543,456 B1 4/2003 Freeman
6,545,384 B1 4/2003 Pelrine et al.
6,547,786 B1 4/2003 Goble
6,550,546 B2 4/2003 Thurler et al.
6,551,333 B2 4/2003 Kuhns et al.
6,554,844 B2 4/2003 Lee et al.
6,554,861 B2 4/2003 Knox et al.
6,555,770 B2 4/2003 Kawase
6,558,378 B2 5/2003 Sherman et al.
6,558,379 B1 5/2003 Batchelor et al.
6,558,429 B2 5/2003 Taylor
6,561,187 B2 5/2003 Schmidt et al.
6,565,560 B1 5/2003 Goble et al.
6,566,619 B2 5/2003 Gillman et al.
6,569,085 B2 5/2003 Kortenbach et al.
6,569,171 B2 5/2003 DeGuillebon et al.
6,569,173 B1 5/2003 Blatter et al.
6,572,629 B2 6/2003 Kalloo et al.
6,575,969 B1 6/2003 Rittman, III et al.
6,578,751 B2 6/2003 Hartwick
6,582,364 B2 6/2003 Butler et al.
6,582,427 B1 6/2003 Goble et al.
6,582,441 B1 6/2003 He et al.
6,583,533 B2 6/2003 Pelrine et al.
6,585,144 B2 7/2003 Adams et al.
6,585,664 B2 7/2003 Burdorff et al.
6,586,898 B2 7/2003 King et al.
6,587,750 B2 7/2003 Gerbi et al.
6,588,277 B2 7/2003 Giordano et al.
6,588,643 B2 7/2003 Bolduc et al.
6,588,931 B2 7/2003 Betzner et al.
6,589,118 B1 7/2003 Soma et al.
6,589,164 B1 7/2003 Flaherty
6,592,538 B1 7/2003 Hotchkiss et al.
6,592,572 B1 7/2003 Suzuta
6,592,597 B2 7/2003 Grant et al.
6,594,552 B1 7/2003 Nowlin et al.
6,595,914 B2 7/2003 Kato
6,596,296 B1 7/2003 Nelson et al.
6,596,304 B1 7/2003 Bayon et al.
6,596,432 B2 7/2003 Kawakami et al.
6,599,295 B1 7/2003 Tornier et al.
6,599,323 B2 7/2003 Melican et al.
D478,665 S 8/2003 Isaacs et al.
D478,986 S 8/2003 Johnston et al.
6,601,749 B2 8/2003 Sullivan et al.
6,602,252 B2 8/2003 Mollenauer
6,602,262 B2 8/2003 Griego et al.
6,603,050 B2 8/2003 Heaton
6,605,078 B2 8/2003 Adams
6,605,669 B2 8/2003 Awokola et al.
6,605,911 B1 8/2003 Klesing
6,607,475 B2 8/2003 Doyle et al.
6,611,793 B1 8/2003 Burnside et al.
6,613,069 B2 9/2003 Boyd et al.
6,616,686 B2 9/2003 Coleman et al.
6,619,529 B2 9/2003 Green et al.
6,620,111 B2 9/2003 Stephens et al.
6,620,161 B2 9/2003 Schulze et al.
6,620,166 B1 9/2003 Wenstrom, Jr. et al.
6,625,517 B1 9/2003 Bogdanov et al.
6,626,834 B2 9/2003 Dunne et al.
6,626,901 B1 9/2003 Treat et al.
6,626,938 B1 9/2003 Butaric et al.
H2086 H 10/2003 Amsler
6,629,630 B2 10/2003 Adams
6,629,974 B2 10/2003 Penny et al.
6,629,988 B2 10/2003 Weadock
6,635,838 B1 10/2003 Kornelson
6,636,412 B2 10/2003 Smith
6,638,108 B2 10/2003 Tachi
6,638,285 B2 10/2003 Gabbay
6,638,297 B1 10/2003 Huitema
RE38,335 E 11/2003 Aust et al.
6,641,528 B2 11/2003 Torii
6,644,532 B2 11/2003 Green et al.
6,645,201 B1 11/2003 Utley et al.
6,646,307 B1 11/2003 Yu et al.
6,648,816 B2 11/2003 Irion et al.
6,648,901 B2 11/2003 Fleischman et al.
6,652,595 B1 11/2003 Nicolo
D484,243 S 12/2003 Ryan et al.
D484,595 S 12/2003 Ryan et al.
D484,596 S 12/2003 Ryan et al.
6,656,177 B2 12/2003 Truckai et al.
6,656,193 B2 12/2003 Grant et al.
6,659,940 B2 12/2003 Adler
6,660,008 B1 12/2003 Foerster et al.
6,663,623 B1 12/2003 Oyama et al.
6,663,641 B1 12/2003 Kovac et al.
6,666,854 B1 12/2003 Lange
6,666,860 B1 12/2003 Takahashi
6,666,875 B1 12/2003 Sakurai et al.
6,667,825 B2 12/2003 Lu et al.
6,669,073 B2 12/2003 Milliman et al.
6,670,806 B2 12/2003 Wendt et al.
6,671,185 B2 12/2003 Duval
D484,977 S 1/2004 Ryan et al.
6,676,660 B2 1/2004 Wampler et al.
6,677,687 B2 1/2004 Ho et al.
6,679,269 B2 1/2004 Swanson
6,679,410 B2 1/2004 Wursch et al.
6,681,978 B2 1/2004 Geiste et al.
6,681,979 B2 1/2004 Whitman
6,682,527 B2 1/2004 Strul
6,682,528 B2 1/2004 Frazier et al.
6,682,544 B2 1/2004 Mastri et al.
6,685,698 B2 2/2004 Morley et al.
6,685,727 B2 2/2004 Fisher et al.
6,689,153 B1 2/2004 Skiba
6,692,507 B2 2/2004 Pugsley et al.
6,692,692 B2 2/2004 Stetzel
6,695,198 B2 2/2004 Adams et al.
6,695,199 B2 2/2004 Whitman

(56) References Cited

U.S. PATENT DOCUMENTS 6,695,774 B2 2/2004 Hale et al.
6,695,849 B2 2/2004 Michelson
6,696,814 B2 2/2004 Henderson et al.
6,697,048 B2 2/2004 Rosenberg et al.
6,698,643 B2 3/2004 Whitman
6,699,177 B1 3/2004 Wang et al.
6,699,214 B2 3/2004 Gellman
6,699,235 B2 3/2004 Wallace et al.
6,704,210 B1 3/2004 Myers
6,705,503 B1 3/2004 Pedicini et al.
6,709,445 B2 3/2004 Boebel et al.
6,712,773 B1 3/2004 Viola
6,716,215 B1 4/2004 David et al.
6,716,223 B2 4/2004 Leopold et al.
6,716,232 B1 4/2004 Vidal et al.
6,716,233 B1 4/2004 Whitman
6,720,734 B2 4/2004 Norris
6,722,550 B1 4/2004 Ricordi et al.
6,722,552 B2 4/2004 Fenton, Jr.
6,723,087 B2 4/2004 O'Neill et al.
6,723,091 B2 4/2004 Goble et al.
6,723,106 B1 4/2004 Charles et al.
6,723,109 B2 4/2004 Solingen
6,726,651 B1 4/2004 Robinson et al.
6,726,697 B2 4/2004 Nicholas et al.
6,726,705 B2 4/2004 Peterson et al.
6,726,706 B2 4/2004 Dominguez
6,729,119 B2 5/2004 Schnipke et al.
6,731,976 B2 5/2004 Penn et al.
6,736,810 B2 5/2004 Hoey et al.
6,736,825 B2 5/2004 Blatter et al.
6,736,854 B2 5/2004 Vadurro et al.
6,740,030 B2 5/2004 Martone et al.
6,743,230 B2 6/2004 Lutze et al.
6,744,385 B2 6/2004 Kazuya et al.
6,747,121 B2 6/2004 Gogolewski
6,747,300 B2 6/2004 Nadd et al.
6,749,560 B1 6/2004 Konstorum et al.
6,749,600 B1 6/2004 Levy
6,752,768 B2 6/2004 Burdorff et al.
6,752,816 B2 6/2004 Culp et al.
6,754,959 B1 6/2004 Guiette, III et al.
6,755,195 B1 6/2004 Lemke et al.
6,755,338 B2 6/2004 Hahnen et al.
6,755,825 B2 6/2004 Shoenman et al.
6,755,843 B2 6/2004 Chung et al.
6,756,705 B2 6/2004 Pulford, Jr.
6,758,846 B2 7/2004 Goble et al.
6,761,685 B2 7/2004 Adams et al.
6,762,339 B1 7/2004 Klun et al.
6,763,307 B2 7/2004 Berg et al.
6,764,445 B2 7/2004 Ramans et al.
6,766,957 B2 7/2004 Matsuura et al.
6,767,352 B2 7/2004 Field et al.
6,767,356 B2 7/2004 Kanner et al.
6,769,590 B2 8/2004 Vresh et al.
6,769,594 B2 8/2004 Orban, III
6,770,027 B2 8/2004 Banik et al.
6,770,070 B1 8/2004 Balbierz
6,770,072 B1 8/2004 Truckai et al.
6,770,078 B2 8/2004 Bonutti
6,773,409 B2 8/2004 Truckai et al.
6,773,437 B2 8/2004 Ogilvie et al.
6,773,438 B1 8/2004 Knodel et al.
6,773,458 B1 8/2004 Brauker et al.
6,775,575 B2 8/2004 Bommannan et al.
6,777,838 B2 8/2004 Miekka et al.
6,778,846 B1 8/2004 Martinez et al.
6,780,151 B2 8/2004 Grabover et al.
6,780,180 B1 8/2004 Goble et al.
6,783,524 B2 8/2004 Anderson et al.
6,784,775 B2 8/2004 Mandell et al.
6,786,382 B1 9/2004 Hoffman
6,786,864 B2 9/2004 Matsuura et al.
6,786,896 B1 9/2004 Madhani et al.
6,788,018 B1 9/2004 Blumenkranz
6,790,173 B2 9/2004 Saadat et al.
6,793,652 B1 9/2004 Whitman et al.
6,793,661 B2 9/2004 Hamilton et al.
6,793,663 B2 9/2004 Kneifel et al.
6,793,669 B2 9/2004 Nakamura et al.
6,796,921 B1 9/2004 Buck et al.
6,799,669 B2 10/2004 Fukumura et al.
6,801,009 B2 10/2004 Makaran et al.
6,802,822 B1 10/2004 Dodge
6,802,843 B2 10/2004 Truckai et al.
6,802,844 B2 10/2004 Ferree
6,805,273 B2 10/2004 Bilotti et al.
6,806,808 B1 10/2004 Watters et al.
6,806,867 B1 10/2004 Arruda et al.
6,808,525 B2 10/2004 Latterell et al.
6,810,359 B2 10/2004 Sakaguchi
6,814,154 B2 11/2004 Chou
6,814,741 B2 11/2004 Bowman et al.
6,817,508 B1 11/2004 Racenet et al.
6,817,509 B2 11/2004 Geiste et al.
6,817,974 B2 11/2004 Cooper et al.
6,818,018 B1 11/2004 Sawhney
6,820,791 B2 11/2004 Adams
6,821,273 B2 11/2004 Mollenauer
6,821,282 B2 11/2004 Perry et al.
6,821,284 B2 11/2004 Sturtz et al.
6,827,246 B2 12/2004 Sullivan et al.
6,827,712 B2 12/2004 Tovey et al.
6,827,725 B2 12/2004 Batchelor et al.
6,828,902 B2 12/2004 Casden
6,830,174 B2 12/2004 Hillstead et al.
6,831,629 B2 12/2004 Nishino et al.
6,832,998 B2 12/2004 Goble
6,834,001 B2 12/2004 Myono
6,835,173 B2 12/2004 Couvillon, Jr.
6,835,199 B2 12/2004 McGuckin, Jr. et al.
6,835,336 B2 12/2004 Watt
6,836,611 B2 12/2004 Popovic et al.
6,837,846 B2 1/2005 Jaffe et al.
6,837,883 B2 1/2005 Moll et al.
6,838,493 B2 1/2005 Williams et al.
6,840,423 B2 1/2005 Adams et al.
6,840,938 B1 1/2005 Morley et al.
6,841,967 B2 1/2005 Kim et al.
6,843,403 B2 1/2005 Whitman
6,843,789 B2 1/2005 Goble
6,843,793 B2 1/2005 Brock et al.
6,846,307 B2 1/2005 Whitman et al.
6,846,308 B2 1/2005 Whitman et al.
6,846,309 B2 1/2005 Whitman et al.
6,847,190 B2 1/2005 Schaefer et al.
6,849,071 B2 2/2005 Whitman et al.
6,850,817 B1 2/2005 Green
6,852,122 B2 2/2005 Rush
6,852,330 B2 2/2005 Bowman et al.
6,853,879 B2 2/2005 Sunaoshi
6,858,005 B2 2/2005 Ohline et al.
6,859,882 B2 2/2005 Fung
RE38,708 E 3/2005 Bolanos et al.
D502,994 S 3/2005 Blake, III
6,860,169 B2 3/2005 Shinozaki
6,861,142 B1 3/2005 Wilkie et al.
6,861,954 B2 3/2005 Levin
6,863,668 B2 3/2005 Gillespie et al.
6,863,694 B1 3/2005 Boyce et al.
6,863,924 B2 3/2005 Ranganathan et al.
6,866,178 B2 3/2005 Adams et al.
6,866,668 B2 3/2005 Giannetti et al.
6,866,671 B2 3/2005 Tierney et al.
6,867,248 B1 3/2005 Martin et al.
6,869,430 B2 3/2005 Balbierz et al.
6,869,435 B2 3/2005 Blake, III
6,872,214 B2 3/2005 Sonnenschein et al.
6,874,669 B2 4/2005 Adams et al.
6,876,850 B2 4/2005 Maeshima et al.
6,877,647 B2 4/2005 Green et al.
6,878,106 B1 4/2005 Herrmann
6,882,127 B2 4/2005 Konigbauer

(56) References Cited

U.S. PATENT DOCUMENTS

| | | | |
|---|---|---|---|
| 6,883,199 | B1 | 4/2005 | Lundell et al. |
| 6,884,392 | B2 | 4/2005 | Malkin et al. |
| 6,884,428 | B2 | 4/2005 | Binette et al. |
| 6,886,730 | B2 | 5/2005 | Fujisawa et al. |
| 6,887,244 | B1 | 5/2005 | Walker et al. |
| 6,887,710 | B2 | 5/2005 | Call et al. |
| 6,889,116 | B2 | 5/2005 | Jinno |
| 6,893,435 | B2 | 5/2005 | Goble |
| 6,894,140 | B2 | 5/2005 | Roby |
| 6,895,176 | B2 | 5/2005 | Archer et al. |
| 6,899,538 | B2 | 5/2005 | Matoba |
| 6,899,593 | B1 | 5/2005 | Moeller et al. |
| 6,899,705 | B2 | 5/2005 | Niemeyer |
| 6,899,915 | B2 | 5/2005 | Yelick et al. |
| 6,905,057 | B2 | 6/2005 | Swayze et al. |
| 6,905,497 | B2 | 6/2005 | Truckai et al. |
| 6,905,498 | B2 | 6/2005 | Hooven |
| 6,908,472 | B2 | 6/2005 | Wiener et al. |
| 6,911,033 | B2 | 6/2005 | de Guillebon et al. |
| 6,911,916 | B1 | 6/2005 | Wang et al. |
| 6,913,579 | B2 | 7/2005 | Truckai et al. |
| 6,913,608 | B2 | 7/2005 | Liddicoat et al. |
| 6,913,613 | B2 | 7/2005 | Schwarz et al. |
| 6,921,397 | B2 | 7/2005 | Corcoran et al. |
| 6,921,412 | B1 | 7/2005 | Black et al. |
| 6,923,093 | B2 | 8/2005 | Ullah |
| 6,923,803 | B2 | 8/2005 | Goble |
| 6,923,819 | B2 | 8/2005 | Meade et al. |
| 6,925,849 | B2 | 8/2005 | Jairam |
| 6,926,716 | B2 | 8/2005 | Baker et al. |
| 6,927,315 | B1 | 8/2005 | Heinecke et al. |
| 6,928,902 | B1 | 8/2005 | Eyssallenne |
| 6,929,641 | B2 | 8/2005 | Goble et al. |
| 6,929,644 | B2 | 8/2005 | Truckai et al. |
| 6,931,830 | B2 | 8/2005 | Liao |
| 6,932,218 | B2 | 8/2005 | Kosann et al. |
| 6,932,810 | B2 | 8/2005 | Ryan |
| 6,936,042 | B2 | 8/2005 | Wallace et al. |
| 6,936,948 | B2 | 8/2005 | Bell et al. |
| D509,297 | S | 9/2005 | Wells |
| D509,589 | S | 9/2005 | Wells |
| 6,938,706 | B2 | 9/2005 | Ng |
| 6,939,358 | B2 | 9/2005 | Palacios et al. |
| 6,942,662 | B2 | 9/2005 | Goble et al. |
| 6,942,674 | B2 | 9/2005 | Belef et al. |
| 6,945,444 | B2 | 9/2005 | Gresham et al. |
| 6,945,981 | B2 | 9/2005 | Donofrio et al. |
| 6,949,196 | B2 | 9/2005 | Schmitz et al. |
| 6,951,562 | B2 | 10/2005 | Zwirnmann |
| 6,953,138 | B1 | 10/2005 | Dworak et al. |
| 6,953,139 | B2 | 10/2005 | Milliman et al. |
| 6,953,461 | B2 | 10/2005 | McClurken et al. |
| 6,957,758 | B2 | 10/2005 | Aranyi |
| 6,958,035 | B2 | 10/2005 | Friedman et al. |
| D511,525 | S | 11/2005 | Hernandez et al. |
| 6,959,851 | B2 | 11/2005 | Heinrich |
| 6,959,852 | B2 | 11/2005 | Shelton, IV et al. |
| 6,960,107 | B1 | 11/2005 | Schaub et al. |
| 6,960,163 | B2 | 11/2005 | Ewers et al. |
| 6,960,220 | B2 | 11/2005 | Marino et al. |
| 6,962,587 | B2 | 11/2005 | Johnson et al. |
| 6,963,792 | B1 | 11/2005 | Green |
| 6,964,363 | B2 | 11/2005 | Wales et al. |
| 6,966,907 | B2 | 11/2005 | Goble |
| 6,966,909 | B2 | 11/2005 | Marshall et al. |
| 6,968,908 | B2 | 11/2005 | Tokunaga et al. |
| 6,969,385 | B2 | 11/2005 | Moreyra |
| 6,969,395 | B2 | 11/2005 | Eskuri |
| 6,971,988 | B2 | 12/2005 | Orban, III |
| 6,972,199 | B2 | 12/2005 | Lebouitz et al. |
| 6,974,435 | B2 | 12/2005 | Daw et al. |
| 6,974,462 | B2 | 12/2005 | Sater |
| 6,978,921 | B2 | 12/2005 | Shelton, IV et al. |
| 6,978,922 | B2 | 12/2005 | Bilotti et al. |
| 6,981,628 | B2 | 1/2006 | Wales |
| 6,981,941 | B2 | 1/2006 | Whitman et al. |
| 6,981,978 | B2 | 1/2006 | Gannoe |
| 6,984,203 | B2 | 1/2006 | Tartaglia et al. |
| 6,984,231 | B2 | 1/2006 | Goble et al. |
| 6,986,451 | B1 | 1/2006 | Mastri et al. |
| 6,988,649 | B2 | 1/2006 | Shelton, IV et al. |
| 6,988,650 | B2 | 1/2006 | Schwemberger et al. |
| 6,989,034 | B2 | 1/2006 | Hammer et al. |
| 6,990,731 | B2 | 1/2006 | Haytayan |
| 6,990,796 | B2 | 1/2006 | Schnipke et al. |
| 6,991,146 | B2 | 1/2006 | Sinisi et al. |
| 6,993,200 | B2 | 1/2006 | Tastl et al. |
| 6,993,413 | B2 | 1/2006 | Sunaoshi |
| 6,994,708 | B2 | 2/2006 | Manzo |
| 6,995,729 | B2 | 2/2006 | Govari et al. |
| 6,996,433 | B2 | 2/2006 | Burbank et al. |
| 6,997,931 | B2 | 2/2006 | Sauer et al. |
| 6,997,935 | B2 | 2/2006 | Anderson et al. |
| 6,998,736 | B2 | 2/2006 | Lee et al. |
| 6,998,816 | B2 | 2/2006 | Wieck et al. |
| 6,999,821 | B2 | 2/2006 | Jenney et al. |
| 7,000,818 | B2 | 2/2006 | Shelton, IV et al. |
| 7,000,819 | B2 | 2/2006 | Swayze et al. |
| 7,000,911 | B2 | 2/2006 | McCormick et al. |
| 7,001,380 | B2 | 2/2006 | Goble |
| 7,001,408 | B2 | 2/2006 | Knodel et al. |
| 7,004,174 | B2 | 2/2006 | Eggers et al. |
| 7,005,828 | B2 | 2/2006 | Karikomi |
| 7,007,176 | B2 | 2/2006 | Goodfellow et al. |
| 7,008,433 | B2 | 3/2006 | Voellmicke et al. |
| 7,008,435 | B2 | 3/2006 | Cummins |
| 7,009,039 | B2 | 3/2006 | Yayon et al. |
| 7,011,213 | B2 | 3/2006 | Clark et al. |
| 7,011,657 | B2 | 3/2006 | Truckai et al. |
| 7,014,640 | B2 | 3/2006 | Kemppainen et al. |
| 7,018,357 | B2 | 3/2006 | Emmons |
| 7,018,390 | B2 | 3/2006 | Turovskiy et al. |
| 7,021,399 | B2 | 4/2006 | Driessen |
| 7,021,669 | B1 | 4/2006 | Lindermeir et al. |
| 7,022,131 | B1 | 4/2006 | Derowe et al. |
| 7,023,159 | B2 | 4/2006 | Gorti et al. |
| 7,025,064 | B2 | 4/2006 | Wang et al. |
| 7,025,732 | B2 | 4/2006 | Thompson et al. |
| 7,025,743 | B2 | 4/2006 | Mann et al. |
| 7,025,774 | B2 | 4/2006 | Freeman et al. |
| 7,025,775 | B2 | 4/2006 | Gadberry et al. |
| 7,028,570 | B2 | 4/2006 | Ohta et al. |
| 7,029,435 | B2 | 4/2006 | Nakao |
| 7,029,439 | B2 | 4/2006 | Roberts et al. |
| 7,030,904 | B2 | 4/2006 | Adair et al. |
| 7,032,798 | B2 | 4/2006 | Whitman et al. |
| 7,032,799 | B2 | 4/2006 | Viola et al. |
| 7,033,356 | B2 | 4/2006 | Latterell et al. |
| 7,033,378 | B2 | 4/2006 | Smith et al. |
| 7,035,716 | B2 | 4/2006 | Harris et al. |
| 7,035,762 | B2 | 4/2006 | Menard et al. |
| 7,036,680 | B1 | 5/2006 | Flannery |
| 7,037,314 | B2 | 5/2006 | Armstrong |
| 7,037,344 | B2 | 5/2006 | Kagan et al. |
| 7,038,421 | B2 | 5/2006 | Trifilo |
| 7,041,088 | B2 | 5/2006 | Nawrocki et al. |
| 7,041,102 | B2 | 5/2006 | Truckai et al. |
| 7,041,868 | B2 | 5/2006 | Greene et al. |
| 7,043,852 | B2 | 5/2006 | Hayashida et al. |
| 7,044,350 | B2 | 5/2006 | Kameyama et al. |
| 7,044,352 | B2 | 5/2006 | Shelton, IV et al. |
| 7,044,353 | B2 | 5/2006 | Mastri et al. |
| 7,046,082 | B2 | 5/2006 | Komiya et al. |
| 7,048,165 | B2 | 5/2006 | Haramiishi |
| 7,048,687 | B1 | 5/2006 | Reuss et al. |
| 7,048,716 | B1 | 5/2006 | Kucharczyk et al. |
| 7,048,745 | B2 | 5/2006 | Tierney et al. |
| 7,052,454 | B2 | 5/2006 | Taylor |
| 7,052,494 | B2 | 5/2006 | Goble et al. |
| 7,052,499 | B2 | 5/2006 | Steger et al. |
| 7,055,730 | B2 | 6/2006 | Ehrenfels et al. |
| 7,055,731 | B2 | 6/2006 | Shelton, IV et al. |
| 7,056,123 | B2 | 6/2006 | Gregorio et al. |
| 7,056,284 | B2 | 6/2006 | Martone et al. |

(56) References Cited

U.S. PATENT DOCUMENTS 7,056,330 B2 6/2006 Gayton
7,059,331 B2 6/2006 Adams et al.
7,059,508 B2 6/2006 Shelton, IV et al.
7,063,671 B2 6/2006 Couvillon, Jr.
7,063,712 B2 6/2006 Vargas et al.
7,064,509 B1 6/2006 Fu et al.
7,066,879 B2 6/2006 Fowler et al.
7,066,944 B2 6/2006 Laufer et al.
7,067,038 B2 6/2006 Trokhan et al.
7,070,083 B2 7/2006 Jankowski
7,070,559 B2 7/2006 Adams et al.
7,070,597 B2 7/2006 Truckai et al.
7,071,287 B2 7/2006 Rhine et al.
7,075,412 B1 7/2006 Reynolds et al.
7,075,770 B1 7/2006 Smith
7,077,856 B2 7/2006 Whitman
7,080,769 B2 7/2006 Vresh et al.
7,081,114 B2 7/2006 Rashidi
7,081,318 B2 7/2006 Lee et al.
7,083,073 B2 8/2006 Yoshie et al.
7,083,075 B2 8/2006 Swayze et al.
7,083,571 B2 8/2006 Wang et al.
7,083,615 B2 8/2006 Peterson et al.
7,083,619 B2 8/2006 Truckai et al.
7,083,620 B2 8/2006 Jahns et al.
7,083,626 B2 8/2006 Hart et al.
7,086,267 B2 8/2006 Dworak et al.
7,087,049 B2 8/2006 Nowlin et al.
7,087,054 B2 8/2006 Truckai et al.
7,087,071 B2 8/2006 Nicholas et al.
7,090,637 B2 8/2006 Danitz et al.
7,090,673 B2 8/2006 Dycus et al.
7,090,683 B2 8/2006 Brock et al.
7,090,684 B2 8/2006 McGuckin, Jr. et al.
7,091,191 B2 8/2006 Laredo et al.
7,091,412 B2 8/2006 Wang et al.
7,093,492 B2 8/2006 Treiber et al.
7,094,202 B2 8/2006 Nobis et al.
7,094,247 B2 8/2006 Monassevitch et al.
7,094,916 B2 8/2006 DeLuca et al.
7,096,972 B2 8/2006 Orozco, Jr.
7,097,089 B2 8/2006 Marczyk
7,097,644 B2 8/2006 Long
7,097,650 B2 8/2006 Weller et al.
7,098,794 B2 8/2006 Lindsay et al.
7,100,949 B2 9/2006 Williams et al.
7,101,187 B1 9/2006 Deconinck et al.
7,101,363 B2 9/2006 Nishizawa et al.
7,101,371 B2 9/2006 Dycus et al.
7,101,394 B2 9/2006 Hamm et al.
7,104,741 B2 9/2006 Krohn
7,108,695 B2 9/2006 Witt et al.
7,108,701 B2 9/2006 Evens et al.
7,108,709 B2 9/2006 Cummins
7,111,768 B2 9/2006 Cummins et al.
7,111,769 B2 9/2006 Wales et al.
7,112,201 B2 9/2006 Truckai et al.
7,112,214 B2 9/2006 Peterson et al.
RE39,358 E 10/2006 Goble
D530,339 S 10/2006 Hernandez et al.
7,114,642 B2 10/2006 Whitman
7,116,100 B1 10/2006 Mock et al.
7,118,020 B2 10/2006 Lee et al.
7,118,528 B1 10/2006 Piskun
7,118,563 B2 10/2006 Weckwerth et al.
7,118,582 B1 10/2006 Wang et al.
7,119,534 B2 10/2006 Butzmann
7,121,446 B2 10/2006 Arad et al.
7,121,773 B2 10/2006 Mikiya et al.
7,122,028 B2 10/2006 Looper et al.
7,125,403 B2 10/2006 Julian et al.
7,125,409 B2 10/2006 Truckai et al.
7,126,303 B2 10/2006 Farritor et al.
7,126,879 B2 10/2006 Snyder
7,128,253 B2 10/2006 Mastri et al.
7,128,254 B2 10/2006 Shelton, IV et al.
7,128,748 B2 10/2006 Mooradian et al.
7,131,445 B2 11/2006 Amoah
7,133,601 B2 11/2006 Phillips et al.
7,134,364 B2 11/2006 Kageler et al.
7,134,587 B2 11/2006 Schwemberger et al.
7,135,027 B2 11/2006 Delmotte
7,137,980 B2 11/2006 Buysse et al.
7,137,981 B2 11/2006 Long
7,139,016 B2 11/2006 Squilla et al.
7,140,527 B2 11/2006 Ehrenfels et al.
7,140,528 B2 11/2006 Shelton, IV
7,141,055 B2 11/2006 Abrams et al.
7,143,923 B2 12/2006 Shelton, IV et al.
7,143,924 B2 12/2006 Scirica et al.
7,143,925 B2 12/2006 Shelton, IV et al.
7,143,926 B2 12/2006 Shelton, IV et al.
7,146,191 B2 12/2006 Kerner et al.
7,147,138 B2 12/2006 Shelton, IV
7,147,139 B2 12/2006 Schwemberger et al.
7,147,140 B2 12/2006 Wukusick et al.
7,147,637 B2 12/2006 Goble
7,147,648 B2 12/2006 Lin
7,147,650 B2 12/2006 Lee
7,150,748 B2 12/2006 Ebbutt et al.
7,153,300 B2 12/2006 Goble
7,153,314 B2 12/2006 Laufer et al.
7,155,316 B2 12/2006 Sutherland et al.
7,156,846 B2 1/2007 Dycus et al.
7,156,863 B2 1/2007 Sonnenschein et al.
7,159,750 B2 1/2007 Racenet et al.
7,160,296 B2 1/2007 Pearson et al.
7,160,299 B2 1/2007 Baily
7,160,311 B2 1/2007 Blatter et al.
7,161,036 B2 1/2007 Oikawa et al.
7,161,580 B2 1/2007 Bailey et al.
7,162,758 B2 1/2007 Skinner
7,163,563 B2 1/2007 Schwartz et al.
7,166,117 B2 1/2007 Hellenkamp
7,166,133 B2 1/2007 Evans et al.
7,168,604 B2 1/2007 Milliman et al.
7,169,146 B2 1/2007 Truckai et al.
7,170,910 B2 1/2007 Chen et al.
7,171,279 B2 1/2007 Buckingham et al.
7,172,104 B2 2/2007 Scirica et al.
7,172,593 B2 2/2007 Trieu et al.
7,172,615 B2 2/2007 Morriss et al.
7,174,202 B2 2/2007 Bladen et al.
7,174,636 B2 2/2007 Lowe
7,177,533 B2 2/2007 McFarlin et al.
7,179,223 B2 2/2007 Motoki et al.
7,179,267 B2 2/2007 Nolan et al.
7,182,239 B1 2/2007 Myers
7,182,763 B2 2/2007 Nardella
7,183,737 B2 2/2007 Kitagawa
7,187,960 B2 3/2007 Abreu
7,188,758 B2 3/2007 Viola et al.
7,189,207 B2 3/2007 Viola
7,190,147 B2 3/2007 Gileff et al.
7,193,199 B2 3/2007 Jang
7,195,627 B2 3/2007 Amoah et al.
7,196,911 B2 3/2007 Takano et al.
D541,418 S 4/2007 Schechter et al.
7,197,965 B1 4/2007 Anderson
7,199,537 B2 4/2007 Okamura et al.
7,199,545 B2 4/2007 Oleynikov et al.
7,202,576 B1 4/2007 Dechene et al.
7,202,653 B2 4/2007 Pai
7,204,404 B2 4/2007 Nguyen et al.
7,204,835 B2 4/2007 Latterell et al.
7,205,959 B2 4/2007 Henriksson
7,206,626 B2 4/2007 Quaid, III
7,207,233 B2 4/2007 Wadge
7,207,471 B2 4/2007 Heinrich et al.
7,207,472 B2 4/2007 Wukusick et al.
7,207,556 B2 4/2007 Saitoh et al.
7,208,005 B2 4/2007 Frecker et al.
7,210,609 B2 5/2007 Leiboff et al.
7,211,081 B2 5/2007 Goble

(56) References Cited

U.S. PATENT DOCUMENTS 7,211,084 B2 5/2007 Goble et al.
7,211,092 B2 5/2007 Hughett
7,211,979 B2 5/2007 Khatib et al.
7,213,736 B2 5/2007 Wales et al.
7,214,224 B2 5/2007 Goble
7,215,517 B2 5/2007 Takamatsu
7,217,285 B2 5/2007 Vargas et al.
7,220,260 B2 5/2007 Fleming et al.
7,220,272 B2 5/2007 Weadock
7,225,959 B2 6/2007 Patton et al.
7,225,963 B2 6/2007 Scirica
7,225,964 B2 6/2007 Mastri et al.
7,226,450 B2 6/2007 Athanasiou et al.
7,226,467 B2 6/2007 Lucatero et al.
7,228,505 B2 6/2007 Shimazu et al.
7,229,408 B2 6/2007 Douglas et al.
7,234,624 B2 6/2007 Gresham et al.
7,235,072 B2 6/2007 Sartor et al.
7,235,089 B1 6/2007 McGuckin, Jr.
7,235,302 B2 6/2007 Jing et al.
7,237,708 B1 7/2007 Guy et al.
7,238,195 B2 7/2007 Viola
7,238,901 B2 7/2007 Kim et al.
7,239,657 B1 7/2007 Gunnarsson
7,241,288 B2 7/2007 Braun
7,241,289 B2 7/2007 Braun
7,246,734 B2 7/2007 Shelton, IV
7,247,161 B2 7/2007 Johnston et al.
7,249,267 B2 7/2007 Chapuis
7,252,641 B2 8/2007 Thompson et al.
7,252,660 B2 8/2007 Kunz
7,255,012 B2 8/2007 Hedtke
7,255,696 B2 8/2007 Goble et al.
7,256,695 B2 8/2007 Hamel et al.
7,258,262 B2 8/2007 Mastri et al.
7,258,546 B2 8/2007 Beier et al.
7,260,431 B2 8/2007 Libbus et al.
7,265,374 B2 9/2007 Lee et al.
7,267,677 B2 9/2007 Johnson et al.
7,267,679 B2 9/2007 McGuckin, Jr. et al.
7,272,002 B2 9/2007 Drapeau
7,273,483 B2 9/2007 Wiener et al.
7,273,488 B2 9/2007 Nakamura et al.
D552,623 S 10/2007 Vong et al.
7,275,674 B2 10/2007 Racenet et al.
7,276,044 B2 10/2007 Ferry et al.
7,276,068 B2 10/2007 Johnson et al.
7,278,562 B2 10/2007 Mastri et al.
7,278,563 B1 10/2007 Green
7,278,949 B2 10/2007 Bader
7,278,994 B2 10/2007 Goble
7,282,048 B2 10/2007 Goble et al.
7,283,096 B2 10/2007 Geisheimer et al.
7,286,850 B2 10/2007 Frielink et al.
7,287,682 B1 10/2007 Ezzat et al.
7,289,139 B2 10/2007 Amling et al.
7,293,685 B2 11/2007 Ehrenfels et al.
7,295,893 B2 11/2007 Sunaoshi
7,295,907 B2 11/2007 Lu et al.
7,296,722 B2 11/2007 Ivanko
7,296,724 B2 11/2007 Green et al.
7,297,149 B2 11/2007 Vitali et al.
7,300,373 B2 11/2007 Jinno et al.
7,300,431 B2 11/2007 Dubrovsky
7,300,450 B2 11/2007 Vleugels et al.
7,303,106 B2 12/2007 Milliman et al.
7,303,107 B2 12/2007 Milliman et al.
7,303,108 B2 12/2007 Shelton, IV
7,303,502 B2 12/2007 Thompson
7,303,556 B2 12/2007 Metzger
7,306,597 B2 12/2007 Manzo
7,308,998 B2 12/2007 Mastri et al.
7,311,238 B2 12/2007 Liu
7,311,709 B2 12/2007 Truckai et al.
7,313,430 B2 12/2007 Urquhart et al.
7,314,473 B2 1/2008 Jinno et al.
7,317,955 B2 1/2008 McGreevy
7,320,704 B2 1/2008 Lashinski et al.
7,322,859 B2 1/2008 Evans
7,322,975 B2 1/2008 Goble et al.
7,322,994 B2 1/2008 Nicholas et al.
7,324,572 B2 1/2008 Chang
7,326,203 B2 2/2008 Papineau et al.
7,326,213 B2 2/2008 Benderev et al.
7,328,828 B2 2/2008 Ortiz et al.
7,328,829 B2 2/2008 Arad et al.
7,330,004 B2 2/2008 DeJonge et al.
7,331,340 B2 2/2008 Barney
7,331,343 B2 2/2008 Schmidt et al.
7,331,403 B2 2/2008 Berry et al.
7,331,406 B2 2/2008 Wottreng, Jr. et al.
7,331,969 B1 2/2008 Inganas et al.
7,334,717 B2 2/2008 Rethy et al.
7,334,718 B2 2/2008 McAlister et al.
7,335,199 B2 2/2008 Goble et al.
7,335,401 B2 2/2008 Finke et al.
7,336,045 B2 2/2008 Clermonts
7,336,048 B2 2/2008 Lohr
7,336,183 B2 2/2008 Reddy et al.
7,336,184 B2 2/2008 Smith et al.
7,337,774 B2 3/2008 Webb
7,338,505 B2 3/2008 Belson
7,338,513 B2 3/2008 Lee et al.
7,341,554 B2 3/2008 Sekine et al.
7,341,555 B2 3/2008 Ootawara et al.
7,341,591 B2 3/2008 Grinberg
7,343,920 B2 3/2008 Toby et al.
7,344,532 B2 3/2008 Goble et al.
7,344,533 B2 3/2008 Pearson et al.
7,346,344 B2 3/2008 Fontaine
7,346,406 B2 3/2008 Brotto et al.
7,348,763 B1 3/2008 Reinhart et al.
7,348,875 B2 3/2008 Hughes et al.
RE40,237 E 4/2008 Bilotti et al.
7,351,258 B2 4/2008 Ricotta et al.
7,354,398 B2 4/2008 Kanazawa
7,354,440 B2 4/2008 Truckal et al.
7,354,447 B2 4/2008 Shelton, IV et al.
7,354,502 B2 4/2008 Polat et al.
7,357,287 B2 4/2008 Shelton, IV et al.
7,357,806 B2 4/2008 Rivera et al.
7,361,168 B2 4/2008 Makower et al.
7,361,195 B2 4/2008 Schwartz et al.
7,362,062 B2 4/2008 Schneider et al.
7,364,060 B2 4/2008 Milliman
7,364,061 B2 4/2008 Swayze et al.
7,367,485 B2 5/2008 Shelton, IV et al.
7,367,973 B2 5/2008 Manzo et al.
7,368,124 B2 5/2008 Chun et al.
7,371,210 B2 5/2008 Brock et al.
7,371,403 B2 5/2008 McCarthy et al.
7,375,493 B2 5/2008 Calhoon et al.
7,377,918 B2 5/2008 Amoah
7,377,928 B2 5/2008 Zubik et al.
7,378,817 B2 5/2008 Calhoon et al.
RE40,388 E 6/2008 Gines
D570,868 S 6/2008 Hosokawa et al.
7,380,695 B2 6/2008 Doll et al.
7,380,696 B2 6/2008 Shelton, IV et al.
7,384,403 B2 6/2008 Sherman
7,384,417 B2 6/2008 Cucin
7,386,365 B2 6/2008 Nixon
7,386,730 B2 6/2008 Uchikubo
7,388,217 B2 6/2008 Buschbeck et al.
7,388,484 B2 6/2008 Hsu
7,391,173 B2 6/2008 Schena
7,394,190 B2 7/2008 Huang
7,396,356 B2 7/2008 Mollenauer
7,397,364 B2 7/2008 Govari
7,398,707 B2 7/2008 Morley et al.
7,398,907 B2 7/2008 Racenet et al.
7,398,908 B2 7/2008 Holsten et al.
7,400,107 B2 7/2008 Schneider et al.
7,400,752 B2 7/2008 Zacharias

(56) References Cited

U.S. PATENT DOCUMENTS 7,401,000 B2 7/2008 Nakamura
7,401,721 B2 7/2008 Holsten et al.
7,404,449 B2 7/2008 Bermingham et al.
7,404,508 B2 7/2008 Smith et al.
7,404,509 B2 7/2008 Ortiz et al.
7,404,822 B2 7/2008 Viart et al.
D575,793 S 8/2008 Ording
7,407,074 B2 8/2008 Ortiz et al.
7,407,075 B2 8/2008 Holsten et al.
7,407,076 B2 8/2008 Racenet et al.
7,407,077 B2 8/2008 Ortiz et al.
7,407,078 B2 8/2008 Shelton, IV et al.
7,408,310 B2 8/2008 Hong et al.
7,410,085 B2 8/2008 Wolf et al.
7,410,086 B2 8/2008 Ortiz et al.
7,410,483 B2 8/2008 Danitz et al.
7,413,563 B2 8/2008 Corcoran et al.
7,416,101 B2 8/2008 Shelton, IV et al.
7,418,078 B2 8/2008 Blanz et al.
RE40,514 E 9/2008 Mastri et al.
7,419,080 B2 9/2008 Smith et al.
7,419,081 B2 9/2008 Ehrenfels et al.
7,419,321 B2 9/2008 Tereschouk
7,419,495 B2 9/2008 Menn et al.
7,422,136 B1 9/2008 Marczyk
7,422,138 B2 9/2008 Bilotti et al.
7,422,139 B2 9/2008 Shelton, IV et al.
7,424,965 B2 9/2008 Racenet et al.
7,427,607 B2 9/2008 Suzuki
D578,644 S 10/2008 Shumer et al.
7,430,772 B2 10/2008 Van Es
7,430,849 B1 10/2008 Coutts et al.
7,431,188 B1 10/2008 Marczyk
7,431,189 B2 10/2008 Shelton, IV et al.
7,431,230 B2 10/2008 McPherson et al.
7,431,694 B2 10/2008 Stefanchik et al.
7,431,730 B2 10/2008 Viola
7,434,715 B2 10/2008 Shelton, IV et al.
7,434,717 B2 10/2008 Shelton, IV et al.
7,435,249 B2 10/2008 Buysse et al.
7,438,209 B1 10/2008 Hess et al.
7,438,718 B2 10/2008 Milliman et al.
7,439,354 B2 10/2008 Lenges et al.
7,441,684 B2 10/2008 Shelton, IV et al.
7,441,685 B1 10/2008 Boudreaux
7,442,201 B2 10/2008 Pugsley et al.
7,443,547 B2 10/2008 Moreno et al.
D580,942 S 11/2008 Oshiro et al.
7,446,131 B1 11/2008 Liu et al.
7,448,525 B2 11/2008 Shelton, IV et al.
7,450,010 B1 11/2008 Gravelle et al.
7,450,991 B2 11/2008 Smith et al.
7,451,904 B2 11/2008 Shelton, IV
7,455,208 B2 11/2008 Wales et al.
7,455,676 B2 11/2008 Holsten et al.
7,455,682 B2 11/2008 Viola
7,455,687 B2 11/2008 Saunders et al.
D582,934 S 12/2008 Byeon
7,461,767 B2 12/2008 Viola et al.
7,462,187 B2 12/2008 Johnston et al.
7,464,845 B2 12/2008 Chou
7,464,846 B2 12/2008 Shelton, IV et al.
7,464,847 B2 12/2008 Viola et al.
7,464,848 B2 12/2008 Green et al.
7,464,849 B2 12/2008 Shelton, IV et al.
7,467,740 B2 12/2008 Shelton, IV et al.
7,467,849 B2 12/2008 Silverbrook et al.
7,472,814 B2 1/2009 Mastri et al.
7,472,815 B2 1/2009 Shelton, IV et al.
7,472,816 B2 1/2009 Holsten et al.
7,473,221 B2 1/2009 Ewers et al.
7,473,253 B2 1/2009 Dycus et al.
7,473,263 B2 1/2009 Johnston et al.
7,476,237 B2 1/2009 Taniguchi et al.
7,479,147 B2 1/2009 Honeycutt et al.
7,479,608 B2 1/2009 Smith
7,481,347 B2 1/2009 Roy
7,481,348 B2 1/2009 Marczyk
7,481,349 B2 1/2009 Holsten et al.
7,481,824 B2 1/2009 Boudreaux et al.
7,485,124 B2 2/2009 Kuhns et al.
7,485,133 B2 2/2009 Cannon et al.
7,485,142 B2 2/2009 Milo
7,487,899 B2 2/2009 Shelton, IV et al.
7,489,055 B2 2/2009 Jeong et al.
7,490,749 B2 2/2009 Schall et al.
7,491,232 B2 2/2009 Bolduc et al.
7,492,261 B2 2/2009 Cambre et al.
7,494,039 B2 2/2009 Racenet et al.
7,494,460 B2 2/2009 Haarstad et al.
7,494,499 B2 2/2009 Nagase et al.
7,494,501 B2 2/2009 Ahlberg et al.
7,497,137 B2 3/2009 Tellenbach et al.
7,500,979 B2 3/2009 Hueil et al.
7,501,198 B2 3/2009 Barlev et al.
7,503,474 B2 3/2009 Hillstead et al.
7,506,790 B2 3/2009 Shelton, IV
7,506,791 B2 3/2009 Omaits et al.
7,507,202 B2 3/2009 Schoellhorn
7,510,107 B2 3/2009 Timm et al.
7,510,534 B2 3/2009 Burdorff et al.
7,510,566 B2 3/2009 Jacobs et al.
7,513,407 B1 4/2009 Chang
7,513,408 B2 4/2009 Shelton, IV et al.
7,517,356 B2 4/2009 Heinrich
7,524,320 B2 4/2009 Tierney et al.
7,527,632 B2 5/2009 Houghton et al.
7,530,984 B2 5/2009 Sonnenschein et al.
7,530,985 B2 5/2009 Takemoto et al.
7,533,790 B1 5/2009 Knodel et al.
7,533,906 B2 5/2009 Luettgen et al.
7,534,259 B2 5/2009 Lashinski et al.
7,540,867 B2 6/2009 Jinno et al.
7,540,872 B2 6/2009 Schechter et al.
7,542,807 B2 6/2009 Bertolero et al.
7,543,730 B1 6/2009 Marczyk
7,544,197 B2 6/2009 Kelsch et al.
7,546,939 B2 6/2009 Adams et al.
7,546,940 B2 6/2009 Milliman et al.
7,547,287 B2 6/2009 Boecker et al.
7,547,312 B2 6/2009 Bauman et al.
7,549,563 B2 6/2009 Mather et al.
7,549,564 B2 6/2009 Boudreaux
7,549,998 B2 6/2009 Braun
7,552,854 B2 6/2009 Wixey et al.
7,553,173 B2 6/2009 Kowalick
7,553,275 B2 6/2009 Padget et al.
7,554,343 B2 6/2009 Bromfield
7,556,185 B2 7/2009 Viola
7,556,186 B2 7/2009 Milliman
7,556,647 B2 7/2009 Drews et al.
7,559,449 B2 7/2009 Viola
7,559,450 B2 7/2009 Wales et al.
7,559,452 B2 7/2009 Wales et al.
7,559,937 B2 7/2009 de la Torre et al.
7,561,637 B2 7/2009 Jonsson et al.
7,562,910 B2 7/2009 Kertesz et al.
7,563,269 B2 7/2009 Hashiguchi
7,563,862 B2 7/2009 Sieg et al.
7,565,993 B2 7/2009 Milliman et al.
7,566,300 B2 7/2009 Devierre et al.
7,567,045 B2 7/2009 Fristedt
7,568,603 B2 8/2009 Shelton, IV et al.
7,568,604 B2 8/2009 Ehrenfels et al.
7,568,619 B2 8/2009 Todd et al.
7,572,285 B2 8/2009 Frey et al.
7,572,298 B2 8/2009 Roller et al.
7,575,144 B2 8/2009 Ortiz et al.
7,578,825 B2 8/2009 Huebner
D600,712 S 9/2009 LaManna et al.
7,583,063 B2 9/2009 Dooley
7,584,880 B2 9/2009 Racenet et al.
7,586,289 B2 9/2009 Andruk et al.
7,588,174 B2 9/2009 Holsten et al.

(56) References Cited

U.S. PATENT DOCUMENTS 7,588,175 B2 9/2009 Timm et al.
7,588,176 B2 9/2009 Timm et al.
7,588,177 B2 9/2009 Racenet
7,591,783 B2 9/2009 Boulais et al.
7,591,818 B2 9/2009 Bertolero et al.
7,593,766 B2 9/2009 Faber et al.
7,595,642 B2 9/2009 Doyle
7,597,229 B2 10/2009 Boudreaux et al.
7,597,230 B2 10/2009 Racenet et al.
7,597,693 B2 10/2009 Garrison
7,597,699 B2 10/2009 Rogers
7,598,972 B2 10/2009 Tomita
7,600,663 B2 10/2009 Green
7,604,118 B2 10/2009 Iio et al.
7,604,150 B2 10/2009 Boudreaux
7,604,151 B2 10/2009 Hess et al.
7,604,668 B2 10/2009 Farnsworth et al.
7,605,826 B2 10/2009 Sauer
7,607,557 B2 10/2009 Shelton, IV et al.
7,608,091 B2 10/2009 Goldfarb et al.
D604,325 S 11/2009 Ebeling et al.
7,611,038 B2 11/2009 Racenet et al.
7,611,474 B2 11/2009 Hibner et al.
7,615,003 B2 11/2009 Stefanchik et al.
7,615,006 B2 11/2009 Abe
7,615,067 B2 11/2009 Lee et al.
7,617,961 B2 11/2009 Viola
7,618,427 B2 11/2009 Ortiz et al.
D605,201 S 12/2009 Lorenz et al.
D606,992 S 12/2009 Liu et al.
D607,010 S 12/2009 Kocmick
7,624,902 B2 12/2009 Marczyk et al.
7,624,903 B2 12/2009 Green et al.
7,625,370 B2 12/2009 Hart et al.
7,625,388 B2 12/2009 Boukhny et al.
7,625,662 B2 12/2009 Vaisnys et al.
7,630,841 B2 12/2009 Comisky et al.
7,631,793 B2 12/2009 Rethy et al.
7,631,794 B2 12/2009 Rethy et al.
7,635,074 B2 12/2009 Olson et al.
7,635,922 B2 12/2009 Becker
7,637,409 B2 12/2009 Marczyk
7,637,410 B2 12/2009 Marczyk
7,638,958 B2 12/2009 Philipp et al.
7,641,091 B2 1/2010 Olson et al.
7,641,092 B2 1/2010 Kruszynski et al.
7,641,093 B2 1/2010 Doll et al.
7,641,095 B2 1/2010 Viola
7,641,671 B2 1/2010 Crainich
7,644,016 B2 1/2010 Nycz et al.
7,644,484 B2 1/2010 Vereschagin
7,644,783 B2 1/2010 Roberts et al.
7,644,848 B2 1/2010 Swayze et al.
7,645,230 B2 1/2010 Mikkaichi et al.
7,648,055 B2 1/2010 Marczyk
7,648,457 B2 1/2010 Stefanchik et al.
7,648,519 B2 1/2010 Lee et al.
7,650,185 B2 1/2010 Maile et al.
7,651,017 B2 1/2010 Ortiz et al.
7,651,498 B2 1/2010 Shifrin et al.
7,654,431 B2 2/2010 Hueil et al.
7,655,003 B2 2/2010 Lorang et al.
7,655,004 B2 2/2010 Long
7,655,288 B2 2/2010 Bauman et al.
7,655,584 B2 2/2010 Biran et al.
7,656,131 B2 2/2010 Embrey et al.
7,658,311 B2 2/2010 Boudreaux
7,658,312 B2 2/2010 Vidal et al.
7,658,705 B2 2/2010 Melvin et al.
7,659,219 B2 2/2010 Biran et al.
7,661,448 B2 2/2010 Kim et al.
7,662,161 B2 2/2010 Briganti et al.
7,665,646 B2 2/2010 Prommersberger
7,665,647 B2 2/2010 Shelton, IV et al.
7,666,195 B2 2/2010 Kelleher et al.
7,669,746 B2 3/2010 Shelton, IV
7,669,747 B2 3/2010 Weisenburgh et al.
7,670,334 B2 3/2010 Hueil et al.
7,670,337 B2 3/2010 Young
7,673,780 B2 3/2010 Shelton, IV et al.
7,673,781 B2 3/2010 Swayze et al.
7,673,782 B2 3/2010 Hess et al.
7,673,783 B2 3/2010 Morgan et al.
7,674,253 B2 3/2010 Fisher et al.
7,674,255 B2 3/2010 Braun
7,674,263 B2 3/2010 Ryan
7,674,270 B2 3/2010 Layer
7,678,121 B1 3/2010 Knodel
7,682,307 B2 3/2010 Danitz et al.
7,682,367 B2 3/2010 Shah et al.
7,682,686 B2 3/2010 Curro et al.
7,686,201 B2 3/2010 Csiky
7,686,804 B2 3/2010 Johnson et al.
7,686,826 B2 3/2010 Lee et al.
7,688,028 B2 3/2010 Phillips et al.
7,690,547 B2 4/2010 Racenet et al.
7,691,098 B2 4/2010 Wallace et al.
7,691,103 B2 4/2010 Fernandez et al.
7,691,106 B2 4/2010 Schenberger et al.
7,694,864 B2 4/2010 Okada et al.
7,694,865 B2 4/2010 Scirica
7,695,485 B2 4/2010 Whitman et al.
7,695,493 B2 4/2010 Saadat et al.
7,699,204 B2 4/2010 Viola
7,699,835 B2 4/2010 Lee et al.
7,699,844 B2 4/2010 Utley et al.
7,699,846 B2 4/2010 Ryan
7,699,856 B2 4/2010 Van Wyk et al.
7,699,859 B2 4/2010 Bombard et al.
7,699,860 B2 4/2010 Huitema et al.
7,699,868 B2 4/2010 Frank et al.
7,703,653 B2 4/2010 Shah et al.
7,705,559 B2 4/2010 Powell et al.
7,706,853 B2 4/2010 Hacker et al.
7,708,180 B2 5/2010 Murray et al.
7,708,181 B2 5/2010 Cole et al.
7,708,182 B2 5/2010 Viola
7,708,758 B2 5/2010 Lee et al.
7,708,768 B2 5/2010 Danek et al.
7,709,136 B2 5/2010 Touchton et al.
7,712,182 B2 5/2010 Zeiler et al.
7,713,190 B2 5/2010 Brock et al.
7,713,542 B2 5/2010 Xu et al.
7,714,239 B2 5/2010 Smith
7,714,334 B2 5/2010 Lin
7,717,312 B2 5/2010 Beetel
7,717,313 B2 5/2010 Criscuolo et al.
7,717,846 B2 5/2010 Zirps et al.
7,717,873 B2 5/2010 Swick
7,717,915 B2 5/2010 Miyazawa
7,717,926 B2 5/2010 Whitfield et al.
7,718,180 B2 5/2010 Karp
7,718,556 B2 5/2010 Matsuda et al.
7,721,930 B2 5/2010 McKenna et al.
7,721,931 B2 5/2010 Shelton, IV et al.
7,721,932 B2 5/2010 Cole et al.
7,721,933 B2 5/2010 Ehrenfels et al.
7,721,934 B2 5/2010 Shelton, IV et al.
7,721,936 B2 5/2010 Shalton, IV et al.
7,722,527 B2 5/2010 Bouchier et al.
7,722,607 B2 5/2010 Dumbauld et al.
7,722,610 B2 5/2010 Viola et al.
7,725,214 B2 5/2010 Diolaiti
7,726,171 B2 6/2010 Langlotz et al.
7,726,537 B2 6/2010 Olson et al.
7,726,538 B2 6/2010 Holsten et al.
7,726,539 B2 6/2010 Holsten et al.
7,727,954 B2 6/2010 McKay
7,728,553 B2 6/2010 Carrier et al.
7,729,742 B2 6/2010 Govari
7,731,072 B2 6/2010 Timm et al.
7,731,073 B2 6/2010 Wixey et al.
7,731,724 B2 6/2010 Huitema et al.
7,735,703 B2 6/2010 Morgan et al.

(56) References Cited

U.S. PATENT DOCUMENTS 7,735,704 B2 6/2010 Bilotti
7,736,254 B2 6/2010 Schena
7,736,306 B2 6/2010 Brustad et al.
7,736,356 B2 6/2010 Cooper et al.
7,736,374 B2 6/2010 Vaughan et al.
7,738,971 B2 6/2010 Swayze et al.
7,740,159 B2 6/2010 Shelton, IV et al.
7,742,036 B2 6/2010 Grant et al.
7,743,960 B2 6/2010 Whitman et al.
7,744,624 B2 6/2010 Bettuchi
7,744,627 B2 6/2010 Orban, III et al.
7,744,628 B2 6/2010 Viola
7,747,146 B2 6/2010 Milano et al.
7,748,587 B2 7/2010 Haramiishi et al.
7,748,632 B2 7/2010 Coleman et al.
7,749,204 B2 7/2010 Dhanaraj et al.
7,749,240 B2 7/2010 Takahashi et al.
7,751,870 B2 7/2010 Whitman
7,753,245 B2 7/2010 Boudreaux et al.
7,753,246 B2 7/2010 Scirica
7,753,904 B2 7/2010 Shelton, IV et al.
7,757,924 B2 7/2010 Gerbi et al.
7,758,594 B2 7/2010 Lamson et al.
7,758,612 B2 7/2010 Shipp
7,758,613 B2 7/2010 Whitman
7,762,462 B2 7/2010 Gelbman
7,762,998 B2 7/2010 Birk et al.
D622,286 S 8/2010 Umezawa
7,766,207 B2 8/2010 Mather et al.
7,766,209 B2 8/2010 Baxter, III et al.
7,766,210 B2 8/2010 Shelton, IV et al.
7,766,821 B2 8/2010 Brunnen et al.
7,766,894 B2 8/2010 Weitzner et al.
7,770,658 B2 8/2010 Ito et al.
7,770,773 B2 8/2010 Whitman et al.
7,770,774 B2 8/2010 Mastri et al.
7,770,775 B2 8/2010 Shelton, IV et al.
7,770,776 B2 8/2010 Chen et al.
7,771,396 B2 8/2010 Stefanchik et al.
7,772,720 B2 8/2010 McGee et al.
7,772,725 B2 8/2010 Siman-Tov
7,775,972 B2 8/2010 Brock et al.
7,776,037 B2 8/2010 Odom
7,776,060 B2 8/2010 Mooradian et al.
7,776,065 B2 8/2010 Griffiths et al.
7,778,004 B2 8/2010 Nerheim et al.
7,779,614 B1 8/2010 McGonagle et al.
7,779,737 B2 8/2010 Newman, Jr. et al.
7,780,054 B2 8/2010 Wales
7,780,055 B2 8/2010 Scirica et al.
7,780,309 B2 8/2010 McMillan et al.
7,780,651 B2 8/2010 Madhani et al.
7,780,663 B2 8/2010 Yates et al.
7,780,685 B2 8/2010 Hunt et al.
7,782,382 B2 8/2010 Fujimura
7,784,662 B2 8/2010 Wales et al.
7,784,663 B2 8/2010 Shelton, IV
7,787,256 B2 8/2010 Chan et al.
7,789,283 B2 9/2010 Shah
7,789,875 B2 9/2010 Brock et al.
7,789,883 B2 9/2010 Takashino et al.
7,789,889 B2 9/2010 Zubik et al.
7,793,812 B2 9/2010 Moore et al.
7,794,475 B2 9/2010 Hess et al.
7,798,386 B2 9/2010 Schall et al.
7,799,039 B2 9/2010 Shelton, IV et al.
7,799,044 B2 9/2010 Johnston et al.
7,799,965 B2 9/2010 Patel et al.
7,803,151 B2 9/2010 Whitman
7,806,871 B2 10/2010 Li et al.
7,806,891 B2 10/2010 Nowlin et al.
7,810,690 B2 10/2010 Bilotti et al.
7,810,691 B2 10/2010 Boyden et al.
7,810,692 B2 10/2010 Hall et al.
7,810,693 B2 10/2010 Broehl et al.
7,811,275 B2 10/2010 Birk et al.
7,814,816 B2 10/2010 Alberti et al.
7,815,092 B2 10/2010 Whitman et al.
7,815,565 B2 10/2010 Stefanchik et al.
7,815,662 B2 10/2010 Spivey et al.
7,819,296 B2 10/2010 Hueil et al.
7,819,297 B2 10/2010 Doll et al.
7,819,298 B2 10/2010 Hall et al.
7,819,299 B2 10/2010 Shelton, IV et al.
7,819,799 B2 10/2010 Merril et al.
7,819,884 B2 10/2010 Lee et al.
7,819,885 B2 10/2010 Cooper
7,819,886 B2 10/2010 Whitfield et al.
7,819,894 B2 10/2010 Mitsuishi et al.
7,823,076 B2 10/2010 Borovsky et al.
7,823,592 B2 11/2010 Bettuchi et al.
7,823,760 B2 11/2010 Zemlok et al.
7,824,401 B2 11/2010 Manzo et al.
7,824,422 B2 11/2010 Benchetrit
7,824,426 B2 11/2010 Racenet et al.
7,828,189 B2 11/2010 Holsten et al.
7,828,794 B2 11/2010 Sartor
7,828,808 B2 11/2010 Hinman et al.
7,829,416 B2 11/2010 Kudou et al.
7,831,292 B2 11/2010 Quaid et al.
7,832,408 B2 11/2010 Shelton, IV et al.
7,832,611 B2 11/2010 Boyden et al.
7,832,612 B2 11/2010 Baxter, III et al.
7,833,234 B2 11/2010 Bailly et al.
7,835,823 B2 11/2010 Sillman et al.
7,836,400 B2 11/2010 May et al.
7,837,079 B2 11/2010 Holsten et al.
7,837,080 B2 11/2010 Schwemberger
7,837,081 B2 11/2010 Holsten et al.
7,837,425 B2 11/2010 Saeki et al.
7,837,685 B2 11/2010 Weinberg et al.
7,837,687 B2 11/2010 Harp
7,837,694 B2 11/2010 Tethrake et al.
7,838,789 B2 11/2010 Stoffers et al.
7,839,109 B2 11/2010 Carmen, Jr. et al.
7,840,253 B2 11/2010 Tremblay et al.
7,841,503 B2 11/2010 Sonnenschein et al.
7,842,025 B2 11/2010 Coleman et al.
7,842,028 B2 11/2010 Lee
7,843,158 B2 11/2010 Prisco
7,845,533 B2 12/2010 Marczyk et al.
7,845,534 B2 12/2010 Viola et al.
7,845,535 B2 12/2010 Scircia
7,845,536 B2 12/2010 Viola et al.
7,845,537 B2 12/2010 Shelton, IV et al.
7,845,538 B2 12/2010 Whitman
7,845,912 B2 12/2010 Sung et al.
7,846,085 B2 12/2010 Silverman et al.
7,846,149 B2 12/2010 Jankowski
7,846,161 B2 12/2010 Dumbauld et al.
7,848,066 B2 12/2010 Yanagishima
7,850,623 B2 12/2010 Griffin et al.
7,850,642 B2 12/2010 Moll et al.
7,850,982 B2 12/2010 Stopek et al.
7,853,813 B2 12/2010 Lee
7,854,735 B2 12/2010 Houser et al.
7,854,736 B2 12/2010 Ryan
7,857,183 B2 12/2010 Shelton, IV
7,857,184 B2 12/2010 Viola
7,857,185 B2 12/2010 Swayze et al.
7,857,186 B2 12/2010 Baxter, III et al.
7,857,813 B2 12/2010 Schmitz et al.
7,861,906 B2 1/2011 Doll et al.
7,862,502 B2 1/2011 Pool et al.
7,862,546 B2 1/2011 Conlon et al.
7,862,579 B2 1/2011 Ortiz et al.
7,866,525 B2 1/2011 Scirica
7,866,527 B2 1/2011 Hall et al.
7,866,528 B2 1/2011 Olson et al.
7,870,989 B2 1/2011 Viola et al.
7,871,418 B2 1/2011 Thompson et al.
7,871,440 B2 1/2011 Schwartz et al.
7,875,055 B2 1/2011 Cichocki, Jr.
7,877,869 B2 2/2011 Mehdizadeh et al.

(56) References Cited

U.S. PATENT DOCUMENTS

| | | | |
|---|---|---|---|
| 7,879,063 | B2 | 2/2011 | Khosravi |
| 7,879,070 | B2 | 2/2011 | Ortiz et al. |
| 7,879,367 | B2 | 2/2011 | Heublein et al. |
| 7,883,461 | B2 | 2/2011 | Albrecht et al. |
| 7,883,465 | B2 | 2/2011 | Donofrio et al. |
| 7,883,540 | B2 | 2/2011 | Niwa et al. |
| 7,886,951 | B2 | 2/2011 | Hessler |
| 7,886,952 | B2 | 2/2011 | Scirica et al. |
| 7,887,530 | B2 | 2/2011 | Zemlok et al. |
| 7,887,535 | B2 | 2/2011 | Lands et al. |
| 7,887,536 | B2 | 2/2011 | Johnson et al. |
| 7,887,563 | B2 | 2/2011 | Cummins |
| 7,887,755 | B2 | 2/2011 | Mingerink et al. |
| 7,891,531 | B1 | 2/2011 | Ward |
| 7,891,532 | B2 | 2/2011 | Mastri et al. |
| 7,892,200 | B2 | 2/2011 | Birk et al. |
| 7,892,245 | B2 | 2/2011 | Liddicoat et al. |
| 7,893,586 | B2 | 2/2011 | West et al. |
| 7,896,214 | B2 | 3/2011 | Farascioni |
| 7,896,215 | B2 | 3/2011 | Adams et al. |
| 7,896,671 | B2 | 3/2011 | Kim et al. |
| 7,896,869 | B2 | 3/2011 | DiSilvestro et al. |
| 7,896,877 | B2 | 3/2011 | Hall et al. |
| 7,896,895 | B2 | 3/2011 | Boudreaux et al. |
| 7,896,897 | B2 | 3/2011 | Gresham et al. |
| 7,896,900 | B2 | 3/2011 | Frank et al. |
| 7,898,198 | B2 | 3/2011 | Murphree |
| 7,900,805 | B2 | 3/2011 | Shelton, IV et al. |
| 7,900,806 | B2 | 3/2011 | Chen et al. |
| 7,901,381 | B2 | 3/2011 | Birk et al. |
| 7,905,380 | B2 | 3/2011 | Shelton, IV et al. |
| 7,905,381 | B2 | 3/2011 | Baxter, III et al. |
| 7,905,881 | B2 | 3/2011 | Masuda et al. |
| 7,905,889 | B2 | 3/2011 | Catanese, III et al. |
| 7,905,890 | B2 | 3/2011 | Whitfield et al. |
| 7,905,902 | B2 | 3/2011 | Huitema et al. |
| 7,909,039 | B2 | 3/2011 | Hur |
| 7,909,191 | B2 | 3/2011 | Baker et al. |
| 7,909,220 | B2 | 3/2011 | Viola |
| 7,909,221 | B2 | 3/2011 | Viola et al. |
| 7,909,224 | B2 | 3/2011 | Prommersberger |
| 7,913,891 | B2 | 3/2011 | Doll et al. |
| 7,913,893 | B2 | 3/2011 | Mastri et al. |
| 7,914,521 | B2 | 3/2011 | Wang et al. |
| 7,914,543 | B2 | 3/2011 | Roth et al. |
| 7,914,551 | B2 | 3/2011 | Ortiz et al. |
| 7,918,230 | B2 | 4/2011 | Whitman et al. |
| 7,918,376 | B1 | 4/2011 | Knodel et al. |
| 7,918,377 | B2 | 4/2011 | Measamer et al. |
| 7,918,845 | B2 | 4/2011 | Saadat et al. |
| 7,918,848 | B2 | 4/2011 | Lau et al. |
| 7,918,861 | B2 | 4/2011 | Brock et al. |
| 7,918,867 | B2 | 4/2011 | Dana et al. |
| 7,922,061 | B2 | 4/2011 | Shelton, IV et al. |
| 7,922,063 | B2 | 4/2011 | Zemlok et al. |
| 7,922,743 | B2 | 4/2011 | Heinrich et al. |
| 7,923,144 | B2 | 4/2011 | Kohn et al. |
| 7,926,691 | B2 | 4/2011 | Viola et al. |
| 7,926,692 | B2 | 4/2011 | Racenet et al. |
| 7,927,328 | B2 | 4/2011 | Orszulak et al. |
| 7,928,281 | B2 | 4/2011 | Augustine |
| 7,930,040 | B1 | 4/2011 | Kelsch et al. |
| 7,930,065 | B2 | 4/2011 | Larkin et al. |
| 7,931,660 | B2 | 4/2011 | Aranyi et al. |
| 7,931,695 | B2 | 4/2011 | Ringeisen |
| 7,931,877 | B2 | 4/2011 | Steffens et al. |
| 7,934,630 | B2 | 5/2011 | Shelton, IV et al. |
| 7,934,631 | B2 | 5/2011 | Balbierz et al. |
| 7,934,896 | B2 | 5/2011 | Schnier |
| 7,935,130 | B2 | 5/2011 | Williams |
| 7,935,773 | B2 | 5/2011 | Hadba et al. |
| 7,936,142 | B2 | 5/2011 | Otsuka et al. |
| 7,938,307 | B2 | 5/2011 | Bettuchi |
| 7,939,152 | B2 | 5/2011 | Haskin et al. |
| 7,941,865 | B2 | 5/2011 | Seman, Jr. et al. |
| 7,942,300 | B2 | 5/2011 | Rethy et al. |
| 7,942,303 | B2 | 5/2011 | Shah |
| 7,942,890 | B2 | 5/2011 | D'Agostino et al. |
| 7,944,175 | B2 | 5/2011 | Mori et al. |
| 7,945,792 | B2 | 5/2011 | Cherpantier |
| 7,945,798 | B2 | 5/2011 | Carlson et al. |
| 7,946,453 | B2 | 5/2011 | Voegele et al. |
| 7,947,011 | B2 | 5/2011 | Birk et al. |
| 7,948,381 | B2 | 5/2011 | Lindsay et al. |
| 7,950,560 | B2 | 5/2011 | Zemlok et al. |
| 7,950,561 | B2 | 5/2011 | Aranyi |
| 7,950,562 | B2 | 5/2011 | Beardsley et al. |
| 7,951,071 | B2 | 5/2011 | Whitman et al. |
| 7,951,166 | B2 | 5/2011 | Orban, III et al. |
| 7,952,464 | B2 | 5/2011 | Nikitin et al. |
| 7,954,682 | B2 | 6/2011 | Giordano et al. |
| 7,954,684 | B2 | 6/2011 | Boudreaux |
| 7,954,685 | B2 | 6/2011 | Viola |
| 7,954,686 | B2 | 6/2011 | Baxter, III et al. |
| 7,954,687 | B2 | 6/2011 | Zemlok et al. |
| 7,954,688 | B2 | 6/2011 | Argentine et al. |
| 7,955,253 | B2 | 6/2011 | Ewers et al. |
| 7,955,257 | B2 | 6/2011 | Frasier et al. |
| 7,955,322 | B2 | 6/2011 | Devengenzo et al. |
| 7,955,327 | B2 | 6/2011 | Sartor et al. |
| 7,955,380 | B2 | 6/2011 | Chu et al. |
| 7,959,050 | B2 | 6/2011 | Smith et al. |
| 7,959,051 | B2 | 6/2011 | Smith et al. |
| 7,959,052 | B2 | 6/2011 | Sonnenschein et al. |
| 7,963,432 | B2 | 6/2011 | Knodel et al. |
| 7,963,433 | B2 | 6/2011 | Whitman et al. |
| 7,963,913 | B2 | 6/2011 | Devengenzo et al. |
| 7,963,963 | B2 | 6/2011 | Francischelli et al. |
| 7,963,964 | B2 | 6/2011 | Santilli et al. |
| 7,964,206 | B2 | 6/2011 | Suokas et al. |
| 7,966,236 | B2 | 6/2011 | Noriega et al. |
| 7,966,269 | B2 | 6/2011 | Bauer et al. |
| 7,966,799 | B2 | 6/2011 | Morgan et al. |
| 7,967,178 | B2 | 6/2011 | Scirica et al. |
| 7,967,179 | B2 | 6/2011 | Olson et al. |
| 7,967,180 | B2 | 6/2011 | Scirica |
| 7,967,181 | B2 | 6/2011 | Viola et al. |
| 7,967,791 | B2 | 6/2011 | Franer et al. |
| 7,967,839 | B2 | 6/2011 | Flock et al. |
| 7,972,298 | B2 | 7/2011 | Wallace et al. |
| 7,972,315 | B2 | 7/2011 | Birk et al. |
| 7,976,213 | B2 | 7/2011 | Bertolotti et al. |
| 7,976,508 | B2 | 7/2011 | Hoag |
| 7,976,563 | B2 | 7/2011 | Summerer |
| 7,979,137 | B2 | 7/2011 | Tracey et al. |
| 7,980,443 | B2 | 7/2011 | Scheib et al. |
| 7,981,025 | B2 | 7/2011 | Pool et al. |
| 7,981,102 | B2 | 7/2011 | Patel et al. |
| 7,981,132 | B2 | 7/2011 | Dubrul et al. |
| 7,987,405 | B2 | 7/2011 | Turner et al. |
| 7,988,015 | B2 | 8/2011 | Mason, II et al. |
| 7,988,026 | B2 | 8/2011 | Knodel et al. |
| 7,988,027 | B2 | 8/2011 | Olson et al. |
| 7,988,028 | B2 | 8/2011 | Farascioni et al. |
| 7,988,779 | B2 | 8/2011 | Disalvo et al. |
| 7,992,757 | B2 | 8/2011 | Wheeler et al. |
| 7,993,360 | B2 | 8/2011 | Hacker et al. |
| 7,994,670 | B2 | 8/2011 | Ji |
| 7,997,054 | B2 | 8/2011 | Bertsch et al. |
| 7,997,468 | B2 | 8/2011 | Farascioni |
| 7,997,469 | B2 | 8/2011 | Olson et al. |
| 8,002,696 | B2 | 8/2011 | Suzuki |
| 8,002,784 | B2 | 8/2011 | Jinno et al. |
| 8,002,785 | B2 | 8/2011 | Weiss et al. |
| 8,002,795 | B2 | 8/2011 | Beetel |
| 8,006,365 | B2 | 8/2011 | Levin et al. |
| 8,006,885 | B2 | 8/2011 | Marczyk |
| 8,006,889 | B2 | 8/2011 | Adams et al. |
| 8,007,370 | B2 | 8/2011 | Hirsch et al. |
| 8,007,465 | B2 | 8/2011 | Birk et al. |
| 8,007,479 | B2 | 8/2011 | Birk et al. |
| 8,007,511 | B2 | 8/2011 | Brock et al. |
| 8,007,513 | B2 | 8/2011 | Nalagatla et al. |
| 8,008,598 | B2 | 8/2011 | Whitman et al. |

(56) References Cited

U.S. PATENT DOCUMENTS

| | | | |
|---|---|---|---|
| 8,010,180 | B2 | 8/2011 | Quaid et al. |
| 8,011,550 | B2 | 9/2011 | Aranyi et al. |
| 8,011,551 | B2 | 9/2011 | Marczyk et al. |
| 8,011,553 | B2 | 9/2011 | Mastri et al. |
| 8,011,555 | B2 | 9/2011 | Tarinelli et al. |
| 8,012,170 | B2 | 9/2011 | Whitman et al. |
| 8,016,176 | B2 | 9/2011 | Kasvikis et al. |
| 8,016,177 | B2 | 9/2011 | Bettuchi et al. |
| 8,016,178 | B2 | 9/2011 | Olson et al. |
| 8,016,849 | B2 | 9/2011 | Wenchell |
| 8,016,855 | B2 | 9/2011 | Whitman et al. |
| 8,016,858 | B2 | 9/2011 | Whitman |
| 8,016,881 | B2 | 9/2011 | Furst |
| 8,020,741 | B2 | 9/2011 | Cole et al. |
| 8,020,742 | B2 | 9/2011 | Marczyk |
| 8,020,743 | B2 | 9/2011 | Shelton, IV |
| 8,021,375 | B2 | 9/2011 | Aldrich et al. |
| 8,025,199 | B2 | 9/2011 | Whitman et al. |
| 8,025,896 | B2 | 9/2011 | Malaviya et al. |
| 8,028,835 | B2 | 10/2011 | Yasuda et al. |
| 8,028,882 | B2 | 10/2011 | Viola |
| 8,028,883 | B2 | 10/2011 | Stopek |
| 8,028,884 | B2 | 10/2011 | Sniffin et al. |
| 8,028,885 | B2 | 10/2011 | Smith et al. |
| 8,029,510 | B2 | 10/2011 | Hoegerle |
| 8,031,069 | B2 | 10/2011 | Cohn et al. |
| 8,033,438 | B2 | 10/2011 | Scirica |
| 8,033,439 | B2 | 10/2011 | Racenet et al. |
| 8,033,440 | B2 | 10/2011 | Wenchell et al. |
| 8,033,442 | B2 | 10/2011 | Racenet et al. |
| 8,034,077 | B2 | 10/2011 | Smith et al. |
| 8,034,337 | B2 | 10/2011 | Simard |
| 8,034,363 | B2 | 10/2011 | Li et al. |
| 8,035,487 | B2 | 10/2011 | Malackowski |
| 8,037,591 | B2 | 10/2011 | Spivey et al. |
| 8,038,044 | B2 | 10/2011 | Viola |
| 8,038,045 | B2 | 10/2011 | Bettuchi et al. |
| 8,038,046 | B2 | 10/2011 | Smith et al. |
| 8,038,686 | B2 | 10/2011 | Huitema et al. |
| 8,043,207 | B2 | 10/2011 | Adams |
| 8,043,328 | B2 | 10/2011 | Hahnen et al. |
| 8,044,536 | B2 | 10/2011 | Nguyen et al. |
| 8,044,604 | B2 | 10/2011 | Hagino et al. |
| 8,047,236 | B2 | 11/2011 | Perry |
| 8,048,503 | B2 | 11/2011 | Farnsworth et al. |
| 8,052,636 | B2 | 11/2011 | Moll et al. |
| 8,052,697 | B2 | 11/2011 | Phillips |
| 8,056,787 | B2 | 11/2011 | Boudreaux et al. |
| 8,056,788 | B2 | 11/2011 | Mastri et al. |
| 8,056,789 | B1 | 11/2011 | White et al. |
| 8,057,508 | B2 | 11/2011 | Shelton, IV |
| 8,058,771 | B2 | 11/2011 | Giordano et al. |
| 8,060,250 | B2 | 11/2011 | Reiland et al. |
| 8,061,014 | B2 | 11/2011 | Smith et al. |
| 8,061,576 | B2 | 11/2011 | Cappola |
| 8,062,236 | B2 | 11/2011 | Soltz |
| 8,062,306 | B2 | 11/2011 | Nobis et al. |
| 8,062,330 | B2 | 11/2011 | Prommersberger et al. |
| 8,063,619 | B2 | 11/2011 | Zhu et al. |
| 8,066,158 | B2 | 11/2011 | Vogel et al. |
| 8,066,166 | B2 | 11/2011 | Demmy et al. |
| 8,066,167 | B2 | 11/2011 | Measamer et al. |
| 8,066,168 | B2 | 11/2011 | Vidal et al. |
| 8,066,720 | B2 | 11/2011 | Knodel et al. |
| D650,074 | S | 12/2011 | Hunt et al. |
| D650,789 | S | 12/2011 | Arnold |
| 8,070,033 | B2 | 12/2011 | Milliman et al. |
| 8,070,034 | B1 | 12/2011 | Knodel |
| 8,070,035 | B2 | 12/2011 | Holsten et al. |
| 8,070,743 | B2 | 12/2011 | Kagan et al. |
| 8,074,858 | B2 | 12/2011 | Marczyk |
| 8,074,859 | B2 | 12/2011 | Kostrzewski |
| 8,074,861 | B2 | 12/2011 | Ehrenfels et al. |
| 8,075,476 | B2 | 12/2011 | Vargas |
| 8,075,571 | B2 | 12/2011 | Vitali et al. |
| 8,079,950 | B2 | 12/2011 | Stern et al. |
| 8,079,989 | B2 | 12/2011 | Birk et al. |
| 8,080,004 | B2 | 12/2011 | Downey et al. |
| 8,083,118 | B2 | 12/2011 | Milliman et al. |
| 8,083,119 | B2 | 12/2011 | Prommersberger |
| 8,083,120 | B2 | 12/2011 | Shelton, IV et al. |
| 8,084,001 | B2 | 12/2011 | Burns et al. |
| 8,084,969 | B2 | 12/2011 | David et al. |
| 8,085,013 | B2 | 12/2011 | Wei et al. |
| 8,087,562 | B1 | 1/2012 | Manoux et al. |
| 8,087,563 | B2 | 1/2012 | Milliman et al. |
| 8,089,509 | B2 | 1/2012 | Chatenever et al. |
| 8,091,753 | B2 | 1/2012 | Viola |
| 8,091,756 | B2 | 1/2012 | Viola |
| 8,092,443 | B2 | 1/2012 | Bischoff |
| 8,092,932 | B2 | 1/2012 | Phillips et al. |
| 8,093,572 | B2 | 1/2012 | Kuduvalli |
| 8,096,458 | B2 | 1/2012 | Hessler |
| 8,096,459 | B2 | 1/2012 | Ortiz et al. |
| 8,097,017 | B2 | 1/2012 | Viola |
| 8,100,310 | B2 | 1/2012 | Zemlok |
| 8,100,824 | B2 | 1/2012 | Hegeman et al. |
| 8,100,872 | B2 | 1/2012 | Patel |
| 8,102,138 | B2 | 1/2012 | Sekine et al. |
| 8,102,278 | B2 | 1/2012 | Deck et al. |
| 8,105,320 | B2 | 1/2012 | Manzo |
| 8,105,350 | B2 | 1/2012 | Lee et al. |
| 8,107,925 | B2 | 1/2012 | Natsuno et al. |
| 8,108,033 | B2 | 1/2012 | Drew et al. |
| 8,108,072 | B2 | 1/2012 | Zhao et al. |
| 8,109,426 | B2 | 2/2012 | Milliman et al. |
| 8,110,208 | B1 | 2/2012 | Hen |
| 8,113,405 | B2 | 2/2012 | Milliman |
| 8,113,407 | B2 | 2/2012 | Holsten et al. |
| 8,113,408 | B2 | 2/2012 | Wenchell et al. |
| 8,113,410 | B2 | 2/2012 | Hall et al. |
| 8,114,017 | B2 | 2/2012 | Bacher |
| 8,114,100 | B2 | 2/2012 | Smith et al. |
| 8,114,345 | B2 | 2/2012 | Dlugos, Jr. et al. |
| 8,118,206 | B2 | 2/2012 | Zand et al. |
| 8,118,207 | B2 | 2/2012 | Racenet et al. |
| 8,120,301 | B2 | 2/2012 | Goldberg et al. |
| 8,122,128 | B2 | 2/2012 | Burke, II et al. |
| 8,123,103 | B2 | 2/2012 | Milliman |
| 8,123,523 | B2 | 2/2012 | Carron et al. |
| 8,123,766 | B2 | 2/2012 | Bauman et al. |
| 8,123,767 | B2 | 2/2012 | Bauman et al. |
| 8,125,168 | B2 | 2/2012 | Johnson et al. |
| 8,127,975 | B2 | 3/2012 | Olson et al. |
| 8,127,976 | B2 | 3/2012 | Scirica et al. |
| 8,128,624 | B2 | 3/2012 | Couture et al. |
| 8,128,643 | B2 | 3/2012 | Aranyi et al. |
| 8,128,645 | B2 | 3/2012 | Sonnenschein et al. |
| 8,128,662 | B2 | 3/2012 | Altarac et al. |
| 8,132,703 | B2 | 3/2012 | Milliman et al. |
| 8,132,705 | B2 | 3/2012 | Viola et al. |
| 8,132,706 | B2 | 3/2012 | Marczyk et al. |
| 8,133,500 | B2 | 3/2012 | Ringeisen et al. |
| 8,134,306 | B2 | 3/2012 | Drader et al. |
| 8,136,711 | B2 | 3/2012 | Beardsley et al. |
| 8,136,712 | B2 | 3/2012 | Zingman |
| 8,136,713 | B2 | 3/2012 | Hathaway et al. |
| 8,137,339 | B2 | 3/2012 | Jinno et al. |
| 8,140,417 | B2 | 3/2012 | Shibata |
| 8,141,762 | B2 | 3/2012 | Bedi et al. |
| 8,141,763 | B2 | 3/2012 | Milliman |
| 8,142,200 | B2 | 3/2012 | Crunkilton et al. |
| 8,142,425 | B2 | 3/2012 | Eggers |
| 8,142,461 | B2 | 3/2012 | Houser et al. |
| 8,142,515 | B2 | 3/2012 | Therin et al. |
| 8,143,520 | B2 | 3/2012 | Cutler |
| 8,146,790 | B2 | 4/2012 | Milliman |
| 8,147,421 | B2 | 4/2012 | Farquhar et al. |
| 8,147,456 | B2 | 4/2012 | Fisher et al. |
| 8,147,485 | B2 | 4/2012 | Wham et al. |
| 8,152,041 | B2 | 4/2012 | Kostrzewski |
| 8,152,756 | B2 | 4/2012 | Webster et al. |
| 8,154,239 | B2 | 4/2012 | Katsuki et al. |
| 8,157,145 | B2 | 4/2012 | Shelton, IV et al. |

(56) References Cited

U.S. PATENT DOCUMENTS 8,157,148 B2 4/2012 Scirica
8,157,151 B2 4/2012 Ingmanson et al.
8,157,152 B2 4/2012 Holsten et al.
8,157,153 B2 4/2012 Shelton, IV et al.
8,157,793 B2 4/2012 Omori et al.
8,157,834 B2 4/2012 Conlon
8,161,977 B2 4/2012 Shelton, IV et al.
8,162,138 B2 4/2012 Bettenhausen et al.
8,162,197 B2 4/2012 Mastri et al.
8,162,668 B2 4/2012 Toly
8,162,933 B2 4/2012 Francischelli et al.
8,162,965 B2 4/2012 Reschke et al.
8,167,185 B2 5/2012 Shelton, IV et al.
8,167,622 B2 5/2012 Zhou
8,167,895 B2 5/2012 D'Agostino et al.
8,167,898 B1 5/2012 Schaller et al.
8,170,241 B2 5/2012 Roe et al.
8,172,004 B2 5/2012 Ho
8,172,120 B2 5/2012 Boyden et al.
8,172,122 B2 5/2012 Kasvikis et al.
8,172,124 B2 5/2012 Shelton, IV et al.
8,177,776 B2 5/2012 Humayun et al.
8,177,797 B2 5/2012 Shimoji et al.
8,179,705 B2 5/2012 Chapuis
8,180,458 B2 5/2012 Kane et al.
8,181,839 B2 5/2012 Beetel
8,181,840 B2 5/2012 Milliman
8,182,422 B2 5/2012 Bayer et al.
8,182,444 B2 5/2012 Uber, III et al.
8,183,807 B2 5/2012 Tsai et al.
8,186,555 B2 5/2012 Shelton, IV et al.
8,186,556 B2 5/2012 Viola
8,186,558 B2 5/2012 Sapienza
8,186,560 B2 5/2012 Hess et al.
8,190,238 B2 5/2012 Moll et al.
8,191,752 B2 6/2012 Scirica
8,192,350 B2 6/2012 Ortiz et al.
8,192,460 B2 6/2012 Orban, III et al.
8,192,651 B2 6/2012 Young et al.
8,193,129 B2 6/2012 Tagawa et al.
8,196,795 B2 6/2012 Moore et al.
8,196,796 B2 6/2012 Shelton, IV et al.
8,197,501 B2 6/2012 Shadeck et al.
8,197,502 B2 6/2012 Smith et al.
8,197,837 B2 6/2012 Jamiolkowski et al.
8,201,720 B2 6/2012 Hessler
8,201,721 B2 6/2012 Zemlok et al.
8,202,549 B2 6/2012 Stucky et al.
8,205,779 B2 6/2012 Ma et al.
8,205,780 B2 6/2012 Sorrentino et al.
8,205,781 B2 6/2012 Baxter, III et al.
8,207,863 B2 6/2012 Neubauer et al.
8,210,411 B2 7/2012 Yates et al.
8,210,414 B2 7/2012 Bettuchi et al.
8,210,415 B2 7/2012 Ward
8,210,416 B2 7/2012 Milliman et al.
8,210,721 B2 7/2012 Chen et al.
8,211,125 B2 7/2012 Spivey
8,214,019 B2 7/2012 Govari et al.
8,215,531 B2 7/2012 Shelton, IV et al.
8,215,532 B2 7/2012 Marczyk
8,215,533 B2 7/2012 Viola et al.
8,220,468 B2 7/2012 Cooper et al.
8,220,688 B2 7/2012 Laurent et al.
8,220,690 B2 7/2012 Hess et al.
8,221,402 B2 7/2012 Francischelli et al.
8,221,424 B2 7/2012 Cha
8,221,433 B2 7/2012 Lozier et al.
8,225,799 B2 7/2012 Bettuchi
8,225,979 B2 7/2012 Farascioni et al.
8,226,553 B2 7/2012 Shelton, IV et al.
8,226,635 B2 7/2012 Petrie et al.
8,226,675 B2 7/2012 Houser et al.
8,226,715 B2 7/2012 Hwang et al.
8,227,946 B2 7/2012 Kim
8,228,020 B2 7/2012 Shin et al.
8,228,048 B2 7/2012 Spencer
8,229,549 B2 7/2012 Whitman et al.
8,230,235 B2 7/2012 Goodman et al.
8,231,040 B2 7/2012 Zemlok et al.
8,231,042 B2 7/2012 Hessler et al.
8,231,043 B2 7/2012 Tarinelli et al.
8,235,272 B2 8/2012 Nicholas et al.
8,235,274 B2 8/2012 Cappola
8,236,010 B2 8/2012 Ortiz et al.
8,236,011 B2 8/2012 Harris et al.
8,236,020 B2 8/2012 Smith et al.
8,237,388 B2 8/2012 Jinno et al.
8,240,537 B2 8/2012 Marczyk
8,241,271 B2 8/2012 Millman et al.
8,241,284 B2 8/2012 Dycus et al.
8,241,308 B2 8/2012 Kortenbach et al.
8,241,322 B2 8/2012 Whitman et al.
8,245,594 B2 8/2012 Rogers et al.
8,245,898 B2 8/2012 Smith et al.
8,245,899 B2 8/2012 Swensgard et al.
8,245,900 B2 8/2012 Scirica
8,245,901 B2 8/2012 Stopek
8,246,608 B2 8/2012 Omori et al.
8,246,637 B2 8/2012 Viola et al.
8,252,009 B2 8/2012 Weller et al.
8,256,654 B2 9/2012 Bettuchi et al.
8,256,655 B2 9/2012 Sniffin et al.
8,256,656 B2 9/2012 Milliman et al.
8,257,251 B2 9/2012 Shelton, IV et al.
8,257,356 B2 9/2012 Bleich et al.
8,257,386 B2 9/2012 Lee et al.
8,257,391 B2 9/2012 Orban, III et al.
8,257,634 B2 9/2012 Scirica
8,258,745 B2 9/2012 Smith et al.
8,261,958 B1 9/2012 Knodel
8,262,560 B2 9/2012 Whitman
8,262,655 B2 9/2012 Ghabrial et al.
8,266,232 B2 9/2012 Piper et al.
8,267,300 B2 9/2012 Boudreaux
8,267,849 B2 9/2012 Wazer et al.
8,267,924 B2 9/2012 Zemlok et al.
8,267,946 B2 9/2012 Whitfield et al.
8,267,951 B2 9/2012 Whayne et al.
8,268,344 B2 9/2012 Ma et al.
8,269,121 B2 9/2012 Smith
8,272,553 B2 9/2012 Mastri et al.
8,272,554 B2 9/2012 Whitman et al.
8,272,918 B2 9/2012 Lam
8,273,404 B2 9/2012 Dave et al.
8,276,594 B2 10/2012 Shah
8,276,801 B2 10/2012 Zemlok et al.
8,276,802 B2 10/2012 Kostrzewski
8,277,473 B2 10/2012 Sunaoshi et al.
8,281,446 B2 10/2012 Moskovich
8,281,973 B2 10/2012 Wenchell et al.
8,281,974 B2 10/2012 Hessler et al.
8,282,654 B2 10/2012 Ferrari et al.
8,285,367 B2 10/2012 Hyde et al.
8,286,723 B2 10/2012 Puzio et al.
8,286,845 B2 10/2012 Perry et al.
8,286,846 B2 10/2012 Smith et al.
8,286,847 B2 10/2012 Taylor
8,287,487 B2 10/2012 Estes
8,287,522 B2 10/2012 Moses et al.
8,287,561 B2 10/2012 Nunez et al.
8,288,984 B2 10/2012 Yang
8,289,403 B2 10/2012 Dobashi et al.
8,290,883 B2 10/2012 Takeuchi et al.
8,292,147 B2 10/2012 Viola
8,292,148 B2 10/2012 Viola
8,292,150 B2 10/2012 Bryant
8,292,151 B2 10/2012 Viola
8,292,152 B2 10/2012 Milliman et al.
8,292,155 B2 10/2012 Shelton, IV et al.
8,292,157 B2 10/2012 Smith et al.
8,292,158 B2 10/2012 Sapienza
8,292,801 B2 10/2012 Dejima et al.
8,292,888 B2 10/2012 Whitman

(56) References Cited

U.S. PATENT DOCUMENTS 8,292,906 B2 10/2012 Taylor et al.
8,294,399 B2 10/2012 Suzuki et al.
8,298,161 B2 10/2012 Vargas
8,298,189 B2 10/2012 Fisher et al.
8,298,233 B2 10/2012 Mueller
8,298,677 B2 10/2012 Wiesner et al.
8,302,323 B2 11/2012 Fortier et al.
8,303,621 B2 11/2012 Miyamoto et al.
8,308,040 B2 11/2012 Huang et al.
8,308,041 B2 11/2012 Kostrzewski
8,308,042 B2 11/2012 Aranyi
8,308,043 B2 11/2012 Bindra et al.
8,308,046 B2 11/2012 Prommersberger
8,308,659 B2 11/2012 Scheibe et al.
8,308,725 B2 11/2012 Bell et al.
8,310,188 B2 11/2012 Nakai
8,313,496 B2 11/2012 Sauer et al.
8,313,499 B2 11/2012 Magnusson et al.
8,313,509 B2 11/2012 Kostrzewski
8,317,070 B2 11/2012 Hueil et al.
8,317,071 B1 11/2012 Knodel
8,317,074 B2 11/2012 Ortiz et al.
8,317,437 B2 11/2012 Merkley et al.
8,317,744 B2 11/2012 Kirschenman
8,317,790 B2 11/2012 Bell et al.
8,319,002 B2 11/2012 Daniels et al.
D672,784 S 12/2012 Clanton et al.
8,322,455 B2 12/2012 Shelton, IV et al.
8,322,589 B2 12/2012 Boudreaux
8,322,590 B2 12/2012 Patel et al.
8,322,901 B2 12/2012 Michelotti
8,323,271 B2 12/2012 Humayun et al.
8,323,789 B2 12/2012 Rozhin et al.
8,324,585 B2 12/2012 McBroom et al.
8,327,514 B2 12/2012 Kim
8,328,061 B2 12/2012 Kasvikis
8,328,062 B2 12/2012 Viola
8,328,063 B2 12/2012 Milliman et al.
8,328,064 B2 12/2012 Racenet et al.
8,328,065 B2 12/2012 Shah
8,328,802 B2 12/2012 Deville et al.
8,328,823 B2 12/2012 Aranyi et al.
8,333,313 B2 12/2012 Boudreaux et al.
8,333,691 B2 12/2012 Schaaf
8,333,764 B2 12/2012 Francischelli et al.
8,333,779 B2 12/2012 Smith et al.
8,334,468 B2 12/2012 Palmer et al.
8,336,753 B2 12/2012 Olson et al.
8,336,754 B2 12/2012 Cappola et al.
8,342,377 B2 1/2013 Milliman et al.
8,342,378 B2 1/2013 Marczyk et al.
8,342,379 B2 1/2013 Whitman et al.
8,342,380 B2 1/2013 Viola
8,343,150 B2 1/2013 Artale
8,347,978 B2 1/2013 Forster et al.
8,348,118 B2 1/2013 Segura
8,348,123 B2 1/2013 Scirica et al.
8,348,124 B2 1/2013 Scirica
8,348,125 B2 1/2013 Viola et al.
8,348,126 B2 1/2013 Olson et al.
8,348,127 B2 1/2013 Marczyk
8,348,129 B2 1/2013 Bedi et al.
8,348,130 B2 1/2013 Shah et al.
8,348,131 B2 1/2013 Omaits et al.
8,348,837 B2 1/2013 Wenchell
8,348,948 B2 1/2013 Bahney
8,348,959 B2 1/2013 Wolford et al.
8,348,972 B2 1/2013 Soltz et al.
8,349,987 B2 1/2013 Kapiamba et al.
8,352,004 B2 1/2013 Mannheimer et al.
8,353,437 B2 1/2013 Boudreaux
8,353,438 B2 1/2013 Baxter, III et al.
8,353,439 B2 1/2013 Baxter, III et al.
8,356,740 B1 1/2013 Knodel
8,357,144 B2 1/2013 Whitman et al.
8,357,158 B2 1/2013 McKenna et al.
8,357,161 B2 1/2013 Mueller
8,359,174 B2 1/2013 Nakashima et al.
8,360,296 B2 1/2013 Zingman
8,360,297 B2 1/2013 Shelton, IV et al.
8,360,298 B2 1/2013 Farascioni et al.
8,360,299 B2 1/2013 Zemlok et al.
8,361,501 B2 1/2013 DiTizio et al.
D676,866 S 2/2013 Chaudhri
8,365,972 B2 2/2013 Aranyi et al.
8,365,973 B1 2/2013 White et al.
8,365,975 B1 2/2013 Manoux et al.
8,365,976 B2 2/2013 Hess et al.
8,366,559 B2 2/2013 Papenfuss et al.
8,366,719 B2 2/2013 Markey et al.
8,366,787 B2 2/2013 Brown et al.
8,368,327 B2 2/2013 Benning et al.
8,369,056 B2 2/2013 Senriuchi et al.
8,371,393 B2 2/2013 Higuchi et al.
8,371,491 B2 2/2013 Huitema et al.
8,371,492 B2 2/2013 Aranyi et al.
8,371,493 B2 2/2013 Aranyi et al.
8,371,494 B2 2/2013 Racenet et al.
8,372,094 B2 2/2013 Bettuchi et al.
8,374,723 B2 2/2013 Zhao et al.
8,376,865 B2 2/2013 Forster et al.
8,377,029 B2 2/2013 Nagao et al.
8,377,044 B2 2/2013 Coe et al.
8,377,059 B2 2/2013 Deville et al.
8,381,828 B2 2/2013 Whitman et al.
8,381,834 B2 2/2013 Barhitte et al.
8,382,773 B2 2/2013 Whitfield et al.
8,382,790 B2 2/2013 Uenohara et al.
D677,273 S 3/2013 Randall et al.
8,387,848 B2 3/2013 Johnson et al.
8,388,633 B2 3/2013 Rousseau et al.
8,389,588 B2 3/2013 Ringeisen et al.
8,393,513 B2 3/2013 Jankowski
8,393,514 B2 3/2013 Shelton, IV et al.
8,393,516 B2 3/2013 Kostrzewski
8,397,832 B2 3/2013 Blickle et al.
8,397,971 B2 3/2013 Yates et al.
8,397,972 B2 3/2013 Kostrzewski
8,397,973 B1 3/2013 Hausen
8,398,633 B2 3/2013 Mueller
8,398,669 B2 3/2013 Kim
8,398,673 B2 3/2013 Hinchliffe et al.
8,398,674 B2 3/2013 Prestel
8,400,108 B2 3/2013 Powell et al.
8,400,851 B2 3/2013 Byun
8,403,138 B2 3/2013 Weisshaupt et al.
8,403,195 B2 3/2013 Beardsley et al.
8,403,196 B2 3/2013 Beardsley et al.
8,403,198 B2 3/2013 Sorrentino et al.
8,403,832 B2 3/2013 Cunningham et al.
8,403,926 B2 3/2013 Nobis et al.
8,403,945 B2 3/2013 Whitfield et al.
8,403,946 B2 3/2013 Whitfield et al.
8,403,950 B2 3/2013 Palmer et al.
D680,646 S 4/2013 Hunt et al.
8,408,439 B2 4/2013 Huang et al.
8,408,442 B2 4/2013 Racenet et al.
8,409,079 B2 4/2013 Okamoto et al.
8,409,174 B2 4/2013 Omori
8,409,175 B2 4/2013 Lee et al.
8,409,211 B2 4/2013 Baroud
8,409,222 B2 4/2013 Whitfield et al.
8,409,223 B2 4/2013 Sorrentino et al.
8,409,234 B2 4/2013 Stahler et al.
8,411,500 B2 4/2013 Gapihan et al.
8,413,661 B2 4/2013 Rousseau et al.
8,413,870 B2 4/2013 Pastorelli et al.
8,413,871 B2 4/2013 Racenet et al.
8,413,872 B2 4/2013 Patel
8,414,469 B2 4/2013 Diolaiti
8,414,577 B2 4/2013 Boudreaux et al.
8,414,598 B2 4/2013 Brock et al.
8,418,073 B2 4/2013 Mohr et al.
8,418,906 B2 4/2013 Farascioni et al.

(56) References Cited

U.S. PATENT DOCUMENTS 8,418,907 B2 4/2013 Johnson et al.
8,418,908 B1 4/2013 Beardsley
8,418,909 B2 4/2013 Kostrzewski
8,419,635 B2 4/2013 Shelton, IV et al.
8,419,717 B2 4/2013 Diolaiti et al.
8,419,747 B2 4/2013 Hinman et al.
8,419,754 B2 4/2013 Laby et al.
8,419,755 B2 4/2013 Deem et al.
8,423,182 B2 4/2013 Robinson et al.
8,424,737 B2 4/2013 Scirica
8,424,739 B2 4/2013 Racenet et al.
8,424,740 B2 4/2013 Shelton, IV et al.
8,424,741 B2 4/2013 McGuckin, Jr. et al.
8,425,600 B2 4/2013 Maxwell
8,427,430 B2 4/2013 Lee et al.
8,430,292 B2 4/2013 Patel et al.
8,430,892 B2 4/2013 Bindra et al.
8,430,898 B2 4/2013 Wiener et al.
8,435,257 B2 5/2013 Smith et al.
8,439,246 B1 5/2013 Knodel
8,439,830 B2 5/2013 Mckinley et al.
8,444,036 B2 5/2013 Shelton, IV
8,444,037 B2 5/2013 Nicholas et al.
8,444,549 B2 5/2013 Viola et al.
8,449,536 B2 5/2013 Selig
8,449,560 B2 5/2013 Roth et al.
8,453,904 B2 6/2013 Eskaros et al.
8,453,906 B2 6/2013 Huang et al.
8,453,907 B2 6/2013 Laurent et al.
8,453,908 B2 6/2013 Bedi et al.
8,453,912 B2 6/2013 Mastri et al.
8,453,914 B2 6/2013 Laurent et al.
8,454,495 B2 6/2013 Kawano et al.
8,454,551 B2 6/2013 Allen et al.
8,454,628 B2 6/2013 Smith et al.
8,454,640 B2 6/2013 Johnston et al.
8,457,757 B2 6/2013 Cauller et al.
8,459,520 B2 6/2013 Giordano et al.
8,459,521 B2 6/2013 Zemlok et al.
8,459,524 B2 6/2013 Pribanic et al.
8,459,525 B2 6/2013 Yates et al.
8,464,922 B2 6/2013 Marczyk
8,464,923 B2 6/2013 Shelton, IV
8,464,924 B2 6/2013 Gresham et al.
8,464,925 B2 6/2013 Hull et al.
8,465,475 B2 6/2013 Isbell, Jr.
8,465,502 B2 6/2013 Zergiebel
8,465,515 B2 6/2013 Drew et al.
8,469,254 B2 6/2013 Czernik et al.
8,469,946 B2 6/2013 Sugita
8,469,973 B2 6/2013 Meade et al.
8,470,355 B2 6/2013 Skalla et al.
D686,240 S 7/2013 Lin
D686,244 S 7/2013 Moriya et al.
8,474,677 B2 7/2013 Woodard, Jr. et al.
8,475,453 B2 7/2013 Marczyk et al.
8,475,454 B1 7/2013 Alshemari
8,475,474 B2 7/2013 Bombard et al.
8,479,968 B2 7/2013 Hodgkinson et al.
8,479,969 B2 7/2013 Shelton, IV
8,480,703 B2 7/2013 Nicholas et al.
8,483,509 B2 7/2013 Matsuzaka
8,485,412 B2 7/2013 Shelton, IV et al.
8,485,413 B2 7/2013 Scheib et al.
8,485,970 B2 7/2013 Widenhouse et al.
8,486,047 B2 7/2013 Stopek
8,487,199 B2 7/2013 Palmer et al.
8,487,487 B2 7/2013 Dietz et al.
8,490,851 B2 7/2013 Blier et al.
8,490,852 B2 7/2013 Viola
8,490,853 B2 7/2013 Criscuolo et al.
8,491,581 B2 7/2013 Deville et al.
8,491,603 B2 7/2013 Yeung et al.
8,496,153 B2 7/2013 Demmy et al.
8,496,154 B2 7/2013 Marczyk et al.
8,496,156 B2 7/2013 Sniffin et al.
8,496,683 B2 7/2013 Prommersberger et al.
8,498,691 B2 7/2013 Moll et al.
8,499,673 B2 8/2013 Keller
8,499,966 B2 8/2013 Palmer et al.
8,499,992 B2 8/2013 Whitman et al.
8,499,993 B2 8/2013 Shelton, IV et al.
8,499,994 B2 8/2013 D'Arcangelo
8,500,721 B2 8/2013 Jinno
8,500,762 B2 8/2013 Sholev et al.
8,502,091 B2 8/2013 Palmer et al.
8,505,799 B2 8/2013 Viola et al.
8,505,801 B2 8/2013 Ehrenfels et al.
8,506,555 B2 8/2013 Ruiz Morales
8,506,557 B2 8/2013 Zemlok et al.
8,506,580 B2 8/2013 Zergiebel et al.
8,506,581 B2 8/2013 Wingardner, III et al.
8,511,308 B2 8/2013 Hecox et al.
8,512,359 B2 8/2013 Whitman et al.
8,512,402 B2 8/2013 Marczyk et al.
8,517,239 B2 8/2013 Scheib et al.
8,517,241 B2 8/2013 Nicholas et al.
8,517,243 B2 8/2013 Giordano et al.
8,517,244 B2 8/2013 Shelton, IV et al.
8,517,938 B2 8/2013 Eisenhardt et al.
8,518,024 B2 8/2013 Williams et al.
8,521,273 B2 8/2013 Kliman
8,523,042 B2 9/2013 Masiakos et al.
8,523,043 B2 9/2013 Ullrich et al.
8,523,787 B2 9/2013 Ludwin et al.
8,523,881 B2 9/2013 Cabiri et al.
8,523,882 B2 9/2013 Huitema et al.
8,523,900 B2 9/2013 Jinno et al.
8,529,588 B2 9/2013 Ahlberg et al.
8,529,599 B2 9/2013 Holsten
8,529,600 B2 9/2013 Woodard, Jr. et al.
8,529,819 B2 9/2013 Ostapoff et al.
8,531,153 B2 9/2013 Baarman et al.
8,532,747 B2 9/2013 Nock et al.
8,534,527 B2 9/2013 Brendel et al.
8,534,528 B2 9/2013 Shelton, IV
8,535,304 B2 9/2013 Sklar et al.
8,535,340 B2 9/2013 Allen
8,539,866 B2 9/2013 Nayak et al.
8,540,128 B2 9/2013 Shelton, IV et al.
8,540,129 B2 9/2013 Baxter, III et al.
8,540,130 B2 9/2013 Moore et al.
8,540,131 B2 9/2013 Swayze
8,540,133 B2 9/2013 Bedi et al.
8,540,646 B2 9/2013 Mendez-Coll
8,540,733 B2 9/2013 Whitman et al.
8,540,735 B2 9/2013 Mitelberg et al.
8,550,984 B2 10/2013 Takemoto
8,551,076 B2 10/2013 Duval et al.
8,555,660 B2 10/2013 Takenaka et al.
8,556,151 B2 10/2013 Viola
8,556,918 B2 10/2013 Bauman et al.
8,556,935 B1 10/2013 Knodel et al.
8,560,147 B2 10/2013 Taylor et al.
8,561,617 B2 10/2013 Lindh et al.
8,561,870 B2 10/2013 Baxter, III et al.
8,561,871 B2 10/2013 Rajappa et al.
8,561,873 B2 10/2013 Ingmanson et al.
8,562,592 B2 10/2013 Conlon et al.
8,562,598 B2 10/2013 Falkenstein et al.
8,567,656 B2 10/2013 Shelton, IV et al.
8,568,416 B2 10/2013 Schmitz et al.
8,568,425 B2 10/2013 Ross et al.
D692,916 S 11/2013 Granchi et al.
8,573,459 B2 11/2013 Smith et al.
8,573,461 B2 11/2013 Shelton, IV et al.
8,573,462 B2 11/2013 Smith et al.
8,573,465 B2 11/2013 Shelton, IV
8,574,199 B2 11/2013 von Bulow et al.
8,574,263 B2 11/2013 Mueller
8,575,880 B2 11/2013 Grantz
8,575,895 B2 11/2013 Garrastacho et al.
8,579,176 B2 11/2013 Smith et al.
8,579,178 B2 11/2013 Holsten et al.

(56) References Cited

U.S. PATENT DOCUMENTS 8,579,897 B2 11/2013 Vakharia et al.
8,579,937 B2 11/2013 Gresham
8,584,919 B2 11/2013 Hueil et al.
8,584,920 B2 11/2013 Hodgkinson
8,584,921 B2 11/2013 Scirica
8,585,583 B2 11/2013 Sakaguchi et al.
8,585,598 B2 11/2013 Razzaque et al.
8,585,721 B2 11/2013 Kirsch
8,590,760 B2 11/2013 Cummins et al.
8,590,762 B2 11/2013 Hess et al.
8,590,764 B2 11/2013 Hartwick et al.
8,591,400 B2 11/2013 Sugiyama
8,596,515 B2 12/2013 Okoniewski
8,597,745 B2 12/2013 Farnsworth et al.
8,599,450 B2 12/2013 Kubo et al.
8,602,125 B2 12/2013 King
8,602,287 B2 12/2013 Yates et al.
8,602,288 B2 12/2013 Shelton, IV et al.
8,603,077 B2 12/2013 Cooper et al.
8,603,089 B2 12/2013 Viola
8,603,110 B2 12/2013 Maruyama et al.
8,603,135 B2 12/2013 Mueller
8,608,043 B2 12/2013 Scirica
8,608,044 B2 12/2013 Hueil et al.
8,608,045 B2 12/2013 Smith et al.
8,608,046 B2 12/2013 Laurent et al.
8,608,745 B2 12/2013 Guzman et al.
8,613,383 B2 12/2013 Beckman et al.
8,613,384 B2 12/2013 Pastorelli et al.
8,616,427 B2 12/2013 Viola
8,616,431 B2 12/2013 Timm et al.
8,617,155 B2 12/2013 Johnson et al.
8,620,473 B2 12/2013 Diolaiti et al.
8,622,274 B2 1/2014 Yates et al.
8,622,275 B2 1/2014 Baxter, III et al.
8,627,993 B2 1/2014 Smith et al.
8,627,994 B2 1/2014 Zemlok et al.
8,627,995 B2 1/2014 Smith et al.
8,628,467 B2 1/2014 Whitman et al.
8,628,518 B2 1/2014 Blumenkranz et al.
8,628,544 B2 1/2014 Farascioni
8,628,545 B2 1/2014 Cabrera et al.
8,631,987 B2 1/2014 Shelton, IV et al.
8,631,992 B1 1/2014 Hausen et al.
8,631,993 B2 1/2014 Kostrzewski
8,632,462 B2 1/2014 Yoo et al.
8,632,525 B2 1/2014 Kerr et al.
8,632,535 B2 1/2014 Shelton, IV et al.
8,632,539 B2 1/2014 Twomey et al.
8,632,563 B2 1/2014 Nagase et al.
8,636,187 B2 1/2014 Hueil et al.
8,636,190 B2 1/2014 Zemlok et al.
8,636,191 B2 1/2014 Meagher
8,636,193 B2 1/2014 Whitman et al.
8,636,736 B2 1/2014 Yates et al.
8,636,766 B2 1/2014 Milliman et al.
8,639,936 B2 1/2014 Hu et al.
8,640,788 B2 2/2014 Dachs, II et al.
8,646,674 B2 2/2014 Schulte et al.
8,647,258 B2 2/2014 Aranyi et al.
8,652,120 B2 2/2014 Giordano et al.
8,652,151 B2 2/2014 Lehman et al.
8,652,155 B2 2/2014 Houser et al.
8,656,929 B2 2/2014 Miller et al.
8,657,174 B2 2/2014 Yates et al.
8,657,175 B2 2/2014 Sonnenschein et al.
8,657,176 B2 2/2014 Shelton, IV et al.
8,657,177 B2 2/2014 Scirica et al.
8,657,178 B2 2/2014 Hueil et al.
8,657,482 B2 2/2014 Malackowski et al.
8,657,808 B2 2/2014 McPherson et al.
8,657,814 B2 2/2014 Werneth et al.
8,657,821 B2 2/2014 Palermo
D701,238 S 3/2014 Lai et al.
8,662,370 B2 3/2014 Takei
8,663,106 B2 3/2014 Stivoric et al.
8,663,192 B2 3/2014 Hester et al.
8,663,245 B2 3/2014 Francischelli et al.
8,663,262 B2 3/2014 Smith et al.
8,663,270 B2 3/2014 Donnigan et al.
8,664,792 B2 3/2014 Rebsdorf
8,668,129 B2 3/2014 Olson
8,668,130 B2 3/2014 Hess et al.
8,672,206 B2 3/2014 Aranyi et al.
8,672,207 B2 3/2014 Shelton, IV et al.
8,672,208 B2 3/2014 Hess et al.
8,672,209 B2 3/2014 Crainich
8,672,922 B2 3/2014 Loh et al.
8,672,935 B2 3/2014 Okada et al.
8,672,951 B2 3/2014 Smith et al.
8,673,210 B2 3/2014 Deshays
8,675,820 B2 3/2014 Baic et al.
8,678,263 B2 3/2014 Viola
8,678,994 B2 3/2014 Sonnenschein et al.
8,679,093 B2 3/2014 Farra
8,679,098 B2 3/2014 Hart
8,679,137 B2 3/2014 Bauman et al.
8,679,154 B2 3/2014 Smith et al.
8,679,156 B2 3/2014 Smith et al.
8,679,454 B2 3/2014 Guire et al.
8,684,248 B2 4/2014 Milliman
8,684,249 B2 4/2014 Racenet et al.
8,684,250 B2 4/2014 Bettuchi et al.
8,684,253 B2 4/2014 Giordano et al.
8,684,962 B2 4/2014 Kirschenman et al.
8,685,004 B2 4/2014 Zemlock et al.
8,685,020 B2 4/2014 Weizman et al.
8,690,893 B2 4/2014 Deitch et al.
8,695,866 B2 4/2014 Leimbach et al.
8,696,665 B2 4/2014 Hunt et al.
8,701,958 B2 4/2014 Shelton, IV et al.
8,701,959 B2 4/2014 Shah
8,706,316 B1 4/2014 Hoevenaar
8,708,210 B2 4/2014 Zemlok et al.
8,708,211 B2 4/2014 Zemlok et al.
8,708,212 B2 4/2014 Williams
8,708,213 B2 4/2014 Shelton, IV et al.
8,709,012 B2 4/2014 Muller
8,714,352 B2 5/2014 Farascioni et al.
8,714,429 B2 5/2014 Demmy
8,714,430 B2 5/2014 Natarajan et al.
8,715,256 B2 5/2014 Greener
8,715,302 B2 5/2014 Ibrahim et al.
8,720,766 B2 5/2014 Hess et al.
8,721,630 B2 5/2014 Ortiz et al.
8,721,666 B2 5/2014 Schroeder et al.
8,727,197 B2 5/2014 Hess et al.
8,727,199 B2 5/2014 Wenchell
8,727,200 B2 5/2014 Roy
8,727,961 B2 5/2014 Ziv
8,728,099 B2 5/2014 Cohn et al.
8,728,119 B2 5/2014 Cummins
8,733,470 B2 5/2014 Matthias et al.
8,733,611 B2 5/2014 Milliman
8,733,612 B2 5/2014 Ma
8,733,613 B2 5/2014 Huitema et al.
8,733,614 B2 5/2014 Ross et al.
8,734,336 B2 5/2014 Bonadio et al.
8,734,359 B2 5/2014 Ibanez et al.
8,734,478 B2 5/2014 Widenhouse et al.
8,734,831 B2 5/2014 Kim et al.
8,739,033 B2 5/2014 Rosenberg
8,739,417 B2 6/2014 Tokunaga et al.
8,740,034 B2 6/2014 Morgan et al.
8,740,037 B2 6/2014 Shelton, IV et al.
8,740,038 B2 6/2014 Shelton, IV et al.
8,740,987 B2 6/2014 Geremakis et al.
8,746,529 B2 6/2014 Shelton, IV et al.
8,746,530 B2 6/2014 Giordano et al.
8,746,533 B2 6/2014 Whitman et al.
8,746,535 B2 6/2014 Shelton, IV et al.
8,747,238 B2 6/2014 Shelton, IV et al.
8,747,441 B2 6/2014 Konieczynski et al.
8,752,264 B2 6/2014 Ackley et al.

(56) References Cited

U.S. PATENT DOCUMENTS 8,752,699 B2 6/2014 Morgan et al.
8,752,747 B2 6/2014 Shelton, IV et al.
8,752,748 B2 6/2014 Whitman et al.
8,752,749 B2 6/2014 Moore et al.
8,753,664 B2 6/2014 Dao et al.
8,757,287 B2 6/2014 Mak et al.
8,757,465 B2 6/2014 Woodard, Jr. et al.
8,758,235 B2 6/2014 Jaworek
8,758,366 B2 6/2014 McLean et al.
8,758,391 B2 6/2014 Swayze et al.
8,758,438 B2 6/2014 Boyce et al.
8,763,875 B2 7/2014 Morgan et al.
8,763,876 B2 7/2014 Kostrzewski
8,763,877 B2 7/2014 Schall et al.
8,763,879 B2 7/2014 Shelton, IV et al.
8,764,732 B2 7/2014 Hartwell
8,765,942 B2 7/2014 Feraud et al.
8,770,458 B2 7/2014 Scirica
8,770,459 B2 7/2014 Racenet et al.
8,770,460 B2 7/2014 Belzer
8,771,169 B2 7/2014 Whitman et al.
8,771,260 B2 7/2014 Conlon et al.
8,777,004 B2 7/2014 Shelton, IV et al.
8,777,082 B2 7/2014 Scirica
8,777,083 B2 7/2014 Racenet et al.
8,777,898 B2 7/2014 Suon et al.
8,783,541 B2 7/2014 Shelton, IV et al.
8,783,542 B2 7/2014 Riestenberg et al.
8,783,543 B2 7/2014 Shelton, IV et al.
8,784,304 B2 7/2014 Mikkaichi et al.
8,784,404 B2 7/2014 Doyle et al.
8,784,415 B2 7/2014 Malackowski et al.
8,789,737 B2 7/2014 Hodgkinson et al.
8,789,739 B2 7/2014 Swensgard
8,789,740 B2 7/2014 Baxter, III et al.
8,789,741 B2 7/2014 Baxter, III et al.
8,790,658 B2 7/2014 Cigarini et al.
8,790,684 B2 7/2014 Dave et al.
D711,905 S 8/2014 Morrison et al.
8,794,496 B2 8/2014 Scirica
8,794,497 B2 8/2014 Zingman
8,795,159 B2 8/2014 Moriyama
8,795,276 B2 8/2014 Dietz et al.
8,795,308 B2 8/2014 Valin
8,795,324 B2 8/2014 Kawai et al.
8,796,995 B2 8/2014 Cunanan et al.
8,800,681 B2 8/2014 Rousson et al.
8,800,837 B2 8/2014 Zemlok
8,800,838 B2 8/2014 Shelton, IV
8,800,839 B2 8/2014 Beetel
8,800,840 B2 8/2014 Jankowski
8,800,841 B2 8/2014 Ellerhorst et al.
8,801,710 B2 8/2014 Ullrich et al.
8,801,734 B2 8/2014 Shelton, IV et al.
8,801,735 B2 8/2014 Shelton, IV et al.
8,801,752 B2 8/2014 Fortier et al.
8,801,801 B2 8/2014 Datta et al.
8,806,973 B2 8/2014 Ross et al.
8,807,414 B2 8/2014 Ross et al.
8,808,161 B2 8/2014 Gregg et al.
8,808,164 B2 8/2014 Hoffman et al.
8,808,274 B2 8/2014 Hartwell
8,808,294 B2 8/2014 Fox et al.
8,808,308 B2 8/2014 Boukhny et al.
8,808,311 B2 8/2014 Heinrich et al.
8,808,325 B2 8/2014 Hess et al.
8,810,197 B2 8/2014 Juergens
8,811,017 B2 8/2014 Fujii et al.
8,813,866 B2 8/2014 Suzuki
8,814,024 B2 8/2014 Woodard, Jr. et al.
8,814,025 B2 8/2014 Miller et al.
8,814,836 B2 8/2014 Ignon et al.
8,815,594 B2 8/2014 Harris et al.
8,818,523 B2 8/2014 Olson et al.
8,820,603 B2 9/2014 Shelton, IV et al.
8,820,605 B2 9/2014 Shelton, IV
8,820,606 B2 9/2014 Hodgkinson
8,820,607 B2 9/2014 Marczyk
8,820,608 B2 9/2014 Miyamoto
8,821,514 B2 9/2014 Aranyi
8,822,934 B2 9/2014 Sayeh et al.
8,825,164 B2 9/2014 Tweden et al.
8,827,133 B2 9/2014 Shelton, IV et al.
8,827,134 B2 9/2014 Viola et al.
8,827,903 B2 9/2014 Shelton, IV et al.
8,828,046 B2 9/2014 Stefanchik et al.
8,831,779 B2 9/2014 Ortmaier et al.
8,833,219 B2 9/2014 Pierce
8,833,630 B2 9/2014 Milliman
8,833,632 B2 9/2014 Swensgard
8,834,353 B2 9/2014 Dejima et al.
8,834,465 B2 9/2014 Ramstein et al.
8,834,498 B2 9/2014 Byrum et al.
8,834,518 B2 9/2014 Faller et al.
8,840,003 B2 9/2014 Morgan et al.
8,840,004 B2 9/2014 Holsten et al.
8,840,603 B2 9/2014 Shelton, IV et al.
8,840,609 B2 9/2014 Stuebe
8,840,876 B2 9/2014 Eemeta et al.
8,844,789 B2 9/2014 Shelton, IV et al.
8,844,790 B2 9/2014 Demmy et al.
8,845,622 B2 9/2014 Paik et al.
8,851,215 B2 10/2014 Goto
8,851,354 B2 10/2014 Swensgard et al.
8,851,355 B2 10/2014 Aranyi et al.
8,852,174 B2 10/2014 Burbank
8,852,185 B2 10/2014 Twomey
8,852,199 B2 10/2014 Deslauriers et al.
8,852,218 B2 10/2014 Hughett, Sr. et al.
8,855,822 B2 10/2014 Bartol et al.
8,857,693 B2 10/2014 Schuckmann et al.
8,857,694 B2 10/2014 Shelton, IV et al.
8,858,538 B2 10/2014 Belson et al.
8,858,547 B2 10/2014 Brogna
8,858,571 B2 10/2014 Shelton, IV et al.
8,858,590 B2 10/2014 Shelton, IV et al.
8,864,007 B2 10/2014 Widenhouse et al.
8,864,009 B2 10/2014 Shelton, IV et al.
8,864,010 B2 10/2014 Williams
8,864,750 B2 10/2014 Ross et al.
8,869,912 B2 10/2014 Roβkamp et al.
8,869,913 B2 10/2014 Matthias et al.
8,870,049 B2 10/2014 Amid et al.
8,870,050 B2 10/2014 Hodgkinson
8,870,867 B2 10/2014 Walberg et al.
8,870,912 B2 10/2014 Brisson et al.
8,871,829 B2 10/2014 Gerold et al.
8,875,971 B2 11/2014 Hall et al.
8,875,972 B2 11/2014 Weisenburgh, II et al.
8,876,698 B2 11/2014 Sakamoto et al.
8,876,857 B2 11/2014 Burbank
8,876,858 B2 11/2014 Braun
8,882,660 B2 11/2014 Phee et al.
8,882,792 B2 11/2014 Dietz et al.
8,884,560 B2 11/2014 Ito
8,887,979 B2 11/2014 Mastri et al.
8,888,688 B2 11/2014 Julian et al.
8,888,695 B2 11/2014 Piskun et al.
8,888,792 B2 11/2014 Harris et al.
8,888,809 B2 11/2014 Davison et al.
8,893,946 B2 11/2014 Boudreaux et al.
8,893,949 B2 11/2014 Shelton, IV et al.
8,894,647 B2 11/2014 Beardsley et al.
8,894,654 B2 11/2014 Anderson
8,899,460 B2 12/2014 Wojcicki
8,899,461 B2 12/2014 Farascioni
8,899,462 B2 12/2014 Kostrzewski et al.
8,899,463 B2 12/2014 Schall et al.
8,899,464 B2 12/2014 Hueil et al.
8,899,465 B2 12/2014 Shelton, IV et al.
8,899,466 B2 12/2014 Baxter, III et al.
8,900,267 B2 12/2014 Woolfson et al.
8,905,287 B2 12/2014 Racenet et al.
8,905,977 B2 12/2014 Shelton et al.

(56) References Cited

U.S. PATENT DOCUMENTS

| | | | |
|---|---|---|---|
| 8,910,846 | B2 | 12/2014 | Viola |
| 8,910,847 | B2 | 12/2014 | Nalagatla et al. |
| 8,911,426 | B2 | 12/2014 | Coppeta et al. |
| 8,911,448 | B2 | 12/2014 | Stein |
| 8,911,460 | B2 | 12/2014 | Neurohr et al. |
| 8,911,471 | B2 | 12/2014 | Spivey et al. |
| 8,912,746 | B2 | 12/2014 | Reid et al. |
| 8,915,842 | B2 | 12/2014 | Weisenburgh, II et al. |
| 8,920,368 | B2 | 12/2014 | Sandhu et al. |
| 8,920,433 | B2 | 12/2014 | Barrier et al. |
| 8,920,435 | B2 | 12/2014 | Smith et al. |
| 8,920,438 | B2 | 12/2014 | Aranyi et al. |
| 8,920,443 | B2 | 12/2014 | Hiles et al. |
| 8,920,444 | B2 | 12/2014 | Hiles et al. |
| 8,922,163 | B2 | 12/2014 | Macdonald |
| 8,925,782 | B2 | 1/2015 | Shelton, IV |
| 8,925,783 | B2 | 1/2015 | Zemlok et al. |
| 8,925,788 | B2 | 1/2015 | Hess et al. |
| 8,926,506 | B2 | 1/2015 | Widenhouse et al. |
| 8,926,598 | B2 | 1/2015 | Mollere et al. |
| 8,931,576 | B2 | 1/2015 | Iwata |
| 8,931,679 | B2 | 1/2015 | Kostrzewski |
| 8,931,680 | B2 | 1/2015 | Milliman |
| 8,931,682 | B2 | 1/2015 | Timm et al. |
| 8,931,692 | B2 | 1/2015 | Sancak |
| 8,936,614 | B2 | 1/2015 | Allen, IV |
| 8,937,408 | B2 | 1/2015 | Ganem et al. |
| 8,939,343 | B2 | 1/2015 | Milliman et al. |
| 8,939,344 | B2 | 1/2015 | Olson et al. |
| 8,939,898 | B2 | 1/2015 | Omoto |
| 8,944,069 | B2 | 2/2015 | Miller et al. |
| 8,945,095 | B2 | 2/2015 | Blumenkranz et al. |
| 8,945,098 | B2 | 2/2015 | Seibold et al. |
| 8,945,163 | B2 | 2/2015 | Voegele et al. |
| 8,955,732 | B2 | 2/2015 | Zemlok et al. |
| 8,956,342 | B1 | 2/2015 | Russo et al. |
| 8,956,390 | B2 | 2/2015 | Shah et al. |
| 8,958,860 | B2 | 2/2015 | Banerjee et al. |
| 8,960,519 | B2 | 2/2015 | Whitman et al. |
| 8,960,520 | B2 | 2/2015 | McCuen |
| 8,960,521 | B2 | 2/2015 | Kostrzewski |
| 8,961,191 | B2 | 2/2015 | Hanshew |
| 8,961,504 | B2 | 2/2015 | Hoarau et al. |
| 8,961,542 | B2 | 2/2015 | Whitfield et al. |
| 8,963,714 | B2 | 2/2015 | Medhal et al. |
| D725,674 | S | 3/2015 | Jung et al. |
| 8,967,443 | B2 | 3/2015 | McCuen |
| 8,967,444 | B2 | 3/2015 | Beetel |
| 8,967,446 | B2 | 3/2015 | Beardsley et al. |
| 8,967,448 | B2 | 3/2015 | Carter et al. |
| 8,968,276 | B2 | 3/2015 | Zemlok et al. |
| 8,968,308 | B2 | 3/2015 | Horner et al. |
| 8,968,312 | B2 | 3/2015 | Marczyk et al. |
| 8,968,337 | B2 | 3/2015 | Whitfield et al. |
| 8,968,340 | B2 | 3/2015 | Chowaniec et al. |
| 8,968,355 | B2 | 3/2015 | Malkowski et al. |
| 8,968,358 | B2 | 3/2015 | Reschke |
| 8,970,507 | B2 | 3/2015 | Holbein et al. |
| 8,973,803 | B2 | 3/2015 | Hall et al. |
| 8,973,804 | B2 | 3/2015 | Hess et al. |
| 8,973,805 | B2 | 3/2015 | Scirica et al. |
| 8,974,440 | B2 | 3/2015 | Farritor et al. |
| 8,974,542 | B2 | 3/2015 | Fujimoto et al. |
| 8,974,932 | B2 | 3/2015 | McGahan et al. |
| 8,978,954 | B2 | 3/2015 | Shelton, IV et al. |
| 8,978,955 | B2 | 3/2015 | Aronhalt et al. |
| 8,978,956 | B2 | 3/2015 | Schall et al. |
| 8,979,843 | B2 | 3/2015 | Timm et al. |
| 8,979,890 | B2 | 3/2015 | Boudreaux |
| 8,982,195 | B2 | 3/2015 | Claus et al. |
| 8,984,711 | B2 | 3/2015 | Ota et al. |
| 8,985,240 | B2 | 3/2015 | Winnard |
| 8,985,429 | B2 | 3/2015 | Balek et al. |
| 8,986,302 | B2 | 3/2015 | Aldridge et al. |
| 8,989,903 | B2 | 3/2015 | Weir et al. |
| 8,991,676 | B2 | 3/2015 | Hess et al. |
| 8,991,677 | B2 | 3/2015 | Moore et al. |
| 8,991,678 | B2 | 3/2015 | Wellman et al. |
| 8,992,042 | B2 | 3/2015 | Eichenholz |
| 8,992,422 | B2 | 3/2015 | Spivey et al. |
| 8,992,565 | B2 | 3/2015 | Brisson et al. |
| 8,996,165 | B2 | 3/2015 | Wang et al. |
| 8,998,058 | B2 | 4/2015 | Moore et al. |
| 8,998,059 | B2 | 4/2015 | Smith et al. |
| 8,998,060 | B2 | 4/2015 | Bruewer et al. |
| 8,998,061 | B2 | 4/2015 | Williams et al. |
| 8,998,939 | B2 | 4/2015 | Price et al. |
| 9,000,720 | B2 | 4/2015 | Stulen et al. |
| 9,002,518 | B2 | 4/2015 | Manzo et al. |
| 9,004,339 | B1 | 4/2015 | Park |
| 9,004,799 | B1 | 4/2015 | Tibbits |
| 9,005,230 | B2 | 4/2015 | Yates et al. |
| 9,005,238 | B2 | 4/2015 | DeSantis et al. |
| 9,005,243 | B2 | 4/2015 | Stopek et al. |
| 9,010,606 | B2 | 4/2015 | Aranyi et al. |
| 9,010,608 | B2 | 4/2015 | Casasanta, Jr. et al. |
| 9,010,611 | B2 | 4/2015 | Ross et al. |
| 9,011,437 | B2 | 4/2015 | Woodruff et al. |
| 9,011,439 | B2 | 4/2015 | Shalaby et al. |
| 9,011,471 | B2 | 4/2015 | Timm et al. |
| 9,014,856 | B2 | 4/2015 | Manzo et al. |
| 9,016,539 | B2 | 4/2015 | Kostrzewski et al. |
| 9,016,540 | B2 | 4/2015 | Whitman et al. |
| 9,016,541 | B2 | 4/2015 | Viola et al. |
| 9,016,542 | B2 | 4/2015 | Shelton, IV et al. |
| 9,016,545 | B2 | 4/2015 | Aranyi et al. |
| 9,017,331 | B2 | 4/2015 | Fox |
| 9,017,355 | B2 | 4/2015 | Smith et al. |
| 9,017,369 | B2 | 4/2015 | Renger et al. |
| 9,017,371 | B2 | 4/2015 | Whitman et al. |
| 9,017,849 | B2 | 4/2015 | Stulen et al. |
| 9,017,851 | B2 | 4/2015 | Felder et al. |
| D729,274 | S | 5/2015 | Clement et al. |
| 9,021,684 | B2 | 5/2015 | Lenker et al. |
| 9,023,014 | B2 | 5/2015 | Chowaniec et al. |
| 9,023,069 | B2 | 5/2015 | Kasvikis et al. |
| 9,023,071 | B2 | 5/2015 | Miller et al. |
| 9,026,347 | B2 | 5/2015 | Gadh et al. |
| 9,027,817 | B2 | 5/2015 | Milliman et al. |
| 9,028,468 | B2 | 5/2015 | Scarfogliero et al. |
| 9,028,494 | B2 | 5/2015 | Shelton, IV et al. |
| 9,028,495 | B2 | 5/2015 | Mueller et al. |
| 9,028,510 | B2 | 5/2015 | Miyamoto et al. |
| 9,028,511 | B2 | 5/2015 | Weller et al. |
| 9,028,519 | B2 | 5/2015 | Yates et al. |
| 9,028,529 | B2 | 5/2015 | Fox et al. |
| 9,030,166 | B2 | 5/2015 | Kano |
| 9,030,169 | B2 | 5/2015 | Christensen et al. |
| 9,033,203 | B2 | 5/2015 | Woodard, Jr. et al. |
| 9,033,204 | B2 | 5/2015 | Shelton, IV et al. |
| 9,034,505 | B2 | 5/2015 | Detry et al. |
| 9,038,881 | B1 | 5/2015 | Schaller et al. |
| 9,039,690 | B2 | 5/2015 | Kersten et al. |
| 9,039,694 | B2 | 5/2015 | Ross et al. |
| 9,039,720 | B2 | 5/2015 | Madan |
| 9,039,736 | B2 | 5/2015 | Scirica et al. |
| 9,040,062 | B2 | 5/2015 | Maeda et al. |
| 9,043,027 | B2 | 5/2015 | Durant et al. |
| 9,044,227 | B2 | 6/2015 | Shelton, IV et al. |
| 9,044,228 | B2 | 6/2015 | Woodard, Jr. et al. |
| 9,044,229 | B2 | 6/2015 | Scheib et al. |
| 9,044,230 | B2 | 6/2015 | Morgan et al. |
| 9,044,238 | B2 | 6/2015 | Orszulak |
| 9,044,241 | B2 | 6/2015 | Barner et al. |
| 9,044,261 | B2 | 6/2015 | Houser |
| 9,044,281 | B2 | 6/2015 | Pool et al. |
| 9,050,083 | B2 | 6/2015 | Yates et al. |
| 9,050,084 | B2 | 6/2015 | Schmid et al. |
| 9,050,089 | B2 | 6/2015 | Orszulak |
| 9,050,100 | B2 | 6/2015 | Yates et al. |
| 9,050,120 | B2 | 6/2015 | Swarup et al. |
| 9,050,123 | B2 | 6/2015 | Krause et al. |
| 9,050,176 | B2 | 6/2015 | Datta et al. |
| 9,050,192 | B2 | 6/2015 | Mansmann |

(56) References Cited

U.S. PATENT DOCUMENTS 9,055,941 B2 6/2015 Schmid et al.
9,055,942 B2 6/2015 Balbierz et al.
9,055,943 B2 6/2015 Zemlok et al.
9,055,944 B2 6/2015 Hodgkinson et al.
9,055,961 B2 6/2015 Manzo et al.
9,060,770 B2 6/2015 Shelton, IV et al.
9,060,776 B2 6/2015 Yates et al.
9,060,794 B2 6/2015 Kang et al.
9,060,894 B2 6/2015 Wubbeling
9,061,392 B2 6/2015 Forgues et al.
9,070,068 B2 6/2015 Coveley et al.
9,072,515 B2 7/2015 Hall et al.
9,072,523 B2 7/2015 Houser et al.
9,072,535 B2 7/2015 Shelton, IV et al.
9,072,536 B2 7/2015 Shelton, IV et al.
9,078,653 B2 7/2015 Leimbach et al.
9,078,654 B2 7/2015 Whitman et al.
9,084,586 B2 7/2015 Hafner et al.
9,084,601 B2 7/2015 Moore et al.
9,084,602 B2 7/2015 Gleiman
9,086,875 B2 7/2015 Harrat et al.
9,089,326 B2 7/2015 Krumanaker et al.
9,089,330 B2 7/2015 Widenhouse et al.
9,089,338 B2 7/2015 Smith et al.
9,089,352 B2 7/2015 Jeong
9,089,360 B2 7/2015 Messerly et al.
9,091,588 B2 7/2015 Lefler
D736,792 S 8/2015 Brinda et al.
9,095,339 B2 8/2015 Moore et al.
9,095,346 B2 8/2015 Houser et al.
9,095,362 B2 8/2015 Dachs, II et al.
9,095,367 B2 8/2015 Olson et al.
9,095,642 B2 8/2015 Harder et al.
9,096,033 B2 8/2015 Holop et al.
9,098,153 B2 8/2015 Shen et al.
9,099,863 B2 8/2015 Smith et al.
9,099,877 B2 8/2015 Banos et al.
9,099,922 B2 8/2015 Toosky et al.
9,101,358 B2 8/2015 Kerr et al.
9,101,359 B2 8/2015 Smith et al.
9,101,385 B2 8/2015 Shelton, IV et al.
9,101,475 B2 8/2015 Wei et al.
9,101,621 B2 8/2015 Zeldis
9,107,663 B2 8/2015 Swensgard
9,107,667 B2 8/2015 Hodgkinson
9,107,690 B2 8/2015 Bales, Jr. et al.
9,110,587 B2 8/2015 Kim et al.
9,113,862 B2 8/2015 Morgan et al.
9,113,864 B2 8/2015 Morgan et al.
9,113,865 B2 8/2015 Shelton, IV et al.
9,113,868 B2 8/2015 Felder et al.
9,113,873 B2 8/2015 Marczyk et al.
9,113,874 B2 8/2015 Shelton, IV et al.
9,113,875 B2 8/2015 Viola et al.
9,113,876 B2 8/2015 Zemlok et al.
9,113,879 B2 8/2015 Felder et al.
9,113,880 B2 8/2015 Zemlok et al.
9,113,881 B2 8/2015 Scirica
9,113,883 B2 8/2015 Aronhalt et al.
9,113,884 B2 8/2015 Shelton, IV et al.
9,113,887 B2 8/2015 Behnke, II et al.
9,119,615 B2 9/2015 Felder et al.
9,119,657 B2 9/2015 Shelton, IV et al.
9,119,898 B2 9/2015 Bayon et al.
9,119,957 B2 9/2015 Gantz et al.
9,123,286 B2 9/2015 Park
9,124,097 B2 9/2015 Cruz
9,125,651 B2 9/2015 Mandakolathur Vasudevan et al.
9,125,654 B2 9/2015 Aronhalt et al.
9,125,662 B2 9/2015 Shelton, IV
9,126,317 B2 9/2015 Lawton et al.
9,131,835 B2 9/2015 Widenhouse et al.
9,131,940 B2 9/2015 Huitema et al.
9,131,950 B2 9/2015 Matthew
9,131,957 B2 9/2015 Skarbnik et al.
9,138,225 B2 9/2015 Huang et al.
9,138,226 B2 9/2015 Racenet et al.
9,144,455 B2 9/2015 Kennedy et al.
D740,414 S 10/2015 Katsura
D741,882 S 10/2015 Shmilov et al.
9,149,274 B2 10/2015 Spivey et al.
9,149,324 B2 10/2015 Huang et al.
9,149,325 B2 10/2015 Worrell et al.
9,153,994 B2 10/2015 Wood et al.
9,154,189 B2 10/2015 Von Novak et al.
9,161,753 B2 10/2015 Prior
9,161,769 B2 10/2015 Stoddard et al.
9,161,803 B2 10/2015 Yates et al.
9,161,807 B2 10/2015 Garrison
9,161,855 B2 10/2015 Rousseau et al.
9,164,271 B2 10/2015 Ebata et al.
9,167,960 B2 10/2015 Yamaguchi et al.
9,168,038 B2 10/2015 Shelton, IV et al.
9,168,039 B1 10/2015 Knodel
9,168,042 B2 10/2015 Milliman
9,168,054 B2 10/2015 Turner et al.
9,168,144 B2 10/2015 Rivin et al.
9,171,244 B2 10/2015 Endou et al.
9,179,832 B2 11/2015 Diolaiti
9,179,911 B2 11/2015 Morgan et al.
9,179,912 B2 11/2015 Yates et al.
9,180,223 B2 11/2015 Yu et al.
9,182,244 B2 11/2015 Luke et al.
9,186,046 B2 11/2015 Ramamurthy et al.
9,186,137 B2 11/2015 Farascioni et al.
9,186,140 B2 11/2015 Hiles et al.
9,186,142 B2 11/2015 Fanelli et al.
9,186,143 B2 11/2015 Timm et al.
9,186,148 B2 11/2015 Felder et al.
9,186,221 B2 11/2015 Burbank
9,192,376 B2 11/2015 Almodovar
9,192,380 B2 11/2015 (Tarinelli) Racenet et al.
9,192,384 B2 11/2015 Bettuchi
9,192,430 B2 11/2015 Rachlin et al.
9,192,434 B2 11/2015 Twomey et al.
9,193,045 B2 11/2015 Saur et al.
9,197,079 B2 11/2015 Yip et al.
D744,528 S 12/2015 Agrawal
D746,459 S 12/2015 Kaercher et al.
9,198,642 B2 12/2015 Storz
9,198,644 B2 12/2015 Balek et al.
9,198,661 B2 12/2015 Swensgard
9,198,662 B2 12/2015 Barton et al.
9,198,683 B2 12/2015 Friedman et al.
9,204,830 B2 12/2015 Zand et al.
9,204,877 B2 12/2015 Whitman et al.
9,204,878 B2 12/2015 Hall et al.
9,204,879 B2 12/2015 Shelton, IV
9,204,880 B2 12/2015 Baxter, III et al.
9,204,881 B2 12/2015 Penna
9,204,923 B2 12/2015 Manzo et al.
9,204,924 B2 12/2015 Marczyk et al.
9,211,120 B2 12/2015 Scheib et al.
9,211,121 B2 12/2015 Hall et al.
9,211,122 B2 12/2015 Hagerty et al.
9,216,013 B2 12/2015 Scirica et al.
9,216,019 B2 12/2015 Schmid et al.
9,216,020 B2 12/2015 Zhang et al.
9,216,030 B2 12/2015 Fan et al.
9,216,062 B2 12/2015 Duque et al.
9,220,500 B2 12/2015 Swayze et al.
9,220,501 B2 12/2015 Baxter, III et al.
9,220,502 B2 12/2015 Zemlok et al.
9,220,504 B2 12/2015 Viola et al.
9,220,508 B2 12/2015 Dannaher
9,220,559 B2 12/2015 Worrell et al.
9,220,570 B2 12/2015 Kim et al.
D746,854 S 1/2016 Shardlow et al.
9,226,686 B2 1/2016 Blair
9,226,750 B2 1/2016 Weir et al.
9,226,751 B2 1/2016 Shelton, IV et al.
9,226,754 B2 1/2016 D'Agostino et al.
9,226,760 B2 1/2016 Shelton, IV
9,226,761 B2 1/2016 Burbank

(56) References Cited

U.S. PATENT DOCUMENTS 9,226,767 B2 1/2016 Stulen et al.
9,226,799 B2 1/2016 Lightcap et al.
9,232,941 B2 1/2016 Mandakolathur Vasudevan et al.
9,232,945 B2 1/2016 Zingman
9,232,979 B2 1/2016 Parihar et al.
9,233,610 B2 1/2016 Kim et al.
9,237,891 B2 1/2016 Shelton, IV
9,237,892 B2 1/2016 Hodgkinson
9,237,895 B2 1/2016 McCarthy et al.
9,237,900 B2 1/2016 Boudreaux et al.
9,237,921 B2 1/2016 Messerly et al.
9,239,064 B2 1/2016 Helbig et al.
9,240,740 B2 1/2016 Zeng et al.
9,241,711 B2 1/2016 Ivanko
9,241,712 B2 1/2016 Zemlok et al.
9,241,714 B2 1/2016 Timm et al.
9,241,716 B2 1/2016 Whitman
9,241,731 B2 1/2016 Boudreaux et al.
9,241,758 B2 1/2016 Franer et al.
9,244,524 B2 1/2016 Inoue et al.
D748,668 S 2/2016 Kim et al.
D749,128 S 2/2016 Perez et al.
D749,623 S 2/2016 Gray et al.
D750,122 S 2/2016 Shardlow et al.
D750,129 S 2/2016 Kwon
9,254,131 B2 2/2016 Soltz et al.
9,254,170 B2 2/2016 Parihar et al.
9,259,265 B2 2/2016 Harris et al.
9,259,268 B2 2/2016 Behnke, II et al.
9,259,274 B2 2/2016 Prisco
9,259,275 B2 2/2016 Burbank
9,261,172 B2 2/2016 Solomon et al.
9,265,500 B2 2/2016 Sorrentino et al.
9,265,510 B2 2/2016 Dietzel et al.
9,265,516 B2 2/2016 Casey et al.
9,265,585 B2 2/2016 Wingardner et al.
9,271,718 B2 3/2016 Milad et al.
9,271,727 B2 3/2016 McGuckin, Jr. et al.
9,271,753 B2 3/2016 Butler et al.
9,271,799 B2 3/2016 Shelton, IV et al.
9,272,406 B2 3/2016 Aronhalt et al.
9,274,095 B2 3/2016 Humayun et al.
9,277,919 B2 3/2016 Timmer et al.
9,277,922 B2 3/2016 Carter et al.
9,277,969 B2 3/2016 Brannan et al.
9,282,962 B2 3/2016 Schmid et al.
9,282,963 B2 3/2016 Bryant
9,282,966 B2 3/2016 Shelton, IV et al.
9,282,974 B2 3/2016 Shelton, IV
9,283,028 B2 3/2016 Johnson
9,283,045 B2 3/2016 Rhee et al.
9,283,054 B2 3/2016 Morgan et al.
9,283,334 B2 3/2016 Mantell et al.
9,289,206 B2 3/2016 Hess et al.
9,289,207 B2 3/2016 Shelton, IV
9,289,210 B2 3/2016 Baxter, III et al.
9,289,211 B2 3/2016 Williams et al.
9,289,212 B2 3/2016 Shelton, IV et al.
9,289,225 B2 3/2016 Shelton, IV et al.
9,289,256 B2 3/2016 Shelton, IV et al.
9,293,757 B2 3/2016 Toussaint et al.
9,295,464 B2 3/2016 Shelton, IV et al.
9,295,465 B2 3/2016 Farascioni
9,295,466 B2 3/2016 Hodgkinson et al.
9,295,467 B2 3/2016 Scirica
9,295,468 B2 3/2016 Heinrich et al.
9,295,514 B2 3/2016 Shelton, IV et al.
9,295,522 B2 3/2016 Kostrzewski
9,295,565 B2 3/2016 McLean
9,295,784 B2 3/2016 Eggert et al.
D753,167 S 4/2016 Yu et al.
9,301,691 B2 4/2016 Hufnagel et al.
9,301,752 B2 4/2016 Mandakolathur Vasudevan et al.
9,301,753 B2 4/2016 Aldridge et al.
9,301,755 B2 4/2016 Shelton, IV et al.
9,301,759 B2 4/2016 Spivey et al.
9,301,811 B2 4/2016 Goldberg et al.
9,307,965 B2 4/2016 Ming et al.
9,307,986 B2 4/2016 Hall et al.
9,307,987 B2 4/2016 Swensgard et al.
9,307,988 B2 4/2016 Shelton, IV
9,307,989 B2 4/2016 Shelton, IV et al.
9,307,994 B2 4/2016 Gresham et al.
9,308,009 B2 4/2016 Madan et al.
9,308,011 B2 4/2016 Chao et al.
9,308,646 B2 4/2016 Lim et al.
9,313,915 B2 4/2016 Niu et al.
9,314,246 B2 4/2016 Shelton, IV et al.
9,314,247 B2 4/2016 Shelton, IV et al.
9,314,261 B2 4/2016 Bales, Jr. et al.
9,314,291 B2 4/2016 Schall et al.
9,314,339 B2 4/2016 Mansmann
9,314,908 B2 4/2016 Tanimoto et al.
9,320,518 B2 4/2016 Henderson et al.
9,320,520 B2 4/2016 Shelton, IV et al.
9,320,521 B2 4/2016 Shelton, IV et al.
9,320,523 B2 4/2016 Shelton, IV et al.
9,325,516 B2 4/2016 Pera et al.
D755,196 S 5/2016 Meyers et al.
D756,373 S 5/2016 Raskin et al.
D756,377 S 5/2016 Connolly et al.
D757,028 S 5/2016 Goldenberg et al.
9,326,767 B2 5/2016 Koch, Jr. et al.
9,326,768 B2 5/2016 Shelton, IV
9,326,769 B2 5/2016 Shelton, IV et al.
9,326,770 B2 5/2016 Shelton, IV et al.
9,326,771 B2 5/2016 Baxter, III et al.
9,326,788 B2 5/2016 Batross et al.
9,326,812 B2 5/2016 Waaler et al.
9,326,824 B2 5/2016 Inoue et al.
9,327,061 B2 5/2016 Govil et al.
9,331,721 B2 5/2016 Martinez Nuevo et al.
9,332,890 B2 5/2016 Ozawa
9,332,974 B2 5/2016 Henderson et al.
9,332,984 B2 5/2016 Weaner et al.
9,332,987 B2 5/2016 Leimbach et al.
9,333,040 B2 5/2016 Shellenberger et al.
9,333,082 B2 5/2016 Wei et al.
9,337,668 B2 5/2016 Yip
9,339,226 B2 5/2016 van der Walt et al.
9,339,342 B2 5/2016 Prisco et al.
9,345,477 B2 5/2016 Anim et al.
9,345,479 B2 5/2016 (Tarinelli) Racenet et al.
9,345,480 B2 5/2016 Hessler et al.
9,345,481 B2 5/2016 Hall et al.
9,345,503 B2 5/2016 Ishida et al.
9,351,726 B2 5/2016 Leimbach et al.
9,351,727 B2 5/2016 Leimbach et al.
9,351,728 B2 5/2016 Sniffin et al.
9,351,730 B2 5/2016 Schmid et al.
9,351,731 B2 5/2016 Carter et al.
9,351,732 B2 5/2016 Hodgkinson
9,352,071 B2 5/2016 Landgrebe et al.
D758,433 S 6/2016 Lee et al.
D759,063 S 6/2016 Chen
9,358,003 B2 6/2016 Hall et al.
9,358,004 B2 6/2016 Sniffin et al.
9,358,005 B2 6/2016 Shelton, IV et al.
9,358,015 B2 6/2016 Sorrentino et al.
9,358,031 B2 6/2016 Manzo
9,358,065 B2 6/2016 Ladtkow et al.
9,364,217 B2 6/2016 Kostrzewski et al.
9,364,219 B2 6/2016 Olson et al.
9,364,220 B2 6/2016 Williams
9,364,223 B2 6/2016 Scirica
9,364,226 B2 6/2016 Zemlok et al.
9,364,228 B2 6/2016 Straehnz et al.
9,364,229 B2 6/2016 D'Agostino et al.
9,364,230 B2 6/2016 Shelton, IV et al.
9,364,231 B2 6/2016 Wenchell
9,364,233 B2 6/2016 Alexander, III et al.
9,364,279 B2 6/2016 Houser et al.
9,368,991 B2 6/2016 Qahouq
9,370,341 B2 6/2016 Ceniccola et al.

(56) References Cited

U.S. PATENT DOCUMENTS 9,370,358 B2 6/2016 Shelton, IV et al.
9,370,361 B2 6/2016 Viola et al.
9,370,362 B2 6/2016 Petty et al.
9,370,364 B2 6/2016 Smith et al.
9,370,400 B2 6/2016 Parihar
9,375,206 B2 6/2016 Vidal et al.
9,375,218 B2 6/2016 Wheeler et al.
9,375,230 B2 6/2016 Ross et al.
9,375,232 B2 6/2016 Hunt et al.
9,375,255 B2 6/2016 Houser et al.
D761,309 S 7/2016 Lee et al.
9,381,058 B2 7/2016 Houser et al.
9,383,881 B2 7/2016 Day et al.
9,385,640 B2 7/2016 Sun et al.
9,386,983 B2 7/2016 Swensgard et al.
9,386,984 B2 7/2016 Aronhalt et al.
9,386,985 B2 7/2016 Koch, Jr. et al.
9,386,988 B2 7/2016 Baxter, III et al.
9,387,003 B2 7/2016 Kaercher et al.
9,392,885 B2 7/2016 Vogler et al.
9,393,015 B2 7/2016 Laurent et al.
9,393,017 B2 7/2016 Flanagan et al.
9,393,018 B2 7/2016 Wang et al.
9,393,354 B2 7/2016 Freedman et al.
9,396,369 B1 7/2016 Whitehurst et al.
9,396,669 B2 7/2016 Karkanias et al.
9,398,905 B2 7/2016 Martin
9,398,911 B2 7/2016 Auld
D763,277 S 8/2016 Ahmed et al.
D764,498 S 8/2016 Capela et al.
9,402,604 B2 8/2016 Williams et al.
9,402,625 B2 8/2016 Coleman et al.
9,402,626 B2 8/2016 Ortiz et al.
9,402,627 B2 8/2016 Stevenson et al.
9,402,629 B2 8/2016 Ehrenfels et al.
9,402,679 B2 8/2016 Ginnebaugh et al.
9,402,682 B2 8/2016 Worrell et al.
9,402,688 B2 8/2016 Min et al.
9,408,604 B2 8/2016 Shelton, IV et al.
9,408,605 B1 8/2016 Knodel et al.
9,408,606 B2 8/2016 Shelton, IV
9,408,622 B2 8/2016 Stulen et al.
9,411,370 B2 8/2016 Benni et al.
9,413,128 B2 8/2016 Tien et al.
9,414,838 B2 8/2016 Shelton, IV et al.
9,414,849 B2 8/2016 Nagashimada
9,414,880 B2 8/2016 Monson et al.
9,420,967 B2 8/2016 Zand et al.
9,421,003 B2 8/2016 Williams et al.
9,421,014 B2 8/2016 Ingmanson et al.
9,421,030 B2 8/2016 Cole et al.
9,421,060 B2 8/2016 Monson et al.
9,421,062 B2 8/2016 Houser et al.
9,421,682 B2 8/2016 McClaskey et al.
9,427,223 B2 8/2016 Park et al.
9,427,231 B2 8/2016 Racenet et al.
9,429,204 B2 8/2016 Stefan et al.
D767,624 S 9/2016 Lee et al.
9,433,411 B2 9/2016 Racenet et al.
9,433,414 B2 9/2016 Chen et al.
9,433,419 B2 9/2016 Gonzalez et al.
9,433,420 B2 9/2016 Hodgkinson
9,439,649 B2 9/2016 Shelton, IV et al.
9,439,650 B2 9/2016 McGuckin, Jr. et al.
9,439,651 B2 9/2016 Smith et al.
9,439,668 B2 9/2016 Timm et al.
9,445,808 B2 9/2016 Woodard, Jr. et al.
9,445,813 B2 9/2016 Shelton, IV et al.
9,445,816 B2 9/2016 Swayze et al.
9,445,817 B2 9/2016 Bettuchi
9,446,226 B2 9/2016 Zilberman
9,451,938 B2 9/2016 Overes et al.
9,451,958 B2 9/2016 Shelton, IV et al.
9,452,020 B2 9/2016 Griffiths et al.
D768,152 S 10/2016 Gutierrez et al.
D768,156 S 10/2016 Frincke
D768,167 S 10/2016 Jones et al.
D769,315 S 10/2016 Scotti
D769,930 S 10/2016 Agrawal
9,461,340 B2 10/2016 Li et al.
9,463,012 B2 10/2016 Bonutti et al.
9,463,040 B2 10/2016 Jeong et al.
9,463,260 B2 10/2016 Stopek
9,468,438 B2 10/2016 Baber et al.
9,468,447 B2 10/2016 Aman et al.
9,470,297 B2 10/2016 Aranyi et al.
9,471,969 B2 10/2016 Zeng et al.
9,474,506 B2 10/2016 Magnin et al.
9,474,513 B2 10/2016 Ishida et al.
9,474,523 B2 10/2016 Meade et al.
9,474,540 B2 10/2016 Stokes et al.
9,475,180 B2 10/2016 Eshleman et al.
9,477,649 B1 10/2016 Davidson et al.
D770,476 S 11/2016 Jitkoff et al.
D770,515 S 11/2016 Cho et al.
D771,116 S 11/2016 Dellinger et al.
D772,905 S 11/2016 Ingenlath
9,480,476 B2 11/2016 Aldridge et al.
9,480,492 B2 11/2016 Aranyi et al.
9,483,095 B2 11/2016 Tran et al.
9,486,186 B2 11/2016 Fiebig et al.
9,486,213 B2 11/2016 Altman et al.
9,486,214 B2 11/2016 Shelton, IV
9,486,215 B2 11/2016 Olson et al.
9,486,302 B2 11/2016 Boey et al.
9,488,197 B2 11/2016 Wi
9,492,146 B2 11/2016 Kostrzewski et al.
9,492,167 B2 11/2016 Shelton, IV et al.
9,492,170 B2 11/2016 Bear et al.
9,492,172 B2 11/2016 Weisshaupt et al.
9,492,189 B2 11/2016 Williams et al.
9,492,192 B2 11/2016 To et al.
9,492,237 B2 11/2016 Kang et al.
9,498,213 B2 11/2016 Marczyk et al.
9,498,219 B2 11/2016 Moore et al.
9,498,231 B2 11/2016 Haider et al.
9,504,455 B2 11/2016 Whitman et al.
9,504,483 B2 11/2016 Houser et al.
9,504,520 B2 11/2016 Worrell et al.
9,504,521 B2 11/2016 Deutmeyer et al.
9,504,528 B2 11/2016 Ivinson et al.
9,507,399 B2 11/2016 Chien
D774,547 S 12/2016 Capela et al.
D775,336 S 12/2016 Shelton, IV et al.
9,510,827 B2 12/2016 Kostrzewski
9,510,828 B2 12/2016 Yates et al.
9,510,830 B2 12/2016 Shelton, IV et al.
9,510,846 B2 12/2016 Sholev et al.
9,510,895 B2 12/2016 Houser et al.
9,510,925 B2 12/2016 Hotter et al.
9,515,366 B2 12/2016 Herbsommer et al.
9,517,063 B2 12/2016 Swayze et al.
9,517,065 B2 12/2016 Simms et al.
9,517,068 B2 12/2016 Shelton, IV et al.
9,517,326 B2 12/2016 Hinman et al.
9,521,996 B2 12/2016 Armstrong
9,522,003 B2 12/2016 Weir et al.
9,522,005 B2 12/2016 Williams et al.
9,522,014 B2 12/2016 Nishizawa et al.
9,522,029 B2 12/2016 Yates et al.
9,526,481 B2 12/2016 Storz et al.
9,526,499 B2 12/2016 Kostrzewski et al.
9,526,563 B2 12/2016 Twomey
9,526,564 B2 12/2016 Rusin
9,526,921 B2 12/2016 Kimball et al.
D776,683 S 1/2017 Gobinski et al.
D777,773 S 1/2017 Shi
9,532,783 B2 1/2017 Swayze et al.
9,539,060 B2 1/2017 Lightcap et al.
9,539,726 B2 1/2017 Simaan et al.
9,545,253 B2 1/2017 Worrell et al.
9,545,258 B2 1/2017 Smith et al.
9,549,732 B2 1/2017 Yates et al.
9,549,733 B2 1/2017 Knodel

(56) References Cited

U.S. PATENT DOCUMENTS

| | | | |
|---|---|---|---|
| 9,549,735 | B2 | 1/2017 | Shelton, IV et al. |
| 9,549,750 | B2 | 1/2017 | Shelton, IV et al. |
| 9,554,794 | B2 | 1/2017 | Baber et al. |
| 9,554,796 | B2 | 1/2017 | Kostrzewski |
| 9,554,803 | B2 | 1/2017 | Smith et al. |
| 9,554,812 | B2 | 1/2017 | Inkpen et al. |
| 9,554,854 | B2 | 1/2017 | Yates et al. |
| 9,559,624 | B2 | 1/2017 | Philipp |
| 9,561,013 | B2 | 2/2017 | Tsuchiya |
| 9,561,029 | B2 | 2/2017 | Scheib et al. |
| 9,561,030 | B2 | 2/2017 | Zhang et al. |
| 9,561,031 | B2 | 2/2017 | Heinrich et al. |
| 9,561,032 | B2 | 2/2017 | Shelton, IV et al. |
| 9,561,038 | B2 | 2/2017 | Shelton, IV et al. |
| 9,561,045 | B2 | 2/2017 | Hinman et al. |
| 9,561,072 | B2 | 2/2017 | Ko |
| 9,561,082 | B2 | 2/2017 | Yen et al. |
| 9,566,061 | B2 | 2/2017 | Aronhalt et al. |
| 9,566,062 | B2 | 2/2017 | Boudreaux |
| 9,566,064 | B2 | 2/2017 | Williams et al. |
| 9,566,065 | B2 | 2/2017 | Knodel |
| 9,566,067 | B2 | 2/2017 | Milliman et al. |
| 9,572,552 | B1 | 2/2017 | Bodor et al. |
| 9,572,574 | B2 | 2/2017 | Shelton, IV et al. |
| 9,572,576 | B2 | 2/2017 | Hodgkinson et al. |
| 9,572,577 | B2 | 2/2017 | Lloyd et al. |
| 9,572,592 | B2 | 2/2017 | Price et al. |
| 9,574,644 | B2 | 2/2017 | Parihar |
| 9,579,088 | B2 | 2/2017 | Farritor et al. |
| 9,579,143 | B2 | 2/2017 | Ullrich et al. |
| 9,579,158 | B2 | 2/2017 | Brianza et al. |
| D780,803 | S | 3/2017 | Gill et al. |
| D781,879 | S | 3/2017 | Butcher et al. |
| D782,530 | S | 3/2017 | Paek et al. |
| 9,585,550 | B2 | 3/2017 | Abel et al. |
| 9,585,657 | B2 | 3/2017 | Shelton, IV et al. |
| 9,585,658 | B2 | 3/2017 | Shelton, IV |
| 9,585,659 | B2 | 3/2017 | Viola et al. |
| 9,585,660 | B2 | 3/2017 | Laurent et al. |
| 9,585,662 | B2 | 3/2017 | Shelton, IV et al. |
| 9,585,663 | B2 | 3/2017 | Shelton, IV et al. |
| 9,585,672 | B2 | 3/2017 | Bastia |
| 9,590,433 | B2 | 3/2017 | Li |
| 9,592,050 | B2 | 3/2017 | Schmid et al. |
| 9,592,052 | B2 | 3/2017 | Shelton, IV |
| 9,592,053 | B2 | 3/2017 | Shelton, IV et al. |
| 9,592,054 | B2 | 3/2017 | Schmid et al. |
| 9,597,073 | B2 | 3/2017 | Sorrentino et al. |
| 9,597,075 | B2 | 3/2017 | Shelton, IV et al. |
| 9,597,078 | B2 | 3/2017 | Scirica et al. |
| 9,597,080 | B2 | 3/2017 | Milliman et al. |
| 9,597,104 | B2 | 3/2017 | Nicholas et al. |
| 9,597,143 | B2 | 3/2017 | Madan et al. |
| 9,603,595 | B2 | 3/2017 | Shelton, IV et al. |
| 9,603,598 | B2 | 3/2017 | Shelton, IV et al. |
| 9,603,599 | B2 | 3/2017 | Miller et al. |
| 9,603,991 | B2 | 3/2017 | Shelton, IV et al. |
| D783,658 | S | 4/2017 | Hurst et al. |
| 9,610,068 | B2 | 4/2017 | Kappel et al. |
| 9,610,079 | B2 | 4/2017 | Kamei et al. |
| 9,610,080 | B2 | 4/2017 | Whitfield et al. |
| 9,610,412 | B2 | 4/2017 | Zemlok et al. |
| 9,614,258 | B2 | 4/2017 | Takahashi et al. |
| 9,615,826 | B2 | 4/2017 | Shelton, IV et al. |
| 9,622,745 | B2 | 4/2017 | Ingmanson et al. |
| 9,622,746 | B2 | 4/2017 | Simms et al. |
| 9,629,623 | B2 | 4/2017 | Lytle, IV et al. |
| 9,629,626 | B2 | 4/2017 | Soltz et al. |
| 9,629,627 | B2 | 4/2017 | Kostrzewski et al. |
| 9,629,628 | B2 | 4/2017 | Aranyi |
| 9,629,629 | B2 | 4/2017 | Leimbach et al. |
| 9,629,631 | B2 | 4/2017 | Nicholas et al. |
| 9,629,632 | B2 | 4/2017 | Linder et al. |
| 9,629,652 | B2 | 4/2017 | Mumaw et al. |
| 9,629,814 | B2 | 4/2017 | Widenhouse et al. |
| D785,794 | S | 5/2017 | Magno, Jr. |
| D786,280 | S | 5/2017 | Ma |
| D786,896 | S | 5/2017 | Kim et al. |
| D787,547 | S | 5/2017 | Basargin et al. |
| D788,123 | S | 5/2017 | Shan et al. |
| D788,140 | S | 5/2017 | Hemsley et al. |
| 9,636,091 | B2 | 5/2017 | Beardsley et al. |
| 9,636,111 | B2 | 5/2017 | Wenchell |
| 9,636,112 | B2 | 5/2017 | Penna et al. |
| 9,636,113 | B2 | 5/2017 | Wenchell |
| 9,636,850 | B2 | 5/2017 | Stopek et al. |
| 9,641,122 | B2 | 5/2017 | Romanowich et al. |
| 9,642,620 | B2 | 5/2017 | Baxter, III et al. |
| 9,642,642 | B2 | 5/2017 | Lim |
| 9,649,096 | B2 | 5/2017 | Sholev |
| 9,649,110 | B2 | 5/2017 | Parihar et al. |
| 9,649,111 | B2 | 5/2017 | Shelton, IV et al. |
| 9,649,190 | B2 | 5/2017 | Mathies |
| 9,651,032 | B2 | 5/2017 | Weaver et al. |
| 9,655,613 | B2 | 5/2017 | Schaller |
| 9,655,614 | B2 | 5/2017 | Swensgard et al. |
| 9,655,615 | B2 | 5/2017 | Knodel et al. |
| 9,655,616 | B2 | 5/2017 | Aranyi |
| 9,655,624 | B2 | 5/2017 | Shelton, IV et al. |
| 9,661,991 | B2 | 5/2017 | Glossop |
| 9,662,108 | B2 | 5/2017 | Williams |
| 9,662,110 | B2 | 5/2017 | Huang et al. |
| 9,662,111 | B2 | 5/2017 | Holsten et al. |
| 9,662,116 | B2 | 5/2017 | Smith et al. |
| 9,662,130 | B2 | 5/2017 | Bartels et al. |
| 9,662,131 | B2 | 5/2017 | Omori et al. |
| D788,792 | S | 6/2017 | Alessandri et al. |
| D789,384 | S | 6/2017 | Lin et al. |
| D790,570 | S | 6/2017 | Butcher et al. |
| 9,668,728 | B2 | 6/2017 | Williams et al. |
| 9,668,729 | B2 | 6/2017 | Williams et al. |
| 9,668,732 | B2 | 6/2017 | Patel et al. |
| 9,668,733 | B2 | 6/2017 | Williams |
| 9,668,734 | B2 | 6/2017 | Kostrzewski et al. |
| 9,668,735 | B2 | 6/2017 | Beetel |
| 9,675,344 | B2 | 6/2017 | Combrowski et al. |
| 9,675,348 | B2 | 6/2017 | Smith et al. |
| 9,675,351 | B2 | 6/2017 | Hodgkinson et al. |
| 9,675,354 | B2 | 6/2017 | Weir et al. |
| 9,675,355 | B2 | 6/2017 | Shelton, IV et al. |
| 9,675,368 | B2 | 6/2017 | Guo et al. |
| 9,675,372 | B2 | 6/2017 | Laurent et al. |
| 9,675,375 | B2 | 6/2017 | Houser et al. |
| 9,675,405 | B2 | 6/2017 | Trees et al. |
| 9,675,819 | B2 | 6/2017 | Dunbar et al. |
| 9,681,870 | B2 | 6/2017 | Baxter, III et al. |
| 9,681,873 | B2 | 6/2017 | Smith et al. |
| 9,681,884 | B2 | 6/2017 | Clem et al. |
| 9,687,230 | B2 | 6/2017 | Leimbach et al. |
| 9,687,231 | B2 | 6/2017 | Baxter, III et al. |
| 9,687,232 | B2 | 6/2017 | Shelton, IV et al. |
| 9,687,233 | B2 | 6/2017 | Fernandez et al. |
| 9,687,236 | B2 | 6/2017 | Leimbach et al. |
| 9,687,237 | B2 | 6/2017 | Schmid et al. |
| 9,687,253 | B2 | 6/2017 | Detry et al. |
| 9,689,466 | B2 | 6/2017 | Kanai et al. |
| 9,690,362 | B2 | 6/2017 | Leimbach et al. |
| 9,693,772 | B2 | 7/2017 | Ingmanson et al. |
| 9,693,774 | B2 | 7/2017 | Gettinger et al. |
| 9,693,775 | B2 | 7/2017 | Agarwal et al. |
| 9,693,777 | B2 | 7/2017 | Schellin et al. |
| 9,700,309 | B2 | 7/2017 | Jaworek et al. |
| 9,700,310 | B2 | 7/2017 | Morgan et al. |
| 9,700,312 | B2 | 7/2017 | Kostrzewski et al. |
| 9,700,314 | B2 | 7/2017 | Marczyk |
| 9,700,315 | B2 | 7/2017 | Chen et al. |
| 9,700,317 | B2 | 7/2017 | Aronhalt et al. |
| 9,700,318 | B2 | 7/2017 | Scirica et al. |
| 9,700,319 | B2 | 7/2017 | Motooka et al. |
| 9,700,320 | B2 | 7/2017 | Dinardo et al. |
| 9,700,321 | B2 | 7/2017 | Shelton, IV et al. |
| 9,700,334 | B2 | 7/2017 | Hinman et al. |
| 9,700,381 | B2 | 7/2017 | Amat Girbau |
| 9,702,823 | B2 | 7/2017 | Maher et al. |

(56) References Cited

U.S. PATENT DOCUMENTS 9,706,674 B2 7/2017 Collins et al.
9,706,981 B2 7/2017 Nicholas et al.
9,706,991 B2 7/2017 Hess et al.
9,706,993 B2 7/2017 Hessler et al.
9,707,003 B2 7/2017 Hoell, Jr. et al.
9,707,005 B2 7/2017 Strobl et al.
9,707,026 B2 7/2017 Malackowski et al.
9,707,033 B2 7/2017 Parihar et al.
9,707,043 B2 7/2017 Bozung
9,707,684 B2 7/2017 Ruiz Morales et al.
9,713,466 B2 7/2017 Kostrzewski
9,713,468 B2 7/2017 Harris et al.
9,713,470 B2 7/2017 Scirica et al.
9,713,474 B2 7/2017 Lorenz
D795,919 S 8/2017 Bischoff et al.
9,717,497 B2 8/2017 Zerkle et al.
9,717,498 B2 8/2017 Aranyi et al.
9,718,190 B2 8/2017 Larkin et al.
9,722,236 B2 8/2017 Sathrum
9,724,091 B2 8/2017 Shelton, IV et al.
9,724,092 B2 8/2017 Baxter, III et al.
9,724,094 B2 8/2017 Baber et al.
9,724,095 B2 8/2017 Gupta et al.
9,724,096 B2 8/2017 Thompson et al.
9,724,098 B2 8/2017 Baxter, III et al.
9,724,118 B2 8/2017 Schulte et al.
9,724,163 B2 8/2017 Orban
9,730,692 B2 8/2017 Shelton, IV et al.
9,730,695 B2 8/2017 Leimbach et al.
9,730,697 B2 8/2017 Morgan et al.
9,730,717 B2 8/2017 Katsuki et al.
9,730,757 B2 8/2017 Brudniok
9,731,410 B2 8/2017 Hirabayashi et al.
9,733,663 B2 8/2017 Leimbach et al.
9,737,297 B2 8/2017 Racenet et al.
9,737,298 B2 8/2017 Isbell, Jr.
9,737,299 B2 8/2017 Yan
9,737,301 B2 8/2017 Baber et al.
9,737,302 B2 8/2017 Shelton, IV et al.
9,737,303 B2 8/2017 Shelton, IV et al.
9,737,323 B2 8/2017 Thapliyal et al.
9,737,365 B2 8/2017 Hegeman et al.
9,743,927 B2 8/2017 Whitman
9,743,928 B2 8/2017 Shelton, IV et al.
9,743,929 B2 8/2017 Leimbach et al.
D798,319 S 9/2017 Bergstrand et al.
9,750,498 B2 9/2017 Timm et al.
9,750,499 B2 9/2017 Leimbach et al.
9,750,501 B2 9/2017 Shelton, IV et al.
9,750,502 B2 9/2017 Scirica et al.
9,750,503 B2 9/2017 Milliman
9,750,639 B2 9/2017 Barnes et al.
9,751,176 B2 9/2017 McRoberts et al.
9,757,123 B2 9/2017 Giordano et al.
9,757,124 B2 9/2017 Schellin et al.
9,757,126 B2 9/2017 Cappola
9,757,128 B2 9/2017 Baber et al.
9,757,129 B2 9/2017 Williams
9,757,130 B2 9/2017 Shelton, IV
9,763,662 B2 9/2017 Shelton, IV et al.
9,763,668 B2 9/2017 Whitfield et al.
9,770,245 B2 9/2017 Swayze et al.
9,770,274 B2 9/2017 Pool et al.
D798,886 S 10/2017 Prophete et al.
D800,742 S 10/2017 Rhodes
D800,744 S 10/2017 Jitkoff et al.
D800,766 S 10/2017 Park et al.
D800,904 S 10/2017 Leimbach et al.
9,775,608 B2 10/2017 Aronhalt et al.
9,775,609 B2 10/2017 Shelton, IV et al.
9,775,610 B2 10/2017 Nicholas et al.
9,775,611 B2 10/2017 Kostrzewski
9,775,613 B2 10/2017 Shelton, IV et al.
9,775,614 B2 10/2017 Shelton, IV et al.
9,775,618 B2 10/2017 Bettuchi et al.
9,775,635 B2 10/2017 Takei
9,775,678 B2 10/2017 Lohmeier
9,782,169 B2 10/2017 Kimsey et al.
9,782,170 B2 10/2017 Zemlok et al.
9,782,180 B2 10/2017 Smith et al.
9,782,187 B2 10/2017 Zergiebel et al.
9,782,193 B2 10/2017 Thistle
9,782,214 B2 10/2017 Houser et al.
9,788,834 B2 10/2017 Schmid et al.
9,788,835 B2 10/2017 Morgan et al.
9,788,836 B2 10/2017 Overmyer et al.
9,788,847 B2 10/2017 Jinno
9,788,851 B2 10/2017 Dannaher et al.
9,788,902 B2 10/2017 Inoue et al.
9,795,379 B2 10/2017 Leimbach et al.
9,795,380 B2 10/2017 Shelton, IV et al.
9,795,381 B2 10/2017 Shelton, IV
9,795,382 B2 10/2017 Shelton, IV
9,795,383 B2 10/2017 Aldridge et al.
9,795,384 B2 10/2017 Weaner et al.
9,797,486 B2 10/2017 Zergiebel et al.
9,801,626 B2 10/2017 Parihar et al.
9,801,627 B2 10/2017 Harris et al.
9,801,628 B2 10/2017 Harris et al.
9,801,634 B2 10/2017 Shelton, IV et al.
9,801,679 B2 10/2017 Trees et al.
9,802,033 B2 10/2017 Hibner et al.
9,804,618 B2 10/2017 Leimbach et al.
D803,234 S 11/2017 Day et al.
D803,235 S 11/2017 Markson et al.
D803,850 S 11/2017 Chang et al.
9,808,244 B2 11/2017 Leimbach et al.
9,808,246 B2 11/2017 Shelton, IV et al.
9,808,247 B2 11/2017 Shelton, IV et al.
9,808,248 B2 11/2017 Hoffman
9,808,249 B2 11/2017 Shelton, IV
9,814,460 B2 11/2017 Kimsey et al.
9,814,462 B2 11/2017 Woodard, Jr. et al.
9,814,463 B2 11/2017 Williams et al.
9,814,530 B2 11/2017 Weir et al.
9,814,561 B2 11/2017 Forsell
9,815,118 B1 11/2017 Schmitt et al.
9,820,445 B2 11/2017 Simpson et al.
9,820,737 B2 11/2017 Beardsley et al.
9,820,738 B2 11/2017 Lytle, IV et al.
9,820,741 B2 11/2017 Kostrzewski
9,820,768 B2 11/2017 Gee et al.
9,825,455 B2 11/2017 Sandhu et al.
9,826,976 B2 11/2017 Parihar et al.
9,826,977 B2 11/2017 Leimbach et al.
9,826,978 B2 11/2017 Shelton, IV et al.
9,829,698 B2 11/2017 Haraguchi et al.
D806,108 S 12/2017 Day
9,833,235 B2 12/2017 Penna et al.
9,833,236 B2 12/2017 Shelton, IV et al.
9,833,238 B2 12/2017 Baxter, III et al.
9,833,239 B2 12/2017 Yates et al.
9,833,241 B2 12/2017 Huitema et al.
9,833,242 B2 12/2017 Baxter, III et al.
9,839,420 B2 12/2017 Shelton, IV et al.
9,839,421 B2 12/2017 Zerkle et al.
9,839,422 B2 12/2017 Schellin et al.
9,839,423 B2 12/2017 Vendely et al.
9,839,427 B2 12/2017 Swayze et al.
9,839,428 B2 12/2017 Baxter, III et al.
9,839,429 B2 12/2017 Weisenburgh et al.
9,839,480 B2 12/2017 Pribanic et al.
9,839,481 B2 12/2017 Blumenkranz et al.
9,844,368 B2 12/2017 Boudreaux et al.
9,844,369 B2 12/2017 Huitema et al.
9,844,372 B2 12/2017 Shelton, IV et al.
9,844,373 B2 12/2017 Swayze et al.
9,844,374 B2 12/2017 Lytle, IV et al.
9,844,375 B2 12/2017 Overmyer et al.
9,844,376 B2 12/2017 Baxter, III et al.
9,844,379 B2 12/2017 Shelton, IV et al.
9,848,871 B2 12/2017 Harris et al.
9,848,873 B2 12/2017 Shelton, IV
9,848,875 B2 12/2017 Aronhalt et al.

(56) References Cited

U.S. PATENT DOCUMENTS 9,848,877 B2 12/2017 Shelton, IV et al.
9,850,994 B2 12/2017 Schena
D808,989 S 1/2018 Ayvazian et al.
9,855,039 B2 1/2018 Racenet et al.
9,855,040 B2 1/2018 Kostrzewski
9,855,662 B2 1/2018 Ruiz Morales et al.
9,861,261 B2 1/2018 Shahinian
9,861,359 B2 1/2018 Shelton, IV et al.
9,861,361 B2 1/2018 Aronhalt et al.
9,861,362 B2 1/2018 Whitman et al.
9,861,366 B2 1/2018 Aranyi
9,861,382 B2 1/2018 Smith et al.
9,861,446 B2 1/2018 Lang
9,867,612 B2 1/2018 Parihar et al.
9,867,613 B2 1/2018 Marczyk et al.
9,867,615 B2 1/2018 Fanelli et al.
9,867,617 B2 1/2018 Ma
9,867,618 B2 1/2018 Hall et al.
9,867,620 B2 1/2018 Fischvogt et al.
9,868,198 B2 1/2018 Nicholas et al.
9,872,682 B2 1/2018 Hess et al.
9,872,683 B2 1/2018 Hopkins et al.
9,872,684 B2 1/2018 Hall et al.
9,872,722 B2 1/2018 Lech
9,877,721 B2 1/2018 Schellin et al.
9,877,722 B2 1/2018 Schellin et al.
9,877,723 B2 1/2018 Hall et al.
9,877,776 B2 1/2018 Boudreaux
D810,099 S 2/2018 Riedel
9,883,843 B2 2/2018 Garlow
9,883,860 B2 2/2018 Leimbach et al.
9,883,861 B2 2/2018 Shelton, IV et al.
9,884,456 B2 2/2018 Schellin et al.
9,888,914 B2 2/2018 Martin et al.
9,888,919 B2 2/2018 Leimbach et al.
9,888,921 B2 2/2018 Williams et al.
9,888,924 B2 2/2018 Ebersole et al.
9,889,230 B2 2/2018 Bennett et al.
9,895,147 B2 2/2018 Shelton, IV
9,895,148 B2 2/2018 Shelton, IV et al.
9,895,813 B2 2/2018 Blumenkranz et al.
9,901,339 B2 2/2018 Farascioni
9,901,341 B2 2/2018 Kostrzewski
9,901,342 B2 2/2018 Shelton, IV et al.
9,901,344 B2 2/2018 Moore et al.
9,901,345 B2 2/2018 Moore et al.
9,901,346 B2 2/2018 Moore et al.
9,901,358 B2 2/2018 Faller et al.
9,901,406 B2 2/2018 State et al.
9,901,412 B2 2/2018 Lathrop et al.
D813,899 S 3/2018 Erant et al.
9,907,456 B2 3/2018 Miyoshi
9,907,552 B2 3/2018 Measamer et al.
9,907,553 B2 3/2018 Cole et al.
9,907,600 B2 3/2018 Stulen et al.
9,907,620 B2 3/2018 Shelton, IV et al.
9,913,641 B2 3/2018 Takemoto et al.
9,913,642 B2 3/2018 Leimbach et al.
9,913,644 B2 3/2018 McCuen
9,913,646 B2 3/2018 Shelton, IV
9,913,647 B2 3/2018 Weisenburgh, II et al.
9,913,648 B2 3/2018 Shelton, IV et al.
9,913,694 B2 3/2018 Brisson
9,913,733 B2 3/2018 Piron et al.
9,918,704 B2 3/2018 Shelton, IV et al.
9,918,714 B2 3/2018 Gibbons, Jr.
9,918,715 B2 3/2018 Menn
9,918,716 B2 3/2018 Baxter, III et al.
9,918,717 B2 3/2018 Czernik
9,918,730 B2 3/2018 Trees et al.
9,924,941 B2 3/2018 Burbank
9,924,942 B2 3/2018 Swayze et al.
9,924,943 B2 3/2018 Mohan Pinjala et al.
9,924,944 B2 3/2018 Shelton, IV et al.
9,924,945 B2 3/2018 Zheng et al.
9,924,946 B2 3/2018 Vendely et al.
9,924,947 B2 3/2018 Shelton, IV et al.
9,924,961 B2 3/2018 Shelton, IV et al.
9,931,106 B2 4/2018 Au et al.
9,931,116 B2 4/2018 Racenet et al.
9,931,117 B2 4/2018 Hathaway et al.
9,931,118 B2 4/2018 Shelton, IV et al.
9,931,120 B2 4/2018 Chen et al.
9,936,949 B2 4/2018 Measamer et al.
9,936,950 B2 4/2018 Shelton, IV et al.
9,936,951 B2 4/2018 Hufnagel et al.
9,936,952 B2 4/2018 Demmy
9,936,954 B2 4/2018 Shelton, IV et al.
9,937,626 B2 4/2018 Rockrohr
9,943,309 B2 4/2018 Shelton, IV et al.
9,943,310 B2 4/2018 Harris et al.
9,943,312 B2 4/2018 Posada et al.
9,949,754 B2 4/2018 Newhauser et al.
9,953,193 B2 4/2018 Butler et al.
D819,072 S 5/2018 Clediere
9,955,954 B2 5/2018 Destoumieux et al.
9,955,965 B2 5/2018 Chen et al.
9,955,966 B2 5/2018 Zergiebel
9,956,677 B2 5/2018 Baskar et al.
9,962,129 B2 5/2018 Jerebko et al.
9,962,157 B2 5/2018 Sapre
9,962,158 B2 5/2018 Hall et al.
9,962,159 B2 5/2018 Heinrich et al.
9,962,161 B2 5/2018 Scheib et al.
9,968,354 B2 5/2018 Shelton, IV et al.
9,968,355 B2 5/2018 Shelton, IV et al.
9,968,356 B2 5/2018 Shelton, IV et al.
9,968,397 B2 5/2018 Taylor et al.
9,974,529 B2 5/2018 Shelton, IV et al.
9,974,538 B2 5/2018 Baxter, III et al.
9,974,539 B2 5/2018 Yates et al.
9,974,541 B2 5/2018 Calderoni
9,974,542 B2 5/2018 Hodgkinson
9,980,713 B2 5/2018 Aronhalt et al.
9,980,724 B2 5/2018 Farascioni et al.
9,980,729 B2 5/2018 Moore et al.
9,980,740 B2 5/2018 Krause et al.
9,980,769 B2 5/2018 Trees et al.
D819,680 S 6/2018 Nguyen
D819,682 S 6/2018 Howard et al.
D819,684 S 6/2018 Dart
D820,307 S 6/2018 Jian et al.
D820,867 S 6/2018 Dickens et al.
9,987,000 B2 6/2018 Shelton, IV et al.
9,987,003 B2 6/2018 Timm et al.
9,987,006 B2 6/2018 Morgan et al.
9,987,008 B2 6/2018 Scirica et al.
9,987,095 B2 6/2018 Chowaniec et al.
9,987,097 B2 6/2018 van der Weide et al.
9,987,099 B2 6/2018 Chen et al.
9,993,248 B2 6/2018 Shelton, IV et al.
9,993,258 B2 6/2018 Shelton, IV et al.
9,993,284 B2 6/2018 Boudreaux
9,999,408 B2 6/2018 Boudreaux et al.
9,999,423 B2 6/2018 Schuckmann et al.
9,999,426 B2 6/2018 Moore et al.
9,999,431 B2 6/2018 Shelton, IV et al.
9,999,472 B2 6/2018 Weir et al.
10,004,497 B2 6/2018 Overmyer et al.
10,004,498 B2 6/2018 Morgan et al.
10,004,500 B2 6/2018 Shelton, IV et al.
10,004,501 B2 6/2018 Shelton, IV et al.
10,004,505 B2 6/2018 Moore et al.
10,004,506 B2 6/2018 Shelton, IV et al.
10,004,552 B1 6/2018 Kleyman et al.
D822,206 S 7/2018 Shelton, IV et al.
10,010,322 B2 7/2018 Shelton, IV et al.
10,010,324 B2 7/2018 Huitema et al.
10,010,395 B2 7/2018 Puckett et al.
10,013,049 B2 7/2018 Leimbach et al.
10,016,199 B2 7/2018 Baber et al.
10,016,656 B2 7/2018 Devor et al.
10,022,120 B2 7/2018 Martin et al.
10,022,123 B2 7/2018 Williams et al.

(56) References Cited

U.S. PATENT DOCUMENTS

| | | | |
|---|---|---|---|
| 10,022,125 | B2 | 7/2018 | (Prommersberger) Stopek et al. |
| 10,024,407 | B2 | 7/2018 | Aranyi et al. |
| 10,028,742 | B2 | 7/2018 | Shelton, IV et al. |
| 10,028,743 | B2 | 7/2018 | Shelton, IV et al. |
| 10,028,744 | B2 | 7/2018 | Shelton, IV et al. |
| 10,028,761 | B2 | 7/2018 | Leimbach et al. |
| 10,029,108 | B2 | 7/2018 | Powers et al. |
| 10,029,125 | B2 | 7/2018 | Shapiro et al. |
| 10,034,344 | B2 | 7/2018 | Yoshida |
| 10,034,668 | B2 | 7/2018 | Ebner |
| D826,405 | S | 8/2018 | Shelton, IV et al. |
| 10,039,440 | B2 | 8/2018 | Fenech et al. |
| 10,039,529 | B2 | 8/2018 | Kerr et al. |
| 10,039,532 | B2 | 8/2018 | Srinivas et al. |
| 10,039,545 | B2 | 8/2018 | Sadowski et al. |
| 10,041,822 | B2 | 8/2018 | Zemlok |
| 10,045,769 | B2 | 8/2018 | Aronhalt et al. |
| 10,045,776 | B2 | 8/2018 | Shelton, IV et al. |
| 10,045,778 | B2 | 8/2018 | Yates et al. |
| 10,045,779 | B2 | 8/2018 | Savage et al. |
| 10,045,781 | B2 | 8/2018 | Cropper et al. |
| 10,045,782 | B2 | 8/2018 | Murthy Aravalli |
| 10,045,869 | B2 | 8/2018 | Forsell |
| 10,046,904 | B2 | 8/2018 | Evans et al. |
| 10,052,044 | B2 | 8/2018 | Shelton, IV et al. |
| 10,052,099 | B2 | 8/2018 | Morgan et al. |
| 10,052,100 | B2 | 8/2018 | Morgan et al. |
| 10,052,102 | B2 | 8/2018 | Baxter, III et al. |
| 10,052,104 | B2 | 8/2018 | Shelton, IV et al. |
| 10,052,164 | B2 | 8/2018 | Overmyer |
| 10,058,317 | B2 | 8/2018 | Fan et al. |
| 10,058,327 | B2 | 8/2018 | Weisenburgh, II et al. |
| 10,058,373 | B2 | 8/2018 | Takashino et al. |
| 10,058,395 | B2 | 8/2018 | Devengenzo et al. |
| 10,058,963 | B2 | 8/2018 | Shelton, IV et al. |
| 10,064,620 | B2 | 9/2018 | Gettinger et al. |
| 10,064,621 | B2 | 9/2018 | Kerr et al. |
| 10,064,622 | B2 | 9/2018 | Murthy Aravalli |
| 10,064,624 | B2 | 9/2018 | Shelton, IV et al. |
| 10,064,639 | B2 | 9/2018 | Ishida et al. |
| 10,064,642 | B2 | 9/2018 | Marczyk et al. |
| 10,064,649 | B2 | 9/2018 | Golebieski et al. |
| 10,064,688 | B2 | 9/2018 | Shelton, IV et al. |
| 10,070,861 | B2 | 9/2018 | Spivey et al. |
| 10,070,863 | B2 | 9/2018 | Swayze et al. |
| 10,071,452 | B2 | 9/2018 | Shelton, IV et al. |
| 10,076,325 | B2 | 9/2018 | Huang et al. |
| 10,076,326 | B2 | 9/2018 | Yates et al. |
| 10,076,340 | B2 | 9/2018 | Belagali et al. |
| 10,080,552 | B2 | 9/2018 | Nicholas et al. |
| D830,550 | S | 10/2018 | Miller et al. |
| D831,209 | S | 10/2018 | Huitema et al. |
| D831,676 | S | 10/2018 | Park et al. |
| D832,301 | S | 10/2018 | Smith |
| 10,085,624 | B2 | 10/2018 | Isoda et al. |
| 10,085,643 | B2 | 10/2018 | Bandic et al. |
| 10,085,728 | B2 | 10/2018 | Jogasaki et al. |
| 10,085,746 | B2 | 10/2018 | Fischvogt |
| 10,085,748 | B2 | 10/2018 | Morgan et al. |
| 10,085,749 | B2 | 10/2018 | Cappola et al. |
| 10,085,750 | B2 | 10/2018 | Zergiebel et al. |
| 10,085,751 | B2 | 10/2018 | Overmyer et al. |
| 10,085,754 | B2 | 10/2018 | Sniffin et al. |
| 10,085,806 | B2 | 10/2018 | Hagn et al. |
| 10,092,290 | B2 | 10/2018 | Yigit et al. |
| 10,092,292 | B2 | 10/2018 | Boudreaux et al. |
| 10,098,635 | B2 | 10/2018 | Burbank |
| 10,098,636 | B2 | 10/2018 | Shelton, IV et al. |
| 10,098,640 | B2 | 10/2018 | Bertolero et al. |
| 10,098,642 | B2 | 10/2018 | Baxter, III et al. |
| 10,099,303 | B2 | 10/2018 | Yoshida et al. |
| 10,101,861 | B2 | 10/2018 | Kiyoto |
| 10,105,126 | B2 | 10/2018 | Sauer |
| 10,105,128 | B2 | 10/2018 | Cooper et al. |
| 10,105,136 | B2 | 10/2018 | Yates et al. |
| 10,105,139 | B2 | 10/2018 | Yates et al. |
| 10,105,140 | B2 | 10/2018 | Malinouskas et al. |
| 10,105,142 | B2 | 10/2018 | Baxter, III et al. |
| 10,105,149 | B2 | 10/2018 | Haider et al. |
| 10,106,932 | B2 | 10/2018 | Anderson et al. |
| 10,111,657 | B2 | 10/2018 | McCuen |
| 10,111,658 | B2 | 10/2018 | Chowaniec et al. |
| 10,111,660 | B2 | 10/2018 | Hemmann |
| 10,111,665 | B2 | 10/2018 | Aranyi et al. |
| 10,111,679 | B2 | 10/2018 | Baber et al. |
| 10,111,698 | B2 | 10/2018 | Scheib et al. |
| 10,111,702 | B2 | 10/2018 | Kostrzewski |
| D833,608 | S | 11/2018 | Miller et al. |
| 10,117,649 | B2 | 11/2018 | Baxter, III et al. |
| 10,117,650 | B2 | 11/2018 | Nicholas et al. |
| 10,117,652 | B2 | 11/2018 | Schmid et al. |
| 10,117,653 | B2 | 11/2018 | Leimbach et al. |
| 10,117,654 | B2 | 11/2018 | Ingmanson et al. |
| 10,123,798 | B2 | 11/2018 | Baxter, III et al. |
| 10,123,845 | B2 | 11/2018 | Yeung |
| 10,124,493 | B2 | 11/2018 | Rothfuss et al. |
| 10,130,352 | B2 | 11/2018 | Widenhouse et al. |
| 10,130,359 | B2 | 11/2018 | Hess et al. |
| 10,130,360 | B2 | 11/2018 | Olson et al. |
| 10,130,361 | B2 | 11/2018 | Yates et al. |
| 10,130,363 | B2 | 11/2018 | Huitema et al. |
| 10,130,366 | B2 | 11/2018 | Shelton, IV et al. |
| 10,130,367 | B2 | 11/2018 | Cappola et al. |
| 10,130,382 | B2 | 11/2018 | Gladstone |
| 10,130,738 | B2 | 11/2018 | Shelton, IV et al. |
| 10,130,830 | B2 | 11/2018 | Miret Carceller et al. |
| 10,133,248 | B2 | 11/2018 | Fitzsimmons et al. |
| 10,135,242 | B2 | 11/2018 | Baber et al. |
| 10,136,879 | B2 | 11/2018 | Ross et al. |
| 10,136,887 | B2 | 11/2018 | Shelton, IV et al. |
| 10,136,889 | B2 | 11/2018 | Shelton, IV et al. |
| 10,136,890 | B2 | 11/2018 | Shelton, IV et al. |
| 10,136,891 | B2 | 11/2018 | Shelton, IV et al. |
| 10,136,949 | B2 | 11/2018 | Felder et al. |
| D835,659 | S | 12/2018 | Anzures et al. |
| D836,124 | S | 12/2018 | Fan |
| 10,143,474 | B2 | 12/2018 | Bucciaglia et al. |
| 10,146,423 | B1 | 12/2018 | Reed et al. |
| 10,149,679 | B2 | 12/2018 | Shelton, IV et al. |
| 10,149,680 | B2 | 12/2018 | Parihar et al. |
| 10,149,682 | B2 | 12/2018 | Shelton, IV et al. |
| 10,149,683 | B2 | 12/2018 | Smith et al. |
| 10,149,712 | B2 | 12/2018 | Manwaring et al. |
| 10,152,789 | B2 | 12/2018 | Carnes et al. |
| 10,154,841 | B2 | 12/2018 | Weaner et al. |
| 10,159,481 | B2 | 12/2018 | Whitman et al. |
| 10,159,482 | B2 | 12/2018 | Swayze et al. |
| 10,159,483 | B2 | 12/2018 | Beckman et al. |
| 10,159,506 | B2 | 12/2018 | Boudreaux et al. |
| 10,161,816 | B2 | 12/2018 | Jackson et al. |
| 10,163,065 | B1 | 12/2018 | Koski et al. |
| 10,163,589 | B2 | 12/2018 | Zergiebel et al. |
| 10,164,466 | B2 | 12/2018 | Calderoni |
| D837,244 | S | 1/2019 | Kuo et al. |
| D837,245 | S | 1/2019 | Kuo et al. |
| 10,166,023 | B2 | 1/2019 | Vendely et al. |
| 10,166,025 | B2 | 1/2019 | Leimbach et al. |
| 10,166,026 | B2 | 1/2019 | Shelton, IV et al. |
| 10,172,611 | B2 | 1/2019 | Shelton, IV et al. |
| 10,172,615 | B2 | 1/2019 | Marczyk et al. |
| 10,172,616 | B2 | 1/2019 | Murray et al. |
| 10,172,617 | B2 | 1/2019 | Shelton, IV et al. |
| 10,172,618 | B2 | 1/2019 | Shelton, IV et al. |
| 10,172,619 | B2 | 1/2019 | Harris et al. |
| 10,172,620 | B2 | 1/2019 | Harris et al. |
| 10,172,636 | B2 | 1/2019 | Stulen et al. |
| 10,172,669 | B2 | 1/2019 | Felder et al. |
| 10,175,127 | B2 | 1/2019 | Collins et al. |
| 10,178,992 | B2 | 1/2019 | Wise et al. |
| 10,180,463 | B2 | 1/2019 | Beckman et al. |
| 10,182,813 | B2 | 1/2019 | Leimbach et al. |
| 10,182,815 | B2 | 1/2019 | Williams et al. |
| 10,182,816 | B2 | 1/2019 | Shelton, IV et al. |
| 10,182,818 | B2 | 1/2019 | Hensel et al. |

(56) References Cited

U.S. PATENT DOCUMENTS 10,182,819 B2 1/2019 Shelton, IV
10,182,868 B2 1/2019 Meier et al.
10,188,385 B2 1/2019 Kerr et al.
10,188,389 B2 1/2019 Vendely et al.
10,188,393 B2 1/2019 Smith et al.
10,188,394 B2 1/2019 Shelton, IV et al.
10,190,888 B2 1/2019 Hryb et al.
D839,900 S 2/2019 Gan
D841,667 S 2/2019 Coren
10,194,801 B2 2/2019 Elhawary et al.
10,194,904 B2 2/2019 Viola et al.
10,194,907 B2 2/2019 Marczyk et al.
10,194,908 B2 2/2019 Duque et al.
10,194,910 B2 2/2019 Shelton, IV et al.
10,194,911 B2 2/2019 Miller et al.
10,194,912 B2 2/2019 Scheib et al.
10,194,913 B2 2/2019 Nalagatla et al.
10,194,976 B2 2/2019 Boudreaux
10,194,992 B2 2/2019 Robinson
10,201,348 B2 2/2019 Scheib et al.
10,201,349 B2 2/2019 Leimbach et al.
10,201,363 B2 2/2019 Shelton, IV
10,201,364 B2 2/2019 Leimbach et al.
10,201,365 B2 2/2019 Boudreaux et al.
10,201,381 B2 2/2019 Zergiebel et al.
10,206,605 B2 2/2019 Shelton, IV et al.
10,206,676 B2 2/2019 Shelton, IV
10,206,677 B2 2/2019 Harris et al.
10,206,678 B2 2/2019 Shelton, IV et al.
10,206,748 B2 2/2019 Burbank
10,210,244 B1 2/2019 Branavan et al.
10,211,586 B2 2/2019 Adams et al.
10,213,198 B2 2/2019 Aronhalt et al.
10,213,201 B2 2/2019 Shelton, IV et al.
10,213,202 B2 2/2019 Flanagan et al.
10,213,203 B2 2/2019 Swayze et al.
10,213,204 B2 2/2019 Aranyi et al.
10,213,262 B2 2/2019 Shelton, IV et al.
D842,328 S 3/2019 Jian et al.
10,219,811 B2 3/2019 Haider et al.
10,219,832 B2 3/2019 Bagwell et al.
10,220,522 B2 3/2019 Rockrohr
10,226,239 B2 3/2019 Nicholas et al.
10,226,249 B2 3/2019 Jaworek et al.
10,226,250 B2 3/2019 Beckman et al.
10,226,251 B2 3/2019 Scheib et al.
10,226,274 B2 3/2019 Worrell et al.
10,231,634 B2 3/2019 Zand et al.
10,231,653 B2 3/2019 Bohm et al.
10,231,734 B2 3/2019 Thompson et al.
10,231,794 B2 3/2019 Shelton, IV et al.
10,238,385 B2 3/2019 Yates et al.
10,238,386 B2 3/2019 Overmyer et al.
10,238,387 B2 3/2019 Yates et al.
10,238,389 B2 3/2019 Yates et al.
10,238,390 B2 3/2019 Harris et al.
10,238,391 B2 3/2019 Leimbach et al.
D844,666 S 4/2019 Espeleta et al.
D844,667 S 4/2019 Espeleta et al.
D845,342 S 4/2019 Espeleta et al.
D847,199 S 4/2019 Whitmore
10,244,991 B2 4/2019 Shademan et al.
10,245,027 B2 4/2019 Shelton, IV et al.
10,245,028 B2 4/2019 Shelton, IV et al.
10,245,029 B2 4/2019 Hunter et al.
10,245,030 B2 4/2019 Hunter et al.
10,245,032 B2 4/2019 Shelton, IV
10,245,033 B2 4/2019 Overmyer et al.
10,245,034 B2 4/2019 Shelton, IV et al.
10,245,035 B2 4/2019 Swayze et al.
10,245,038 B2 4/2019 Hopkins et al.
10,245,058 B2 4/2019 Omori et al.
10,251,645 B2 4/2019 Kostrzewski
10,251,648 B2 4/2019 Harris et al.
10,251,649 B2 4/2019 Schellin et al.
10,251,725 B2 4/2019 Valentine et al.
10,258,322 B2 4/2019 Fanton et al.
10,258,330 B2 4/2019 Shelton, IV et al.
10,258,331 B2 4/2019 Shelton, IV et al.
10,258,332 B2 4/2019 Schmid et al.
10,258,333 B2 4/2019 Shelton, IV et al.
10,258,336 B2 4/2019 Baxter, III et al.
10,258,363 B2 4/2019 Worrell et al.
10,258,418 B2 4/2019 Shelton, IV et al.
10,264,797 B2 4/2019 Zhang et al.
10,265,065 B2 4/2019 Shelton, IV et al.
10,265,067 B2 4/2019 Yates et al.
10,265,068 B2 4/2019 Harris et al.
10,265,072 B2 4/2019 Shelton, IV et al.
10,265,073 B2 4/2019 Scheib et al.
10,265,074 B2 4/2019 Shelton, IV et al.
10,265,090 B2 4/2019 Ingmanson et al.
10,271,840 B2 4/2019 Sapre
10,271,844 B2 4/2019 Valentine et al.
10,271,845 B2 4/2019 Shelton, IV
10,271,846 B2 4/2019 Shelton, IV et al.
10,271,847 B2 4/2019 Racenet et al.
10,271,849 B2 4/2019 Vendely et al.
10,271,851 B2 4/2019 Shelton, IV et al.
D847,989 S 5/2019 Shelton, IV et al.
D848,473 S 5/2019 Zhu et al.
D849,046 S 5/2019 Kuo et al.
10,278,696 B2 5/2019 Gurumurthy et al.
10,278,697 B2 5/2019 Shelton, IV et al.
10,278,702 B2 5/2019 Shelton, IV et al.
10,278,703 B2 5/2019 Nativ et al.
10,278,707 B2 5/2019 Thompson et al.
10,278,722 B2 5/2019 Shelton, IV et al.
10,278,780 B2 5/2019 Shelton, IV
10,285,694 B2 5/2019 Viola et al.
10,285,695 B2 5/2019 Jaworek et al.
10,285,699 B2 5/2019 Vendely et al.
10,285,700 B2 5/2019 Scheib
10,285,705 B2 5/2019 Shelton, IV et al.
10,285,724 B2 5/2019 Faller et al.
10,285,750 B2 5/2019 Coulson et al.
10,292,701 B2 5/2019 Scheib et al.
10,292,704 B2 5/2019 Harris et al.
10,292,707 B2 5/2019 Shelton, IV et al.
10,293,100 B2 5/2019 Shelton, IV et al.
10,293,553 B2 5/2019 Racenet et al.
10,299,787 B2 5/2019 Shelton, IV
10,299,788 B2 5/2019 Heinrich et al.
10,299,789 B2 5/2019 Marczyk et al.
10,299,790 B2 5/2019 Beardsley
10,299,792 B2 5/2019 Huitema et al.
10,299,817 B2 5/2019 Shelton, IV et al.
10,299,818 B2 5/2019 Riva
10,299,878 B2 5/2019 Shelton, IV et al.
10,303,851 B2 5/2019 Nguyen et al.
D850,617 S 6/2019 Shelton, IV et al.
D851,676 S 6/2019 Foss et al.
D851,762 S 6/2019 Shelton, IV et al.
10,307,159 B2 6/2019 Harris et al.
10,307,160 B2 6/2019 Vendely et al.
10,307,161 B2 6/2019 Jankowski
10,307,163 B2 6/2019 Moore et al.
10,307,170 B2 6/2019 Parfett et al.
10,307,202 B2 6/2019 Smith et al.
10,314,559 B2 6/2019 Razzaque et al.
10,314,577 B2 6/2019 Laurent et al.
10,314,578 B2 6/2019 Leimbach et al.
10,314,579 B2 6/2019 Chowaniec et al.
10,314,580 B2 6/2019 Scheib et al.
10,314,582 B2 6/2019 Shelton, IV et al.
10,314,584 B2 6/2019 Scirica et al.
10,314,587 B2 6/2019 Harris et al.
10,314,588 B2 6/2019 Turner et al.
10,314,589 B2 6/2019 Shelton, IV et al.
10,314,590 B2 6/2019 Shelton, IV et al.
10,315,566 B2 6/2019 Choi et al.
10,321,907 B2 6/2019 Shelton, IV et al.
10,321,909 B2 6/2019 Shelton, IV et al.
10,321,927 B2 6/2019 Hinman

(56) References Cited

U.S. PATENT DOCUMENTS 10,327,743 B2 6/2019 St. Goar et al.
10,327,764 B2 6/2019 Harris et al.
10,327,765 B2 6/2019 Timm et al.
10,327,767 B2 6/2019 Shelton, IV et al.
10,327,769 B2 6/2019 Overmyer et al.
10,327,776 B2 6/2019 Harris et al.
10,327,777 B2 6/2019 Harris et al.
D854,032 S 7/2019 Jones et al.
D854,151 S 7/2019 Shelton, IV et al.
10,335,144 B2 7/2019 Shelton, IV et al.
10,335,145 B2 7/2019 Harris et al.
10,335,147 B2 7/2019 Rector et al.
10,335,148 B2 7/2019 Shelton, IV et al.
10,335,149 B2 7/2019 Baxter, III et al.
10,335,150 B2 7/2019 Shelton, IV
10,335,151 B2 7/2019 Shelton, IV et al.
10,337,148 B2 7/2019 Rouse et al.
10,342,533 B2 7/2019 Shelton, IV et al.
10,342,535 B2 7/2019 Scheib et al.
10,342,541 B2 7/2019 Shelton, IV et al.
10,342,543 B2 7/2019 Shelton, IV et al.
10,342,623 B2 7/2019 Huelman et al.
10,349,937 B2 7/2019 Williams
10,349,939 B2 7/2019 Shelton, IV et al.
10,349,941 B2 7/2019 Marczyk et al.
10,349,963 B2 7/2019 Fiksen et al.
10,350,016 B2 7/2019 Burbank et al.
10,357,246 B2 7/2019 Shelton, IV et al.
10,357,247 B2 7/2019 Shelton, IV et al.
10,357,248 B2 7/2019 Dalessandro et al.
10,357,252 B2 7/2019 Harris et al.
10,363,031 B2 7/2019 Alexander, III et al.
10,363,033 B2 7/2019 Timm et al.
10,363,036 B2 7/2019 Yates et al.
10,363,037 B2 7/2019 Aronhalt et al.
D855,634 S 8/2019 Kim
D856,359 S 8/2019 Huang et al.
10,368,838 B2 8/2019 Williams et al.
10,368,861 B2 8/2019 Baxter, III et al.
10,368,863 B2 8/2019 Timm et al.
10,368,864 B2 8/2019 Harris et al.
10,368,865 B2 8/2019 Harris et al.
10,368,866 B2 8/2019 Wang et al.
10,368,867 B2 8/2019 Harris et al.
10,368,892 B2 8/2019 Stulen et al.
10,374,544 B2 8/2019 Yokoyama et al.
10,376,263 B2 8/2019 Morgan et al.
10,383,626 B2 8/2019 Soltz
10,383,628 B2 8/2019 Kang et al.
10,383,629 B2 8/2019 Ross et al.
10,383,630 B2 8/2019 Shelton, IV et al.
10,383,631 B2 8/2019 Collings et al.
10,383,633 B2 8/2019 Shelton, IV et al.
10,383,634 B2 8/2019 Shelton, IV et al.
10,390,823 B2 8/2019 Shelton, IV et al.
10,390,825 B2 8/2019 Shelton, IV et al.
10,390,828 B2 8/2019 Vendely et al.
10,390,829 B2 8/2019 Eckert et al.
10,390,830 B2 8/2019 Schulz
10,390,841 B2 8/2019 Shelton, IV et al.
10,390,897 B2 8/2019 Kostrzewski
D859,466 S 9/2019 Okada et al.
D860,219 S 9/2019 Rasmussen et al.
D861,035 S 9/2019 Park et al.
10,398,433 B2 9/2019 Boudreaux et al.
10,398,434 B2 9/2019 Shelton, IV et al.
10,398,436 B2 9/2019 Shelton, IV et al.
10,398,460 B2 9/2019 Overmyer
10,404,136 B2 9/2019 Oktavec et al.
10,405,854 B2 9/2019 Schmid et al.
10,405,857 B2 9/2019 Shelton, IV et al.
10,405,859 B2 9/2019 Harris et al.
10,405,863 B2 9/2019 Wise et al.
10,405,914 B2 9/2019 Manwaring et al.
10,405,932 B2 9/2019 Overmyer
10,405,937 B2 9/2019 Black et al.
10,413,155 B2 9/2019 Inoue
10,413,291 B2 9/2019 Worthington et al.
10,413,293 B2 9/2019 Shelton, IV et al.
10,413,294 B2 9/2019 Shelton, IV et al.
10,413,297 B2 9/2019 Harris et al.
10,413,370 B2 9/2019 Yates et al.
10,413,373 B2 9/2019 Yates et al.
10,420,548 B2 9/2019 Whitman et al.
10,420,549 B2 9/2019 Yates et al.
10,420,550 B2 9/2019 Shelton, IV
10,420,551 B2 9/2019 Calderoni
10,420,552 B2 9/2019 Shelton, IV et al.
10,420,553 B2 9/2019 Shelton, IV et al.
10,420,554 B2 9/2019 Collings et al.
10,420,555 B2 9/2019 Shelton, IV et al.
10,420,558 B2 9/2019 Nalagatla et al.
10,420,559 B2 9/2019 Marczyk et al.
10,420,560 B2 9/2019 Shelton, IV et al.
10,420,561 B2 9/2019 Shelton, IV et al.
10,420,577 B2 9/2019 Chowaniec et al.
D861,707 S 10/2019 Yang
D862,518 S 10/2019 Niven et al.
D863,343 S 10/2019 Mazlish et al.
D864,388 S 10/2019 Barber
D865,174 S 10/2019 Auld et al.
D865,175 S 10/2019 Widenhouse et al.
10,426,463 B2 10/2019 Shelton, IV et al.
10,426,466 B2 10/2019 Contini et al.
10,426,467 B2 10/2019 Miller et al.
10,426,468 B2 10/2019 Contini et al.
10,426,469 B2 10/2019 Shelton, IV et al.
10,426,471 B2 10/2019 Shelton, IV et al.
10,426,476 B2 10/2019 Harris et al.
10,426,477 B2 10/2019 Harris et al.
10,426,478 B2 10/2019 Shelton, IV et al.
10,426,481 B2 10/2019 Aronhalt et al.
10,426,555 B2 10/2019 Crowley et al.
10,433,837 B2 10/2019 Worthington et al.
10,433,839 B2 10/2019 Scheib et al.
10,433,840 B2 10/2019 Shelton, IV et al.
10,433,842 B2 10/2019 Amariglio et al.
10,433,844 B2 10/2019 Shelton, IV et al.
10,433,845 B2 10/2019 Baxter, III et al.
10,433,846 B2 10/2019 Vendely et al.
10,433,849 B2 10/2019 Shelton, IV et al.
10,433,918 B2 10/2019 Shelton, IV et al.
10,441,279 B2 10/2019 Shelton, IV et al.
10,441,280 B2 10/2019 Timm et al.
10,441,281 B2 10/2019 Shelton, IV et al.
10,441,285 B2 10/2019 Shelton, IV et al.
10,441,286 B2 10/2019 Shelton, IV et al.
10,441,345 B2 10/2019 Aldridge et al.
10,441,369 B2 10/2019 Shelton, IV et al.
10,448,948 B2 10/2019 Shelton, IV et al.
10,448,950 B2 10/2019 Shelton, IV et al.
10,448,952 B2 10/2019 Shelton, IV et al.
10,456,122 B2 10/2019 Koltz et al.
10,456,132 B2 10/2019 Gettinger et al.
10,456,133 B2 10/2019 Yates et al.
10,456,137 B2 10/2019 Vendely et al.
10,456,140 B2 10/2019 Shelton, IV et al.
D865,796 S 11/2019 Xu et al.
10,463,367 B2 11/2019 Kostrzewski et al.
10,463,369 B2 11/2019 Shelton, IV et al.
10,463,370 B2 11/2019 Yates et al.
10,463,371 B2 11/2019 Kostrzewski
10,463,372 B2 11/2019 Shelton, IV et al.
10,463,373 B2 11/2019 Mozdzierz et al.
10,463,382 B2 11/2019 Ingmanson et al.
10,463,383 B2 11/2019 Shelton, IV et al.
10,463,384 B2 11/2019 Shelton, IV et al.
10,470,762 B2 11/2019 Leimbach et al.
10,470,763 B2 11/2019 Yates et al.
10,470,764 B2 11/2019 Baxter, III et al.
10,470,767 B2 11/2019 Gleiman et al.
10,470,768 B2 11/2019 Harris et al.
10,470,769 B2 11/2019 Shelton, IV et al.
10,471,282 B2 11/2019 Kirk et al.

(56) References Cited

U.S. PATENT DOCUMENTS 10,471,576 B2 11/2019 Totsu
10,471,607 B2 11/2019 Butt et al.
10,478,181 B2 11/2019 Shelton, IV et al.
10,478,182 B2 11/2019 Taylor
10,478,185 B2 11/2019 Nicholas
10,478,187 B2 11/2019 Shelton, IV et al.
10,478,188 B2 11/2019 Harris et al.
10,478,189 B2 11/2019 Bear et al.
10,478,190 B2 11/2019 Miller et al.
10,478,207 B2 11/2019 Lathrop
10,482,292 B2 11/2019 Clouser et al.
10,485,536 B2 11/2019 Ming et al.
10,485,537 B2 11/2019 Yates et al.
10,485,539 B2 11/2019 Shelton, IV et al.
10,485,541 B2 11/2019 Shelton, IV et al.
10,485,542 B2 11/2019 Shelton, IV et al.
10,485,543 B2 11/2019 Shelton, IV et al.
10,485,546 B2 11/2019 Shelton, IV et al.
10,485,547 B2 11/2019 Shelton, IV et al.
D869,655 S 12/2019 Shelton, IV et al.
D870,742 S 12/2019 Cornell
10,492,783 B2 12/2019 Shelton, IV et al.
10,492,785 B2 12/2019 Overmyer et al.
10,492,787 B2 12/2019 Smith et al.
10,492,814 B2 12/2019 Snow et al.
10,492,847 B2 12/2019 Godara et al.
10,492,851 B2 12/2019 Hughett, Sr. et al.
10,498,269 B2 12/2019 Zemlok et al.
10,499,890 B2 12/2019 Shelton, IV et al.
10,499,914 B2 12/2019 Huang et al.
10,499,917 B2 12/2019 Scheib et al.
10,499,918 B2 12/2019 Schellin et al.
10,500,000 B2 12/2019 Swayze et al.
10,500,004 B2 12/2019 Hanuschik et al.
10,500,309 B2 12/2019 Shah et al.
10,507,034 B2 12/2019 Timm
10,508,720 B2 12/2019 Nicholas
10,512,461 B2 12/2019 Gupta et al.
10,512,462 B2 12/2019 Felder et al.
10,512,464 B2 12/2019 Park et al.
10,517,590 B2 12/2019 Giordano et al.
10,517,592 B2 12/2019 Shelton, IV et al.
10,517,594 B2 12/2019 Shelton, IV et al.
10,517,595 B2 12/2019 Hunter et al.
10,517,596 B2 12/2019 Hunter et al.
10,517,599 B2 12/2019 Baxter, III et al.
10,517,682 B2 12/2019 Giordano et al.
10,524,784 B2 1/2020 Kostrzewski
10,524,787 B2 1/2020 Shelton, IV et al.
10,524,788 B2 1/2020 Vendely et al.
10,524,789 B2 1/2020 Swayze et al.
10,524,790 B2 1/2020 Shelton, IV et al.
10,524,795 B2 1/2020 Nalagatla et al.
10,524,870 B2 1/2020 Saraliev et al.
10,531,874 B2 1/2020 Morgan et al.
10,531,887 B2 1/2020 Shelton, IV et al.
10,537,324 B2 1/2020 Shelton, IV et al.
10,537,325 B2 1/2020 Bakos et al.
10,537,351 B2 1/2020 Shelton, IV et al.
10,542,908 B2 1/2020 Mei et al.
10,542,974 B2 1/2020 Yates et al.
10,542,976 B2 1/2020 Calderoni et al.
10,542,978 B2 1/2020 Chowaniec et al.
10,542,979 B2 1/2020 Shelton, IV et al.
10,542,982 B2 1/2020 Beckman et al.
10,542,985 B2 1/2020 Zhan et al.
10,542,988 B2 1/2020 Schellin et al.
10,542,991 B2 1/2020 Shelton, IV et al.
10,548,504 B2 2/2020 Shelton, IV et al.
10,548,593 B2 2/2020 Shelton, IV et al.
10,548,600 B2 2/2020 Shelton, IV et al.
10,548,673 B2 2/2020 Harris et al.
10,561,412 B2 2/2020 Bookbinder et al.
10,561,418 B2 2/2020 Richard et al.
10,561,419 B2 2/2020 Beardsley
10,561,420 B2 2/2020 Harris et al.
10,561,422 B2 2/2020 Schellin et al.
10,561,432 B2 2/2020 Estrella et al.
10,561,474 B2 2/2020 Adams et al.
10,562,160 B2 2/2020 Iwata et al.
10,568,493 B2 2/2020 Blase et al.
10,568,621 B2 2/2020 Shelton, IV et al.
10,568,624 B2 2/2020 Shelton, IV et al.
10,568,625 B2 2/2020 Harris et al.
10,568,626 B2 2/2020 Shelton, IV et al.
10,568,629 B2 2/2020 Shelton, IV et al.
10,568,632 B2 2/2020 Miller et al.
10,568,652 B2 2/2020 Hess et al.
10,569,071 B2 2/2020 Harris et al.
D879,808 S 3/2020 Harris et al.
D879,809 S 3/2020 Harris et al.
10,575,868 B2 3/2020 Hall et al.
10,580,320 B2 3/2020 Kamiguchi et al.
10,582,928 B2 3/2020 Hunter et al.
10,588,231 B2 3/2020 Sgroi, Jr. et al.
10,588,623 B2 3/2020 Schmid et al.
10,588,625 B2 3/2020 Weaner et al.
10,588,626 B2 3/2020 Overmyer et al.
10,588,629 B2 3/2020 Malinouskas et al.
10,588,630 B2 3/2020 Shelton, IV et al.
10,588,631 B2 3/2020 Shelton, IV et al.
10,588,632 B2 3/2020 Shelton, IV et al.
10,588,633 B2 3/2020 Shelton, IV et al.
10,589,410 B2 3/2020 Aho
10,595,835 B2 3/2020 Kerr et al.
10,595,862 B2 3/2020 Shelton, IV et al.
10,595,882 B2 3/2020 Parfett et al.
10,595,887 B2 3/2020 Shelton, IV et al.
10,595,929 B2 3/2020 Boudreaux et al.
10,603,036 B2 3/2020 Hunter et al.
10,603,039 B2 3/2020 Vendely et al.
10,603,041 B2 3/2020 Miller et al.
10,603,117 B2 3/2020 Schings et al.
10,603,128 B2 3/2020 Zergiebel et al.
D882,783 S 4/2020 Shelton, IV et al.
10,610,224 B2 4/2020 Shelton, IV et al.
10,610,225 B2 4/2020 Reed et al.
10,610,236 B2 4/2020 Baril
10,610,313 B2 4/2020 Bailey et al.
10,610,346 B2 4/2020 Schwartz
10,617,411 B2 4/2020 Williams
10,617,412 B2 4/2020 Shelton, IV et al.
10,617,413 B2 4/2020 Shelton, IV et al.
10,617,414 B2 4/2020 Shelton, IV et al.
10,617,416 B2 4/2020 Leimbach et al.
10,617,417 B2 4/2020 Baxter, III et al.
10,617,418 B2 4/2020 Barton et al.
10,617,420 B2 4/2020 Shelton, IV et al.
10,617,438 B2 4/2020 O'Keefe et al.
10,624,616 B2 4/2020 Mukherjee et al.
10,624,630 B2 4/2020 Deville et al.
10,624,633 B2 4/2020 Shelton, IV et al.
10,624,634 B2 4/2020 Shelton, IV et al.
10,624,635 B2 4/2020 Harris et al.
10,624,709 B2 4/2020 Remm
10,624,861 B2 4/2020 Widenhouse et al.
10,625,062 B2 4/2020 Matlock et al.
10,631,857 B2 4/2020 Kostrzewski
10,631,858 B2 4/2020 Burbank
10,631,859 B2 4/2020 Shelton, IV et al.
10,631,860 B2 4/2020 Bakos et al.
10,636,104 B2 4/2020 Mazar et al.
10,639,018 B2 5/2020 Shelton, IV et al.
10,639,034 B2 5/2020 Harris et al.
10,639,035 B2 5/2020 Shelton, IV et al.
10,639,036 B2 5/2020 Yates et al.
10,639,037 B2 5/2020 Shelton, IV et al.
10,639,089 B2 5/2020 Manwaring et al.
10,639,115 B2 5/2020 Shelton, IV et al.
10,642,633 B1 5/2020 Chopra et al.
10,645,905 B2 5/2020 Gandola et al.
10,646,220 B2 5/2020 Shelton, IV et al.
10,646,292 B2 5/2020 Solomon et al.
10,653,413 B2 5/2020 Worthington et al.

(56) References Cited

U.S. PATENT DOCUMENTS 10,653,417 B2 5/2020 Shelton, IV et al.
10,653,435 B2 5/2020 Shelton, IV et al.
10,660,640 B2 5/2020 Yates et al.
10,667,408 B2 5/2020 Sgroi, Jr. et al.
D888,953 S 6/2020 Baxter, III et al.
10,667,808 B2 6/2020 Baxter, III et al.
10,667,809 B2 6/2020 Bakos et al.
10,667,810 B2 6/2020 Shelton, IV et al.
10,667,811 B2 6/2020 Harris et al.
10,667,818 B2 6/2020 McLain et al.
10,674,895 B2 6/2020 Yeung et al.
10,675,021 B2 6/2020 Harris et al.
10,675,024 B2 6/2020 Shelton, IV et al.
10,675,025 B2 6/2020 Swayze et al.
10,675,026 B2 6/2020 Harris et al.
10,675,028 B2 6/2020 Shelton, IV et al.
10,675,035 B2 6/2020 Zingman
10,675,080 B2 6/2020 Woloszko et al.
10,675,102 B2 6/2020 Forgione et al.
10,677,035 B2 6/2020 Balan et al.
10,682,134 B2 6/2020 Shelton, IV et al.
10,682,136 B2 6/2020 Harris et al.
10,682,137 B2 6/2020 Stokes et al.
10,682,138 B2 6/2020 Shelton, IV et al.
10,682,141 B2 6/2020 Moore et al.
10,682,142 B2 6/2020 Shelton, IV et al.
10,687,806 B2 6/2020 Shelton, IV et al.
10,687,809 B2 6/2020 Shelton, IV et al.
10,687,810 B2 6/2020 Shelton, IV et al.
10,687,812 B2 6/2020 Shelton, IV et al.
10,687,813 B2 6/2020 Shelton, IV et al.
10,687,817 B2 6/2020 Shelton, IV et al.
10,687,819 B2 6/2020 Stokes et al.
10,687,904 B2 6/2020 Harris et al.
10,695,053 B2 6/2020 Hess et al.
10,695,055 B2 6/2020 Shelton, IV et al.
10,695,057 B2 6/2020 Shelton, IV et al.
10,695,058 B2 6/2020 Lytle, IV et al.
10,695,062 B2 6/2020 Leimbach et al.
10,695,063 B2 6/2020 Morgan et al.
10,695,074 B2 6/2020 Carusillo
10,695,081 B2 6/2020 Shelton, IV et al.
10,695,119 B2 6/2020 Smith
10,695,123 B2 6/2020 Allen, IV
10,695,187 B2 6/2020 Moskowitz et al.
D890,784 S 7/2020 Shelton, IV et al.
10,702,266 B2 7/2020 Parihar et al.
10,702,267 B2 7/2020 Hess et al.
10,702,270 B2 7/2020 Shelton, IV et al.
10,702,271 B2 7/2020 Aranyi et al.
10,705,660 B2 7/2020 Xiao
10,709,446 B2 7/2020 Harris et al.
10,709,468 B2 7/2020 Shelton, IV et al.
10,709,469 B2 7/2020 Shelton, IV et al.
10,709,496 B2 7/2020 Moua et al.
10,716,563 B2 7/2020 Shelton, IV et al.
10,716,565 B2 7/2020 Shelton, IV et al.
10,716,568 B2 7/2020 Hall et al.
10,716,614 B2 7/2020 Yates et al.
10,717,179 B2 7/2020 Koenig et al.
10,722,232 B2 7/2020 Yates et al.
10,722,233 B2 7/2020 Wellman
10,722,292 B2 7/2020 Arya et al.
10,722,293 B2 7/2020 Arya et al.
10,722,317 B2 7/2020 Ward et al.
D893,717 S 8/2020 Messerly et al.
10,729,432 B2 8/2020 Shelton, IV et al.
10,729,434 B2 8/2020 Harris et al.
10,729,435 B2 8/2020 Richard
10,729,436 B2 8/2020 Shelton, IV et al.
10,729,443 B2 8/2020 Cabrera et al.
10,729,458 B2 8/2020 Stoddard et al.
10,729,501 B2 8/2020 Leimbach et al.
10,729,509 B2 8/2020 Shelton, IV et al.
10,736,616 B2 8/2020 Scheib et al.
10,736,628 B2 8/2020 Yates et al.
10,736,629 B2 8/2020 Shelton, IV et al.
10,736,630 B2 8/2020 Huang et al.
10,736,633 B2 8/2020 Vendely et al.
10,736,634 B2 8/2020 Shelton, IV et al.
10,736,636 B2 8/2020 Baxter, III et al.
10,736,644 B2 8/2020 Windolf et al.
10,736,702 B2 8/2020 Harris et al.
10,737,398 B2 8/2020 Remirez et al.
10,743,849 B2 8/2020 Shelton, IV et al.
10,743,850 B2 8/2020 Hibner et al.
10,743,851 B2 8/2020 Swayze et al.
10,743,868 B2 8/2020 Shelton, IV et al.
10,743,870 B2 8/2020 Hall et al.
10,743,872 B2 8/2020 Leimbach et al.
10,743,873 B2 8/2020 Overmyer et al.
10,743,874 B2 8/2020 Shelton, IV et al.
10,743,875 B2 8/2020 Shelton, IV et al.
10,743,877 B2 8/2020 Shelton, IV et al.
10,743,930 B2 8/2020 Nagtegaal
10,751,048 B2 8/2020 Whitman et al.
10,751,053 B2 8/2020 Harris et al.
10,751,076 B2 8/2020 Laurent et al.
10,751,138 B2 8/2020 Giordano et al.
10,758,229 B2 9/2020 Shelton, IV et al.
10,758,230 B2 9/2020 Shelton, IV et al.
10,758,232 B2 9/2020 Shelton, IV et al.
10,758,233 B2 9/2020 Scheib et al.
10,758,259 B2 9/2020 Demmy et al.
10,765,425 B2 9/2020 Yates et al.
10,765,427 B2 9/2020 Shelton, IV et al.
10,765,429 B2 9/2020 Leimbach et al.
10,765,430 B2 9/2020 Wixey
10,765,432 B2 9/2020 Moore et al.
10,765,442 B2 9/2020 Strobl
10,772,625 B2 9/2020 Shelton, IV et al.
10,772,628 B2 9/2020 Chen et al.
10,772,629 B2 9/2020 Shelton, IV et al.
10,772,630 B2 9/2020 Wixey
10,772,631 B2 9/2020 Zergiebel et al.
10,772,632 B2 9/2020 Kostrzewski
10,772,651 B2 9/2020 Shelton, IV et al.
10,779,818 B2 9/2020 Zemlok et al.
10,779,820 B2 9/2020 Harris et al.
10,779,821 B2 9/2020 Harris et al.
10,779,822 B2 9/2020 Yates et al.
10,779,823 B2 9/2020 Shelton, IV et al.
10,779,824 B2 9/2020 Shelton, IV et al.
10,779,825 B2 9/2020 Shelton, IV et al.
10,779,826 B2 9/2020 Shelton, IV et al.
10,779,903 B2 9/2020 Wise et al.
10,780,539 B2 9/2020 Shelton, IV et al.
10,786,248 B2 9/2020 Rousseau et al.
10,786,253 B2 9/2020 Shelton, IV et al.
10,786,255 B2 9/2020 Hodgkinson et al.
10,792,038 B2 10/2020 Becerra et al.
10,796,471 B2 10/2020 Leimbach et al.
10,799,240 B2 10/2020 Shelton, IV et al.
10,799,306 B2 10/2020 Robinson et al.
10,806,448 B2 10/2020 Shelton, IV et al.
10,806,449 B2 10/2020 Shelton, IV et al.
10,806,450 B2 10/2020 Yates et al.
10,806,451 B2 10/2020 Harris et al.
10,806,453 B2 10/2020 Chen et al.
10,806,479 B2 10/2020 Shelton, IV et al.
10,813,638 B2 10/2020 Shelton, IV et al.
10,813,639 B2 10/2020 Shelton, IV et al.
10,813,640 B2 10/2020 Adams et al.
10,813,641 B2 10/2020 Setser et al.
10,813,683 B2 10/2020 Baxter, III et al.
10,813,705 B2 10/2020 Hares et al.
10,813,710 B2 10/2020 Grubbs
10,820,939 B2 11/2020 Sartor
10,828,028 B2 11/2020 Harris et al.
10,828,030 B2 11/2020 Weir et al.
10,828,032 B2 11/2020 Leimbach et al.
10,828,033 B2 11/2020 Shelton, IV et al.
10,828,089 B2 11/2020 Clark et al.
10,835,245 B2 11/2020 Swayze et al.

(56) References Cited

U.S. PATENT DOCUMENTS 10,835,246 B2 11/2020 Shelton, IV et al.
10,835,247 B2 11/2020 Shelton, IV et al.
10,835,249 B2 11/2020 Schellin et al.
10,835,251 B2 11/2020 Shelton, IV et al.
10,835,330 B2 11/2020 Shelton, IV et al.
10,842,357 B2 11/2020 Moskowitz et al.
10,842,473 B2 11/2020 Scheib et al.
10,842,488 B2 11/2020 Swayze et al.
10,842,489 B2 11/2020 Shelton, IV
10,842,490 B2 11/2020 DiNardo et al.
10,842,491 B2 11/2020 Shelton, IV et al.
10,842,492 B2 11/2020 Shelton, IV et al.
D904,612 S 12/2020 Wynn et al.
D904,613 S 12/2020 Wynn et al.
D906,355 S 12/2020 Messerly et al.
10,849,621 B2 12/2020 Whitfield et al.
10,849,623 B2 12/2020 Dunki-Jacobs et al.
10,849,697 B2 12/2020 Yates et al.
10,856,866 B2 12/2020 Shelton, IV et al.
10,856,867 B2 12/2020 Shelton, IV et al.
10,856,868 B2 12/2020 Shelton, IV et al.
10,856,869 B2 12/2020 Shelton, IV et al.
10,856,870 B2 12/2020 Harris et al.
10,863,981 B2 12/2020 Overmyer et al.
10,863,984 B2 12/2020 Shelton, IV et al.
10,863,986 B2 12/2020 Yates et al.
10,869,663 B2 12/2020 Shelton, IV et al.
10,869,664 B2 12/2020 Shelton, IV
10,869,665 B2 12/2020 Shelton, IV et al.
10,869,666 B2 12/2020 Shelton, IV et al.
10,869,669 B2 12/2020 Shelton, IV et al.
10,874,290 B2 12/2020 Walen et al.
10,874,391 B2 12/2020 Shelton, IV et al.
10,874,392 B2 12/2020 Scirica et al.
10,874,393 B2 12/2020 Satti, III et al.
10,874,396 B2 12/2020 Moore et al.
10,874,399 B2 12/2020 Zhang
10,879,275 B2 12/2020 Li et al.
D907,647 S 1/2021 Siebel et al.
D907,648 S 1/2021 Siebel et al.
D908,216 S 1/2021 Messerly et al.
10,881,395 B2 1/2021 Merchant et al.
10,881,396 B2 1/2021 Shelton, IV et al.
10,881,399 B2 1/2021 Shelton, IV et al.
10,881,401 B2 1/2021 Baber et al.
10,881,446 B2 1/2021 Strobl
10,888,318 B2 1/2021 Parihar et al.
10,888,321 B2 1/2021 Shelton, IV et al.
10,888,322 B2 1/2021 Morgan et al.
10,888,323 B2 1/2021 Chen et al.
10,888,325 B2 1/2021 Harris et al.
10,888,328 B2 1/2021 Shelton, IV et al.
10,888,329 B2 1/2021 Moore et al.
10,888,330 B2 1/2021 Moore et al.
10,888,369 B2 1/2021 Messerly et al.
10,892,899 B2 1/2021 Shelton, IV et al.
10,893,853 B2 1/2021 Shelton, IV et al.
10,893,863 B2 1/2021 Shelton, IV et al.
10,893,864 B2 1/2021 Harris et al.
10,893,867 B2 1/2021 Leimbach et al.
10,898,183 B2 1/2021 Shelton, IV et al.
10,898,184 B2 1/2021 Yates et al.
10,898,185 B2 1/2021 Overmyer et al.
10,898,186 B2 1/2021 Bakos et al.
10,898,190 B2 1/2021 Yates et al.
10,898,193 B2 1/2021 Shelton, IV et al.
10,898,194 B2 1/2021 Moore et al.
10,898,195 B2 1/2021 Moore et al.
10,903,685 B2 1/2021 Yates et al.
D910,847 S 2/2021 Shelton, IV et al.
10,905,415 B2 2/2021 DiNardo et al.
10,905,418 B2 2/2021 Shelton, IV et al.
10,905,420 B2 2/2021 Jasemian et al.
10,905,422 B2 2/2021 Bakos et al.
10,905,423 B2 2/2021 Baber et al.
10,905,426 B2 2/2021 Moore et al.
10,905,427 B2 2/2021 Moore et al.
10,911,515 B2 2/2021 Biasi et al.
10,912,559 B2 2/2021 Harris et al.
10,912,562 B2 2/2021 Dunki-Jacobs et al.
10,912,575 B2 2/2021 Shelton, IV et al.
10,918,364 B2 2/2021 Applegate et al.
10,918,380 B2 2/2021 Morgan et al.
10,918,385 B2 2/2021 Overmyer et al.
10,918,386 B2 2/2021 Shelton, IV et al.
10,919,156 B2 2/2021 Roberts et al.
10,925,600 B2 2/2021 McCuen
10,925,605 B2 2/2021 Moore et al.
D914,878 S 3/2021 Shelton, IV et al.
10,932,772 B2 3/2021 Shelton, IV et al.
10,932,774 B2 3/2021 Shelton, IV
10,932,775 B2 3/2021 Shelton, IV et al.
10,932,778 B2 3/2021 Smith et al.
10,932,779 B2 3/2021 Vendely et al.
10,932,784 B2 3/2021 Mozdzierz et al.
10,932,804 B2 3/2021 Scheib et al.
10,932,806 B2 3/2021 Shelton, IV et al.
10,932,872 B2 3/2021 Shelton, IV et al.
10,944,728 B2 3/2021 Wiener et al.
10,945,727 B2 3/2021 Shelton, IV et al.
10,945,728 B2 3/2021 Morgan et al.
10,945,729 B2 3/2021 Shelton, IV et al.
10,945,731 B2 3/2021 Baxter, III et al.
10,952,708 B2 3/2021 Scheib et al.
10,952,726 B2 3/2021 Chowaniec
10,952,727 B2 3/2021 Giordano et al.
10,952,728 B2 3/2021 Shelton, IV et al.
10,952,759 B2 3/2021 Messerly et al.
10,952,767 B2 3/2021 Kostrzewski et al.
10,959,722 B2 3/2021 Morgan et al.
10,959,725 B2 3/2021 Kerr et al.
10,959,726 B2 3/2021 Williams et al.
10,959,727 B2 3/2021 Hunter et al.
10,959,731 B2 3/2021 Casasanta, Jr. et al.
10,959,744 B2 3/2021 Shelton, IV et al.
10,959,797 B2 3/2021 Licht et al.
D917,500 S 4/2021 Siebel et al.
10,966,627 B2 4/2021 Shelton, IV et al.
10,966,717 B2 4/2021 Shah et al.
10,966,718 B2 4/2021 Shelton, IV et al.
10,966,791 B2 4/2021 Harris et al.
10,973,515 B2 4/2021 Harris et al.
10,973,516 B2 4/2021 Shelton, IV et al.
10,973,517 B2 4/2021 Wixey
10,973,519 B2 4/2021 Weir et al.
10,973,520 B2 4/2021 Shelton, IV et al.
10,980,534 B2 4/2021 Yates et al.
10,980,535 B2 4/2021 Yates et al.
10,980,536 B2 4/2021 Weaner et al.
10,980,537 B2 4/2021 Shelton, IV et al.
10,980,538 B2 4/2021 Nalagatla et al.
10,980,539 B2 4/2021 Harris et al.
10,980,560 B2 4/2021 Shelton, IV et al.
10,983,646 B2 4/2021 Yoon et al.
10,987,102 B2 4/2021 Gonzalez et al.
10,987,178 B2 4/2021 Shelton, IV et al.
10,993,713 B2 5/2021 Shelton, IV et al.
10,993,715 B2 5/2021 Shelton, IV et al.
10,993,716 B2 5/2021 Shelton, IV et al.
10,993,717 B2 5/2021 Shelton, IV et al.
11,000,274 B2 5/2021 Shelton, IV et al.
11,000,275 B2 5/2021 Shelton, IV et al.
11,000,277 B2 5/2021 Giordano et al.
11,000,278 B2 5/2021 Shelton, IV et al.
11,000,279 B2 5/2021 Shelton, IV et al.
11,005,291 B2 5/2021 Calderoni
11,006,951 B2 5/2021 Giordano et al.
11,006,955 B2 5/2021 Shelton, IV et al.
11,007,004 B2 5/2021 Shelton, IV et al.
11,007,022 B2 5/2021 Shelton, IV et al.
11,013,511 B2 5/2021 Huang et al.
11,013,552 B2 5/2021 Widenhouse et al.
11,013,563 B2 5/2021 Shelton, IV et al.
11,020,016 B2 6/2021 Wallace et al.

(56) References Cited

U.S. PATENT DOCUMENTS

| | | | |
|---|---|---|---|
| 11,020,112 | B2 | 6/2021 | Shelton, IV et al. |
| 11,020,113 | B2 | 6/2021 | Shelton, IV et al. |
| 11,020,114 | B2 | 6/2021 | Shelton, IV et al. |
| 11,020,115 | B2 | 6/2021 | Scheib et al. |
| 11,026,678 | B2 | 6/2021 | Overmyer et al. |
| 11,026,680 | B2 | 6/2021 | Shelton, IV et al. |
| 11,026,684 | B2 | 6/2021 | Shelton, IV et al. |
| 11,026,687 | B2 | 6/2021 | Shelton, IV et al. |
| 11,026,712 | B2 | 6/2021 | Shelton, IV et al. |
| 11,026,713 | B2 | 6/2021 | Stokes et al. |
| 11,026,751 | B2 | 6/2021 | Shelton, IV et al. |
| 11,033,267 | B2 | 6/2021 | Shelton, IV et al. |
| 11,039,834 | B2 | 6/2021 | Harris et al. |
| 11,039,836 | B2 | 6/2021 | Shelton, IV et al. |
| 11,039,837 | B2 | 6/2021 | Shelton, IV et al. |
| 11,039,849 | B2 | 6/2021 | Bucciaglia et al. |
| 11,045,189 | B2 | 6/2021 | Yates et al. |
| 11,045,191 | B2 | 6/2021 | Shelton, IV et al. |
| 11,045,192 | B2 | 6/2021 | Harris et al. |
| 11,045,196 | B2 | 6/2021 | Olson et al. |
| 11,045,197 | B2 | 6/2021 | Shelton, IV et al. |
| 11,045,199 | B2 | 6/2021 | Mozdzierz et al. |
| 11,045,270 | B2 | 6/2021 | Shelton, IV et al. |
| 11,051,807 | B2 | 7/2021 | Shelton, IV et al. |
| 11,051,810 | B2 | 7/2021 | Harris et al. |
| 11,051,811 | B2 | 7/2021 | Shelton, IV et al. |
| 11,051,813 | B2 | 7/2021 | Shelton, IV et al. |
| 11,051,836 | B2 | 7/2021 | Shelton, IV et al. |
| 11,051,840 | B2 | 7/2021 | Shelton, IV et al. |
| 11,051,873 | B2 | 7/2021 | Wiener et al. |
| 11,058,418 | B2 | 7/2021 | Shelton, IV et al. |
| 11,058,420 | B2 | 7/2021 | Shelton, IV et al. |
| 11,058,422 | B2 | 7/2021 | Harris et al. |
| 11,058,423 | B2 | 7/2021 | Shelton, IV et al. |
| 11,058,424 | B2 | 7/2021 | Shelton, IV et al. |
| 11,058,425 | B2 | 7/2021 | Widenhouse et al. |
| 11,058,426 | B2 | 7/2021 | Nalagatla et al. |
| 11,058,498 | B2 | 7/2021 | Shelton, IV et al. |
| 11,064,997 | B2 | 7/2021 | Shelton, IV et al. |
| 11,064,998 | B2 | 7/2021 | Shelton, IV |
| 11,065,048 | B2 | 7/2021 | Messerly et al. |
| 11,069,012 | B2 | 7/2021 | Shelton, IV et al. |
| 11,071,542 | B2 | 7/2021 | Chen et al. |
| 11,071,543 | B2 | 7/2021 | Shelton, IV et al. |
| 11,071,545 | B2 | 7/2021 | Baber et al. |
| 11,071,554 | B2 | 7/2021 | Parfett et al. |
| 11,071,560 | B2 | 7/2021 | Deck et al. |
| 11,076,853 | B2 | 8/2021 | Parfett et al. |
| 11,076,854 | B2 | 8/2021 | Baber et al. |
| 11,076,921 | B2 | 8/2021 | Shelton, IV et al. |
| 11,076,929 | B2 | 8/2021 | Shelton, IV et al. |
| 11,083,452 | B2 | 8/2021 | Schmid et al. |
| 11,083,453 | B2 | 8/2021 | Shelton, IV et al. |
| 11,083,454 | B2 | 8/2021 | Harris et al. |
| 11,083,455 | B2 | 8/2021 | Shelton, IV et al. |
| 11,083,456 | B2 | 8/2021 | Shelton, IV et al. |
| 11,083,457 | B2 | 8/2021 | Shelton, IV et al. |
| 11,083,458 | B2 | 8/2021 | Harris et al. |
| 11,090,045 | B2 | 8/2021 | Shelton, IV |
| 11,090,046 | B2 | 8/2021 | Shelton, IV et al. |
| 11,090,047 | B2 | 8/2021 | Shelton, IV et al. |
| 11,090,048 | B2 | 8/2021 | Fanelli et al. |
| 11,090,049 | B2 | 8/2021 | Bakos et al. |
| 11,090,075 | B2 | 8/2021 | Hunter et al. |
| 11,096,688 | B2 | 8/2021 | Shelton, IV et al. |
| 11,096,689 | B2 | 8/2021 | Overmyer et al. |
| 11,100,631 | B2 | 8/2021 | Yates et al. |
| 11,103,241 | B2 | 8/2021 | Yates et al. |
| 11,103,248 | B2 | 8/2021 | Shelton, IV et al. |
| 11,103,268 | B2 | 8/2021 | Shelton, IV et al. |
| 11,103,269 | B2 | 8/2021 | Shelton, IV et al. |
| 11,109,858 | B2 | 9/2021 | Shelton, IV et al. |
| 11,109,859 | B2 | 9/2021 | Overmyer et al. |
| 11,109,860 | B2 | 9/2021 | Shelton, IV et al. |
| 11,109,866 | B2 | 9/2021 | Shelton, IV et al. |
| 11,109,878 | B2 | 9/2021 | Shelton, IV et al. |
| 11,109,925 | B2 | 9/2021 | Cooper et al. |
| 11,116,485 | B2 | 9/2021 | Scheib et al. |
| 11,116,502 | B2 | 9/2021 | Shelton, IV et al. |
| 11,116,594 | B2 | 9/2021 | Beardsley |
| 11,123,069 | B2 | 9/2021 | Baxter, III et al. |
| 11,123,070 | B2 | 9/2021 | Shelton, IV et al. |
| 11,129,611 | B2 | 9/2021 | Shelton, IV et al. |
| 11,129,613 | B2 | 9/2021 | Harris et al. |
| 11,129,615 | B2 | 9/2021 | Scheib et al. |
| 11,129,616 | B2 | 9/2021 | Shelton, IV et al. |
| 11,129,634 | B2 | 9/2021 | Scheib et al. |
| 11,129,636 | B2 | 9/2021 | Shelton, IV et al. |
| 11,129,666 | B2 | 9/2021 | Messerly et al. |
| 11,129,680 | B2 | 9/2021 | Shelton, IV et al. |
| 11,132,462 | B2 | 9/2021 | Shelton, IV et al. |
| 11,133,106 | B2 | 9/2021 | Shelton, IV et al. |
| 11,134,938 | B2 | 10/2021 | Timm et al. |
| 11,134,940 | B2 | 10/2021 | Shelton, IV et al. |
| 11,134,942 | B2 | 10/2021 | Harris et al. |
| 11,134,943 | B2 | 10/2021 | Giordano et al. |
| 11,134,944 | B2 | 10/2021 | Wise et al. |
| 11,134,947 | B2 | 10/2021 | Shelton, IV et al. |
| 11,135,352 | B2 | 10/2021 | Shelton, IV et al. |
| 11,141,153 | B2 | 10/2021 | Shelton, IV et al. |
| 11,141,154 | B2 | 10/2021 | Shelton, IV et al. |
| 11,141,155 | B2 | 10/2021 | Shelton, IV |
| 11,141,156 | B2 | 10/2021 | Shelton, IV |
| 11,141,159 | B2 | 10/2021 | Scheib et al. |
| 11,141,160 | B2 | 10/2021 | Shelton, IV et al. |
| 11,147,547 | B2 | 10/2021 | Shelton, IV et al. |
| 11,147,549 | B2 | 10/2021 | Timm et al. |
| 11,147,551 | B2 | 10/2021 | Shelton, IV |
| 11,147,553 | B2 | 10/2021 | Shelton, IV |
| 11,147,554 | B2 | 10/2021 | Aronhalt et al. |
| 11,154,296 | B2 | 10/2021 | Aronhalt et al. |
| 11,154,297 | B2 | 10/2021 | Swayze et al. |
| 11,154,298 | B2 | 10/2021 | Timm et al. |
| 11,154,299 | B2 | 10/2021 | Shelton, IV et al. |
| 11,154,300 | B2 | 10/2021 | Nalagatla et al. |
| 11,154,301 | B2 | 10/2021 | Beckman et al. |
| 11,160,551 | B2 | 11/2021 | Shelton, IV et al. |
| 11,160,553 | B2 | 11/2021 | Simms et al. |
| 11,160,601 | B2 | 11/2021 | Worrell et al. |
| 11,166,716 | B2 | 11/2021 | Shelton, IV et al. |
| 11,166,717 | B2 | 11/2021 | Shelton, IV et al. |
| 11,166,720 | B2 | 11/2021 | Giordano et al. |
| 11,166,772 | B2 | 11/2021 | Shelton, IV et al. |
| 11,166,773 | B2 | 11/2021 | Ragosta et al. |
| 11,172,580 | B2 | 11/2021 | Gaertner, II |
| 11,172,927 | B2 | 11/2021 | Shelton, IV |
| 11,172,929 | B2 | 11/2021 | Shelton, IV |
| 11,179,150 | B2 | 11/2021 | Yates et al. |
| 11,179,151 | B2 | 11/2021 | Shelton, IV et al. |
| 11,179,152 | B2 | 11/2021 | Morgan et al. |
| 11,179,153 | B2 | 11/2021 | Shelton, IV |
| 11,179,155 | B2 | 11/2021 | Shelton, IV et al. |
| 11,179,208 | B2 | 11/2021 | Yates et al. |
| 11,185,325 | B2 | 11/2021 | Shelton, IV et al. |
| 11,185,330 | B2 | 11/2021 | Huitema et al. |
| 11,191,539 | B2 | 12/2021 | Overmyer et al. |
| 11,191,540 | B2 | 12/2021 | Aronhalt et al. |
| 11,191,543 | B2 | 12/2021 | Overmyer et al. |
| 11,191,545 | B2 | 12/2021 | Vendely et al. |
| 11,197,668 | B2 | 12/2021 | Shelton, IV et al. |
| 11,197,670 | B2 | 12/2021 | Shelton, IV et al. |
| 11,197,671 | B2 | 12/2021 | Shelton, IV et al. |
| 11,197,672 | B2 | 12/2021 | Dunki-Jacobs et al. |
| 11,202,570 | B2 | 12/2021 | Shelton, IV et al. |
| 11,202,631 | B2 | 12/2021 | Shelton, IV et al. |
| 11,202,633 | B2 | 12/2021 | Harris et al. |
| 11,207,064 | B2 | 12/2021 | Shelton, IV et al. |
| 11,207,065 | B2 | 12/2021 | Harris et al. |
| 11,207,067 | B2 | 12/2021 | Shelton, IV et al. |
| 11,207,089 | B2 | 12/2021 | Kostrzewski et al. |
| 11,207,090 | B2 | 12/2021 | Shelton, IV et al. |
| 11,207,146 | B2 | 12/2021 | Shelton, IV et al. |
| 11,213,293 | B2 | 1/2022 | Worthington et al. |
| 11,213,294 | B2 | 1/2022 | Shelton, IV et al. |

(56) References Cited

U.S. PATENT DOCUMENTS

| | | | |
|---|---|---|---|
| 11,213,302 | B2 | 1/2022 | Parfett et al. |
| 11,213,359 | B2 | 1/2022 | Shelton, IV et al. |
| 11,219,453 | B2 | 1/2022 | Shelton, IV et al. |
| 11,219,455 | B2 | 1/2022 | Shelton, IV et al. |
| 11,224,423 | B2 | 1/2022 | Shelton, IV et al. |
| 11,224,426 | B2 | 1/2022 | Shelton, IV et al. |
| 11,224,427 | B2 | 1/2022 | Shelton, IV et al. |
| 11,224,428 | B2 | 1/2022 | Scott et al. |
| 11,224,454 | B2 | 1/2022 | Shelton, IV et al. |
| 11,224,497 | B2 | 1/2022 | Shelton, IV et al. |
| 11,229,436 | B2 | 1/2022 | Shelton, IV et al. |
| 11,229,437 | B2 | 1/2022 | Shelton, IV et al. |
| 11,234,698 | B2 | 2/2022 | Shelton, IV et al. |
| 11,234,700 | B2 | 2/2022 | Ragosta et al. |
| 11,241,229 | B2 | 2/2022 | Shelton, IV et al. |
| 11,241,230 | B2 | 2/2022 | Shelton, IV et al. |
| 11,241,235 | B2 | 2/2022 | Shelton, IV et al. |
| 11,246,590 | B2 | 2/2022 | Swayze et al. |
| 11,246,592 | B2 | 2/2022 | Shelton, IV et al. |
| 11,246,616 | B2 | 2/2022 | Shelton, IV et al. |
| 11,246,618 | B2 | 2/2022 | Hall et al. |
| 11,246,678 | B2 | 2/2022 | Shelton, IV et al. |
| 11,253,254 | B2 | 2/2022 | Kimball et al. |
| 11,253,256 | B2 | 2/2022 | Harris et al. |
| 11,259,799 | B2 | 3/2022 | Overmyer et al. |
| 11,259,803 | B2 | 3/2022 | Shelton, IV et al. |
| 11,259,805 | B2 | 3/2022 | Shelton, IV et al. |
| 11,259,806 | B2 | 3/2022 | Shelton, IV et al. |
| 11,259,807 | B2 | 3/2022 | Shelton, IV et al. |
| 11,266,405 | B2 | 3/2022 | Shelton, IV et al. |
| 11,266,406 | B2 | 3/2022 | Leimbach et al. |
| 11,266,409 | B2 | 3/2022 | Huitema et al. |
| 11,266,410 | B2 | 3/2022 | Shelton, IV et al. |
| 11,266,468 | B2 | 3/2022 | Shelton, IV et al. |
| 11,272,927 | B2 | 3/2022 | Swayze et al. |
| 11,272,928 | B2 | 3/2022 | Shelton, IV |
| 11,272,931 | B2 | 3/2022 | Boudreaux et al. |
| 11,272,938 | B2 | 3/2022 | Shelton, IV et al. |
| 11,278,279 | B2 | 3/2022 | Morgan et al. |
| 11,278,280 | B2 | 3/2022 | Shelton, IV et al. |
| 11,278,284 | B2 | 3/2022 | Shelton, IV et al. |
| 11,284,890 | B2 | 3/2022 | Nalagatla et al. |
| 11,284,891 | B2 | 3/2022 | Shelton, IV et al. |
| 11,284,898 | B2 | 3/2022 | Baxter et al. |
| 11,284,953 | B2 | 3/2022 | Shelton, IV et al. |
| 11,291,440 | B2 | 4/2022 | Harris et al. |
| 11,291,441 | B2 | 4/2022 | Giordano et al. |
| 11,291,443 | B2 | 4/2022 | Viola et al. |
| 11,291,444 | B2 | 4/2022 | Boudreaux et al. |
| 11,291,445 | B2 | 4/2022 | Shelton, IV et al. |
| 11,291,447 | B2 | 4/2022 | Shelton, IV et al. |
| 11,291,449 | B2 | 4/2022 | Swensgard et al. |
| 11,291,451 | B2 | 4/2022 | Shelton, IV |
| 11,291,465 | B2 | 4/2022 | Parihar et al. |
| 11,291,510 | B2 | 4/2022 | Shelton, IV et al. |
| 11,298,125 | B2 | 4/2022 | Ming et al. |
| 11,298,127 | B2 | 4/2022 | Shelton, IV |
| 11,298,128 | B2 | 4/2022 | Messerly et al. |
| 11,298,129 | B2 | 4/2022 | Bakos et al. |
| 11,298,130 | B2 | 4/2022 | Bakos et al. |
| 11,298,132 | B2 | 4/2022 | Shelton, IV et al. |
| 11,298,134 | B2 | 4/2022 | Huitema et al. |
| 11,304,695 | B2 | 4/2022 | Shelton, IV et al. |
| 11,304,696 | B2 | 4/2022 | Shelton, IV et al. |
| 11,304,697 | B2 | 4/2022 | Fanelli et al. |
| 11,304,699 | B2 | 4/2022 | Shelton, IV et al. |
| 11,304,704 | B2 | 4/2022 | Thomas et al. |
| 11,311,290 | B2 | 4/2022 | Shelton, IV et al. |
| 11,311,292 | B2 | 4/2022 | Shelton, IV et al. |
| 11,311,294 | B2 | 4/2022 | Swayze et al. |
| 11,311,295 | B2 | 4/2022 | Wingardner et al. |
| 11,311,342 | B2 | 4/2022 | Parihar et al. |
| D950,728 | S | 5/2022 | Bakos et al. |
| D952,144 | S | 5/2022 | Boudreaux |
| 11,317,910 | B2 | 5/2022 | Miller et al. |
| 11,317,912 | B2 | 5/2022 | Jenkins et al. |
| 11,317,913 | B2 | 5/2022 | Shelton, IV et al. |
| 11,317,915 | B2 | 5/2022 | Boudreaux et al. |
| 11,317,917 | B2 | 5/2022 | Shelton, IV et al. |
| 11,317,919 | B2 | 5/2022 | Shelton, IV et al. |
| 11,317,978 | B2 | 5/2022 | Cameron et al. |
| 11,324,501 | B2 | 5/2022 | Shelton, IV et al. |
| 11,324,503 | B2 | 5/2022 | Shelton, IV et al. |
| 11,324,506 | B2 | 5/2022 | Beckman et al. |
| 11,324,557 | B2 | 5/2022 | Shelton, IV et al. |
| 11,331,100 | B2 | 5/2022 | Boudreaux et al. |
| 11,331,101 | B2 | 5/2022 | Harris et al. |
| 11,337,691 | B2 | 5/2022 | Widenhouse et al. |
| 11,337,693 | B2 | 5/2022 | Hess et al. |
| 11,337,698 | B2 | 5/2022 | Baxter, III et al. |
| 11,344,299 | B2 | 5/2022 | Yates et al. |
| 11,344,303 | B2 | 5/2022 | Shelton, IV et al. |
| 11,350,843 | B2 | 6/2022 | Shelton, IV et al. |
| 11,350,916 | B2 | 6/2022 | Shelton, IV et al. |
| 11,350,928 | B2 | 6/2022 | Shelton, IV et al. |
| 11,350,929 | B2 | 6/2022 | Giordano et al. |
| 11,350,932 | B2 | 6/2022 | Shelton, IV et al. |
| 11,350,934 | B2 | 6/2022 | Bakos et al. |
| 11,350,935 | B2 | 6/2022 | Shelton, IV et al. |
| 11,350,938 | B2 | 6/2022 | Shelton, IV et al. |
| 11,357,503 | B2 | 6/2022 | Bakos et al. |
| 11,361,176 | B2 | 6/2022 | Shelton, IV et al. |
| 11,364,027 | B2 | 6/2022 | Harris et al. |
| 11,364,046 | B2 | 6/2022 | Shelton, IV et al. |
| 11,369,368 | B2 | 6/2022 | Shelton, IV et al. |
| 11,369,376 | B2 | 6/2022 | Simms et al. |
| 11,369,377 | B2 | 6/2022 | Boudreaux et al. |
| 11,373,755 | B2 | 6/2022 | Shelton, IV et al. |
| 11,376,001 | B2 | 7/2022 | Shelton, IV et al. |
| 11,376,082 | B2 | 7/2022 | Shelton, IV et al. |
| 11,376,098 | B2 | 7/2022 | Shelton, IV et al. |
| 11,382,625 | B2 | 7/2022 | Huitema et al. |
| 11,382,626 | B2 | 7/2022 | Shelton, IV et al. |
| 11,382,627 | B2 | 7/2022 | Huitema et al. |
| 11,382,628 | B2 | 7/2022 | Baxter, III et al. |
| 11,382,638 | B2 | 7/2022 | Harris et al. |
| 11,382,697 | B2 | 7/2022 | Shelton, IV et al. |
| 11,389,160 | B2 | 7/2022 | Shelton, IV et al. |
| 11,389,161 | B2 | 7/2022 | Shelton, IV et al. |
| 11,389,162 | B2 | 7/2022 | Baber et al. |
| 11,389,164 | B2 | 7/2022 | Yates et al. |
| 11,395,651 | B2 | 7/2022 | Shelton, IV et al. |
| 11,395,652 | B2 | 7/2022 | Parihar et al. |
| 11,399,828 | B2 | 8/2022 | Swayze et al. |
| 11,399,829 | B2 | 8/2022 | Leimbach et al. |
| 11,399,831 | B2 | 8/2022 | Overmyer et al. |
| 11,399,837 | B2 | 8/2022 | Shelton, IV et al. |
| 11,406,377 | B2 | 8/2022 | Schmid et al. |
| 11,406,378 | B2 | 8/2022 | Baxter, III et al. |
| 11,406,380 | B2 | 8/2022 | Yates et al. |
| 11,406,381 | B2 | 8/2022 | Parihar et al. |
| 11,406,382 | B2 | 8/2022 | Shelton, IV et al. |
| 11,406,386 | B2 | 8/2022 | Baber et al. |
| 11,406,390 | B2 | 8/2022 | Shelton, IV et al. |
| 11,406,442 | B2 | 8/2022 | Davison et al. |
| 11,410,259 | B2 | 8/2022 | Harris et al. |
| 11,413,041 | B2 | 8/2022 | Viola et al. |
| 11,413,042 | B2 | 8/2022 | Shelton, IV et al. |
| 11,413,102 | B2 | 8/2022 | Shelton, IV et al. |
| 11,419,606 | B2 | 8/2022 | Overmyer et al. |
| 11,419,630 | B2 | 8/2022 | Yates et al. |
| 11,424,027 | B2 | 8/2022 | Shelton, IV |
| 11,426,160 | B2 | 8/2022 | Shelton, IV et al. |
| 11,426,167 | B2 | 8/2022 | Shelton, IV et al. |
| 11,426,251 | B2 | 8/2022 | Kimball et al. |
| D964,564 | S | 9/2022 | Boudreaux |
| 11,432,816 | B2 | 9/2022 | Leimbach et al. |
| 11,432,885 | B2 | 9/2022 | Shelton, IV et al. |
| 11,439,391 | B2 | 9/2022 | Bruns et al. |
| 11,439,470 | B2 | 9/2022 | Spivey et al. |
| 11,446,029 | B2 | 9/2022 | Shelton, IV et al. |
| 11,446,034 | B2 | 9/2022 | Shelton, IV et al. |
| 11,452,526 | B2 | 9/2022 | Ross et al. |
| 11,452,528 | B2 | 9/2022 | Leimbach et al. |

(56) References Cited

U.S. PATENT DOCUMENTS

| | | | |
|---|---|---|---|
| D966,512 | S | 10/2022 | Shelton, IV et al. |
| D967,421 | S | 10/2022 | Shelton, IV et al. |
| 11,457,918 | B2 | 10/2022 | Shelton, IV et al. |
| 11,464,511 | B2 | 10/2022 | Timm et al. |
| 11,464,512 | B2 | 10/2022 | Shelton, IV et al. |
| 11,464,513 | B2 | 10/2022 | Shelton, IV et al. |
| 11,464,514 | B2 | 10/2022 | Yates et al. |
| 11,464,601 | B2 | 10/2022 | Shelton, IV et al. |
| 11,471,155 | B2 | 10/2022 | Shelton, IV et al. |
| 11,471,156 | B2 | 10/2022 | Shelton, IV et al. |
| 11,471,157 | B2 | 10/2022 | Baxter, III et al. |
| 11,478,241 | B2 | 10/2022 | Shelton, IV et al. |
| 11,478,242 | B2 | 10/2022 | Shelton, IV et al. |
| 11,478,244 | B2 | 10/2022 | DiNardo et al. |
| D971,232 | S | 11/2022 | Siebel et al. |
| 11,484,307 | B2 | 11/2022 | Hall et al. |
| 11,484,309 | B2 | 11/2022 | Harris et al. |
| 11,484,310 | B2 | 11/2022 | Shelton, IV et al. |
| 11,484,311 | B2 | 11/2022 | Shelton, IV et al. |
| 11,484,312 | B2 | 11/2022 | Shelton, IV et al. |
| 11,490,889 | B2 | 11/2022 | Overmyer et al. |
| 11,497,488 | B2 | 11/2022 | Leimbach et al. |
| 11,497,489 | B2 | 11/2022 | Baxter, III et al. |
| 11,497,492 | B2 | 11/2022 | Shelton, IV |
| 11,497,499 | B2 | 11/2022 | Shelton, IV et al. |
| 11,504,116 | B2 | 11/2022 | Schmid et al. |
| 11,504,119 | B2 | 11/2022 | Shelton, IV et al. |
| 11,504,122 | B2 | 11/2022 | Shelton, IV et al. |
| 11,504,192 | B2 | 11/2022 | Shelton, IV et al. |
| 11,510,671 | B2 | 11/2022 | Shelton, IV et al. |
| 11,510,741 | B2 | 11/2022 | Shelton, IV et al. |
| 11,517,304 | B2 | 12/2022 | Yates et al. |
| 11,517,306 | B2 | 12/2022 | Miller et al. |
| 11,517,309 | B2 | 12/2022 | Bakos et al. |
| 11,517,311 | B2 | 12/2022 | Lytle, IV et al. |
| 11,517,315 | B2 | 12/2022 | Huitema et al. |
| 11,517,325 | B2 | 12/2022 | Shelton, IV et al. |
| 11,517,390 | B2 | 12/2022 | Baxter, III |
| 11,523,821 | B2 | 12/2022 | Harris et al. |
| 11,523,822 | B2 | 12/2022 | Shelton, IV et al. |
| 11,523,823 | B2 | 12/2022 | Hunter et al. |
| 11,523,859 | B2 | 12/2022 | Shelton, IV et al. |
| 11,529,137 | B2 | 12/2022 | Shelton, IV et al. |
| 11,529,138 | B2 | 12/2022 | Jaworek et al. |
| 11,529,139 | B2 | 12/2022 | Shelton, IV et al. |
| 11,529,140 | B2 | 12/2022 | Shelton, IV et al. |
| 11,529,142 | B2 | 12/2022 | Leimbach et al. |
| 11,534,162 | B2 | 12/2022 | Shelton, IV |
| 11,534,259 | B2 | 12/2022 | Leimbach et al. |
| D974,560 | S | 1/2023 | Shelton, IV et al. |
| D975,278 | S | 1/2023 | Shelton, IV et al. |
| D975,850 | S | 1/2023 | Shelton, IV et al. |
| D975,851 | S | 1/2023 | Shelton, IV et al. |
| D976,401 | S | 1/2023 | Shelton, IV et al. |
| 11,540,824 | B2 | 1/2023 | Shelton, IV et al. |
| 11,540,829 | B2 | 1/2023 | Shelton, IV et al. |
| 11,547,403 | B2 | 1/2023 | Shelton, IV et al. |
| 11,547,404 | B2 | 1/2023 | Shelton, IV et al. |
| 11,553,911 | B2 | 1/2023 | Shelton, IV et al. |
| 11,553,916 | B2 | 1/2023 | Vendely et al. |
| 11,553,919 | B2 | 1/2023 | Shelton, IV et al. |
| 11,553,971 | B2 | 1/2023 | Shelton, IV et al. |
| 11,559,302 | B2 | 1/2023 | Timm et al. |
| 11,559,303 | B2 | 1/2023 | Shelton, IV et al. |
| 11,559,304 | B2 | 1/2023 | Boudreaux et al. |
| 11,559,307 | B2 | 1/2023 | Shelton, IV et al. |
| 11,559,308 | B2 | 1/2023 | Yates et al. |
| 11,559,496 | B2 | 1/2023 | Widenhouse et al. |
| 11,564,679 | B2 | 1/2023 | Parihar et al. |
| 11,564,682 | B2 | 1/2023 | Timm et al. |
| 11,564,686 | B2 | 1/2023 | Yates et al. |
| 11,564,688 | B2 | 1/2023 | Swayze et al. |
| 11,564,703 | B2 | 1/2023 | Shelton, IV et al. |
| 11,564,756 | B2 | 1/2023 | Shelton, IV et al. |
| 11,571,207 | B2 | 2/2023 | Shelton, IV et al. |
| 11,571,210 | B2 | 2/2023 | Shelton, IV et al. |
| 11,571,212 | B2 | 2/2023 | Yates et al. |
| 11,571,215 | B2 | 2/2023 | Shelton, IV et al. |
| 11,571,231 | B2 | 2/2023 | Hess et al. |
| 11,576,668 | B2 | 2/2023 | Shelton, IV et al. |
| 11,576,672 | B2 | 2/2023 | Shelton, IV et al. |
| 11,576,673 | B2 | 2/2023 | Shelton, IV |
| 11,576,677 | B2 | 2/2023 | Shelton, IV et al. |
| 11,583,274 | B2 | 2/2023 | Widenhouse et al. |
| 11,583,277 | B2 | 2/2023 | Shelton, IV et al. |
| 11,583,278 | B2 | 2/2023 | Shelton, IV et al. |
| 11,583,279 | B2 | 2/2023 | Smith et al. |
| 2001/0000531 | A1 | 4/2001 | Casscells et al. |
| 2001/0025183 | A1 | 9/2001 | Shahidi |
| 2001/0025184 | A1 | 9/2001 | Messerly |
| 2001/0030219 | A1 | 10/2001 | Green et al. |
| 2001/0034530 | A1 | 10/2001 | Malackowski et al. |
| 2001/0045442 | A1 | 11/2001 | Whitman |
| 2002/0014510 | A1 | 2/2002 | Richter et al. |
| 2002/0022810 | A1 | 2/2002 | Urich |
| 2002/0022836 | A1 | 2/2002 | Goble et al. |
| 2002/0022861 | A1 | 2/2002 | Jacobs et al. |
| 2002/0023126 | A1 | 2/2002 | Flavin |
| 2002/0029032 | A1 | 3/2002 | Arkin |
| 2002/0029036 | A1 | 3/2002 | Goble et al. |
| 2002/0042620 | A1 | 4/2002 | Julian et al. |
| 2002/0054158 | A1 | 5/2002 | Asami |
| 2002/0065535 | A1 | 5/2002 | Kneifel et al. |
| 2002/0066764 | A1 | 6/2002 | Perry et al. |
| 2002/0082612 | A1 | 6/2002 | Moll et al. |
| 2002/0087048 | A1 | 7/2002 | Brock et al. |
| 2002/0087148 | A1 | 7/2002 | Brock et al. |
| 2002/0091374 | A1 | 7/2002 | Cooper |
| 2002/0095175 | A1 | 7/2002 | Brock et al. |
| 2002/0103494 | A1 | 8/2002 | Pacey |
| 2002/0111621 | A1 | 8/2002 | Wallace et al. |
| 2002/0111624 | A1 | 8/2002 | Witt et al. |
| 2002/0116063 | A1 | 8/2002 | Giannetti et al. |
| 2002/0117533 | A1 | 8/2002 | Milliman et al. |
| 2002/0117534 | A1 | 8/2002 | Green et al. |
| 2002/0127265 | A1 | 9/2002 | Bowman et al. |
| 2002/0128633 | A1 | 9/2002 | Brock et al. |
| 2002/0133236 | A1 | 9/2002 | Rousseau |
| 2002/0134811 | A1 | 9/2002 | Napier et al. |
| 2002/0135474 | A1 | 9/2002 | Sylliassen |
| 2002/0138086 | A1 | 9/2002 | Sixto et al. |
| 2002/0143340 | A1 | 10/2002 | Kaneko |
| 2002/0151770 | A1 | 10/2002 | Noll et al. |
| 2002/0158593 | A1 | 10/2002 | Henderson et al. |
| 2002/0161277 | A1 | 10/2002 | Boone et al. |
| 2002/0177848 | A1 | 11/2002 | Truckai et al. |
| 2002/0185514 | A1 | 12/2002 | Adams et al. |
| 2002/0188170 | A1 | 12/2002 | Santamore et al. |
| 2002/0188287 | A1 | 12/2002 | Zvuloni et al. |
| 2003/0009193 | A1 | 1/2003 | Corsaro |
| 2003/0011245 | A1 | 1/2003 | Fiebig |
| 2003/0012805 | A1 | 1/2003 | Chen et al. |
| 2003/0018323 | A1 | 1/2003 | Wallace et al. |
| 2003/0028236 | A1 | 2/2003 | Gillick et al. |
| 2003/0040670 | A1 | 2/2003 | Govari |
| 2003/0045835 | A1 | 3/2003 | Anderson et al. |
| 2003/0047230 | A1 | 3/2003 | Kim |
| 2003/0047582 | A1 | 3/2003 | Sonnenschein et al. |
| 2003/0050628 | A1 | 3/2003 | Whitman et al. |
| 2003/0050654 | A1 | 3/2003 | Whitman et al. |
| 2003/0066858 | A1 | 4/2003 | Holgersson |
| 2003/0078647 | A1 | 4/2003 | Vallana et al. |
| 2003/0083648 | A1 | 5/2003 | Wang et al. |
| 2003/0084983 | A1 | 5/2003 | Rangachari et al. |
| 2003/0093103 | A1 | 5/2003 | Malackowski et al. |
| 2003/0094356 | A1 | 5/2003 | Waldron |
| 2003/0096158 | A1 | 5/2003 | Takano et al. |
| 2003/0105475 | A1 | 6/2003 | Sancoff et al. |
| 2003/0114851 | A1 | 6/2003 | Truckai et al. |
| 2003/0121586 | A1 | 7/2003 | Mitra et al. |
| 2003/0135204 | A1 | 7/2003 | Lee et al. |
| 2003/0135388 | A1 | 7/2003 | Martucci et al. |
| 2003/0139741 | A1 | 7/2003 | Goble et al. |
| 2003/0144660 | A1 | 7/2003 | Mollenauer |

(56) References Cited

U.S. PATENT DOCUMENTS

| | | | |
|---|---|---|---|
| 2003/0149406 | A1 | 8/2003 | Martineau et al. |
| 2003/0153908 | A1 | 8/2003 | Goble et al. |
| 2003/0153968 | A1 | 8/2003 | Geis et al. |
| 2003/0158463 | A1 | 8/2003 | Julian et al. |
| 2003/0163029 | A1 | 8/2003 | Sonnenschein et al. |
| 2003/0163085 | A1 | 8/2003 | Tanner et al. |
| 2003/0164172 | A1 | 9/2003 | Chumas et al. |
| 2003/0181800 | A1 | 9/2003 | Bonutti |
| 2003/0181900 | A1 | 9/2003 | Long |
| 2003/0190584 | A1 | 10/2003 | Heasley |
| 2003/0195387 | A1 | 10/2003 | Kortenbach et al. |
| 2003/0205029 | A1 | 11/2003 | Chapolini et al. |
| 2003/0212005 | A1 | 11/2003 | Petito et al. |
| 2003/0216619 | A1 | 11/2003 | Scirica et al. |
| 2003/0216732 | A1 | 11/2003 | Truckai et al. |
| 2003/0236505 | A1 | 12/2003 | Bonadio et al. |
| 2004/0006335 | A1 | 1/2004 | Garrison |
| 2004/0006340 | A1 | 1/2004 | Latterell et al. |
| 2004/0007608 | A1 | 1/2004 | Ehrenfels et al. |
| 2004/0024457 | A1 | 2/2004 | Boyce et al. |
| 2004/0028502 | A1 | 2/2004 | Cummins |
| 2004/0030333 | A1 | 2/2004 | Goble |
| 2004/0034287 | A1 | 2/2004 | Hickle |
| 2004/0034357 | A1 | 2/2004 | Beane et al. |
| 2004/0044295 | A1 | 3/2004 | Reinert et al. |
| 2004/0044364 | A1 | 3/2004 | DeVries et al. |
| 2004/0049121 | A1 | 3/2004 | Yaron |
| 2004/0049172 | A1 | 3/2004 | Root et al. |
| 2004/0059362 | A1 | 3/2004 | Knodel et al. |
| 2004/0068161 | A1 | 4/2004 | Couvillon |
| 2004/0068224 | A1 | 4/2004 | Couvillon et al. |
| 2004/0068307 | A1 | 4/2004 | Goble |
| 2004/0070369 | A1 | 4/2004 | Sakakibara |
| 2004/0073222 | A1 | 4/2004 | Koseki |
| 2004/0078037 | A1 | 4/2004 | Batchelor et al. |
| 2004/0082952 | A1 | 4/2004 | Dycus et al. |
| 2004/0085180 | A1 | 5/2004 | Juang |
| 2004/0092992 | A1 | 5/2004 | Adams et al. |
| 2004/0093020 | A1 | 5/2004 | Sinton |
| 2004/0093024 | A1 | 5/2004 | Lousararian et al. |
| 2004/0098040 | A1 | 5/2004 | Taniguchi et al. |
| 2004/0101822 | A1 | 5/2004 | Wiesner et al. |
| 2004/0102783 | A1 | 5/2004 | Sutterlin et al. |
| 2004/0108357 | A1 | 6/2004 | Milliman et al. |
| 2004/0110439 | A1 | 6/2004 | Chaikof et al. |
| 2004/0115022 | A1 | 6/2004 | Albertson et al. |
| 2004/0116952 | A1 | 6/2004 | Sakurai et al. |
| 2004/0119185 | A1 | 6/2004 | Chen |
| 2004/0122419 | A1 | 6/2004 | Neuberger |
| 2004/0122423 | A1 | 6/2004 | Dycus et al. |
| 2004/0133095 | A1 | 7/2004 | Dunki-Jacobs et al. |
| 2004/0133189 | A1 | 7/2004 | Sakurai |
| 2004/0143297 | A1 | 7/2004 | Ramsey |
| 2004/0147909 | A1 | 7/2004 | Johnston et al. |
| 2004/0153100 | A1 | 8/2004 | Ahlberg et al. |
| 2004/0158261 | A1 | 8/2004 | Vu |
| 2004/0164123 | A1 | 8/2004 | Racenet et al. |
| 2004/0166169 | A1 | 8/2004 | Malaviya et al. |
| 2004/0167572 | A1 | 8/2004 | Roth et al. |
| 2004/0181219 | A1 | 9/2004 | Goble et al. |
| 2004/0193189 | A1 | 9/2004 | Kortenbach et al. |
| 2004/0197367 | A1 | 10/2004 | Rezania et al. |
| 2004/0199181 | A1 | 10/2004 | Knodel et al. |
| 2004/0204735 | A1 | 10/2004 | Shiroff et al. |
| 2004/0218451 | A1 | 11/2004 | Said et al. |
| 2004/0222268 | A1 | 11/2004 | Bilotti et al. |
| 2004/0225186 | A1 | 11/2004 | Horne et al. |
| 2004/0231870 | A1 | 11/2004 | McCormick et al. |
| 2004/0232201 | A1 | 11/2004 | Wenchell et al. |
| 2004/0236352 | A1 | 11/2004 | Wang et al. |
| 2004/0239582 | A1 | 12/2004 | Seymour |
| 2004/0243147 | A1 | 12/2004 | Lipow |
| 2004/0243151 | A1 | 12/2004 | Demmy et al. |
| 2004/0243163 | A1 | 12/2004 | Casiano et al. |
| 2004/0247415 | A1 | 12/2004 | Mangone |
| 2004/0249366 | A1 | 12/2004 | Kunz |
| 2004/0254455 | A1 | 12/2004 | Iddan |
| 2004/0254566 | A1 | 12/2004 | Plicchi et al. |
| 2004/0254590 | A1 | 12/2004 | Hoffman et al. |
| 2004/0254680 | A1 | 12/2004 | Sunaoshi |
| 2004/0260315 | A1 | 12/2004 | Dell et al. |
| 2004/0267310 | A1 | 12/2004 | Racenet et al. |
| 2005/0010158 | A1 | 1/2005 | Brugger et al. |
| 2005/0010213 | A1 | 1/2005 | Stad et al. |
| 2005/0021078 | A1 | 1/2005 | Vleugels et al. |
| 2005/0023325 | A1 | 2/2005 | Gresham et al. |
| 2005/0032511 | A1 | 2/2005 | Malone et al. |
| 2005/0033352 | A1 | 2/2005 | Zepf et al. |
| 2005/0044489 | A1 | 2/2005 | Yamagami et al. |
| 2005/0051163 | A1 | 3/2005 | Deem et al. |
| 2005/0054946 | A1 | 3/2005 | Krzyzanowski |
| 2005/0057225 | A1 | 3/2005 | Marquet |
| 2005/0058890 | A1 | 3/2005 | Brazell et al. |
| 2005/0059997 | A1 | 3/2005 | Bauman et al. |
| 2005/0067548 | A1 | 3/2005 | Inoue |
| 2005/0070929 | A1 | 3/2005 | Dalessandro et al. |
| 2005/0075561 | A1 | 4/2005 | Golden |
| 2005/0079088 | A1 | 4/2005 | Wirth et al. |
| 2005/0080342 | A1 | 4/2005 | Gilreath et al. |
| 2005/0085693 | A1 | 4/2005 | Belson et al. |
| 2005/0085838 | A1 | 4/2005 | Thompson et al. |
| 2005/0090709 | A1 | 4/2005 | Okada et al. |
| 2005/0090817 | A1 | 4/2005 | Phan |
| 2005/0096683 | A1 | 5/2005 | Ellins et al. |
| 2005/0116673 | A1 | 6/2005 | Carl et al. |
| 2005/0119524 | A1 | 6/2005 | Sekine et al. |
| 2005/0120836 | A1 | 6/2005 | Anderson |
| 2005/0124855 | A1 | 6/2005 | Jaffe et al. |
| 2005/0125028 | A1 | 6/2005 | Looper et al. |
| 2005/0125897 | A1 | 6/2005 | Wyslucha et al. |
| 2005/0129735 | A1 | 6/2005 | Cook et al. |
| 2005/0130682 | A1 | 6/2005 | Takara et al. |
| 2005/0131173 | A1 | 6/2005 | McDaniel et al. |
| 2005/0131211 | A1 | 6/2005 | Bayley et al. |
| 2005/0131390 | A1 | 6/2005 | Heinrich et al. |
| 2005/0131436 | A1 | 6/2005 | Johnston et al. |
| 2005/0131457 | A1 | 6/2005 | Douglas et al. |
| 2005/0137454 | A1 | 6/2005 | Saadat et al. |
| 2005/0137455 | A1 | 6/2005 | Ewers et al. |
| 2005/0139636 | A1 | 6/2005 | Schwemberger et al. |
| 2005/0143759 | A1 | 6/2005 | Kelly |
| 2005/0143769 | A1 | 6/2005 | White et al. |
| 2005/0145671 | A1 | 7/2005 | Viola |
| 2005/0145672 | A1 | 7/2005 | Schwemberger et al. |
| 2005/0150928 | A1 | 7/2005 | Kameyama et al. |
| 2005/0154258 | A1 | 7/2005 | Tartaglia et al. |
| 2005/0154406 | A1 | 7/2005 | Bombard et al. |
| 2005/0159778 | A1 | 7/2005 | Heinrich et al. |
| 2005/0165419 | A1 | 7/2005 | Sauer et al. |
| 2005/0169974 | A1 | 8/2005 | Tenerz et al. |
| 2005/0171522 | A1 | 8/2005 | Christopherson |
| 2005/0177176 | A1 | 8/2005 | Gerbi et al. |
| 2005/0177181 | A1 | 8/2005 | Kagan et al. |
| 2005/0177249 | A1 | 8/2005 | Kladakis et al. |
| 2005/0182298 | A1 | 8/2005 | Ikeda et al. |
| 2005/0182443 | A1 | 8/2005 | Jonn et al. |
| 2005/0184121 | A1 | 8/2005 | Heinrich |
| 2005/0186240 | A1 | 8/2005 | Ringeisen et al. |
| 2005/0187545 | A1 | 8/2005 | Hooven et al. |
| 2005/0191936 | A1 | 9/2005 | Marine et al. |
| 2005/0197859 | A1 | 9/2005 | Wilson et al. |
| 2005/0203550 | A1 | 9/2005 | Laufer et al. |
| 2005/0209614 | A1 | 9/2005 | Fenter et al. |
| 2005/0216055 | A1 | 9/2005 | Scirica et al. |
| 2005/0222587 | A1 | 10/2005 | Jinno et al. |
| 2005/0222611 | A1 | 10/2005 | Weitkamp |
| 2005/0222616 | A1 | 10/2005 | Rethy et al. |
| 2005/0222665 | A1 | 10/2005 | Aranyi |
| 2005/0228224 | A1 | 10/2005 | Okada et al. |
| 2005/0228446 | A1 | 10/2005 | Mooradian et al. |
| 2005/0230453 | A1 | 10/2005 | Viola |
| 2005/0240178 | A1 | 10/2005 | Morley et al. |
| 2005/0242950 | A1 | 11/2005 | Lindsay et al. |
| 2005/0245965 | A1 | 11/2005 | Orban, III et al. |

(56) References Cited

U.S. PATENT DOCUMENTS

| | | | |
|---|---|---|---|
| 2005/0246881 | A1 | 11/2005 | Kelly et al. |
| 2005/0251063 | A1 | 11/2005 | Basude |
| 2005/0256452 | A1 | 11/2005 | DeMarchi et al. |
| 2005/0256546 | A1 | 11/2005 | Vaisnys et al. |
| 2005/0258963 | A1 | 11/2005 | Rodriguez et al. |
| 2005/0261676 | A1 | 11/2005 | Hall et al. |
| 2005/0263563 | A1 | 12/2005 | Racenet et al. |
| 2005/0267455 | A1 | 12/2005 | Eggers et al. |
| 2005/0267464 | A1 | 12/2005 | Truckai et al. |
| 2005/0267529 | A1 | 12/2005 | Crockett et al. |
| 2005/0274034 | A1 | 12/2005 | Hayashida et al. |
| 2005/0283188 | A1 | 12/2005 | Loshakove et al. |
| 2005/0283226 | A1 | 12/2005 | Haverkost |
| 2006/0008787 | A1 | 1/2006 | Hayman et al. |
| 2006/0011698 | A1 | 1/2006 | Okada et al. |
| 2006/0015009 | A1 | 1/2006 | Jaffe et al. |
| 2006/0020167 | A1 | 1/2006 | Sitzmann |
| 2006/0020258 | A1 | 1/2006 | Strauss et al. |
| 2006/0020272 | A1 | 1/2006 | Gildenberg |
| 2006/0020336 | A1 | 1/2006 | Liddicoat |
| 2006/0025812 | A1 | 2/2006 | Shelton |
| 2006/0041188 | A1 | 2/2006 | Dirusso et al. |
| 2006/0047275 | A1 | 3/2006 | Goble |
| 2006/0049229 | A1 | 3/2006 | Milliman et al. |
| 2006/0052824 | A1 | 3/2006 | Ransick et al. |
| 2006/0052825 | A1 | 3/2006 | Ransick et al. |
| 2006/0064086 | A1 | 3/2006 | Odom |
| 2006/0079735 | A1 | 4/2006 | Martone et al. |
| 2006/0079874 | A1 | 4/2006 | Faller et al. |
| 2006/0079879 | A1 | 4/2006 | Faller et al. |
| 2006/0086032 | A1 | 4/2006 | Valencic et al. |
| 2006/0087746 | A1 | 4/2006 | Lipow |
| 2006/0089535 | A1 | 4/2006 | Raz et al. |
| 2006/0097699 | A1 | 5/2006 | Kamenoff |
| 2006/0100643 | A1 | 5/2006 | Laufer et al. |
| 2006/0100649 | A1 | 5/2006 | Hart |
| 2006/0106369 | A1 | 5/2006 | Desai et al. |
| 2006/0111711 | A1 | 5/2006 | Goble |
| 2006/0111723 | A1 | 5/2006 | Chapolini et al. |
| 2006/0116634 | A1 | 6/2006 | Shachar |
| 2006/0142656 | A1 | 6/2006 | Malackowski et al. |
| 2006/0142772 | A1 | 6/2006 | Ralph et al. |
| 2006/0144898 | A1 | 7/2006 | Bilotti et al. |
| 2006/0154546 | A1 | 7/2006 | Murphy et al. |
| 2006/0161050 | A1 | 7/2006 | Butler et al. |
| 2006/0161185 | A1 | 7/2006 | Saadat et al. |
| 2006/0167471 | A1 | 7/2006 | Phillips |
| 2006/0173290 | A1 | 8/2006 | Lavallee et al. |
| 2006/0173470 | A1 | 8/2006 | Oray et al. |
| 2006/0176031 | A1 | 8/2006 | Forman et al. |
| 2006/0176242 | A1 | 8/2006 | Jaramaz et al. |
| 2006/0178556 | A1 | 8/2006 | Hasser et al. |
| 2006/0180633 | A1 | 8/2006 | Emmons |
| 2006/0180634 | A1 | 8/2006 | Shelton et al. |
| 2006/0185682 | A1 | 8/2006 | Marczyk |
| 2006/0199999 | A1 | 9/2006 | Ikeda et al. |
| 2006/0201989 | A1 | 9/2006 | Ojeda |
| 2006/0206100 | A1 | 9/2006 | Eskridge et al. |
| 2006/0217729 | A1 | 9/2006 | Eskridge et al. |
| 2006/0226196 | A1 | 10/2006 | Hueil et al. |
| 2006/0226957 | A1 | 10/2006 | Miller et al. |
| 2006/0235368 | A1 | 10/2006 | Oz |
| 2006/0241666 | A1 | 10/2006 | Briggs et al. |
| 2006/0241691 | A1 | 10/2006 | Wilk |
| 2006/0244460 | A1 | 11/2006 | Weaver |
| 2006/0247584 | A1 | 11/2006 | Sheetz et al. |
| 2006/0252981 | A1 | 11/2006 | Matsuda et al. |
| 2006/0252990 | A1 | 11/2006 | Kubach |
| 2006/0252993 | A1 | 11/2006 | Freed et al. |
| 2006/0258904 | A1 | 11/2006 | Stefanchik et al. |
| 2006/0259073 | A1 | 11/2006 | Miyamoto et al. |
| 2006/0261763 | A1 | 11/2006 | Iott et al. |
| 2006/0263444 | A1 | 11/2006 | Ming et al. |
| 2006/0264831 | A1 | 11/2006 | Skwarek et al. |
| 2006/0264929 | A1 | 11/2006 | Goble et al. |
| 2006/0271042 | A1 | 11/2006 | Latterell et al. |
| 2006/0271102 | A1 | 11/2006 | Bosshard et al. |
| 2006/0282064 | A1 | 12/2006 | Shimizu et al. |
| 2006/0284730 | A1 | 12/2006 | Schmid et al. |
| 2006/0287576 | A1 | 12/2006 | Tsuji et al. |
| 2006/0289600 | A1 | 12/2006 | Wales et al. |
| 2006/0289602 | A1 | 12/2006 | Wales et al. |
| 2006/0291981 | A1 | 12/2006 | Viola et al. |
| 2007/0005045 | A1 | 1/2007 | Mintz et al. |
| 2007/0009570 | A1 | 1/2007 | Kim et al. |
| 2007/0010702 | A1 | 1/2007 | Wang et al. |
| 2007/0010838 | A1 | 1/2007 | Shelton et al. |
| 2007/0016235 | A1 | 1/2007 | Tanaka et al. |
| 2007/0018958 | A1 | 1/2007 | Tavakoli et al. |
| 2007/0026039 | A1 | 2/2007 | Drumheller et al. |
| 2007/0026040 | A1 | 2/2007 | Crawley et al. |
| 2007/0027459 | A1 | 2/2007 | Horvath et al. |
| 2007/0027468 | A1 | 2/2007 | Wales et al. |
| 2007/0027551 | A1 | 2/2007 | Farnsworth et al. |
| 2007/0043338 | A1 | 2/2007 | Moll et al. |
| 2007/0043387 | A1 | 2/2007 | Vargas et al. |
| 2007/0049951 | A1 | 3/2007 | Menn |
| 2007/0049966 | A1 | 3/2007 | Bonadio et al. |
| 2007/0051375 | A1 | 3/2007 | Milliman |
| 2007/0055228 | A1 | 3/2007 | Berg et al. |
| 2007/0055305 | A1 | 3/2007 | Schnyder et al. |
| 2007/0069851 | A1 | 3/2007 | Sung et al. |
| 2007/0073341 | A1 | 3/2007 | Smith et al. |
| 2007/0073389 | A1 | 3/2007 | Bolduc et al. |
| 2007/0078328 | A1 | 4/2007 | Ozaki et al. |
| 2007/0078484 | A1 | 4/2007 | Talarico et al. |
| 2007/0084897 | A1 | 4/2007 | Shelton et al. |
| 2007/0088376 | A1 | 4/2007 | Zacharias |
| 2007/0090788 | A1 | 4/2007 | Hansford et al. |
| 2007/0093869 | A1 | 4/2007 | Bloom et al. |
| 2007/0102472 | A1 | 5/2007 | Shelton |
| 2007/0103437 | A1 | 5/2007 | Rosenberg |
| 2007/0106113 | A1 | 5/2007 | Ravo |
| 2007/0106317 | A1 | 5/2007 | Shelton et al. |
| 2007/0118115 | A1 | 5/2007 | Artale et al. |
| 2007/0134251 | A1 | 6/2007 | Ashkenazi et al. |
| 2007/0135686 | A1 | 6/2007 | Pruitt et al. |
| 2007/0135803 | A1 | 6/2007 | Belson |
| 2007/0152612 | A1 | 7/2007 | Chen et al. |
| 2007/0152829 | A1 | 7/2007 | Lindsay et al. |
| 2007/0155010 | A1 | 7/2007 | Farnsworth et al. |
| 2007/0162056 | A1 | 7/2007 | Gerbi et al. |
| 2007/0170225 | A1 | 7/2007 | Shelton et al. |
| 2007/0173687 | A1 | 7/2007 | Shima et al. |
| 2007/0173813 | A1 | 7/2007 | Odom |
| 2007/0173872 | A1 | 7/2007 | Neuenfeldt |
| 2007/0175950 | A1 | 8/2007 | Shelton et al. |
| 2007/0175951 | A1 | 8/2007 | Shelton et al. |
| 2007/0175955 | A1 | 8/2007 | Shelton et al. |
| 2007/0175956 | A1 | 8/2007 | Swayze et al. |
| 2007/0179476 | A1 | 8/2007 | Shelton et al. |
| 2007/0179477 | A1 | 8/2007 | Danger |
| 2007/0185545 | A1 | 8/2007 | Duke |
| 2007/0187857 | A1 | 8/2007 | Riley et al. |
| 2007/0190110 | A1 | 8/2007 | Pameijer et al. |
| 2007/0191868 | A1 | 8/2007 | Theroux et al. |
| 2007/0191915 | A1 | 8/2007 | Strother et al. |
| 2007/0194079 | A1 | 8/2007 | Hueil et al. |
| 2007/0194081 | A1 | 8/2007 | Hueil et al. |
| 2007/0194082 | A1 | 8/2007 | Morgan et al. |
| 2007/0197954 | A1 | 8/2007 | Keenan |
| 2007/0198039 | A1 | 8/2007 | Jones et al. |
| 2007/0203510 | A1 | 8/2007 | Bettuchi |
| 2007/0207010 | A1 | 9/2007 | Caspi |
| 2007/0208359 | A1 | 9/2007 | Hoffman |
| 2007/0208375 | A1 | 9/2007 | Nishizawa et al. |
| 2007/0213750 | A1 | 9/2007 | Weadock |
| 2007/0221701 | A1 | 9/2007 | Ortiz et al. |
| 2007/0225562 | A1 | 9/2007 | Spivey et al. |
| 2007/0233163 | A1 | 10/2007 | Bombard et al. |
| 2007/0243227 | A1 | 10/2007 | Gertner |
| 2007/0244471 | A1 | 10/2007 | Malackowski |
| 2007/0244496 | A1 | 10/2007 | Hellenkamp |
| 2007/0246505 | A1 | 10/2007 | Pace-Floridia et al. |

(56) References Cited

U.S. PATENT DOCUMENTS

2007/0260132 A1 11/2007 Sterling
2007/0260242 A1 11/2007 Dycus et al.
2007/0262592 A1 11/2007 Hwang et al.
2007/0270660 A1 11/2007 Caylor et al.
2007/0275035 A1 11/2007 Herman et al.
2007/0276409 A1 11/2007 Ortiz et al.
2007/0279011 A1 12/2007 Jones et al.
2007/0286892 A1 12/2007 Herzberg et al.
2007/0290027 A1 12/2007 Maatta et al.
2007/0296286 A1 12/2007 Avenell
2008/0000941 A1 1/2008 Sonnenschein et al.
2008/0003196 A1 1/2008 Jonn et al.
2008/0007237 A1 1/2008 Nagashima et al.
2008/0015598 A1 1/2008 Prommersberger
2008/0021486 A1 1/2008 Oyola et al.
2008/0029570 A1 2/2008 Shelton et al.
2008/0029573 A1 2/2008 Shelton et al.
2008/0029574 A1 2/2008 Shelton et al.
2008/0029575 A1 2/2008 Shelton et al.
2008/0030170 A1 2/2008 Dacquay et al.
2008/0039746 A1 2/2008 Hissong et al.
2008/0042861 A1 2/2008 Dacquay et al.
2008/0046000 A1 2/2008 Lee et al.
2008/0051833 A1 2/2008 Gramuglia et al.
2008/0064920 A1 3/2008 Bakos et al.
2008/0064921 A1 3/2008 Larkin et al.
2008/0065153 A1 3/2008 Allard et al.
2008/0069736 A1 3/2008 Mingerink et al.
2008/0071328 A1 3/2008 Haubrich et al.
2008/0077158 A1 3/2008 Haider et al.
2008/0078802 A1 4/2008 Hess et al.
2008/0081948 A1 4/2008 Weisenburgh et al.
2008/0082114 A1 4/2008 McKenna et al.
2008/0082125 A1 4/2008 Murray et al.
2008/0082126 A1 4/2008 Murray et al.
2008/0083807 A1 4/2008 Beardsley et al.
2008/0083811 A1 4/2008 Marczyk
2008/0085296 A1 4/2008 Powell et al.
2008/0086078 A1 4/2008 Powell et al.
2008/0091072 A1 4/2008 Omori et al.
2008/0094228 A1 4/2008 Welch et al.
2008/0108443 A1 5/2008 Jinno et al.
2008/0114250 A1 5/2008 Urbano et al.
2008/0125634 A1 5/2008 Ryan et al.
2008/0125749 A1 5/2008 Olson
2008/0126984 A1 5/2008 Fleishman et al.
2008/0128469 A1 6/2008 Dalessandro et al.
2008/0129253 A1 6/2008 Shiue et al.
2008/0135600 A1 6/2008 Hiranuma et al.
2008/0140115 A1 6/2008 Stopek
2008/0140159 A1 6/2008 Bornhoft et al.
2008/0149682 A1 6/2008 Uhm
2008/0154299 A1 6/2008 Livneh
2008/0154335 A1 6/2008 Thrope et al.
2008/0169328 A1 7/2008 Shelton
2008/0169332 A1 7/2008 Shelton et al.
2008/0169333 A1 7/2008 Shelton et al.
2008/0172087 A1 7/2008 Fuchs et al.
2008/0177392 A1 7/2008 Williams et al.
2008/0190989 A1 8/2008 Crews et al.
2008/0196253 A1 8/2008 Ezra et al.
2008/0196419 A1 8/2008 Dube
2008/0197167 A1 8/2008 Viola et al.
2008/0200755 A1 8/2008 Bakos
2008/0200762 A1 8/2008 Stokes et al.
2008/0200835 A1 8/2008 Monson et al.
2008/0200911 A1 8/2008 Long
2008/0200933 A1 8/2008 Bakos et al.
2008/0200934 A1 8/2008 Fox
2008/0206186 A1 8/2008 Butler et al.
2008/0208058 A1 8/2008 Sabata et al.
2008/0216704 A1 9/2008 Eisenbeis et al.
2008/0217376 A1 9/2008 Clauson et al.
2008/0234709 A1 9/2008 Houser
2008/0234866 A1 9/2008 Kishi et al.
2008/0242939 A1 10/2008 Johnston
2008/0243088 A1 10/2008 Evans
2008/0243143 A1 10/2008 Kuhns et al.
2008/0249536 A1 10/2008 Stahler et al.
2008/0249608 A1 10/2008 Dave
2008/0255413 A1 10/2008 Zemlok et al.
2008/0255420 A1 10/2008 Lee et al.
2008/0255421 A1 10/2008 Hegeman et al.
2008/0255663 A1 10/2008 Akpek et al.
2008/0262654 A1 10/2008 Omori et al.
2008/0269596 A1 10/2008 Revie et al.
2008/0281171 A1 11/2008 Fennell et al.
2008/0281332 A1 11/2008 Taylor
2008/0287944 A1 11/2008 Pearson et al.
2008/0293910 A1 11/2008 Kapiamba et al.
2008/0294179 A1 11/2008 Balbierz et al.
2008/0296346 A1 12/2008 Shelton, IV et al.
2008/0296347 A1 12/2008 Shelton, IV et al.
2008/0297287 A1 12/2008 Shachar et al.
2008/0298784 A1 12/2008 Kastner
2008/0308504 A1 12/2008 Hallan et al.
2008/0308602 A1 12/2008 Timm et al.
2008/0308603 A1 12/2008 Shelton et al.
2008/0308607 A1 12/2008 Timm et al.
2008/0308807 A1 12/2008 Yamazaki et al.
2008/0312686 A1 12/2008 Ellingwood
2008/0312687 A1 12/2008 Blier
2008/0315829 A1 12/2008 Jones et al.
2009/0001121 A1 1/2009 Hess et al.
2009/0001130 A1 1/2009 Hess et al.
2009/0004455 A1 1/2009 Gravagna et al.
2009/0005809 A1 1/2009 Hess et al.
2009/0007014 A1 1/2009 Coomer et al.
2009/0012534 A1 1/2009 Madhani et al.
2009/0015195 A1 1/2009 Loth-Krausser
2009/0020958 A1 1/2009 Soul
2009/0030437 A1 1/2009 Houser et al.
2009/0043253 A1 2/2009 Podaima
2009/0048583 A1 2/2009 Williams et al.
2009/0048589 A1 2/2009 Takashino et al.
2009/0053288 A1 2/2009 Eskridge, Jr. et al.
2009/0057369 A1 3/2009 Smith et al.
2009/0069806 A1 3/2009 De La Mora Levy et al.
2009/0076506 A1 3/2009 Baker
2009/0078736 A1 3/2009 Van Lue
2009/0081313 A1 3/2009 Aghion et al.
2009/0088659 A1 4/2009 Graham et al.
2009/0090763 A1 4/2009 Zemlok et al.
2009/0099579 A1 4/2009 Nentwick et al.
2009/0099876 A1 4/2009 Whitman
2009/0110533 A1 4/2009 Jinno
2009/0112234 A1 4/2009 Crainich et al.
2009/0114701 A1 5/2009 Zemlok et al.
2009/0118762 A1 5/2009 Crainch et al.
2009/0119011 A1 5/2009 Kondo et al.
2009/0120994 A1 5/2009 Murray et al.
2009/0131819 A1 5/2009 Ritchie et al.
2009/0132400 A1 5/2009 Conway
2009/0135280 A1 5/2009 Johnston et al.
2009/0138003 A1 5/2009 Deville et al.
2009/0143797 A1 6/2009 Smith et al.
2009/0143855 A1 6/2009 Weber et al.
2009/0149871 A9 6/2009 Kagan et al.
2009/0167548 A1 7/2009 Sugahara
2009/0171147 A1 7/2009 Lee et al.
2009/0177218 A1 7/2009 Young et al.
2009/0177226 A1 7/2009 Reinprecht et al.
2009/0181290 A1 7/2009 Baldwin et al.
2009/0188964 A1 7/2009 Orlov
2009/0192534 A1 7/2009 Ortiz et al.
2009/0198272 A1 8/2009 Kerver et al.
2009/0204108 A1 8/2009 Steffen
2009/0204109 A1 8/2009 Grove et al.
2009/0204126 A1 8/2009 Le
2009/0204925 A1 8/2009 Bhat et al.
2009/0206125 A1 8/2009 Huitema et al.
2009/0206126 A1 8/2009 Huitema et al.
2009/0206131 A1 8/2009 Weisenburgh, II et al.
2009/0206133 A1 8/2009 Morgan et al.

(56) References Cited

U.S. PATENT DOCUMENTS

| | | | |
|---|---|---|---|
| 2009/0206137 | A1 | 8/2009 | Hall et al. |
| 2009/0206139 | A1 | 8/2009 | Hall et al. |
| 2009/0206141 | A1 | 8/2009 | Huitema et al. |
| 2009/0206142 | A1 | 8/2009 | Huitema et al. |
| 2009/0206143 | A1 | 8/2009 | Huitema et al. |
| 2009/0221993 | A1 | 9/2009 | Sohi et al. |
| 2009/0227834 | A1 | 9/2009 | Nakamoto et al. |
| 2009/0234273 | A1 | 9/2009 | Intoccia et al. |
| 2009/0236401 | A1 | 9/2009 | Cole et al. |
| 2009/0242610 | A1 | 10/2009 | Shelton, IV et al. |
| 2009/0246873 | A1 | 10/2009 | Yamamoto et al. |
| 2009/0247368 | A1 | 10/2009 | Chiang |
| 2009/0247901 | A1 | 10/2009 | Zimmer |
| 2009/0248100 | A1 | 10/2009 | Vaisnys et al. |
| 2009/0253959 | A1 | 10/2009 | Yoshie et al. |
| 2009/0255974 | A1 | 10/2009 | Viola |
| 2009/0261141 | A1 | 10/2009 | Stratton et al. |
| 2009/0262078 | A1 | 10/2009 | Pizzi |
| 2009/0264940 | A1 | 10/2009 | Beale et al. |
| 2009/0270895 | A1 | 10/2009 | Churchill et al. |
| 2009/0273353 | A1 | 11/2009 | Kroh et al. |
| 2009/0277288 | A1 | 11/2009 | Doepker et al. |
| 2009/0278406 | A1 | 11/2009 | Hoffman |
| 2009/0290016 | A1 | 11/2009 | Suda |
| 2009/0292283 | A1 | 11/2009 | Odom |
| 2009/0306639 | A1 | 12/2009 | Nevo et al. |
| 2009/0308907 | A1 | 12/2009 | Nalagatla et al. |
| 2009/0318557 | A1 | 12/2009 | Stockel |
| 2009/0318936 | A1 | 12/2009 | Harris et al. |
| 2009/0325859 | A1 | 12/2009 | Ameer et al. |
| 2010/0002013 | A1 | 1/2010 | Kagaya |
| 2010/0005035 | A1 | 1/2010 | Carpenter et al. |
| 2010/0012703 | A1 | 1/2010 | Calabrese et al. |
| 2010/0015104 | A1 | 1/2010 | Fraser et al. |
| 2010/0016853 | A1 | 1/2010 | Burbank |
| 2010/0016888 | A1 | 1/2010 | Calabrese et al. |
| 2010/0017715 | A1 | 1/2010 | Balassanian |
| 2010/0023024 | A1 | 1/2010 | Zeiner et al. |
| 2010/0030233 | A1 | 2/2010 | Whitman et al. |
| 2010/0030239 | A1 | 2/2010 | Viola et al. |
| 2010/0032179 | A1 | 2/2010 | Hanspers et al. |
| 2010/0036370 | A1 | 2/2010 | Mirel et al. |
| 2010/0036441 | A1 | 2/2010 | Procter |
| 2010/0051668 | A1 | 3/2010 | Milliman et al. |
| 2010/0057118 | A1 | 3/2010 | Dietz et al. |
| 2010/0065604 | A1 | 3/2010 | Weng |
| 2010/0069833 | A1 | 3/2010 | Wenderow et al. |
| 2010/0069942 | A1 | 3/2010 | Shelton, IV |
| 2010/0076475 | A1 | 3/2010 | Yates et al. |
| 2010/0076483 | A1 | 3/2010 | Imuta |
| 2010/0076489 | A1 | 3/2010 | Stopek et al. |
| 2010/0081883 | A1 | 4/2010 | Murray et al. |
| 2010/0089970 | A1* | 4/2010 | Smith ................ A61B 17/0686 227/175.1 |
| 2010/0094312 | A1 | 4/2010 | Ruiz Morales et al. |
| 2010/0094340 | A1 | 4/2010 | Stopek et al. |
| 2010/0094400 | A1 | 4/2010 | Bolduc et al. |
| 2010/0100123 | A1 | 4/2010 | Bennett |
| 2010/0100124 | A1 | 4/2010 | Calabrese et al. |
| 2010/0106167 | A1 | 4/2010 | Boulnois et al. |
| 2010/0116519 | A1 | 5/2010 | Gareis |
| 2010/0122339 | A1 | 5/2010 | Boccacci |
| 2010/0125786 | A1 | 5/2010 | Ozawa et al. |
| 2010/0133317 | A1 | 6/2010 | Shelton, IV et al. |
| 2010/0137990 | A1 | 6/2010 | Apatsidis et al. |
| 2010/0138659 | A1 | 6/2010 | Carmichael et al. |
| 2010/0145146 | A1 | 6/2010 | Melder |
| 2010/0147921 | A1 | 6/2010 | Olson |
| 2010/0147922 | A1 | 6/2010 | Olson |
| 2010/0159435 | A1 | 6/2010 | Mueller et al. |
| 2010/0168741 | A1 | 7/2010 | Sanai et al. |
| 2010/0179022 | A1 | 7/2010 | Shirokoshi |
| 2010/0180711 | A1 | 7/2010 | Kilibarda et al. |
| 2010/0187285 | A1 | 7/2010 | Harris et al. |
| 2010/0191255 | A1 | 7/2010 | Crainich et al. |
| 2010/0191262 | A1 | 7/2010 | Harris et al. |
| 2010/0191292 | A1 | 7/2010 | DeMeo et al. |
| 2010/0193566 | A1 | 8/2010 | Scheib et al. |
| 2010/0194541 | A1 | 8/2010 | Stevenson et al. |
| 2010/0198159 | A1 | 8/2010 | Voss et al. |
| 2010/0204717 | A1 | 8/2010 | Knodel |
| 2010/0204721 | A1 | 8/2010 | Young et al. |
| 2010/0217281 | A1 | 8/2010 | Matsuoka et al. |
| 2010/0222901 | A1 | 9/2010 | Swayze et al. |
| 2010/0228250 | A1 | 9/2010 | Brogna |
| 2010/0234687 | A1 | 9/2010 | Azarbarzin et al. |
| 2010/0241115 | A1 | 9/2010 | Benamou et al. |
| 2010/0241137 | A1 | 9/2010 | Doyle et al. |
| 2010/0245102 | A1 | 9/2010 | Yokoi |
| 2010/0249497 | A1 | 9/2010 | Peine et al. |
| 2010/0249947 | A1 | 9/2010 | Lesh et al. |
| 2010/0256675 | A1 | 10/2010 | Romans |
| 2010/0258327 | A1 | 10/2010 | Esenwein et al. |
| 2010/0267525 | A1 | 10/2010 | Tanner |
| 2010/0267662 | A1 | 10/2010 | Fielder et al. |
| 2010/0274160 | A1 | 10/2010 | Yachi et al. |
| 2010/0291184 | A1 | 11/2010 | Clark et al. |
| 2010/0292540 | A1 | 11/2010 | Hess et al. |
| 2010/0298636 | A1 | 11/2010 | Castro et al. |
| 2010/0301097 | A1 | 12/2010 | Scirica et al. |
| 2010/0310623 | A1 | 12/2010 | Laurencin et al. |
| 2010/0312261 | A1 | 12/2010 | Suzuki et al. |
| 2010/0318085 | A1 | 12/2010 | Austin et al. |
| 2010/0325568 | A1 | 12/2010 | Pedersen et al. |
| 2010/0327041 | A1 | 12/2010 | Milliman et al. |
| 2010/0331856 | A1 | 12/2010 | Carlson et al. |
| 2011/0006101 | A1 | 1/2011 | Hall et al. |
| 2011/0009694 | A1 | 1/2011 | Schultz et al. |
| 2011/0011916 | A1 | 1/2011 | Levine |
| 2011/0016960 | A1 | 1/2011 | Debrailly |
| 2011/0021871 | A1 | 1/2011 | Berkelaar |
| 2011/0022032 | A1 | 1/2011 | Zemlok et al. |
| 2011/0024477 | A1 | 2/2011 | Hall |
| 2011/0024478 | A1 | 2/2011 | Shelton, IV |
| 2011/0025311 | A1 | 2/2011 | Chauvin et al. |
| 2011/0028991 | A1 | 2/2011 | Ikeda et al. |
| 2011/0029003 | A1 | 2/2011 | Lavigne et al. |
| 2011/0029270 | A1 | 2/2011 | Mueglitz |
| 2011/0036891 | A1 | 2/2011 | Zemlok et al. |
| 2011/0046667 | A1 | 2/2011 | Culligan et al. |
| 2011/0052660 | A1 | 3/2011 | Yang et al. |
| 2011/0056717 | A1 | 3/2011 | Herisse |
| 2011/0060363 | A1 | 3/2011 | Hess et al. |
| 2011/0066156 | A1 | 3/2011 | McGahan et al. |
| 2011/0082538 | A1 | 4/2011 | Dahlgren et al. |
| 2011/0087276 | A1 | 4/2011 | Bedi et al. |
| 2011/0088921 | A1 | 4/2011 | Forgues et al. |
| 2011/0091515 | A1 | 4/2011 | Zilberman et al. |
| 2011/0095064 | A1 | 4/2011 | Taylor et al. |
| 2011/0095067 | A1 | 4/2011 | Ohdaira |
| 2011/0101069 | A1 | 5/2011 | Bombard et al. |
| 2011/0101794 | A1 | 5/2011 | Schroeder et al. |
| 2011/0112517 | A1 | 5/2011 | Peine et al. |
| 2011/0112530 | A1 | 5/2011 | Keller |
| 2011/0114697 | A1 | 5/2011 | Baxter, III et al. |
| 2011/0118708 | A1 | 5/2011 | Burbank et al. |
| 2011/0118754 | A1 | 5/2011 | Dachs, II et al. |
| 2011/0125149 | A1 | 5/2011 | El-Galley et al. |
| 2011/0125176 | A1 | 5/2011 | Yates et al. |
| 2011/0127945 | A1 | 6/2011 | Yoneda |
| 2011/0129706 | A1 | 6/2011 | Takahashi et al. |
| 2011/0144764 | A1 | 6/2011 | Bagga et al. |
| 2011/0147433 | A1 | 6/2011 | Shelton, IV et al. |
| 2011/0160725 | A1 | 6/2011 | Kabaya et al. |
| 2011/0163146 | A1 | 7/2011 | Ortiz et al. |
| 2011/0172495 | A1 | 7/2011 | Armstrong |
| 2011/0174861 | A1 | 7/2011 | Shelton, IV et al. |
| 2011/0192882 | A1 | 8/2011 | Hess et al. |
| 2011/0198381 | A1 | 8/2011 | McCardle et al. |
| 2011/0199225 | A1 | 8/2011 | Touchberry et al. |
| 2011/0218400 | A1 | 9/2011 | Ma et al. |
| 2011/0218550 | A1 | 9/2011 | Ma |
| 2011/0220381 | A1 | 9/2011 | Friese et al. |
| 2011/0224543 | A1 | 9/2011 | Johnson et al. |

(56) References Cited

U.S. PATENT DOCUMENTS

| | | | |
|---|---|---|---|
| 2011/0225105 | A1 | 9/2011 | Scholer et al. |
| 2011/0230713 | A1 | 9/2011 | Kleemann et al. |
| 2011/0235168 | A1 | 9/2011 | Sander |
| 2011/0238044 | A1 | 9/2011 | Main et al. |
| 2011/0241597 | A1 | 10/2011 | Zhu et al. |
| 2011/0251606 | A1 | 10/2011 | Kerr |
| 2011/0256266 | A1 | 10/2011 | Orme et al. |
| 2011/0271186 | A1 | 11/2011 | Owens |
| 2011/0275901 | A1 | 11/2011 | Shelton, IV |
| 2011/0276083 | A1 | 11/2011 | Shelton, IV et al. |
| 2011/0278035 | A1 | 11/2011 | Chen |
| 2011/0278343 | A1 | 11/2011 | Knodel et al. |
| 2011/0279268 | A1 | 11/2011 | Konishi et al. |
| 2011/0285507 | A1 | 11/2011 | Nelson |
| 2011/0290856 | A1 | 12/2011 | Shelton, IV et al. |
| 2011/0290858 | A1 | 12/2011 | Whitman et al. |
| 2011/0292258 | A1 | 12/2011 | Adler et al. |
| 2011/0293690 | A1 | 12/2011 | Griffin et al. |
| 2011/0295295 | A1 | 12/2011 | Shelton, IV et al. |
| 2011/0295299 | A1 | 12/2011 | Braithwaite et al. |
| 2011/0313894 | A1 | 12/2011 | Dye et al. |
| 2011/0315413 | A1 | 12/2011 | Fisher et al. |
| 2012/0004636 | A1 | 1/2012 | Lo |
| 2012/0007442 | A1 | 1/2012 | Rhodes et al. |
| 2012/0008880 | A1 | 1/2012 | Toth |
| 2012/0010615 | A1 | 1/2012 | Cummings et al. |
| 2012/0016239 | A1 | 1/2012 | Barthe et al. |
| 2012/0016413 | A1 | 1/2012 | Timm et al. |
| 2012/0016467 | A1 | 1/2012 | Chen et al. |
| 2012/0029272 | A1 | 2/2012 | Shelton, IV et al. |
| 2012/0029550 | A1 | 2/2012 | Forsell |
| 2012/0033360 | A1 | 2/2012 | Hsu |
| 2012/0059286 | A1 | 3/2012 | Hastings et al. |
| 2012/0064483 | A1 | 3/2012 | Lint et al. |
| 2012/0074200 | A1 | 3/2012 | Schmid et al. |
| 2012/0078243 | A1 | 3/2012 | Worrell et al. |
| 2012/0078244 | A1 | 3/2012 | Worrell et al. |
| 2012/0080336 | A1 | 4/2012 | Shelton, IV et al. |
| 2012/0080344 | A1 | 4/2012 | Shelton, IV |
| 2012/0080478 | A1 | 4/2012 | Morgan et al. |
| 2012/0080491 | A1 | 4/2012 | Shelton, IV et al. |
| 2012/0080498 | A1 | 4/2012 | Shelton, IV et al. |
| 2012/0086276 | A1 | 4/2012 | Sawyers |
| 2012/0095458 | A1 | 4/2012 | Cybulski et al. |
| 2012/0101488 | A1 | 4/2012 | Aldridge et al. |
| 2012/0109186 | A1 | 5/2012 | Parrott et al. |
| 2012/0116261 | A1 | 5/2012 | Mumaw et al. |
| 2012/0116262 | A1 | 5/2012 | Houser et al. |
| 2012/0116263 | A1 | 5/2012 | Houser et al. |
| 2012/0116265 | A1 | 5/2012 | Houser et al. |
| 2012/0116266 | A1 | 5/2012 | Houser et al. |
| 2012/0116381 | A1 | 5/2012 | Houser et al. |
| 2012/0118595 | A1 | 5/2012 | Pellenc |
| 2012/0123463 | A1 | 5/2012 | Jacobs |
| 2012/0125792 | A1 | 5/2012 | Cassivi |
| 2012/0130217 | A1 | 5/2012 | Kauphusman et al. |
| 2012/0132286 | A1 | 5/2012 | Lim et al. |
| 2012/0132663 | A1 | 5/2012 | Kasvikis et al. |
| 2012/0143175 | A1 | 6/2012 | Hermann et al. |
| 2012/0171539 | A1 | 7/2012 | Rejman et al. |
| 2012/0175398 | A1 | 7/2012 | Sandborn et al. |
| 2012/0190964 | A1 | 7/2012 | Hyde et al. |
| 2012/0197239 | A1 | 8/2012 | Smith et al. |
| 2012/0197272 | A1 | 8/2012 | Oray et al. |
| 2012/0203213 | A1 | 8/2012 | Kimball et al. |
| 2012/0211542 | A1 | 8/2012 | Racenet |
| 2012/0220990 | A1 | 8/2012 | Mckenzie et al. |
| 2012/0233298 | A1 | 9/2012 | Verbandt et al. |
| 2012/0234895 | A1 | 9/2012 | O'Connor et al. |
| 2012/0234897 | A1 | 9/2012 | Shelton, IV et al. |
| 2012/0239068 | A1 | 9/2012 | Morris et al. |
| 2012/0241494 | A1 | 9/2012 | Marczyk |
| 2012/0241503 | A1 | 9/2012 | Baxter, III et al. |
| 2012/0248169 | A1 | 10/2012 | Widenhouse et al. |
| 2012/0251861 | A1 | 10/2012 | Liang et al. |
| 2012/0253328 | A1 | 10/2012 | Cunningham et al. |
| 2012/0256494 | A1 | 10/2012 | Kesler et al. |
| 2012/0271327 | A1 | 10/2012 | West et al. |
| 2012/0283707 | A1 | 11/2012 | Giordano et al. |
| 2012/0286019 | A1 | 11/2012 | Hueil et al. |
| 2012/0289811 | A1 | 11/2012 | Viola et al. |
| 2012/0289979 | A1 | 11/2012 | Eskaros et al. |
| 2012/0292367 | A1 | 11/2012 | Morgan et al. |
| 2012/0296316 | A1 | 11/2012 | Imuta |
| 2012/0296342 | A1 | 11/2012 | Haglund Wendelschafer |
| 2012/0298722 | A1 | 11/2012 | Hess et al. |
| 2012/0301498 | A1 | 11/2012 | Altreuter et al. |
| 2012/0310254 | A1 | 12/2012 | Manzo et al. |
| 2012/0312861 | A1 | 12/2012 | Gurumurthy et al. |
| 2012/0316424 | A1 | 12/2012 | Stopek |
| 2012/0330285 | A1 | 12/2012 | Hartoumbekis et al. |
| 2012/0330329 | A1 | 12/2012 | Harris et al. |
| 2013/0006227 | A1 | 1/2013 | Takashino |
| 2013/0008937 | A1 | 1/2013 | Viola |
| 2013/0012983 | A1 | 1/2013 | Kleyman |
| 2013/0018400 | A1 | 1/2013 | Milton et al. |
| 2013/0020375 | A1 | 1/2013 | Shelton, IV et al. |
| 2013/0020376 | A1 | 1/2013 | Shelton, IV et al. |
| 2013/0023861 | A1 | 1/2013 | Shelton, IV et al. |
| 2013/0023910 | A1 | 1/2013 | Solomon et al. |
| 2013/0026208 | A1 | 1/2013 | Shelton, IV et al. |
| 2013/0026210 | A1 | 1/2013 | Shelton, IV et al. |
| 2013/0030462 | A1 | 1/2013 | Keating et al. |
| 2013/0041292 | A1 | 2/2013 | Cunningham |
| 2013/0057162 | A1 | 3/2013 | Pollischansky |
| 2013/0068816 | A1 | 3/2013 | Mandakolathur Vasudevan et al. |
| 2013/0069088 | A1 | 3/2013 | Speck et al. |
| 2013/0075447 | A1 | 3/2013 | Weisenburgh, II et al. |
| 2013/0087597 | A1 | 4/2013 | Shelton, IV et al. |
| 2013/0090534 | A1 | 4/2013 | Burns et al. |
| 2013/0096568 | A1 | 4/2013 | Justis |
| 2013/0098970 | A1 | 4/2013 | Racenet et al. |
| 2013/0106352 | A1 | 5/2013 | Nagamine |
| 2013/0112729 | A1 | 5/2013 | Beardsley et al. |
| 2013/0116669 | A1 | 5/2013 | Shelton, IV et al. |
| 2013/0123816 | A1 | 5/2013 | Hodgkinson et al. |
| 2013/0126202 | A1 | 5/2013 | Oomori et al. |
| 2013/0131476 | A1 | 5/2013 | Siu et al. |
| 2013/0131651 | A1 | 5/2013 | Strobl et al. |
| 2013/0136969 | A1 | 5/2013 | Yasui et al. |
| 2013/0153639 | A1 | 6/2013 | Hodgkinson et al. |
| 2013/0153641 | A1 | 6/2013 | Shelton, IV et al. |
| 2013/0158390 | A1 | 6/2013 | Tan et al. |
| 2013/0162198 | A1 | 6/2013 | Yokota et al. |
| 2013/0165908 | A1 | 6/2013 | Purdy et al. |
| 2013/0169217 | A1 | 7/2013 | Watanabe et al. |
| 2013/0172713 | A1 | 7/2013 | Kirschenman |
| 2013/0172878 | A1 | 7/2013 | Smith |
| 2013/0175315 | A1 | 7/2013 | Milliman |
| 2013/0175317 | A1 | 7/2013 | Yates et al. |
| 2013/0183769 | A1 | 7/2013 | Tajima |
| 2013/0211244 | A1 | 8/2013 | Nathaniel |
| 2013/0214025 | A1 | 8/2013 | Zemlok et al. |
| 2013/0215449 | A1 | 8/2013 | Yamasaki |
| 2013/0231681 | A1 | 9/2013 | Robinson et al. |
| 2013/0233906 | A1 | 9/2013 | Hess et al. |
| 2013/0238021 | A1 | 9/2013 | Gross et al. |
| 2013/0248578 | A1 | 9/2013 | Arteaga Gonzalez |
| 2013/0253480 | A1 | 9/2013 | Kimball et al. |
| 2013/0256373 | A1 | 10/2013 | Schmid et al. |
| 2013/0256380 | A1 | 10/2013 | Schmid et al. |
| 2013/0267950 | A1 | 10/2013 | Rosa et al. |
| 2013/0267978 | A1 | 10/2013 | Trissel |
| 2013/0270322 | A1 | 10/2013 | Scheib et al. |
| 2013/0277410 | A1 | 10/2013 | Fernandez et al. |
| 2013/0284792 | A1 | 10/2013 | Ma |
| 2013/0289565 | A1 | 10/2013 | Hassler, Jr. |
| 2013/0293353 | A1 | 11/2013 | McPherson et al. |
| 2013/0303845 | A1 | 11/2013 | Skula et al. |
| 2013/0304084 | A1 | 11/2013 | Beira et al. |
| 2013/0306704 | A1 | 11/2013 | Balbierz et al. |
| 2013/0327552 | A1 | 12/2013 | Lovelass et al. |
| 2013/0333910 | A1 | 12/2013 | Tanimoto et al. |
| 2013/0334280 | A1 | 12/2013 | Krehel et al. |

(56) References Cited

U.S. PATENT DOCUMENTS

| | | | |
|---|---|---|---|
| 2013/0334283 | A1 | 12/2013 | Swayze et al. |
| 2013/0334285 | A1 | 12/2013 | Swayze et al. |
| 2013/0341374 | A1 | 12/2013 | Shelton, IV et al. |
| 2014/0001231 | A1 | 1/2014 | Shelton, IV et al. |
| 2014/0001234 | A1 | 1/2014 | Shelton, IV et al. |
| 2014/0002322 | A1 | 1/2014 | Kanome et al. |
| 2014/0005550 | A1 | 1/2014 | Lu et al. |
| 2014/0005640 | A1 | 1/2014 | Shelton, IV et al. |
| 2014/0005678 | A1 | 1/2014 | Shelton, IV et al. |
| 2014/0005702 | A1 | 1/2014 | Timm et al. |
| 2014/0005718 | A1 | 1/2014 | Shelton, IV et al. |
| 2014/0008289 | A1 | 1/2014 | Williams et al. |
| 2014/0014704 | A1 | 1/2014 | Onukuri et al. |
| 2014/0014705 | A1 | 1/2014 | Baxter, III |
| 2014/0014707 | A1 | 1/2014 | Onukuri et al. |
| 2014/0018832 | A1 | 1/2014 | Shelton, IV |
| 2014/0022283 | A1 | 1/2014 | Chan et al. |
| 2014/0039549 | A1 | 2/2014 | Belsky et al. |
| 2014/0041191 | A1 | 2/2014 | Knodel |
| 2014/0048580 | A1 | 2/2014 | Merchant et al. |
| 2014/0069240 | A1 | 3/2014 | Dauvin et al. |
| 2014/0078715 | A1 | 3/2014 | Pickard et al. |
| 2014/0081176 | A1 | 3/2014 | Hassan |
| 2014/0088614 | A1 | 3/2014 | Blumenkranz |
| 2014/0088639 | A1 | 3/2014 | Bartels et al. |
| 2014/0094681 | A1 | 4/2014 | Valentine et al. |
| 2014/0100558 | A1 | 4/2014 | Schmitz et al. |
| 2014/0107697 | A1 | 4/2014 | Patani et al. |
| 2014/0110453 | A1 | 4/2014 | Wingardner et al. |
| 2014/0115229 | A1 | 4/2014 | Kothamasu et al. |
| 2014/0131418 | A1 | 5/2014 | Kostrzewski |
| 2014/0131419 | A1 | 5/2014 | Bettuchi |
| 2014/0135832 | A1 | 5/2014 | Park et al. |
| 2014/0148803 | A1 | 5/2014 | Taylor |
| 2014/0151433 | A1 | 6/2014 | Shelton, IV et al. |
| 2014/0155916 | A1 | 6/2014 | Hodgkinson et al. |
| 2014/0158747 | A1 | 6/2014 | Measamer et al. |
| 2014/0166723 | A1 | 6/2014 | Beardsley et al. |
| 2014/0166724 | A1 | 6/2014 | Schellin et al. |
| 2014/0166725 | A1 | 6/2014 | Schellin et al. |
| 2014/0166726 | A1 | 6/2014 | Schellin et al. |
| 2014/0175147 | A1 | 6/2014 | Manoux et al. |
| 2014/0175150 | A1 | 6/2014 | Shelton, IV et al. |
| 2014/0175152 | A1 | 6/2014 | Hess et al. |
| 2014/0181710 | A1 | 6/2014 | Baalu et al. |
| 2014/0183244 | A1 | 7/2014 | Duque et al. |
| 2014/0188091 | A1 | 7/2014 | Vidal et al. |
| 2014/0188101 | A1 | 7/2014 | Bales, Jr. et al. |
| 2014/0188159 | A1 | 7/2014 | Steege |
| 2014/0207124 | A1 | 7/2014 | Aldridge et al. |
| 2014/0209658 | A1 | 7/2014 | Skalla et al. |
| 2014/0224857 | A1 | 8/2014 | Schmid |
| 2014/0228632 | A1 | 8/2014 | Sholev et al. |
| 2014/0228867 | A1 | 8/2014 | Thomas et al. |
| 2014/0239047 | A1 | 8/2014 | Hodgkinson et al. |
| 2014/0243865 | A1 | 8/2014 | Swayze et al. |
| 2014/0246475 | A1 | 9/2014 | Hall et al. |
| 2014/0248167 | A1 | 9/2014 | Sugimoto et al. |
| 2014/0249557 | A1 | 9/2014 | Koch, Jr. et al. |
| 2014/0249573 | A1 | 9/2014 | Arav |
| 2014/0262408 | A1 | 9/2014 | Woodard |
| 2014/0263541 | A1 | 9/2014 | Leimbach et al. |
| 2014/0263552 | A1 | 9/2014 | Hall et al. |
| 2014/0263558 | A1 | 9/2014 | Hausen et al. |
| 2014/0276730 | A1 | 9/2014 | Boudreaux et al. |
| 2014/0276776 | A1 | 9/2014 | Parihar et al. |
| 2014/0284371 | A1 | 9/2014 | Morgan et al. |
| 2014/0287703 | A1 | 9/2014 | Herbsommer et al. |
| 2014/0288460 | A1 | 9/2014 | Ouyang et al. |
| 2014/0291379 | A1 | 10/2014 | Schellin et al. |
| 2014/0291383 | A1 | 10/2014 | Spivey et al. |
| 2014/0299648 | A1 | 10/2014 | Shelton, IV et al. |
| 2014/0303645 | A1 | 10/2014 | Morgan et al. |
| 2014/0303660 | A1 | 10/2014 | Boyden et al. |
| 2014/0330161 | A1 | 11/2014 | Swayze et al. |
| 2014/0330298 | A1 | 11/2014 | Arshonsky et al. |
| 2014/0330579 | A1 | 11/2014 | Cashman et al. |
| 2014/0358163 | A1 | 12/2014 | Farin et al. |
| 2014/0367445 | A1 | 12/2014 | Ingmanson et al. |
| 2014/0371764 | A1 | 12/2014 | Oyola et al. |
| 2014/0373003 | A1 | 12/2014 | Grez et al. |
| 2014/0374130 | A1 | 12/2014 | Nakamura et al. |
| 2014/0378950 | A1 | 12/2014 | Chiu |
| 2015/0001272 | A1 | 1/2015 | Sniffin et al. |
| 2015/0002089 | A1 | 1/2015 | Rejman et al. |
| 2015/0022012 | A1 | 1/2015 | Kim et al. |
| 2015/0025549 | A1 | 1/2015 | Kilroy et al. |
| 2015/0025571 | A1 | 1/2015 | Suzuki et al. |
| 2015/0034697 | A1 | 2/2015 | Mastri et al. |
| 2015/0039010 | A1 | 2/2015 | Beardsley et al. |
| 2015/0053737 | A1 | 2/2015 | Leimbach et al. |
| 2015/0053743 | A1 | 2/2015 | Yates et al. |
| 2015/0053746 | A1 | 2/2015 | Shelton, IV et al. |
| 2015/0053748 | A1 | 2/2015 | Yates et al. |
| 2015/0060516 | A1 | 3/2015 | Collings et al. |
| 2015/0060519 | A1 | 3/2015 | Shelton, IV et al. |
| 2015/0060520 | A1 | 3/2015 | Shelton, IV et al. |
| 2015/0060521 | A1 | 3/2015 | Weisenburgh, II et al. |
| 2015/0066000 | A1 | 3/2015 | An et al. |
| 2015/0067582 | A1 | 3/2015 | Donnelly et al. |
| 2015/0076208 | A1 | 3/2015 | Shelton, IV |
| 2015/0076209 | A1 | 3/2015 | Shelton, IV et al. |
| 2015/0076210 | A1 | 3/2015 | Shelton, IV et al. |
| 2015/0076211 | A1 | 3/2015 | Irka et al. |
| 2015/0080883 | A1 | 3/2015 | Haverkost et al. |
| 2015/0082624 | A1 | 3/2015 | Craig et al. |
| 2015/0083781 | A1 | 3/2015 | Giordano et al. |
| 2015/0087952 | A1 | 3/2015 | Albert et al. |
| 2015/0088127 | A1 | 3/2015 | Craig et al. |
| 2015/0088547 | A1 | 3/2015 | Balram et al. |
| 2015/0090760 | A1 | 4/2015 | Giordano et al. |
| 2015/0090762 | A1 | 4/2015 | Giordano et al. |
| 2015/0127021 | A1 | 5/2015 | Harris et al. |
| 2015/0134077 | A1 | 5/2015 | Shelton, IV et al. |
| 2015/0150620 | A1 | 6/2015 | Miyamoto et al. |
| 2015/0173749 | A1 | 6/2015 | Shelton, IV et al. |
| 2015/0173756 | A1 | 6/2015 | Baxter, III et al. |
| 2015/0173789 | A1 | 6/2015 | Baxter, III et al. |
| 2015/0196295 | A1 | 7/2015 | Shelton, IV et al. |
| 2015/0196299 | A1 | 7/2015 | Swayze et al. |
| 2015/0201918 | A1 | 7/2015 | Kumar et al. |
| 2015/0201932 | A1 | 7/2015 | Swayze et al. |
| 2015/0201936 | A1 | 7/2015 | Swayze et al. |
| 2015/0201937 | A1 | 7/2015 | Swayze et al. |
| 2015/0201938 | A1 | 7/2015 | Swayze et al. |
| 2015/0201939 | A1 | 7/2015 | Swayze et al. |
| 2015/0201940 | A1 | 7/2015 | Swayze et al. |
| 2015/0201941 | A1 | 7/2015 | Swayze et al. |
| 2015/0209045 | A1 | 7/2015 | Hodgkinson et al. |
| 2015/0216605 | A1 | 8/2015 | Baldwin |
| 2015/0222212 | A1 | 8/2015 | Iwata |
| 2015/0223868 | A1 | 8/2015 | Brandt et al. |
| 2015/0230697 | A1 | 8/2015 | Phee et al. |
| 2015/0230794 | A1 | 8/2015 | Wellman et al. |
| 2015/0230861 | A1 | 8/2015 | Woloszko et al. |
| 2015/0231409 | A1 | 8/2015 | Racenet et al. |
| 2015/0238118 | A1 | 8/2015 | Legassey et al. |
| 2015/0272557 | A1 | 10/2015 | Overmyer et al. |
| 2015/0272571 | A1 | 10/2015 | Leimbach et al. |
| 2015/0272580 | A1 | 10/2015 | Leimbach et al. |
| 2015/0272582 | A1 | 10/2015 | Leimbach et al. |
| 2015/0272606 | A1 | 10/2015 | Nobis |
| 2015/0297200 | A1 | 10/2015 | Fitzsimmons et al. |
| 2015/0297222 | A1 | 10/2015 | Huitema et al. |
| 2015/0297223 | A1 | 10/2015 | Huitema et al. |
| 2015/0297225 | A1 | 10/2015 | Huitema et al. |
| 2015/0297824 | A1 | 10/2015 | Cabiri et al. |
| 2015/0303417 | A1 | 10/2015 | Koeder et al. |
| 2015/0305743 | A1 | 10/2015 | Casasanta et al. |
| 2015/0313594 | A1 | 11/2015 | Shelton, IV et al. |
| 2015/0324317 | A1 | 11/2015 | Collins et al. |
| 2015/0352699 | A1 | 12/2015 | Sakai et al. |
| 2015/0366585 | A1 | 12/2015 | Lemay et al. |
| 2015/0367497 | A1 | 12/2015 | Ito et al. |

(56) References Cited

U.S. PATENT DOCUMENTS

2015/0372265 A1 12/2015 Morisaku et al.
2015/0374372 A1 12/2015 Zergiebel et al.
2015/0374378 A1 12/2015 Giordano et al.
2016/0000437 A1 1/2016 Giordano et al.
2016/0000452 A1 1/2016 Yates et al.
2016/0000453 A1 1/2016 Yates et al.
2016/0029998 A1 2/2016 Brister et al.
2016/0030042 A1 2/2016 Heinrich et al.
2016/0030043 A1 2/2016 Fanelli et al.
2016/0030076 A1 2/2016 Faller et al.
2016/0051316 A1 2/2016 Boudreaux
2016/0066913 A1 3/2016 Swayze et al.
2016/0069449 A1 3/2016 Kanai et al.
2016/0074035 A1 3/2016 Whitman et al.
2016/0074040 A1 3/2016 Widenhouse et al.
2016/0081678 A1 3/2016 Kappel et al.
2016/0082161 A1 3/2016 Zilberman et al.
2016/0089175 A1 3/2016 Hibner et al.
2016/0100838 A1 4/2016 Beaupré et al.
2016/0118201 A1 4/2016 Nicholas et al.
2016/0132026 A1 5/2016 Wingardner et al.
2016/0135835 A1 5/2016 Onuma
2016/0135895 A1 5/2016 Faasse et al.
2016/0139666 A1 5/2016 Rubin et al.
2016/0174969 A1 6/2016 Kerr et al.
2016/0174983 A1 6/2016 Shelton, IV et al.
2016/0175021 A1 6/2016 Hassler, Jr.
2016/0183939 A1 6/2016 Shelton, IV et al.
2016/0183943 A1 6/2016 Shelton, IV
2016/0183944 A1 6/2016 Swensgard et al.
2016/0192927 A1 7/2016 Kostrzewski
2016/0192960 A1 7/2016 Bueno et al.
2016/0199063 A1 7/2016 Mandakolathur Vasudevan et al.
2016/0199956 A1 7/2016 Shelton, IV et al.
2016/0220150 A1 8/2016 Sharonov
2016/0235494 A1 8/2016 Shelton, IV et al.
2016/0242783 A1 8/2016 Shelton, IV et al.
2016/0242855 A1 8/2016 Fichtinger et al.
2016/0249910 A1 9/2016 Shelton, IV et al.
2016/0249922 A1 9/2016 Morgan et al.
2016/0249929 A1 9/2016 Cappola et al.
2016/0256159 A1 9/2016 Pinjala et al.
2016/0256184 A1 9/2016 Shelton, IV et al.
2016/0256221 A1 9/2016 Smith
2016/0256229 A1 9/2016 Morgan et al.
2016/0262745 A1 9/2016 Morgan et al.
2016/0262921 A1 9/2016 Balbierz et al.
2016/0270781 A1 9/2016 Scirica
2016/0287265 A1 10/2016 Macdonald et al.
2016/0287279 A1 10/2016 Bovay et al.
2016/0302820 A1 10/2016 Hibner et al.
2016/0310143 A1 10/2016 Bettuchi
2016/0314716 A1 10/2016 Grubbs
2016/0314717 A1 10/2016 Grubbs
2016/0345972 A1 12/2016 Beardsley et al.
2016/0367122 A1 12/2016 Ichimura et al.
2016/0374669 A1 12/2016 Overmyer et al.
2016/0374716 A1 12/2016 Kessler
2017/0000549 A1 1/2017 Gilbert et al.
2017/0007234 A1 1/2017 Chin et al.
2017/0007244 A1 1/2017 Shelton, IV et al.
2017/0007245 A1 1/2017 Shelton, IV et al.
2017/0007347 A1 1/2017 Jaworek et al.
2017/0020616 A1 1/2017 Vale et al.
2017/0035419 A1 2/2017 Decker et al.
2017/0055819 A1 3/2017 Hansen et al.
2017/0055980 A1 3/2017 Vendely et al.
2017/0056008 A1 3/2017 Shelton, IV et al.
2017/0056016 A1 3/2017 Barton et al.
2017/0056018 A1 3/2017 Zeiner et al.
2017/0066054 A1 3/2017 Birky
2017/0079642 A1 3/2017 Overmyer et al.
2017/0086829 A1 3/2017 Vendely et al.
2017/0086830 A1 3/2017 Yates et al.
2017/0086842 A1 3/2017 Shelton, IV et al.
2017/0086930 A1 3/2017 Thompson et al.
2017/0086932 A1 3/2017 Auld et al.
2017/0095922 A1 4/2017 Licht et al.
2017/0105727 A1 4/2017 Scheib et al.
2017/0105733 A1 4/2017 Scheib et al.
2017/0105786 A1 4/2017 Scheib et al.
2017/0106302 A1 4/2017 Cummings et al.
2017/0135711 A1 5/2017 Overmyer et al.
2017/0135717 A1 5/2017 Boudreaux et al.
2017/0135747 A1 5/2017 Broderick et al.
2017/0143336 A1 5/2017 Shah et al.
2017/0168187 A1 6/2017 Calderoni et al.
2017/0172382 A1 6/2017 Nir et al.
2017/0172549 A1 6/2017 Smaby et al.
2017/0172662 A1 6/2017 Panescu et al.
2017/0181803 A1 6/2017 Mayer-Ullmann et al.
2017/0182195 A1 6/2017 Wagner
2017/0182211 A1 6/2017 Raxworthy et al.
2017/0196558 A1 7/2017 Morgan et al.
2017/0196649 A1 7/2017 Yates et al.
2017/0202605 A1 7/2017 Shelton, IV et al.
2017/0202607 A1 7/2017 Shelton, IV et al.
2017/0202770 A1 7/2017 Friedrich et al.
2017/0224332 A1 8/2017 Hunter et al.
2017/0231628 A1 8/2017 Shelton, IV et al.
2017/0231629 A1 8/2017 Stopek et al.
2017/0238962 A1 8/2017 Hansen et al.
2017/0242455 A1 8/2017 Dickens
2017/0245949 A1 8/2017 Randle
2017/0249431 A1 8/2017 Shelton, IV et al.
2017/0252060 A1 9/2017 Ellingson et al.
2017/0255799 A1 9/2017 Zhao et al.
2017/0262110 A1 9/2017 Polishchuk et al.
2017/0265774 A1 9/2017 Johnson et al.
2017/0281186 A1 10/2017 Shelton, IV et al.
2017/0296173 A1 10/2017 Shelton, IV et al.
2017/0296185 A1 10/2017 Swensgard et al.
2017/0296213 A1 10/2017 Swensgard et al.
2017/0303984 A1 10/2017 Malackowski
2017/0312042 A1 11/2017 Giordano et al.
2017/0319047 A1 11/2017 Poulsen et al.
2017/0319201 A1 11/2017 Morgan et al.
2017/0333034 A1 11/2017 Morgan et al.
2017/0333035 A1 11/2017 Morgan et al.
2017/0348010 A1 12/2017 Chiang
2017/0348043 A1 12/2017 Wang et al.
2017/0354413 A1 12/2017 Chen et al.
2017/0358052 A1 12/2017 Yuan
2017/0360441 A1 12/2017 Sgroi
2018/0008265 A1 1/2018 Hatanaka et al.
2018/0042610 A1 2/2018 Sgroi, Jr.
2018/0042689 A1 2/2018 Mozdzierz et al.
2018/0049738 A1 2/2018 Meloul et al.
2018/0049794 A1 2/2018 Swayze et al.
2018/0051780 A1 2/2018 Shelton, IV et al.
2018/0055501 A1 3/2018 Zemlok et al.
2018/0067004 A1 3/2018 Sgroi, Jr.
2018/0085117 A1 3/2018 Shelton, IV et al.
2018/0085120 A1 3/2018 Viola
2018/0092710 A1 4/2018 Bosisio et al.
2018/0114591 A1 4/2018 Pribanic et al.
2018/0116658 A1 5/2018 Aronhalt, IV et al.
2018/0125481 A1 5/2018 Yates et al.
2018/0125487 A1 5/2018 Beardsley
2018/0125488 A1 5/2018 Morgan et al.
2018/0125594 A1 5/2018 Beardsley
2018/0132849 A1 5/2018 Miller et al.
2018/0132850 A1 5/2018 Leimbach et al.
2018/0132926 A1 5/2018 Asher et al.
2018/0132952 A1 5/2018 Spivey et al.
2018/0133521 A1 5/2018 Frushour et al.
2018/0140299 A1 5/2018 Weaner et al.
2018/0146960 A1 5/2018 Shelton, IV et al.
2018/0153542 A1 6/2018 Shelton, IV et al.
2018/0153634 A1 6/2018 Zemlok et al.
2018/0161034 A1 6/2018 Scheib et al.
2018/0168572 A1 6/2018 Burbank
2018/0168574 A1 6/2018 Robinson et al.
2018/0168575 A1 6/2018 Simms et al.

(56) References Cited

U.S. PATENT DOCUMENTS

2018/0168577 A1 6/2018 Aronhalt et al.
2018/0168579 A1 6/2018 Aronhalt et al.
2018/0168598 A1 6/2018 Shelton, IV et al.
2018/0168608 A1 6/2018 Shelton, IV et al.
2018/0168609 A1 6/2018 Fanelli et al.
2018/0168615 A1 6/2018 Shelton, IV et al.
2018/0168618 A1 6/2018 Scott et al.
2018/0168619 A1 6/2018 Scott et al.
2018/0168623 A1 6/2018 Simms et al.
2018/0168625 A1 6/2018 Posada et al.
2018/0168633 A1 6/2018 Shelton, IV et al.
2018/0168647 A1 6/2018 Shelton, IV et al.
2018/0168648 A1 6/2018 Shelton, IV et al.
2018/0168650 A1 6/2018 Shelton, IV et al.
2018/0168754 A1 6/2018 Overmyer
2018/0168756 A1 6/2018 Liao et al.
2018/0206904 A1 7/2018 Felder et al.
2018/0228490 A1 8/2018 Richard et al.
2018/0231111 A1 8/2018 Mika et al.
2018/0231475 A1 8/2018 Brown et al.
2018/0235609 A1 8/2018 Harris et al.
2018/0235617 A1 8/2018 Shelton, IV et al.
2018/0235618 A1 8/2018 Kostrzewski
2018/0235626 A1 8/2018 Shelton, IV et al.
2018/0236181 A1 8/2018 Marlin et al.
2018/0242970 A1 8/2018 Mozdzierz
2018/0247711 A1 8/2018 Terry
2018/0250002 A1 9/2018 Eschbach
2018/0271553 A1 9/2018 Worrell
2018/0271604 A1 9/2018 Grout et al.
2018/0273597 A1 9/2018 Stimson
2018/0279994 A1 10/2018 Schaer et al.
2018/0280073 A1 10/2018 Sanai et al.
2018/0289371 A1 10/2018 Wang et al.
2018/0296216 A1 10/2018 Shelton, IV et al.
2018/0296290 A1 10/2018 Namiki et al.
2018/0317905 A1 11/2018 Olson et al.
2018/0317915 A1 11/2018 Mcdonald, II
2018/0325514 A1 11/2018 Harris et al.
2018/0333169 A1 11/2018 Leimbach et al.
2018/0360446 A1 12/2018 Shelton, IV et al.
2018/0360456 A1 12/2018 Shelton, IV et al.
2018/0368066 A1 12/2018 Howell et al.
2018/0368844 A1 12/2018 Bakos et al.
2018/0372806 A1 12/2018 Laughery et al.
2018/0375165 A1 12/2018 Shelton, IV et al.
2019/0000459 A1 1/2019 Shelton, IV et al.
2019/0000461 A1 1/2019 Shelton, IV et al.
2019/0000475 A1 1/2019 Shelton, IV et al.
2019/0000477 A1 1/2019 Shelton, IV et al.
2019/0000481 A1 1/2019 Harris et al.
2019/0000535 A1 1/2019 Messerly et al.
2019/0000536 A1 1/2019 Yates et al.
2019/0006047 A1 1/2019 Gorek et al.
2019/0008515 A1 1/2019 Beardsley et al.
2019/0015102 A1 1/2019 Baber et al.
2019/0015165 A1 1/2019 Giordano et al.
2019/0017311 A1 1/2019 McGettrick et al.
2019/0021733 A1 1/2019 Burbank
2019/0029682 A1 1/2019 Huitema et al.
2019/0029701 A1 1/2019 Shelton, IV et al.
2019/0038281 A1 2/2019 Shelton, IV et al.
2019/0038283 A1 2/2019 Shelton, IV et al.
2019/0038285 A1 2/2019 Mozdzierz
2019/0059986 A1 2/2019 Shelton, IV et al.
2019/0076143 A1 3/2019 Smith
2019/0090871 A1 3/2019 Shelton, IV et al.
2019/0091183 A1 3/2019 Tomat et al.
2019/0104919 A1 4/2019 Shelton, IV et al.
2019/0105035 A1 4/2019 Shelton, IV et al.
2019/0105036 A1 4/2019 Morgan et al.
2019/0105037 A1 4/2019 Morgan et al.
2019/0105039 A1 4/2019 Morgan et al.
2019/0105044 A1 4/2019 Shelton, IV et al.
2019/0110779 A1 4/2019 Gardner et al.
2019/0110791 A1 4/2019 Shelton, IV et al.
2019/0117224 A1 4/2019 Setser et al.
2019/0125320 A1 5/2019 Shelton, IV et al.
2019/0125336 A1 5/2019 Deck et al.
2019/0125338 A1 5/2019 Shelton, IV et al.
2019/0125342 A1 5/2019 Beardsley et al.
2019/0125344 A1 5/2019 DiNardo et al.
2019/0125361 A1 5/2019 Shelton, IV et al.
2019/0125377 A1 5/2019 Shelton, IV
2019/0125378 A1 5/2019 Shelton, IV et al.
2019/0125388 A1 5/2019 Shelton, IV et al.
2019/0125430 A1 5/2019 Shelton, IV et al.
2019/0125431 A1 5/2019 Shelton, IV et al.
2019/0125432 A1 5/2019 Shelton, IV et al.
2019/0125454 A1 5/2019 Stokes et al.
2019/0125476 A1 5/2019 Shelton, IV et al.
2019/0133422 A1 5/2019 Nakamura
2019/0133577 A1 5/2019 Weadock et al.
2019/0138770 A1 5/2019 Compaijen et al.
2019/0142423 A1 5/2019 Satti, III et al.
2019/0150925 A1 5/2019 Marczyk et al.
2019/0151029 A1 5/2019 Robinson
2019/0175847 A1 6/2019 Pocreva, III et al.
2019/0183502 A1 6/2019 Shelton, IV et al.
2019/0192147 A1 6/2019 Shelton, IV et al.
2019/0192148 A1 6/2019 Shelton, IV et al.
2019/0192151 A1 6/2019 Shelton, IV et al.
2019/0192153 A1 6/2019 Shelton, IV et al.
2019/0192155 A1 6/2019 Shelton, IV et al.
2019/0192157 A1 6/2019 Scott et al.
2019/0200844 A1 7/2019 Shelton, IV et al.
2019/0200905 A1 7/2019 Shelton, IV et al.
2019/0200906 A1 7/2019 Shelton, IV et al.
2019/0200977 A1 7/2019 Shelton, IV et al.
2019/0200981 A1 7/2019 Harris et al.
2019/0200986 A1 7/2019 Shelton, IV et al.
2019/0200987 A1 7/2019 Shelton, IV et al.
2019/0200988 A1 7/2019 Shelton, IV
2019/0200989 A1 7/2019 Burbank et al.
2019/0200997 A1 7/2019 Shelton, IV et al.
2019/0200998 A1 7/2019 Shelton, IV et al.
2019/0201020 A1 7/2019 Shelton, IV et al.
2019/0201024 A1 7/2019 Shelton, IV et al.
2019/0201025 A1 7/2019 Shelton, IV et al.
2019/0201026 A1 7/2019 Shelton, IV et al.
2019/0201027 A1 7/2019 Shelton, IV et al.
2019/0201029 A1 7/2019 Shelton, IV et al.
2019/0201030 A1 7/2019 Shelton, IV et al.
2019/0201034 A1 7/2019 Shelton, IV et al.
2019/0201045 A1 7/2019 Yates et al.
2019/0201046 A1 7/2019 Shelton, IV et al.
2019/0201079 A1 7/2019 Shelton, IV et al.
2019/0201104 A1 7/2019 Shelton, IV et al.
2019/0201112 A1 7/2019 Wiener et al.
2019/0201113 A1 7/2019 Shelton, IV et al.
2019/0201115 A1 7/2019 Shelton, IV et al.
2019/0201118 A1 7/2019 Shelton, IV et al.
2019/0201136 A1 7/2019 Shelton, IV et al.
2019/0201139 A1 7/2019 Shelton, IV et al.
2019/0201140 A1 7/2019 Yates et al.
2019/0201142 A1 7/2019 Shelton, IV et al.
2019/0201158 A1 7/2019 Shelton, IV et al.
2019/0201594 A1 7/2019 Shelton, IV et al.
2019/0205001 A1 7/2019 Messerly et al.
2019/0205567 A1 7/2019 Shelton, IV et al.
2019/0206551 A1 7/2019 Yates et al.
2019/0206555 A1 7/2019 Morgan et al.
2019/0206561 A1 7/2019 Shelton, IV et al.
2019/0206564 A1 7/2019 Shelton, IV et al.
2019/0206569 A1 7/2019 Shelton, IV et al.
2019/0209172 A1 7/2019 Shelton, IV et al.
2019/0209247 A1 7/2019 Giordano et al.
2019/0209248 A1 7/2019 Giordano et al.
2019/0209249 A1 7/2019 Giordano et al.
2019/0209250 A1 7/2019 Giordano et al.
2019/0216558 A1 7/2019 Giordano et al.
2019/0239873 A1 8/2019 Laurent et al.
2019/0247048 A1 8/2019 Gasparovich et al.
2019/0261982 A1 8/2019 Holsten

(56) References Cited

U.S. PATENT DOCUMENTS

2019/0261983 A1 8/2019 Granger et al.
2019/0261984 A1 8/2019 Nelson et al.
2019/0261987 A1 8/2019 Viola et al.
2019/0262153 A1 8/2019 Tassoni et al.
2019/0269400 A1 9/2019 Mandakolathur Vasudevan et al.
2019/0269402 A1 9/2019 Murray et al.
2019/0269428 A1 9/2019 Allen et al.
2019/0274685 A1 9/2019 Olson et al.
2019/0282233 A1 9/2019 Burbank et al.
2019/0290264 A1 9/2019 Morgan et al.
2019/0290266 A1 9/2019 Scheib et al.
2019/0290267 A1 9/2019 Baxter, III et al.
2019/0290297 A1 9/2019 Haider et al.
2019/0298350 A1 10/2019 Shelton, IV et al.
2019/0298353 A1 10/2019 Shelton, IV et al.
2019/0298360 A1 10/2019 Shelton, IV et al.
2019/0298361 A1 10/2019 Shelton, IV et al.
2019/0298362 A1 10/2019 Shelton, IV et al.
2019/0298381 A1 10/2019 Kreidler et al.
2019/0307452 A1 10/2019 Shelton, IV et al.
2019/0307453 A1 10/2019 Shelton, IV et al.
2019/0307454 A1 10/2019 Shelton, IV et al.
2019/0307456 A1 10/2019 Shelton, IV et al.
2019/0314015 A1 10/2019 Shelton, IV et al.
2019/0321040 A1 10/2019 Shelton, IV
2019/0321062 A1 10/2019 Williams
2019/0328387 A1 10/2019 Overmyer et al.
2019/0343515 A1 11/2019 Morgan et al.
2019/0357909 A1 11/2019 Huitema et al.
2019/0388091 A1 12/2019 Eschbach et al.
2020/0000531 A1 1/2020 Giordano et al.
2020/0008802 A1 1/2020 Aronhalt et al.
2020/0008809 A1 1/2020 Shelton, IV et al.
2020/0008827 A1 1/2020 Dearden et al.
2020/0015817 A1 1/2020 Harris et al.
2020/0015915 A1 1/2020 Swayze et al.
2020/0030020 A1 1/2020 Wang et al.
2020/0037939 A1 2/2020 Castagna et al.
2020/0038016 A1 2/2020 Shelton, IV et al.
2020/0038018 A1 2/2020 Shelton, IV et al.
2020/0038020 A1 2/2020 Yates et al.
2020/0046355 A1 2/2020 Harris et al.
2020/0046356 A1 2/2020 Baxter, III et al.
2020/0054320 A1 2/2020 Harris et al.
2020/0054321 A1 2/2020 Harris et al.
2020/0054329 A1 2/2020 Shelton, IV et al.
2020/0054332 A1 2/2020 Shelton, IV et al.
2020/0054333 A1 2/2020 Shelton, IV et al.
2020/0054334 A1 2/2020 Shelton, IV et al.
2020/0054355 A1 2/2020 Laurent et al.
2020/0060523 A1 2/2020 Matsuda et al.
2020/0060713 A1 2/2020 Leimbach et al.
2020/0061385 A1 2/2020 Schwarz et al.
2020/0085431 A1 3/2020 Swayze et al.
2020/0085435 A1 3/2020 Shelton, IV et al.
2020/0085518 A1 3/2020 Giordano et al.
2020/0093484 A1 3/2020 Shelton, IV et al.
2020/0093506 A1 3/2020 Leimbach et al.
2020/0093550 A1 3/2020 Spivey et al.
2020/0100783 A1 4/2020 Yates et al.
2020/0107829 A1 4/2020 Shelton, IV et al.
2020/0114505 A1 4/2020 Kikuchi
2020/0138436 A1 5/2020 Yates et al.
2020/0138507 A1 5/2020 Davison et al.
2020/0138534 A1 5/2020 Garcia Kilroy et al.
2020/0146741 A1 5/2020 Long et al.
2020/0187943 A1 6/2020 Shelton, IV et al.
2020/0197027 A1 6/2020 Hershberger et al.
2020/0205810 A1 7/2020 Posey et al.
2020/0205811 A1 7/2020 Posey et al.
2020/0205823 A1 7/2020 Vendely et al.
2020/0214706 A1 7/2020 Vendely et al.
2020/0214731 A1 7/2020 Shelton, IV et al.
2020/0229814 A1 7/2020 Amariglio et al.
2020/0237371 A1 7/2020 Huitema et al.
2020/0261086 A1 8/2020 Zeiner et al.
2020/0268377 A1 8/2020 Schmid et al.
2020/0275927 A1 9/2020 Shelton, IV et al.
2020/0275930 A1 9/2020 Harris et al.
2020/0280219 A1 9/2020 Laughery et al.
2020/0289112 A1 9/2020 Whitfield et al.
2020/0297341 A1 9/2020 Yates et al.
2020/0305862 A1 10/2020 Yates et al.
2020/0305863 A1 10/2020 Yates et al.
2020/0305864 A1 10/2020 Yates et al.
2020/0305870 A1 10/2020 Shelton, IV
2020/0305872 A1 10/2020 Weidner et al.
2020/0305874 A1 10/2020 Huitema et al.
2020/0315623 A1 10/2020 Eisinger et al.
2020/0323526 A1 10/2020 Huang et al.
2020/0330092 A1 10/2020 Shelton, IV et al.
2020/0330096 A1 10/2020 Shelton, IV et al.
2020/0330181 A1 10/2020 Junger et al.
2020/0337791 A1 10/2020 Shelton, IV et al.
2020/0345346 A1 11/2020 Shelton, IV et al.
2020/0345349 A1 11/2020 Kimball et al.
2020/0345352 A1 11/2020 Shelton, IV et al.
2020/0345353 A1 11/2020 Leimbach et al.
2020/0345356 A1 11/2020 Leimbach et al.
2020/0345357 A1 11/2020 Leimbach et al.
2020/0345358 A1 11/2020 Jenkins
2020/0345359 A1 11/2020 Baxter, III et al.
2020/0345363 A1 11/2020 Shelton, IV et al.
2020/0345435 A1 11/2020 Traina
2020/0352562 A1 11/2020 Timm et al.
2020/0367886 A1 11/2020 Shelton, IV et al.
2020/0375585 A1 12/2020 Swayze et al.
2020/0375597 A1 12/2020 Shelton, IV et al.
2020/0390444 A1 12/2020 Harris et al.
2020/0397430 A1 12/2020 Patel et al.
2020/0405292 A1 12/2020 Shelton, IV et al.
2020/0405293 A1 12/2020 Shelton, IV et al.
2020/0405296 A1 12/2020 Shelton, IV et al.
2020/0405302 A1 12/2020 Shelton, IV et al.
2020/0405304 A1 12/2020 Mozdzierz et al.
2020/0405306 A1 12/2020 Shelton, IV et al.
2020/0405307 A1 12/2020 Shelton, IV et al.
2020/0405308 A1 12/2020 Shelton, IV
2020/0405316 A1 12/2020 Shelton, IV et al.
2020/0405341 A1 12/2020 Hess et al.
2020/0405403 A1 12/2020 Shelton, IV et al.
2020/0405404 A1 12/2020 Shelton, IV et al.
2020/0405410 A1 12/2020 Shelton, IV
2020/0405439 A1 12/2020 Shelton, IV et al.
2020/0410177 A1 12/2020 Shelton, IV
2021/0000466 A1 1/2021 Leimbach et al.
2021/0000467 A1 1/2021 Shelton, IV et al.
2021/0007742 A1 1/2021 Rector et al.
2021/0015480 A1 1/2021 Shelton, IV et al.
2021/0030416 A1 2/2021 Shelton, IV et al.
2021/0045742 A1 2/2021 Shelton, IV et al.
2021/0052271 A1 2/2021 Harris et al.
2021/0059661 A1 3/2021 Schmid et al.
2021/0059662 A1 3/2021 Shelton, IV
2021/0059664 A1 3/2021 Hensel et al.
2021/0059670 A1 3/2021 Overmyer et al.
2021/0059672 A1 3/2021 Giordano et al.
2021/0059673 A1 3/2021 Shelton, IV et al.
2021/0068829 A1 3/2021 Miller et al.
2021/0068835 A1 3/2021 Shelton, IV et al.
2021/0077099 A1 3/2021 Shelton, IV et al.
2021/0077100 A1 3/2021 Shelton, IV et al.
2021/0077109 A1 3/2021 Harris et al.
2021/0085313 A1 3/2021 Morgan et al.
2021/0085314 A1 3/2021 Schmid et al.
2021/0085315 A1 3/2021 Aronhalt et al.
2021/0085316 A1 3/2021 Harris et al.
2021/0085320 A1 3/2021 Leimbach et al.
2021/0085321 A1 3/2021 Shelton, IV et al.
2021/0085325 A1 3/2021 Shelton, IV et al.
2021/0093321 A1 4/2021 Auld et al.
2021/0093323 A1 4/2021 Scirica et al.
2021/0100541 A1 4/2021 Shelton, IV et al.
2021/0100982 A1 4/2021 Laby et al.

(56) References Cited

U.S. PATENT DOCUMENTS

2021/0106333 A1 4/2021 Shelton, IV et al.
2021/0107031 A1 4/2021 Bales, Jr. et al.
2021/0121175 A1 4/2021 Yates et al.
2021/0128146 A1 5/2021 Shelton, IV et al.
2021/0128153 A1 5/2021 Sgroi
2021/0137522 A1 5/2021 Shelton, IV et al.
2021/0153866 A1 5/2021 Knapp et al.
2021/0177401 A1 6/2021 Abramek et al.
2021/0177411 A1 6/2021 Williams
2021/0186492 A1 6/2021 Shelton, IV et al.
2021/0186495 A1 6/2021 Shelton, IV et al.
2021/0186497 A1 6/2021 Shelton, IV et al.
2021/0186499 A1 6/2021 Shelton, IV et al.
2021/0186501 A1 6/2021 Shelton, IV et al.
2021/0186502 A1 6/2021 Shelton, IV et al.
2021/0204941 A1 7/2021 Dewaele et al.
2021/0204951 A1 7/2021 Sgroi et al.
2021/0212671 A1 7/2021 Ramadan et al.
2021/0212691 A1 7/2021 Smith et al.
2021/0212776 A1 7/2021 Schmitt et al.
2021/0228209 A1 7/2021 Shelton, IV et al.
2021/0236117 A1 8/2021 Morgan et al.
2021/0236124 A1 8/2021 Shelton, IV et al.
2021/0244406 A1 8/2021 Kerr et al.
2021/0244407 A1 8/2021 Shelton, IV et al.
2021/0244410 A1 8/2021 Swayze et al.
2021/0244411 A1 8/2021 Smith et al.
2021/0244412 A1 8/2021 Vendely et al.
2021/0259681 A1 8/2021 Shelton, IV et al.
2021/0259687 A1 8/2021 Gonzalez et al.
2021/0259986 A1 8/2021 Widenhouse et al.
2021/0259987 A1 8/2021 Widenhouse et al.
2021/0267589 A1 9/2021 Swayze et al.
2021/0267594 A1 9/2021 Morgan et al.
2021/0267595 A1 9/2021 Posada et al.
2021/0267596 A1 9/2021 Fanelli et al.
2021/0275053 A1 9/2021 Shelton, IV et al.
2021/0275172 A1 9/2021 Harris et al.
2021/0275173 A1 9/2021 Shelton, IV et al.
2021/0275175 A1 9/2021 Vadali et al.
2021/0275176 A1 9/2021 Beckman et al.
2021/0282767 A1 9/2021 Shelton, IV et al.
2021/0282769 A1 9/2021 Baxter, III et al.
2021/0282774 A1 9/2021 Shelton, IV et al.
2021/0282776 A1 9/2021 Overmyer et al.
2021/0290226 A1 9/2021 Mandakolathur Vasudevan et al.
2021/0290231 A1 9/2021 Baxter, III et al.
2021/0290232 A1 9/2021 Harris et al.
2021/0290233 A1 9/2021 Shelton, IV et al.
2021/0290236 A1 9/2021 Moore et al.
2021/0290322 A1 9/2021 Traina
2021/0298745 A1 9/2021 Leimbach et al.
2021/0298746 A1 9/2021 Leimbach et al.
2021/0307744 A1 10/2021 Walcott et al.
2021/0307748 A1 10/2021 Harris et al.
2021/0315566 A1 10/2021 Yates et al.
2021/0315570 A1 10/2021 Shelton, IV
2021/0315571 A1 10/2021 Swayze et al.
2021/0315573 A1 10/2021 Shelton, IV et al.
2021/0315574 A1 10/2021 Shelton, IV et al.
2021/0315576 A1 10/2021 Shelton, IV et al.
2021/0315577 A1 10/2021 Shelton, IV et al.
2021/0322009 A1 10/2021 Huang et al.
2021/0330321 A1 10/2021 Leimbach et al.
2021/0338233 A1 11/2021 Shelton, IV et al.
2021/0338234 A1 11/2021 Shelton, IV et al.
2021/0338260 A1 11/2021 Le Rolland et al.
2021/0353284 A1 11/2021 Yang et al.
2021/0369271 A1 12/2021 Schings et al.
2021/0369273 A1 12/2021 Yates et al.
2021/0378669 A1 12/2021 Shelton, IV et al.
2021/0393260 A1 12/2021 Shelton, IV et al.
2021/0393261 A1 12/2021 Harris et al.
2021/0393262 A1 12/2021 Shelton, IV et al.
2021/0393268 A1 12/2021 Shelton, IV et al.
2021/0393366 A1 12/2021 Shelton, IV et al.
2022/0000478 A1 1/2022 Shelton, IV et al.
2022/0000479 A1 1/2022 Shelton, IV et al.
2022/0015760 A1 1/2022 Beardsley et al.
2022/0031313 A1 2/2022 Bakos et al.
2022/0031314 A1 2/2022 Bakos et al.
2022/0031315 A1 2/2022 Bakos et al.
2022/0031319 A1 2/2022 Witte et al.
2022/0031320 A1 2/2022 Hall et al.
2022/0031322 A1 2/2022 Parks
2022/0031323 A1 2/2022 Witte
2022/0031324 A1 2/2022 Hall et al.
2022/0031345 A1 2/2022 Witte
2022/0031346 A1 2/2022 Parks
2022/0031350 A1 2/2022 Witte
2022/0031351 A1 2/2022 Moubarak et al.
2022/0049593 A1 2/2022 Groover et al.
2022/0054125 A1 2/2022 Ji et al.
2022/0054130 A1 2/2022 Overmyer et al.
2022/0061836 A1 3/2022 Parihar et al.
2022/0061843 A1 3/2022 Vendely et al.
2022/0061845 A1 3/2022 Shelton, IV et al.
2022/0061862 A1 3/2022 Shelton, IV et al.
2022/0071630 A1 3/2022 Swayze et al.
2022/0071631 A1 3/2022 Harris et al.
2022/0071632 A1 3/2022 Patel et al.
2022/0071635 A1 3/2022 Shelton, IV et al.
2022/0079580 A1 3/2022 Vendely et al.
2022/0079586 A1 3/2022 Shelton, IV et al.
2022/0079588 A1 3/2022 Harris et al.
2022/0079589 A1 3/2022 Harris et al.
2022/0079590 A1 3/2022 Harris et al.
2022/0079595 A1 3/2022 Huitema et al.
2022/0079596 A1 3/2022 Huitema et al.
2022/0087676 A1 3/2022 Shelton, IV et al.
2022/0104816 A1 4/2022 Fernandes et al.
2022/0104820 A1 4/2022 Shelton, IV et al.
2022/0117602 A1 4/2022 Wise et al.
2022/0133299 A1 5/2022 Baxter, III
2022/0133300 A1 5/2022 Leimbach et al.
2022/0133301 A1 5/2022 Leimbach
2022/0133302 A1 5/2022 Zerkle et al.
2022/0133303 A1 5/2022 Huang
2022/0133304 A1 5/2022 Leimbach et al.
2022/0133310 A1 5/2022 Ross
2022/0133311 A1 5/2022 Huang
2022/0133312 A1 5/2022 Huang
2022/0142643 A1 5/2022 Shelton, IV et al.
2022/0151611 A1 5/2022 Shelton, IV et al.
2022/0151613 A1 5/2022 Vendely et al.
2022/0151614 A1 5/2022 Vendely et al.
2022/0151615 A1 5/2022 Shelton, IV et al.
2022/0151616 A1 5/2022 Shelton, IV et al.
2022/0160358 A1 5/2022 Wixey
2022/0167968 A1 6/2022 Worthington et al.
2022/0167970 A1 6/2022 Aronhalt et al.
2022/0167971 A1 6/2022 Shelton, IV et al.
2022/0167972 A1 6/2022 Shelton, IV et al.
2022/0167973 A1 6/2022 Shelton, IV et al.
2022/0167974 A1 6/2022 Shelton, IV et al.
2022/0167975 A1 6/2022 Shelton, IV et al.
2022/0167977 A1 6/2022 Shelton, IV et al.
2022/0167979 A1 6/2022 Yates et al.
2022/0167980 A1 6/2022 Shelton, IV et al.
2022/0167981 A1 6/2022 Shelton, IV et al.
2022/0167982 A1 6/2022 Shelton, IV et al.
2022/0167983 A1 6/2022 Shelton, IV et al.
2022/0167984 A1 6/2022 Shelton, IV et al.
2022/0167995 A1 6/2022 Parfett et al.
2022/0168038 A1 6/2022 Shelton, IV et al.
2022/0175370 A1 6/2022 Shelton, IV et al.
2022/0175371 A1 6/2022 Hess et al.
2022/0175372 A1 6/2022 Shelton, IV et al.
2022/0175375 A1 6/2022 Harris et al.
2022/0175378 A1 6/2022 Leimbach et al.
2022/0175381 A1 6/2022 Scheib et al.
2022/0183685 A1 6/2022 Shelton, IV et al.
2022/0211367 A1 7/2022 Schmid et al.
2022/0218332 A1 7/2022 Shelton, IV et al.

(56) References Cited

U.S. PATENT DOCUMENTS

| | | | |
|---|---|---|---|
| 2022/0218333 | A1 | 7/2022 | Parihar et al. |
| 2022/0218334 | A1 | 7/2022 | Parihar et al. |
| 2022/0218336 | A1 | 7/2022 | Timm et al. |
| 2022/0218337 | A1 | 7/2022 | Timm et al. |
| 2022/0218338 | A1 | 7/2022 | Shelton, IV et al. |
| 2022/0218340 | A1 | 7/2022 | Harris et al. |
| 2022/0218344 | A1 | 7/2022 | Leimbach et al. |
| 2022/0218345 | A1 | 7/2022 | Shelton, IV et al. |
| 2022/0218346 | A1 | 7/2022 | Shelton, IV et al. |
| 2022/0218347 | A1 | 7/2022 | Shelton, IV et al. |
| 2022/0218348 | A1 | 7/2022 | Swensgard et al. |
| 2022/0218349 | A1 | 7/2022 | Shelton, IV et al. |
| 2022/0218350 | A1 | 7/2022 | Shelton, IV et al. |
| 2022/0218351 | A1 | 7/2022 | Shelton, IV et al. |
| 2022/0218376 | A1 | 7/2022 | Shelton, IV et al. |
| 2022/0218378 | A1 | 7/2022 | Shelton, IV et al. |
| 2022/0218381 | A1 | 7/2022 | Leimbach et al. |
| 2022/0218382 | A1 | 7/2022 | Leimbach et al. |
| 2022/0225980 | A1 | 7/2022 | Shelton, IV et al. |
| 2022/0225982 | A1 | 7/2022 | Yates et al. |
| 2022/0225986 | A1 | 7/2022 | Shelton, IV et al. |
| 2022/0225993 | A1 | 7/2022 | Huitema et al. |
| 2022/0225994 | A1 | 7/2022 | Setser et al. |
| 2022/0226012 | A1 | 7/2022 | Shelton, IV et al. |
| 2022/0226013 | A1 | 7/2022 | Hall et al. |
| 2022/0233184 | A1 | 7/2022 | Parihar et al. |
| 2022/0233185 | A1 | 7/2022 | Parihar et al. |
| 2022/0233186 | A1 | 7/2022 | Timm et al. |
| 2022/0233187 | A1 | 7/2022 | Timm et al. |
| 2022/0233188 | A1 | 7/2022 | Timm et al. |
| 2022/0233194 | A1 | 7/2022 | Baxter, III et al. |
| 2022/0233195 | A1 | 7/2022 | Shelton, IV et al. |
| 2022/0233257 | A1 | 7/2022 | Shelton, IV et al. |
| 2022/0240928 | A1 | 8/2022 | Timm et al. |
| 2022/0240929 | A1 | 8/2022 | Timm et al. |
| 2022/0240930 | A1 | 8/2022 | Yates et al. |
| 2022/0240936 | A1 | 8/2022 | Huitema et al. |
| 2022/0240937 | A1 | 8/2022 | Shelton, IV et al. |
| 2022/0249095 | A1 | 8/2022 | Shelton, IV et al. |
| 2022/0265272 | A1 | 8/2022 | Li et al. |
| 2022/0273291 | A1 | 9/2022 | Shelton, IV et al. |
| 2022/0273292 | A1 | 9/2022 | Shelton, IV et al. |
| 2022/0273293 | A1 | 9/2022 | Shelton, IV et al. |
| 2022/0273294 | A1 | 9/2022 | Creamer et al. |
| 2022/0273299 | A1 | 9/2022 | Shelton, IV et al. |
| 2022/0273300 | A1 | 9/2022 | Shelton, IV et al. |
| 2022/0273301 | A1 | 9/2022 | Creamer et al. |
| 2022/0273302 | A1 | 9/2022 | Shelton, IV et al. |
| 2022/0273303 | A1 | 9/2022 | Creamer et al. |
| 2022/0273304 | A1 | 9/2022 | Shelton, IV et al. |
| 2022/0273305 | A1 | 9/2022 | Shelton, IV et al. |
| 2022/0273306 | A1 | 9/2022 | Shelton, IV et al. |
| 2022/0273307 | A1 | 9/2022 | Shelton, IV et al. |
| 2022/0273308 | A1 | 9/2022 | Shelton, IV et al. |
| 2022/0278438 | A1 | 9/2022 | Shelton, IV et al. |
| 2022/0287711 | A1 | 9/2022 | Ming et al. |
| 2022/0296230 | A1 | 9/2022 | Adams et al. |
| 2022/0296231 | A1 | 9/2022 | Adams et al. |
| 2022/0296232 | A1 | 9/2022 | Adams et al. |
| 2022/0296233 | A1 | 9/2022 | Morgan et al. |
| 2022/0296234 | A1 | 9/2022 | Shelton, IV et al. |
| 2022/0296235 | A1 | 9/2022 | Morgan et al. |
| 2022/0296236 | A1 | 9/2022 | Bakos et al. |
| 2022/0296237 | A1 | 9/2022 | Bakos et al. |
| 2022/0304679 | A1 | 9/2022 | Bakos et al. |
| 2022/0304680 | A1 | 9/2022 | Shelton, IV et al. |
| 2022/0304681 | A1 | 9/2022 | Shelton, IV et al. |
| 2022/0304682 | A1 | 9/2022 | Shelton, IV et al. |
| 2022/0304683 | A1 | 9/2022 | Shelton, IV et al. |
| 2022/0304684 | A1 | 9/2022 | Bakos et al. |
| 2022/0304685 | A1 | 9/2022 | Bakos et al. |
| 2022/0304686 | A1 | 9/2022 | Shelton, IV et al. |
| 2022/0304687 | A1 | 9/2022 | Shelton, IV et al. |
| 2022/0304688 | A1 | 9/2022 | Shelton, IV et al. |
| 2022/0304689 | A1 | 9/2022 | Shelton, IV |
| 2022/0304690 | A1 | 9/2022 | Baxter, III et al. |
| 2022/0304714 | A1 | 9/2022 | Shelton, IV et al. |
| 2022/0304715 | A1 | 9/2022 | Shelton, IV |
| 2022/0313253 | A1 | 10/2022 | Shelton, IV et al. |
| 2022/0313263 | A1 | 10/2022 | Huitema et al. |
| 2022/0313619 | A1 | 10/2022 | Schmid et al. |
| 2022/0323067 | A1 | 10/2022 | Overmyer et al. |
| 2022/0323070 | A1 | 10/2022 | Ross et al. |
| 2022/0330940 | A1 | 10/2022 | Shelton, IV et al. |
| 2022/0338870 | A1 | 10/2022 | Swayze et al. |
| 2022/0346774 | A1 | 11/2022 | Hess et al. |
| 2022/0346775 | A1 | 11/2022 | Hess et al. |
| 2022/0354493 | A1 | 11/2022 | Shelton, IV et al. |
| 2022/0354495 | A1 | 11/2022 | Baxter, III et al. |
| 2022/0361879 | A1 | 11/2022 | Baxter, III et al. |
| 2022/0370069 | A1 | 11/2022 | Simms et al. |
| 2022/0378418 | A1 | 12/2022 | Huang et al. |
| 2022/0378420 | A1 | 12/2022 | Leimbach et al. |
| 2022/0378424 | A1 | 12/2022 | Huang et al. |
| 2022/0378425 | A1 | 12/2022 | Huang et al. |
| 2022/0378426 | A1 | 12/2022 | Huang et al. |
| 2022/0378427 | A1 | 12/2022 | Huang et al. |
| 2022/0378428 | A1 | 12/2022 | Shelton, IV et al. |
| 2022/0378435 | A1 | 12/2022 | Dholakia et al. |
| 2022/0387030 | A1 | 12/2022 | Shelton, IV et al. |
| 2022/0387031 | A1 | 12/2022 | Yates et al. |
| 2022/0387032 | A1 | 12/2022 | Huitema et al. |
| 2022/0387033 | A1 | 12/2022 | Huitema et al. |
| 2022/0387034 | A1 | 12/2022 | Huitema et al. |
| 2022/0387035 | A1 | 12/2022 | Huitema et al. |
| 2022/0387036 | A1 | 12/2022 | Huitema et al. |
| 2022/0387037 | A1 | 12/2022 | Huitema et al. |
| 2022/0387038 | A1 | 12/2022 | Huitema et al. |
| 2022/0387125 | A1 | 12/2022 | Leimbach et al. |

FOREIGN PATENT DOCUMENTS

| | | | |
|---|---|---|---|
| AU | 2012268848 | A1 | 1/2013 |
| AU | 2011218702 | B2 | 6/2013 |
| AU | 2012200178 | B2 | 7/2013 |
| BR | 112013007744 | A2 | 6/2016 |
| BR | 112013027777 | A2 | 1/2017 |
| CA | 1015829 | A | 8/1977 |
| CA | 1125615 | A | 6/1982 |
| CA | 2520413 | A1 | 3/2007 |
| CA | 2725181 | A1 | 11/2007 |
| CA | 2851239 | A1 | 11/2007 |
| CA | 2664874 | A1 | 11/2009 |
| CA | 2813230 | A1 | 4/2012 |
| CA | 2940510 | A1 | 8/2015 |
| CA | 2698728 | C | 8/2016 |
| CN | 1163558 | A | 10/1997 |
| CN | 2488482 | Y | 5/2002 |
| CN | 1634601 | A | 7/2005 |
| CN | 2716900 | Y | 8/2005 |
| CN | 2738962 | Y | 11/2005 |
| CN | 1777406 | A | 5/2006 |
| CN | 2785249 | Y | 5/2006 |
| CN | 2796654 | Y | 7/2006 |
| CN | 2868212 | Y | 2/2007 |
| CN | 200942099 | Y | 9/2007 |
| CN | 200984209 | Y | 12/2007 |
| CN | 200991269 | Y | 12/2007 |
| CN | 201001747 | Y | 1/2008 |
| CN | 101143105 | A | 3/2008 |
| CN | 201029899 | Y | 3/2008 |
| CN | 101188900 | A | 5/2008 |
| CN | 101203085 | A | 6/2008 |
| CN | 101273908 | A | 10/2008 |
| CN | 101378791 | A | 3/2009 |
| CN | 101507635 | A | 8/2009 |
| CN | 101522120 | A | 9/2009 |
| CN | 101669833 | A | 3/2010 |
| CN | 101716090 | A | 6/2010 |
| CN | 101721236 | A | 6/2010 |
| CN | 101756727 | A | 6/2010 |
| CN | 101828940 | A | 9/2010 |
| CN | 101856250 | A | 10/2010 |
| CN | 101873834 | A | 10/2010 |

(56) References Cited

FOREIGN PATENT DOCUMENTS

| | | | |
|---|---|---|---|
| CN | 201719298 | U | 1/2011 |
| CN | 102038532 | A | 5/2011 |
| CN | 201879759 | U | 6/2011 |
| CN | 201949071 | U | 8/2011 |
| CN | 102217961 | A | 10/2011 |
| CN | 102217963 | A | 10/2011 |
| CN | 102243850 | A | 11/2011 |
| CN | 102247182 | A | 11/2011 |
| CN | 102247183 | A | 11/2011 |
| CN | 101779977 | B | 12/2011 |
| CN | 102309352 | A | 1/2012 |
| CN | 101912284 | B | 7/2012 |
| CN | 102125450 | B | 7/2012 |
| CN | 202313537 | U | 7/2012 |
| CN | 202397539 | U | 8/2012 |
| CN | 202426586 | U | 9/2012 |
| CN | 102743201 | A | 10/2012 |
| CN | 202489990 | U | 10/2012 |
| CN | 102228387 | B | 11/2012 |
| CN | 102835977 | A | 12/2012 |
| CN | 202568350 | U | 12/2012 |
| CN | 103037781 | A | 4/2013 |
| CN | 103083053 | A | 5/2013 |
| CN | 103391037 | A | 11/2013 |
| CN | 203328751 | U | 12/2013 |
| CN | 103505264 | A | 1/2014 |
| CN | 103584893 | A | 2/2014 |
| CN | 103635150 | A | 3/2014 |
| CN | 103690212 | A | 4/2014 |
| CN | 103764046 | A | 4/2014 |
| CN | 203564285 | U | 4/2014 |
| CN | 203564287 | U | 4/2014 |
| CN | 203597997 | U | 5/2014 |
| CN | 103829981 | A | 6/2014 |
| CN | 103829983 | A | 6/2014 |
| CN | 103860221 | A | 6/2014 |
| CN | 103908313 | A | 7/2014 |
| CN | 203693685 | U | 7/2014 |
| CN | 203736251 | U | 7/2014 |
| CN | 103981635 | A | 8/2014 |
| CN | 104027145 | A | 9/2014 |
| CN | 203815517 | U | 9/2014 |
| CN | 102783741 | B | 10/2014 |
| CN | 102973300 | B | 10/2014 |
| CN | 204092074 | U | 1/2015 |
| CN | 104337556 | A | 2/2015 |
| CN | 204158440 | U | 2/2015 |
| CN | 204158441 | U | 2/2015 |
| CN | 102469995 | B | 3/2015 |
| CN | 104422849 | A | 3/2015 |
| CN | 104586463 | A | 5/2015 |
| CN | 204520822 | U | 8/2015 |
| CN | 204636451 | U | 9/2015 |
| CN | 103860225 | B | 3/2016 |
| CN | 103750872 | B | 5/2016 |
| CN | 105919642 | A | 9/2016 |
| CN | 103648410 | B | 10/2016 |
| CN | 105997173 | A | 10/2016 |
| CN | 106344091 | A | 1/2017 |
| CN | 104921730 | B | 9/2017 |
| CN | 104349800 | B | 11/2017 |
| CN | 107635483 | A | 1/2018 |
| CN | 208625784 | U | 3/2019 |
| DE | 273689 | C | 5/1914 |
| DE | 1775926 | A | 1/1972 |
| DE | 3036217 | A1 | 4/1982 |
| DE | 3210466 | A1 | 9/1983 |
| DE | 3709067 | A1 | 9/1988 |
| DE | 19534043 | A1 | 3/1997 |
| DE | 19851291 | A1 | 1/2000 |
| DE | 19924311 | A1 | 11/2000 |
| DE | 20016423 | U1 | 2/2001 |
| DE | 20112837 | U1 | 10/2001 |
| DE | 20121753 | U1 | 4/2003 |
| DE | 202004012389 | U1 | 9/2004 |
| DE | 10314072 | A1 | 10/2004 |
| DE | 102004014011 | A1 | 10/2005 |
| DE | 102004041871 | A1 | 3/2006 |
| DE | 102004063606 | A1 | 7/2006 |
| DE | 202007003114 | U1 | 6/2007 |
| DE | 102010013150 | A1 | 9/2011 |
| DE | 102012213322 | A1 | 1/2014 |
| DE | 102013101158 | A1 | 8/2014 |
| EM | 002220467-0008 | | 4/2013 |
| EP | 0000756 | A1 | 2/1979 |
| EP | 0122046 | A1 | 10/1984 |
| EP | 0129442 | B1 | 11/1987 |
| EP | 0251444 | A1 | 1/1988 |
| EP | 0255631 | A1 | 2/1988 |
| EP | 0169044 | B1 | 6/1991 |
| EP | 0541950 | A1 | 5/1993 |
| EP | 0548998 | A1 | 6/1993 |
| EP | 0594148 | A1 | 4/1994 |
| EP | 0646357 | A1 | 4/1995 |
| EP | 0505036 | B1 | 5/1995 |
| EP | 0669104 | A1 | 8/1995 |
| EP | 0516544 | B1 | 3/1996 |
| EP | 0705571 | A1 | 4/1996 |
| EP | 0528478 | B1 | 5/1996 |
| EP | 0770355 | A1 | 5/1997 |
| EP | 0625335 | B1 | 11/1997 |
| EP | 0879742 | A1 | 11/1998 |
| EP | 0650701 | B1 | 3/1999 |
| EP | 0923907 | A1 | 6/1999 |
| EP | 0484677 | B2 | 7/2000 |
| EP | 1034747 | A1 | 9/2000 |
| EP | 1034748 | A1 | 9/2000 |
| EP | 0726632 | B1 | 10/2000 |
| EP | 1053719 | A1 | 11/2000 |
| EP | 1055399 | A1 | 11/2000 |
| EP | 1055400 | A1 | 11/2000 |
| EP | 1064882 | A1 | 1/2001 |
| EP | 1080694 | A1 | 3/2001 |
| EP | 1090592 | A1 | 4/2001 |
| EP | 1095627 | A1 | 5/2001 |
| EP | 0806914 | B1 | 9/2001 |
| EP | 1234587 | A1 | 8/2002 |
| EP | 1284120 | A1 | 2/2003 |
| EP | 0717967 | B1 | 5/2003 |
| EP | 0869742 | B1 | 5/2003 |
| EP | 1374788 | A1 | 1/2004 |
| EP | 1407719 | A2 | 4/2004 |
| EP | 0996378 | B1 | 6/2004 |
| EP | 1558161 | A1 | 8/2005 |
| EP | 1157666 | B1 | 9/2005 |
| EP | 0880338 | B1 | 10/2005 |
| EP | 1158917 | B1 | 11/2005 |
| EP | 1344498 | B1 | 11/2005 |
| EP | 1330989 | B1 | 12/2005 |
| EP | 1632191 | A2 | 3/2006 |
| EP | 1082944 | B1 | 5/2006 |
| EP | 1253866 | B1 | 7/2006 |
| EP | 1723914 | A1 | 11/2006 |
| EP | 1285633 | B1 | 12/2006 |
| EP | 1011494 | B1 | 1/2007 |
| EP | 1767163 | A1 | 3/2007 |
| EP | 1813207 | A1 | 8/2007 |
| EP | 1837041 | A1 | 9/2007 |
| EP | 0922435 | B1 | 10/2007 |
| EP | 1599146 | B1 | 10/2007 |
| EP | 1330201 | B1 | 6/2008 |
| EP | 2039302 | A2 | 3/2009 |
| EP | 1719461 | B1 | 6/2009 |
| EP | 2090238 | A1 | 8/2009 |
| EP | 2090240 | A1 | 8/2009 |
| EP | 2116196 | A2 | 11/2009 |
| EP | 2153793 | A2 | 2/2010 |
| EP | 1769754 | B1 | 6/2010 |
| EP | 1627605 | B1 | 12/2010 |
| EP | 2316345 | A1 | 5/2011 |
| EP | 1962711 | B1 | 2/2012 |
| EP | 2486862 | A2 | 8/2012 |
| EP | 2486868 | A2 | 8/2012 |
| EP | 2517638 | A1 | 10/2012 |

(56) References Cited

FOREIGN PATENT DOCUMENTS

| | | | |
|---|---|---|---|
| EP | 2529671 | A2 | 12/2012 |
| EP | 2606812 | A1 | 6/2013 |
| EP | 2649948 | A1 | 10/2013 |
| EP | 2649949 | A1 | 10/2013 |
| EP | 2668910 | A2 | 12/2013 |
| EP | 2687164 | A2 | 1/2014 |
| EP | 2713902 | A1 | 4/2014 |
| EP | 2743042 | A2 | 6/2014 |
| EP | 2764827 | A2 | 8/2014 |
| EP | 2777524 | A2 | 9/2014 |
| EP | 2789299 | A1 | 10/2014 |
| EP | 2842500 | A1 | 3/2015 |
| EP | 2853220 | A1 | 4/2015 |
| EP | 2878274 | A1 | 6/2015 |
| EP | 2298220 | B1 | 6/2016 |
| EP | 2510891 | B1 | 6/2016 |
| EP | 3031404 | A1 | 6/2016 |
| EP | 3047806 | A1 | 7/2016 |
| EP | 3078334 | A1 | 10/2016 |
| EP | 2364651 | B1 | 11/2016 |
| EP | 2747235 | B1 | 11/2016 |
| EP | 3095399 | A2 | 11/2016 |
| EP | 3120781 | A2 | 1/2017 |
| EP | 3135225 | A2 | 3/2017 |
| EP | 2789299 | B1 | 5/2017 |
| EP | 3225190 | A2 | 10/2017 |
| EP | 3235445 | A1 | 10/2017 |
| EP | 3326548 | A1 | 5/2018 |
| EP | 3363378 | A1 | 8/2018 |
| EP | 3409216 | A1 | 12/2018 |
| EP | 3476301 | A1 | 5/2019 |
| EP | 3476334 | A1 | 5/2019 |
| EP | 3275378 | B1 | 7/2019 |
| EP | 3505095 | A1 | 7/2019 |
| EP | 3791810 | A1 | 3/2021 |
| ES | 1070456 | U | 9/2009 |
| FR | 459743 | A | 11/1913 |
| FR | 999646 | A | 2/1952 |
| FR | 1112936 | A | 3/1956 |
| FR | 2598905 | A1 | 11/1987 |
| FR | 2689749 | B1 | 7/1994 |
| FR | 2765794 | A1 | 1/1999 |
| FR | 2815842 | A1 | 5/2002 |
| GB | 939929 | A | 10/1963 |
| GB | 1210522 | A | 10/1970 |
| GB | 1217159 | A | 12/1970 |
| GB | 1339394 | A | 12/1973 |
| GB | 2024012 | A | 1/1980 |
| GB | 2109241 | A | 6/1983 |
| GB | 2090534 | B | 6/1984 |
| GB | 2272159 | A | 5/1994 |
| GB | 2336214 | A | 10/1999 |
| GB | 2509523 | A | 7/2014 |
| GR | 930100110 | A | 11/1993 |
| JP | S4711908 | Y1 | 5/1972 |
| JP | S5033988 | U | 4/1975 |
| JP | S5367286 | A | 6/1978 |
| JP | S56112235 | A | 9/1981 |
| JP | S60113007 | A | 6/1985 |
| JP | S62170011 | U | 10/1987 |
| JP | S6333137 | A | 2/1988 |
| JP | S63270040 | A | 11/1988 |
| JP | S63318824 | A | 12/1988 |
| JP | H0129503 | B2 | 6/1989 |
| JP | H02106189 | A | 4/1990 |
| JP | H0378514 | U | 8/1991 |
| JP | H0385009 | U | 8/1991 |
| JP | H0489041 | A | 3/1992 |
| JP | H04215747 | A | 8/1992 |
| JP | H04131860 | U | 12/1992 |
| JP | H0584252 | A | 4/1993 |
| JP | H05123325 | A | 5/1993 |
| JP | H05226945 | A | 9/1993 |
| JP | H0630945 | A | 2/1994 |
| JP | H0636757 | A | 2/1994 |
| JP | H06237937 | A | 8/1994 |
| JP | H06304176 | A | 11/1994 |
| JP | H06327684 | A | 11/1994 |
| JP | H079622 | U | 2/1995 |
| JP | H07124166 | A | 5/1995 |
| JP | H07163573 | A | 6/1995 |
| JP | H07255735 | A | 10/1995 |
| JP | H07285089 | A | 10/1995 |
| JP | H0833642 | A | 2/1996 |
| JP | H08164141 | A | 6/1996 |
| JP | H08182684 | A | 7/1996 |
| JP | H08507708 | A | 8/1996 |
| JP | H08229050 | A | 9/1996 |
| JP | H08289895 | A | 11/1996 |
| JP | H0950795 | A | 2/1997 |
| JP | H09-323068 | A | 12/1997 |
| JP | H10118090 | A | 5/1998 |
| JP | H10-200699 | A | 7/1998 |
| JP | H10296660 | A | 11/1998 |
| JP | 2000014632 | A | 1/2000 |
| JP | 2000033071 | A | 2/2000 |
| JP | 2000112002 | A | 4/2000 |
| JP | 2000166932 | A | 6/2000 |
| JP | 2000171730 | A | 6/2000 |
| JP | 2000210299 | A | 8/2000 |
| JP | 2000271141 | A | 10/2000 |
| JP | 2000287987 | A | 10/2000 |
| JP | 2000325303 | A | 11/2000 |
| JP | 2001-69758 | A | 3/2001 |
| JP | 2001087272 | A | 4/2001 |
| JP | 2001208655 | A | 8/2001 |
| JP | 2001514541 | A | 9/2001 |
| JP | 2001276091 | A | 10/2001 |
| JP | 2002051974 | A | 2/2002 |
| JP | 2002054903 | A | 2/2002 |
| JP | 2002085415 | A | 3/2002 |
| JP | 2002143078 | A | 5/2002 |
| JP | 2002153481 | A | 5/2002 |
| JP | 2002528161 | A | 9/2002 |
| JP | 2002314298 | A | 10/2002 |
| JP | 2003135473 | A | 5/2003 |
| JP | 2003521301 | A | 7/2003 |
| JP | 3442423 | B2 | 9/2003 |
| JP | 2003300416 | A | 10/2003 |
| JP | 2004147701 | A | 5/2004 |
| JP | 2004162035 | A | 6/2004 |
| JP | 2004229976 | A | 8/2004 |
| JP | 2005013573 | A | 1/2005 |
| JP | 2005080702 | A | 3/2005 |
| JP | 2005131163 | A | 5/2005 |
| JP | 2005131164 | A | 5/2005 |
| JP | 2005131173 | A | 5/2005 |
| JP | 2005131211 | A | 5/2005 |
| JP | 2005131212 | A | 5/2005 |
| JP | 2005137423 | A | 6/2005 |
| JP | 2005187954 | A | 7/2005 |
| JP | 2005211455 | A | 8/2005 |
| JP | 2005328882 | A | 12/2005 |
| JP | 2005335432 | A | 12/2005 |
| JP | 2005342267 | A | 12/2005 |
| JP | 3791856 | B2 | 6/2006 |
| JP | 2006187649 | A | 7/2006 |
| JP | 2006218228 | A | 8/2006 |
| JP | 2006281405 | A | 10/2006 |
| JP | 2006291180 | A | 10/2006 |
| JP | 2006346445 | A | 12/2006 |
| JP | 2007-97252 | A | 4/2007 |
| JP | 2007289715 | A | 11/2007 |
| JP | 2007304057 | A | 11/2007 |
| JP | 2007306710 | A | 11/2007 |
| JP | D1322057 | | 2/2008 |
| JP | 2008154804 | A | 7/2008 |
| JP | 2008220032 | A | 9/2008 |
| JP | 2009507526 | A | 2/2009 |
| JP | 2009189838 | A | 8/2009 |
| JP | 2009189846 | A | 8/2009 |
| JP | 2009207260 | A | 9/2009 |
| JP | 2009226028 | A | 10/2009 |
| JP | 2009538684 | A | 11/2009 |

(56) References Cited

FOREIGN PATENT DOCUMENTS

| | | | |
|---|---|---|---|
| JP | 2009539420 | A | 11/2009 |
| JP | D1383743 | | 2/2010 |
| JP | 2010065594 | A | 3/2010 |
| JP | 2010069307 | A | 4/2010 |
| JP | 2010069310 | A | 4/2010 |
| JP | 2010098844 | A | 4/2010 |
| JP | 2010214128 | A | 9/2010 |
| JP | 2011072574 | A | 4/2011 |
| JP | 4722849 | B2 | 7/2011 |
| JP | 4728996 | B2 | 7/2011 |
| JP | 2011524199 | A | 9/2011 |
| JP | 2011200665 | A | 10/2011 |
| JP | D1432094 | | 12/2011 |
| JP | 1433631 | S | 2/2012 |
| JP | 2012115542 | A | 6/2012 |
| JP | 2012143283 | A | 8/2012 |
| JP | 5154710 | B1 | 2/2013 |
| JP | 2013099551 | A | 5/2013 |
| JP | 2013126430 | A | 6/2013 |
| JP | D1481426 | | 9/2013 |
| JP | 2013541982 | A | 11/2013 |
| JP | 2013541983 | A | 11/2013 |
| JP | 2013541997 | A | 11/2013 |
| JP | 2014018667 | A | 2/2014 |
| JP | D1492363 | | 2/2014 |
| JP | 2014121599 | A | 7/2014 |
| JP | 2014171879 | A | 9/2014 |
| JP | 1517663 | S | 2/2015 |
| JP | 2015512725 | A | 4/2015 |
| JP | 2015513956 | A | 5/2015 |
| JP | 2015513958 | A | 5/2015 |
| JP | 2015514471 | A | 5/2015 |
| JP | 2015516838 | A | 6/2015 |
| JP | 2015521524 | A | 7/2015 |
| JP | 2015521525 | A | 7/2015 |
| JP | 2016007800 | A | 1/2016 |
| JP | 2016508792 | A | 3/2016 |
| JP | 2016512057 | A | 4/2016 |
| JP | 2016530949 | A | 10/2016 |
| JP | 2017513563 | A | 6/2017 |
| JP | 1601498 | S | 4/2018 |
| JP | 2019513530 | A | 5/2019 |
| JP | 2020501797 | A | 1/2020 |
| JP | D1677030 | S | 1/2021 |
| JP | D1696539 | S | 10/2021 |
| KR | 20100110134 | A | 10/2010 |
| KR | 20110003229 | A | 1/2011 |
| KR | 300631507 | | 3/2012 |
| KR | 300747646 | | 6/2014 |
| KR | 20180053811 | A | 5/2018 |
| RU | 1814161 | C | 5/1993 |
| RU | 2008830 | C1 | 3/1994 |
| RU | 2052979 | C1 | 1/1996 |
| RU | 2066128 | C1 | 9/1996 |
| RU | 2069981 | C1 | 12/1996 |
| RU | 2098025 | C1 | 12/1997 |
| RU | 2104671 | C1 | 2/1998 |
| RU | 2110965 | C1 | 5/1998 |
| RU | 2141279 | C1 | 11/1999 |
| RU | 2144791 | C1 | 1/2000 |
| RU | 2161450 | C1 | 1/2001 |
| RU | 2181566 | C2 | 4/2002 |
| RU | 2187249 | C2 | 8/2002 |
| RU | 32984 | U1 | 10/2003 |
| RU | 2225170 | C2 | 3/2004 |
| RU | 42750 | U1 | 12/2004 |
| RU | 61114 | U1 | 2/2007 |
| RU | 61122 | U1 | 2/2007 |
| RU | 2430692 | C2 | 10/2011 |
| SU | 189517 | A | 1/1967 |
| SU | 297156 | A | 5/1971 |
| SU | 328636 | A | 9/1972 |
| SU | 511939 | A1 | 4/1976 |
| SU | 674747 | A1 | 7/1979 |
| SU | 728848 | A1 | 4/1980 |
| SU | 1009439 | A | 4/1983 |
| SU | 1042742 | A1 | 9/1983 |
| SU | 1271497 | A1 | 11/1986 |
| SU | 1333319 | A2 | 8/1987 |
| SU | 1377052 | A1 | 2/1988 |
| SU | 1377053 | A1 | 2/1988 |
| SU | 1443874 | A1 | 12/1988 |
| SU | 1509051 | A1 | 9/1989 |
| SU | 1561964 | A1 | 5/1990 |
| SU | 1708312 | A1 | 1/1992 |
| SU | 1722476 | A1 | 3/1992 |
| SU | 1752361 | A1 | 8/1992 |
| SU | 1814161 | A1 | 5/1993 |
| WO | WO-9308754 | A1 | 5/1993 |
| WO | WO-9315648 | A1 | 8/1993 |
| WO | WO-9420030 | A1 | 9/1994 |
| WO | WO-9517855 | A1 | 7/1995 |
| WO | WO-9520360 | A1 | 8/1995 |
| WO | WO-9623448 | A1 | 8/1996 |
| WO | WO-9635464 | A1 | 11/1996 |
| WO | WO-9639086 | A1 | 12/1996 |
| WO | WO-9639088 | A1 | 12/1996 |
| WO | WO-9724073 | A1 | 7/1997 |
| WO | WO-9734533 | A1 | 9/1997 |
| WO | WO-9827870 | A1 | 7/1998 |
| WO | WO-9903407 | A1 | 1/1999 |
| WO | WO-9903409 | A1 | 1/1999 |
| WO | WO-9948430 | A1 | 9/1999 |
| WO | WO-0024322 | A1 | 5/2000 |
| WO | WO-0024330 | A1 | 5/2000 |
| WO | WO-0036690 | A2 | 6/2000 |
| WO | WO-0053112 | A2 | 9/2000 |
| WO | WO-0024448 | A2 | 10/2000 |
| WO | WO-0057796 | A1 | 10/2000 |
| WO | WO-0105702 | A1 | 1/2001 |
| WO | WO-0154594 | A1 | 8/2001 |
| WO | WO-0158371 | A1 | 8/2001 |
| WO | WO-0162164 | A2 | 8/2001 |
| WO | WO-0162169 | A2 | 8/2001 |
| WO | WO-0191646 | A1 | 12/2001 |
| WO | WO-0219932 | A1 | 3/2002 |
| WO | WO-0226143 | A1 | 4/2002 |
| WO | WO-0236028 | A1 | 5/2002 |
| WO | WO-02065933 | A2 | 8/2002 |
| WO | WO-03055402 | A1 | 7/2003 |
| WO | WO-03094747 | A1 | 11/2003 |
| WO | WO-03079909 | A3 | 3/2004 |
| WO | WO-2004019803 | A1 | 3/2004 |
| WO | WO-2004032783 | A1 | 4/2004 |
| WO | WO-2004047626 | A1 | 6/2004 |
| WO | WO-2004047653 | A2 | 6/2004 |
| WO | WO-2004056277 | A1 | 7/2004 |
| WO | WO-2004078050 | A2 | 9/2004 |
| WO | WO-2004078051 | A2 | 9/2004 |
| WO | WO-2004096015 | A2 | 11/2004 |
| WO | WO-2006044581 | A2 | 4/2006 |
| WO | WO-2006051252 | A1 | 5/2006 |
| WO | WO-2006059067 | A1 | 6/2006 |
| WO | WO-2006073581 | A2 | 7/2006 |
| WO | WO-2006085389 | A1 | 8/2006 |
| WO | WO-2007015971 | A2 | 2/2007 |
| WO | WO-2007074430 | A1 | 7/2007 |
| WO | WO-2007129121 | A1 | 11/2007 |
| WO | WO-2007137304 | A2 | 11/2007 |
| WO | WO-2007142625 | A2 | 12/2007 |
| WO | WO-2008021969 | A2 | 2/2008 |
| WO | WO-2008061566 | A1 | 5/2008 |
| WO | WO-2008089404 | A2 | 7/2008 |
| WO | WO-2009005969 | A2 | 1/2009 |
| WO | 2009/046394 | A1 | 4/2009 |
| WO | WO-2009067649 | A2 | 5/2009 |
| WO | WO-2009091497 | A2 | 7/2009 |
| WO | WO-2010126129 | A1 | 11/2010 |
| WO | WO-2010134913 | A1 | 11/2010 |
| WO | WO-2011008672 | A2 | 1/2011 |
| WO | WO-2011044343 | A2 | 4/2011 |
| WO | WO-2012006306 | A2 | 1/2012 |
| WO | WO-2012013577 | A1 | 2/2012 |
| WO | WO-2012044606 | A2 | 4/2012 |

(56) References Cited

FOREIGN PATENT DOCUMENTS

| | | | |
|---|---|---|---|
| WO | WO-2012061725 | A1 | 5/2012 |
| WO | WO-2012072133 | A1 | 6/2012 |
| WO | WO-2012166503 | A1 | 12/2012 |
| WO | WO-2013087092 | A1 | 6/2013 |
| WO | WO-2013151888 | A1 | 10/2013 |
| WO | WO-2014004209 | A2 | 1/2014 |
| WO | WO-2014113438 | A1 | 7/2014 |
| WO | WO-2014175894 | A1 | 10/2014 |
| WO | WO-2015032797 | A1 | 3/2015 |
| WO | WO-2015076780 | A1 | 5/2015 |
| WO | WO-2015137040 | A1 | 9/2015 |
| WO | WO-2015138760 | A1 | 9/2015 |
| WO | WO-2015187107 | A1 | 12/2015 |
| WO | WO-2016100682 | A1 | 6/2016 |
| WO | WO-2016107448 | A1 | 7/2016 |
| WO | WO-2017138905 | A1 | 8/2017 |
| WO | WO-2018011664 | A1 | 1/2018 |
| WO | WO-2019036490 | A1 | 2/2019 |
| WO | WO-2019130087 | A1 | 7/2019 |
| WO | WO-2019130089 | A1 | 7/2019 |
| WO | WO-2019208902 | A1 | 10/2019 |
| WO | WO-2021189234 | A1 | 9/2021 |

OTHER PUBLICATIONS

ASTM procedure D2240-05, "Standard Test Method for Rubber Property-Durometer Hardness," (Published Apr. 2010).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
Disclosed Anonymously, "Motor-Driven Surgical Stapler Improvements," Research Disclosure Database No. 526041, Published: Feb. 2008.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
D. Tuite, Ed., "Get The Lowdown on Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Covidien Brochure, "Endo GIA™ Ultra Universal Stapler," (2010), 2 pages.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Peppas, Editor "Hydrogels in Medicine and Pharmacy," vol. I, Fundamentals, CRC Press, 1986.
Young, "Microcellular foams via phase separation," Journal of Vacuum Science & Technology A 4(3), (May/Jun. 1986).
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.
Solorio et al., "Gelatin Microspheres Crosslinked with Genipin for Local Delivery of Growth Factors," J. Tissue Eng. Regen. Med. (2010), 4(7): pp. 514-523.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien Brochure "iDrive™ Ultra Powered Stapling System," (6 pages).
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Pitt et al., "Attachment of Hyaluronan to Metallic Surfaces," J. Biomed. Mater. Res. 68A: pp. 95-106, 2004.
Indian Standard: Automotive Vehicles—Brakes and Braking Systems (IS 11852-1:2001), Mar. 1, 2001.
Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.
Byrne et al., "Molecular Imprinting Within Hydrogels," Advanced Drug Delivery Reviews, 54 (2002) pp. 149-161.
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Chen et al., "Elastomeric Biomaterials for Tissue Engineering," Progress in Polymer Science 38 (2013), pp. 584-671.
Matsuda, "Thermodynamics of Formation of Porous Polymeric Membrane from Solutions," Polymer Journal, vol. 23, No. 5, pp. 435-444 (1991).
Covidien Brochure, "Endo GIA™ Black Reload with Tri-Staple™ Technology," (2012), 2 pages.
Biomedical Coatings, Fort Wayne Metals, Research Products Corporation, obtained online at www.fwmetals.com on Jun. 21, 2010 (1 page).
The Sodem Aseptic Battery Transfer Kit, Sodem Systems, 2000, 3 pages.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileId=db3a304332d040720132d939503e5f17 [retrieved on Oct. 18, 2016].
Mouser Electronics, "LM317M 3—Terminal Adjustable Regulator with Overcurrent/Overtemperature Self Protection", Mar. 31, 2014 (Mar. 31, 2014), XP0555246104, Retrieved from the Internet: URL: http://www.mouser.com/ds/2/405/lm317m-440423.pdf, pp. 1-8.

(56) References Cited

OTHER PUBLICATIONS

Mouser Electronics, "LM317 3—Terminal Adjustable Regulator with Overcurrent/Overtemperature Self Protection", Sep. 30, 2016 (Sep. 30, 2016), XP0555246104, Retrieved from the Internet: URL: http://www.mouser.com/ds/2/405/lm317m-440423.pdf, pp. 1-9.
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
Yan et al., Comparison of the effects of Mg—6Zn and Ti—3Al-2.5V alloys on TGF-β/TNF-α/VEGF/b-FGF in the healing of the intestinal track in vivo, Biomed. Mater. 9 (2014), 11 pages.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Anonymous, Analog Devices Wiki, Chapter 11: The Current Mirror, Aug. 20, 2017, 22 pages. https://wiki.analog.com/university/courses/electronics/text/chapter-11?rev=1503222341.
Yan et al., "Comparison of the effects of Mg—6Zn and titanium on intestinal tract in vivo," J Mater Sci: Mater Med (2013), 11 pages.
Brar et al., "Investigation of the mechanical and degradation properties of Mg—Sr and Mg—Zn—Sr alloys for use as potential biodegradable implant materials," J. Mech. Behavior of Biomed. Mater. 7 (2012) pp. 87-95.
Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.
Qiu Li Loh et al.: "Three-Dimensional Scaffolds for Tissue Engineering Applications: Role of Porosity and Pore Size", Tissue Engineering Part B—Reviews, vol. 19, No. 6, Dec. 1, 2013, pp. 485-502.
Gao et al., "Mechanical Signature Enhancement of Response Vibrations in the Time Lag Domain," Fifth International Congress on Sound and Vibration, Dec. 15-18, 1997, pp. 1-8.
Trendafilova et al., "Vibration-based Methods for Structural and Machinery Fault Diagnosis Based on Nonlinear Dynamics Tools," In: Fault Diagnosis in Robotic and Industrial Systems, IConcept Press LTD, 2012, pp. 1-29.
Youtube.com; video by Fibran (retrieved from URL https://www.youtube.com/watch?v=vN2Qjt51gFQ); (Year: 2018).
Foot and Ankle: Core Knowledge in Orthopaedics; by DiGiovanni MD, Elsevier; (p. 27, left column heading "Materials for Soft Orthoses", 7th bullet point); (Year: 2007).
Lee, Youbok, "Antenna Circuit Design for RFID Applications," 2003, pp. 1-50, DS00710C, Microchip Technology Inc., Available: http://ww1.microchip.com/downloads/en/AppNotes/00710c.pdf.
Kawamura, Atsuo, et al. "Wireless Transmission of Power and Information Through One High-Frequency Resonant AC Link Inverter for Robot Manipulator Applications," Journal, May/Jun. 1996, pp. 503-508, vol. 32, No. 3, IEEE Transactions on Industry Applications.
Honda HS1332AT and ATD Model Info, powerequipment.honda.com [online], published on or before Mar. 22, 2016, [retrieved on May 31, 2019], retrieved from the Internet [URL: https://powerequipment.honda.com/snowblowers/models/hss1332at-hss1332atd] {Year: 2016).
Slow Safety Sign, shutterstock.com [online], published on or before May 9, 2017, [retrieved on May 31, 2019], retrieved from the https://www.shutterstock.com/image-victor/slow-safety-sign-twodimensional-turtle-symbolizing- . . . see PDF in file for full URL] (Year: 2017).
Warning Sign Beveled Buttons, by Peter, flarestock.com [online], published on or before Jan. 1, 2017, [retrieved on Jun. 4, 2019], retrieved from the Internet [URL: https://www.flarestock.com/stock-images/warning-sign-beveled-buttons/70257] (Year: 2017).
Arrow Sign Icon Next Button, by Blan-k, shutterstock.com [online], published on or before Aug. 6, 2014, [retrieved on Jun. 4, 2019], retrieved from the Internet [URL:https://www.shutterstock.com/de/image-vector/arrow-sign-icon-next-button-navigation-207700303?irgwc=1&utm . . . see PDF in file for full URL] (Year: 2014).
Elite Icons, by smart/icons, iconfinder.com [online], published on Aug. 18, 2016, [retrieved on Jun. 4, 2019], retrieved from the Internet [URL: https://www.iconfinder.com/iconsets/elite] (Year: 2016).
Tutorial overview of inductively coupled RFID Systems, UPM, May 2003, pp. 1-7, UPM Rafsec, <http://cdn.mobiusconsulting.com/papers/rfidsystems.pdf>.
Schroeter, John, "Demystifying UHF Gen 2 RFID, HF RFID," Online Article, Jun. 2, 2008, pp. 1-3, <https://www.edn.com/design/industrial-control/4019123/Demystifying-UHF-Gen-2-RFID-HF-RFID>.
Adeeb, et al., "An Inductive Link-Based Wireless Power Transfer System for Biomedical Applications." Research Article, Nov. 14, 2011, pp. 1-12, vol. 2012, Article ID 879294, Hindawi Publishing Corporation.
Pushing Pixels (GIF), published on dribble.com, 2013.
Sodium stearate C18H35NaO2, Chemspider Search and Share Chemistry, Royal Society of Chemistry, pp. 1-3, 2015, http://www.chemspider.com/Chemical-Structure.12639.html, accessed May 23, 2016.
NF Monographs: Sodium Stearate, U.S. Pharmacopeia, http://www.pharmacopeia.cn/v29240/usp29nf24s0_m77360.html, accessed May 23, 2016.
Fischer, Martin H, "Colloid-Chemical Studies on Soaps", The Chemical Engineer, pp. 184-193, Aug. 1919.
V.K. Ahluwalia and Madhuri Goyal, A Textbook of Organic Chemistry, Section 19.11.3, p. 356, 2000.
A.V. Kasture and S.G. Wadodkar, Pharmaceutical Chemistry—II: Second Year Diploma in Pharmacy, Nirali Prakashan, p. 339, 2007.
Forum discussion regarding "Speed is Faster", published on Oct. 1, 2014 and retrieved on Nov. 8, 2019 from URL https://english.stackexchange.com/questions/199018/how-is-that-correct-speed-is-faster-or-prices-are-cheaper (Year: 2014).
"Understanding the Requirements of ISO/IEC 14443 for Type B Proximity Contactless Identification Cards," retrieved from https://www.digchip.com/application-notes/22/15746.php on Mar. 2, 2020, pp. 1-28 (Nov. 2005).
Jauchem, J.R., "Effects of low-level radio-frequency (3 kHz to 300 GHz) enery on human cardiovascular, reproductive, immune, and other systems: A review of the recent literatured," Int. J. Hyg. Environ. Health 211 (2008) 1-29.
Sandvik, "Welding Handbook," https://www.meting.rs/wp-content/uploads/2018/05/welding-handbook.pdf, retrieved on Jun. 22, 2020. pp. 5-6.
Ludois, Daniel C., "Capacitive Power Transfer for Rotor Field Current in Synchronous Machines," IEEE Transactions on Power Electronics, Institute of Electrical and Electronics Engineers, USA, vol. 27, No. 11, Nov. 1, 2012, pp. 4638-4645.
Rotary Systems: Sealed Slip Ring Categories, Rotary Systems, May 22, 2017, retrieved from the internet: http://web.archive.org/we/20170522174710/http:/rotarysystems.com: 80/slip-rings/sealed/, retrieved on Aug. 12, 2020, pp. 1-2.
IEEE Std 802.3-2012 (Revision of IEEE Std 802.3-2008, published Dec. 28, 2012.
"ATM-MPLS Network Interworking Version 2.0, af-aic-0178.001" ATM Standard, The ATM Forum Technical Committee, published Aug. 2003.
Yang et al.; "4D printing reconfigurable, deployable and mechanically tunable metamaterials," Material Horizions, vol. 6, pp. 1244-1250 (2019).
"Council Directive 93/42/EEC of Jun. 14, 1993 Concerning Medical Devices," Official Journal of the European Communities, L&C. Ligislation and Competition, S, No. L 169, Jun. 14, 1993, pp. 1-43.
Arjo Loeve et al., Scopes Too Flexible . . . and Too Stiff, 2010, IEEE Pulse, Nov./Dec. 2010 (Year: 2010), 16 pages.
Molina, "Low Level Reader Protocol (LLRP)," Oct. 13, 2010, pp. 1-198.
Makerbot, 10 Advantages of 3D Printing, 2020 (retrieved via the wayback machine), Makerbot.com (Year: 2020).
U.S. Appl. No. 62/798,651, filed Jan. 30, 2019.
U.S. Appl. No. 62/840,602, filed Apr. 30, 2019.

(56) References Cited

OTHER PUBLICATIONS

Australian Office Action dated Nov. 7, 2013, for Application No. 2011307329, 3 pages.
Canadian first Office Action dated Oct. 13, 2017, for Application No. 2,813,383, 6 pages.
Canadian second Office Action dated Jun. 11, 2018, for Application No. 2,813,383, 3 pages.
Chinese Office Action dated Jan. 28, 2015, For Application No. 201180057826.6, 10 pages.
European Communication dated Feb. 21, 2017, for Application No. 11767867.2, 5 pages.
European Communication dated Nov. 23, 2020, for Application No. 11767867.2, 5 pages.
International Search Report and Written Opinion dated Nov. 30, 2011, for International Application No. PCT/US2011/053393, 11 pages.
Japanese Office Action dated Aug. 18, 2015, for Application No. 2013-531705, 3 pages.

* cited by examiner

SURGICAL INSTRUMENT HAVING A POWER CONTROL CIRCUIT

CROSS-REFERENCE TO RELATED APPLICATIONS

This application is a continuation of application claiming priority under 35 U.S.C. § 120 to U.S. patent application Ser. No. 16/902,443, entitled SURGICAL INSTRUMENT HAVING A POWER CONTROL CIRCUIT, filed Jun. 16, 2020, now U.S. Patent Application Publication No. 2021/0000470, issued as U.S. Pat. No. 11,529,142 on Nov. 30, 2022, which is a continuation application claiming priority under 35 U.S.C. § 120 to U.S. patent application Ser. No. 15/592,820, entitled SURGICAL INSTRUMENT INCLUDING A RETRACTABLE FIRING MEMBER, filed May 11, 2017, which issued on Jun. 30, 2020 as U.S. Pat. No. 10,695,062, which is a continuation application claiming priority under 35 U.S.C. § 120 to U.S. patent application Ser. No. 14/188,199, entitled SURGICAL INSTRUMENT HAVING A POWER CONTROL CIRCUIT, filed Feb. 24, 2014, which issued on Jun. 27, 2017 as U.S. Pat. No. 9,687,236, which is a continuation application claiming priority under 35 U.S.C. § 120 to U.S. patent application Ser. No. 12/896,381, entitled SURGICAL INSTRUMENT HAVING A POWER CONTROL CIRCUIT, filed Oct. 1, 2010, which issued on Apr. 15, 2014 as U.S. Pat. No. 8,695,866, the entire disclosures of which are hereby incorporated by reference herein.

BACKGROUND

Traditionally, surgical devices have been hand operated, with the force to fire and/or manipulate the instruments provided directly by the clinician. A growing number of surgical instruments, however, are powered surgical instruments where the force to fire and/or manipulate the instrument are provided by an automated device, such as an electric motor, pneumatic or hydraulic device, etc. Examples of powered surgical instruments may include such as cutters, graspers, and/or staplers, for example. Such powered instruments free instrument designers from the need to limit the amount of force required to fire to that which can reasonably be provided by a human clinician. Powered instruments may also be more easily used by smaller clinicians and/or clinicians with less physical strength.

One significant challenge of powered instruments, however, is lack of feedback to the clinician. When a clinician uses a manually powered surgical instrument, the clinician is able to know the state of the instrument based on the amount of force that the clinician has already provided to the instrument, the position of the handle trigger or other device for receiving clinician force, etc. In a powered instrument, however, such feedback may be absent. Accordingly, there is a need to compensate for the lack of feedback from powered surgical instruments.

DRAWINGS

The features of the various embodiments are set forth with particularity in the appended claims. The various embodiments, however, both as to organization and methods of operation, together with advantages thereof, may best be understood by reference to the following description, taken in conjunction with the accompanying drawings as follows:

Figure 1:
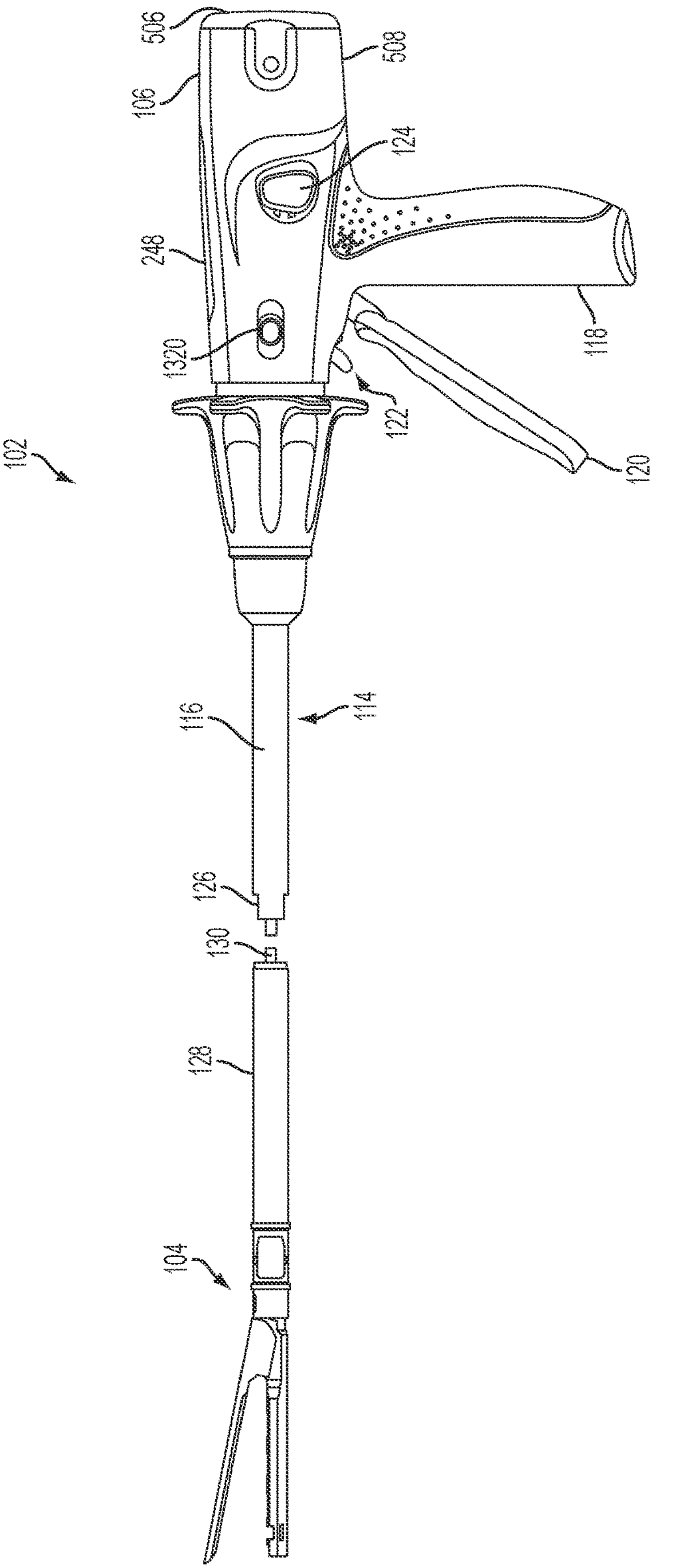
FIG. 1 shows one embodiment of a surgical stapling and cutting instrument with an electrically powered firing feature.
Figure 27:
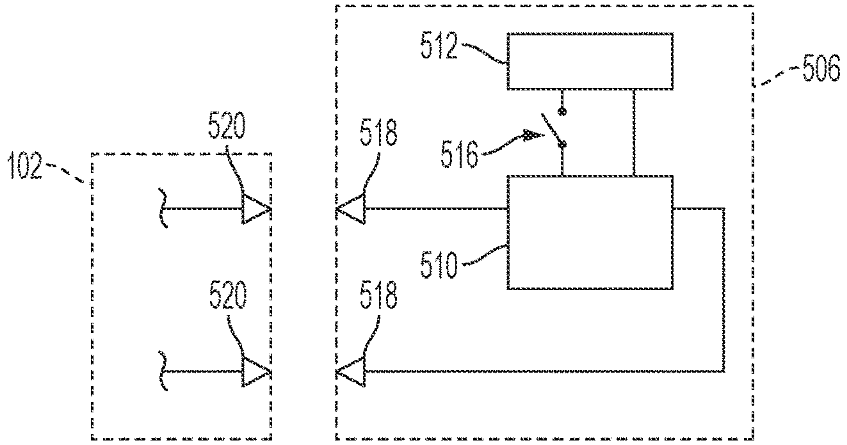
Figure 28:
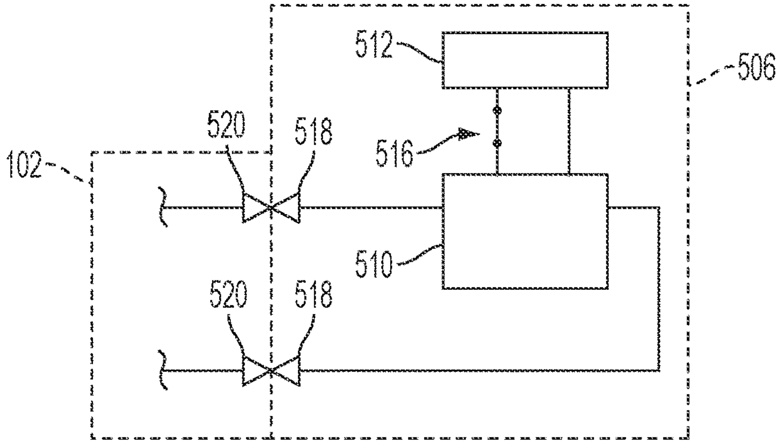
Figure 29:
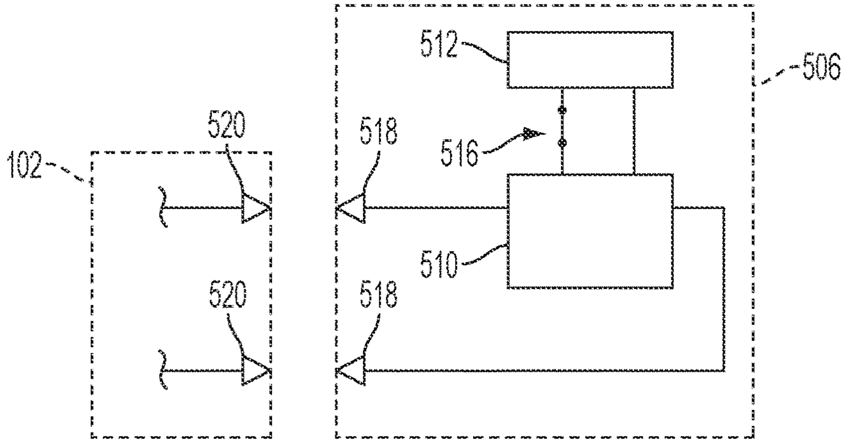

FIGS. 27-29 schematically illustrate one embodiment of a battery unit and a portion of the instrument of FIG. 1 showing the attachment and detachment of the battery unit to the instrument.

Figure 30:
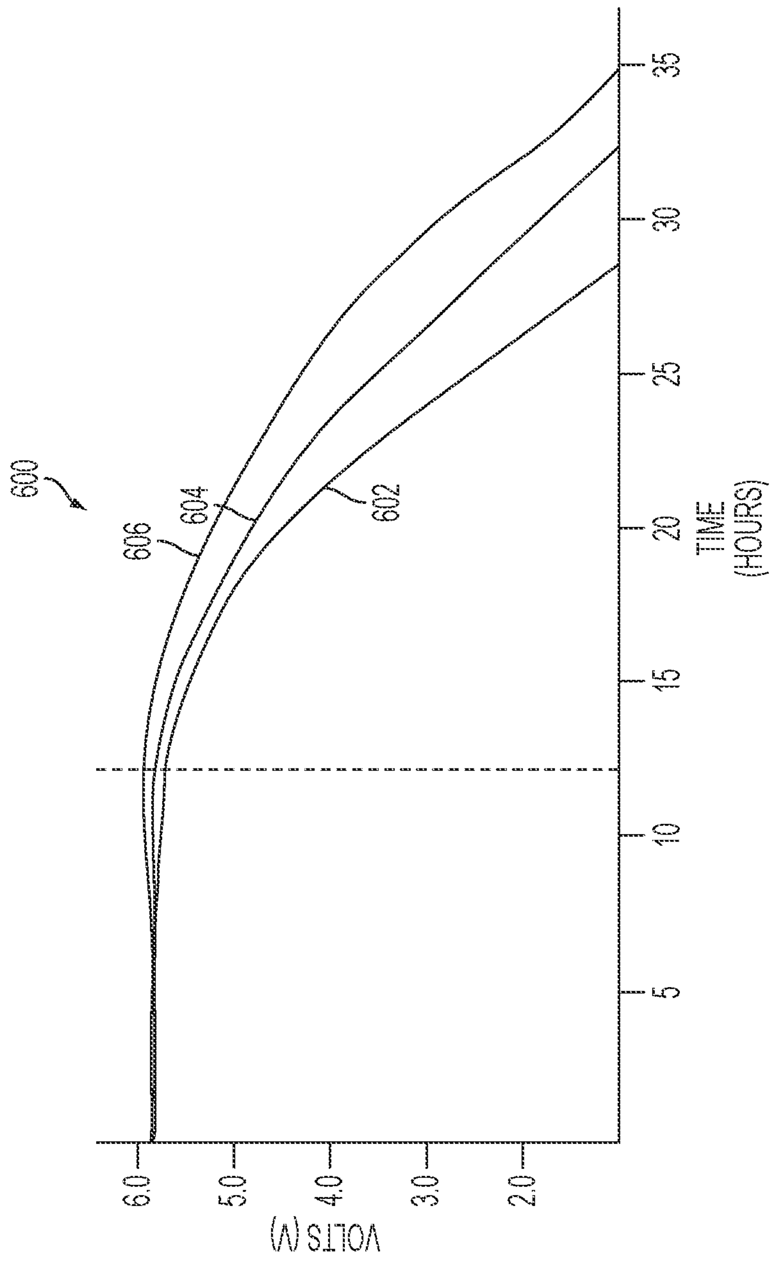

FIG. 30 illustrates a graph of the voltage level of one embodiment of the battery unit of FIGS. 27, 28 and 29 over time, as measured from the time of attachment to the instrument of FIG. 1.

Figure 31:
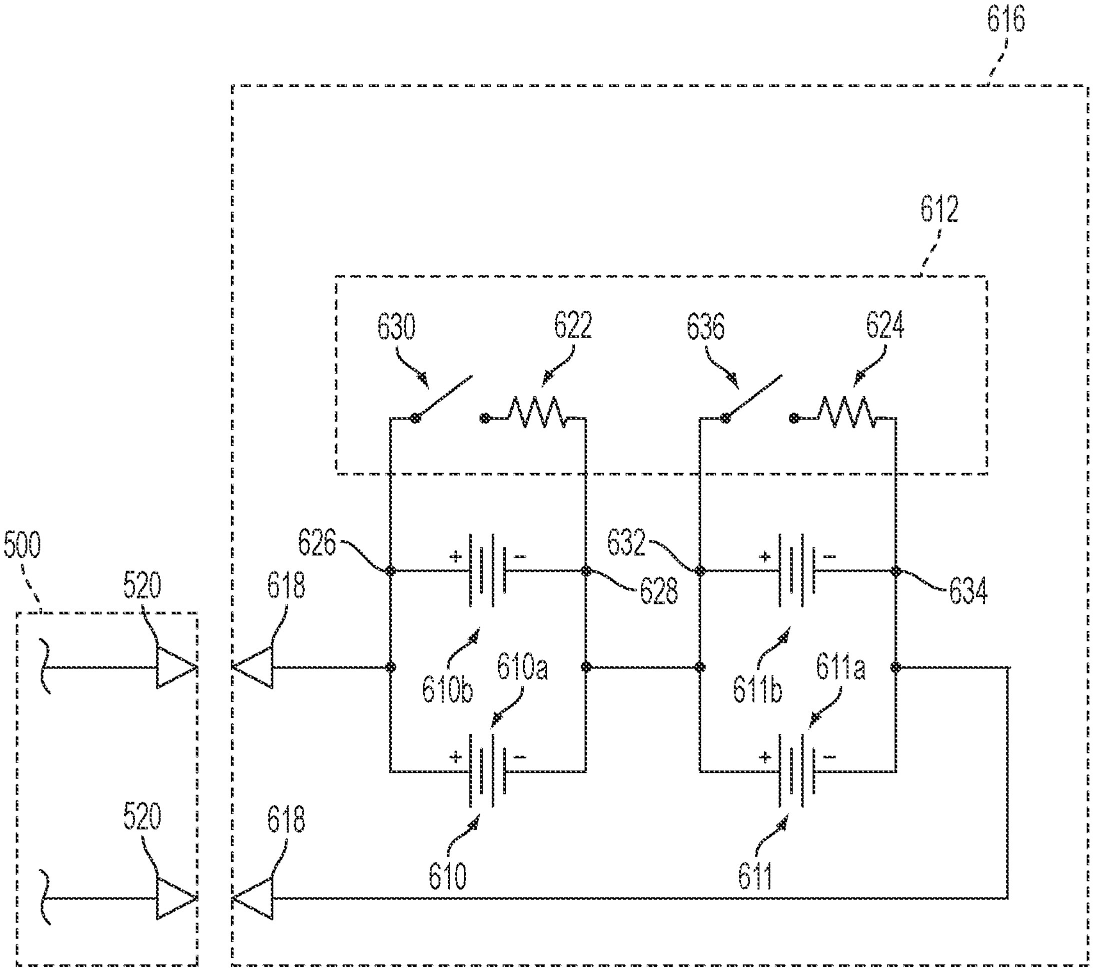

FIG. 31 shows one embodiment of a simplified circuit diagram of one embodiment of a battery unit comprising a drain.

Figure 32:
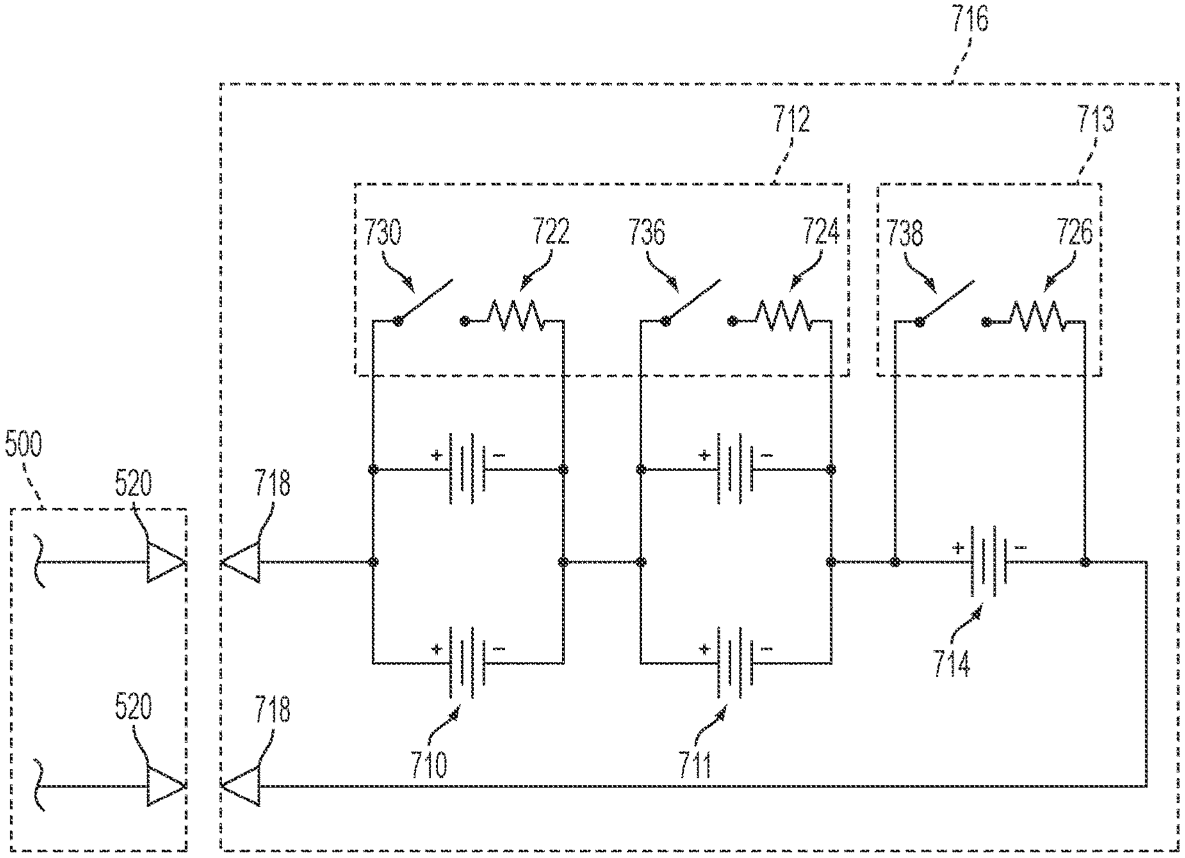
Figure 33:
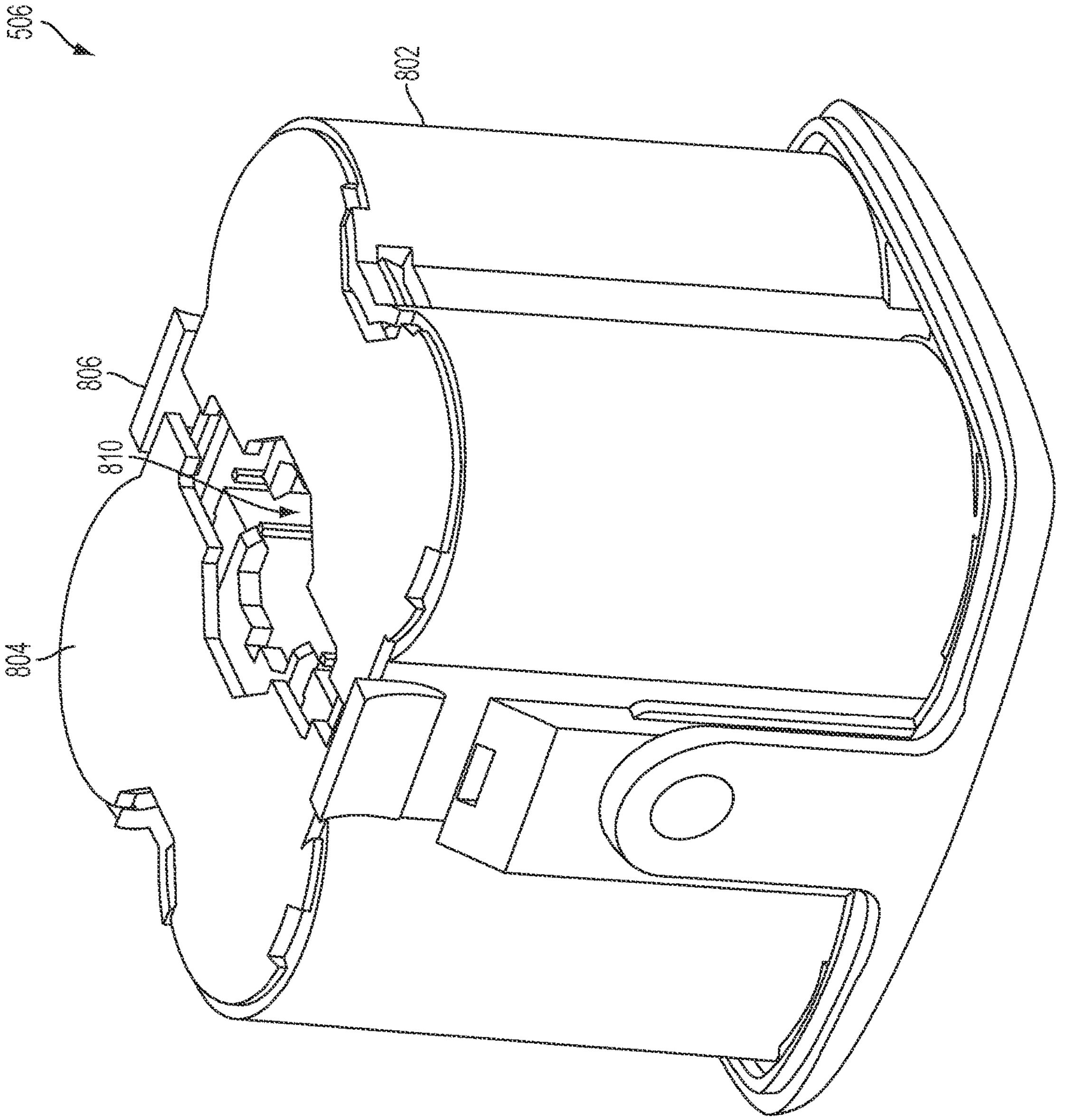

FIG. 32 is one embodiment of a simplified circuit diagram of one embodiment of a battery unit comprising a first drain and a second drain.

FIGS. 33-36 are perspective views of one embodiment of a battery unit.

Figure 35:
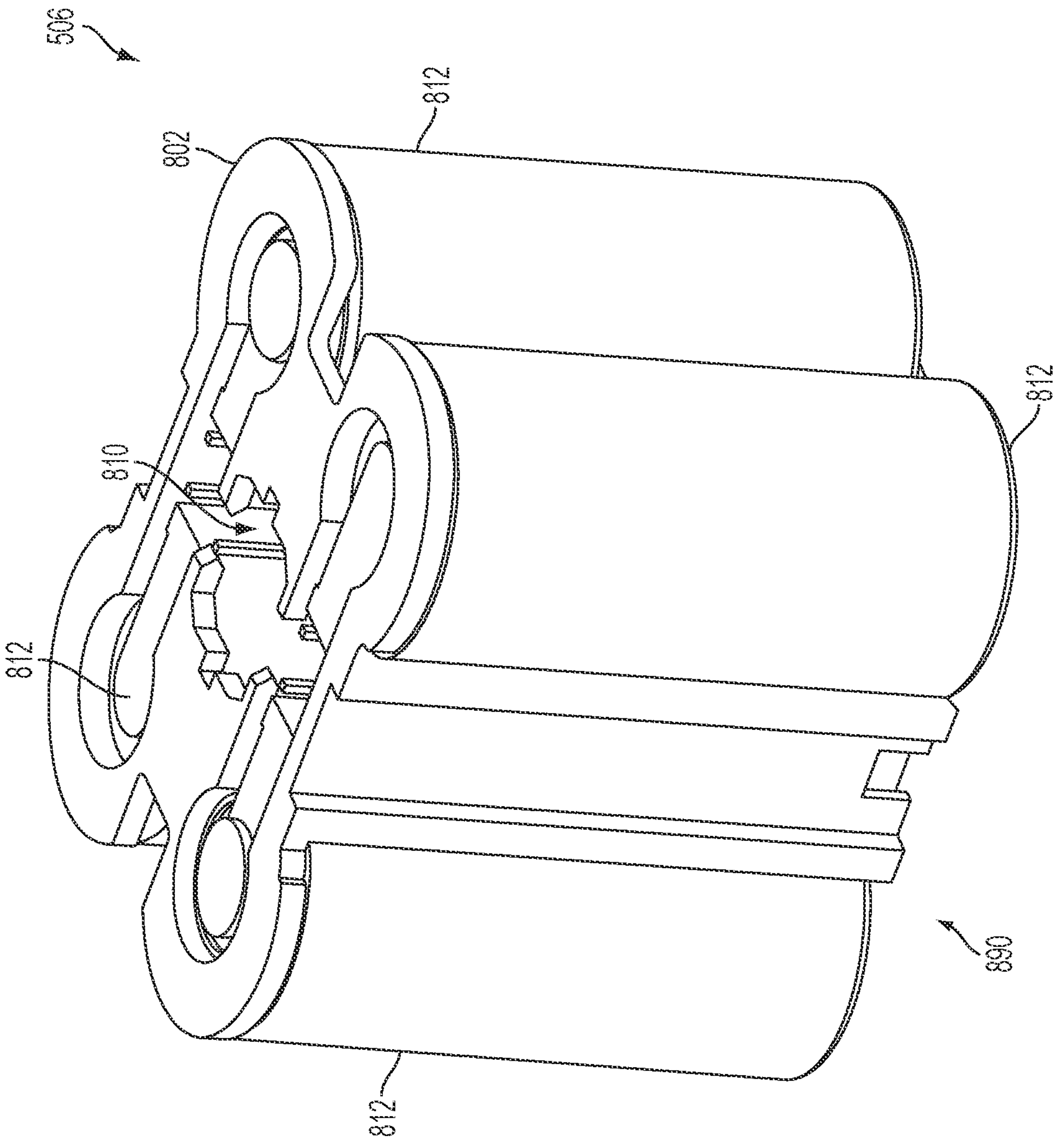
Figure 36:
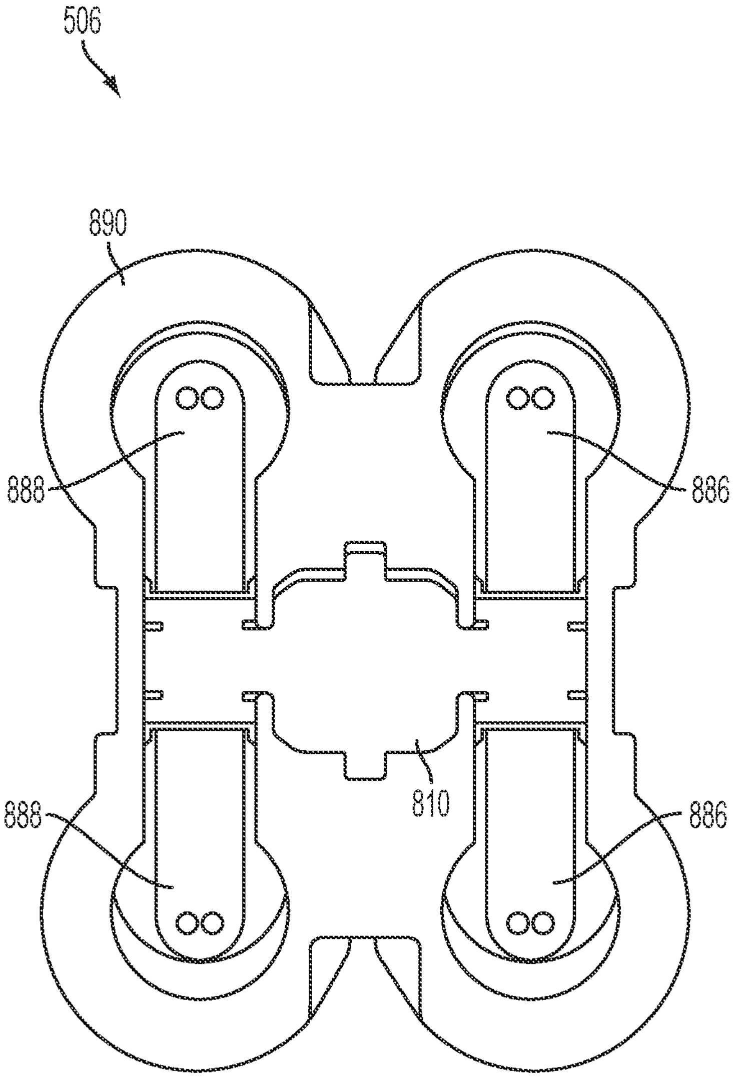
Figure 37:
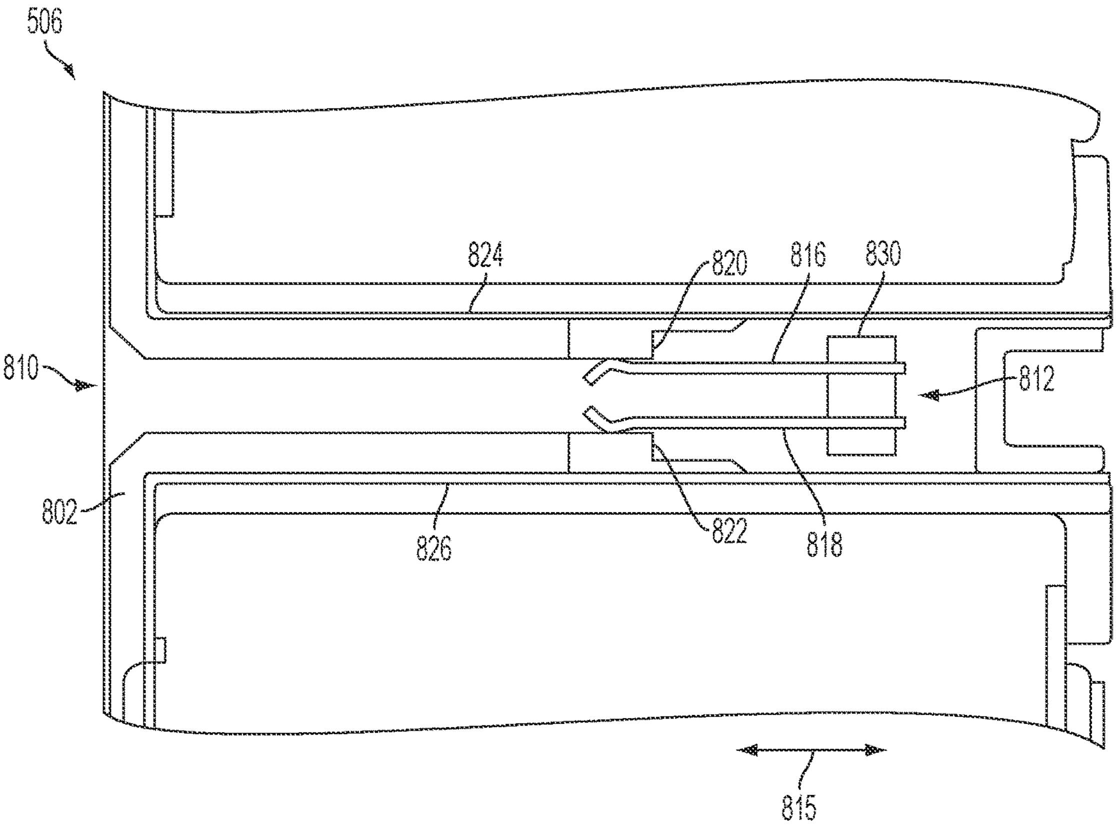
Figure 38:
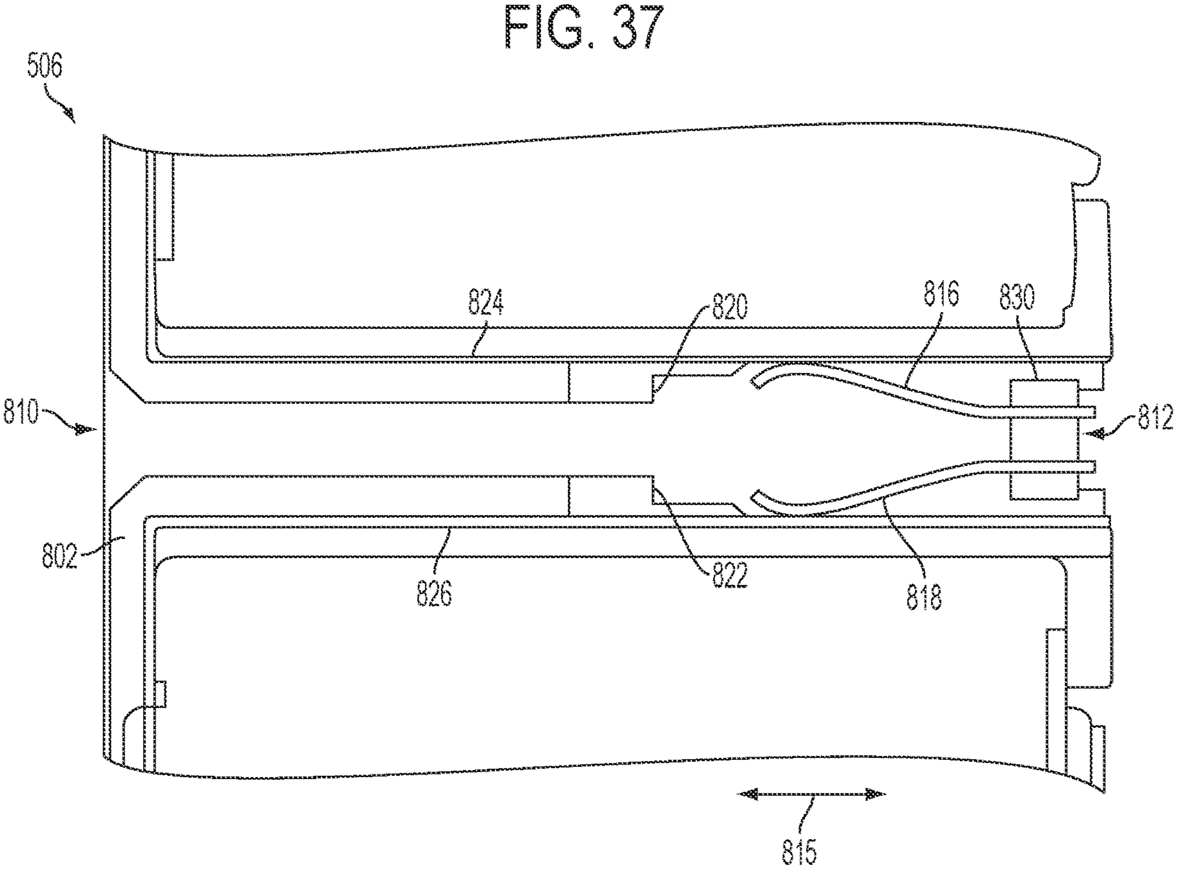
Figure 39:
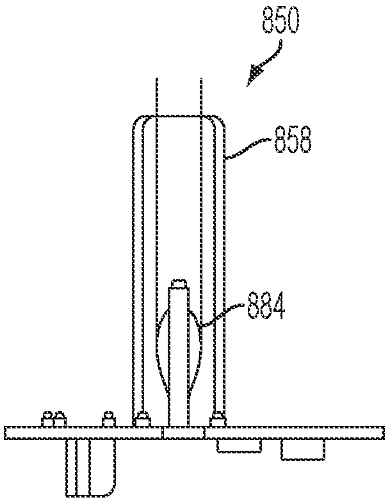
Figure 40:
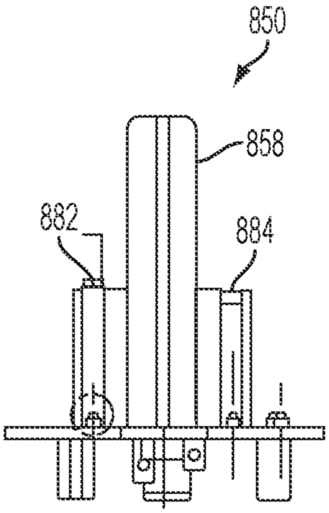
Figure 41:
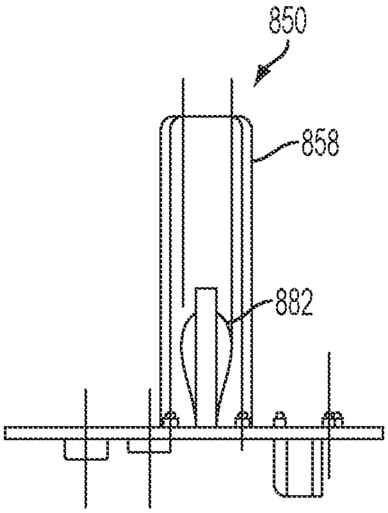
Figure 42:
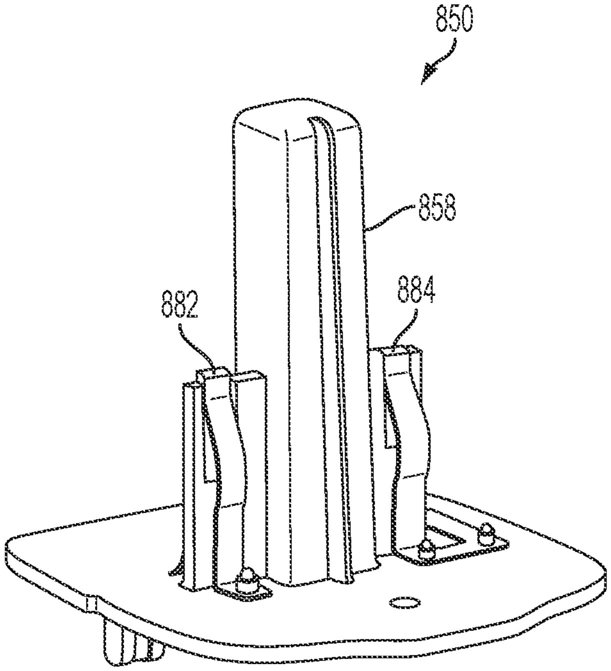

FIGS. 37 and 38 illustrate cross-sectional views of one embodiment of the battery unit of FIGS. 33-36 including a translatable drain.

FIGS. 39-42 show multiple views of one embodiment of a battery dock.

Figure 43:
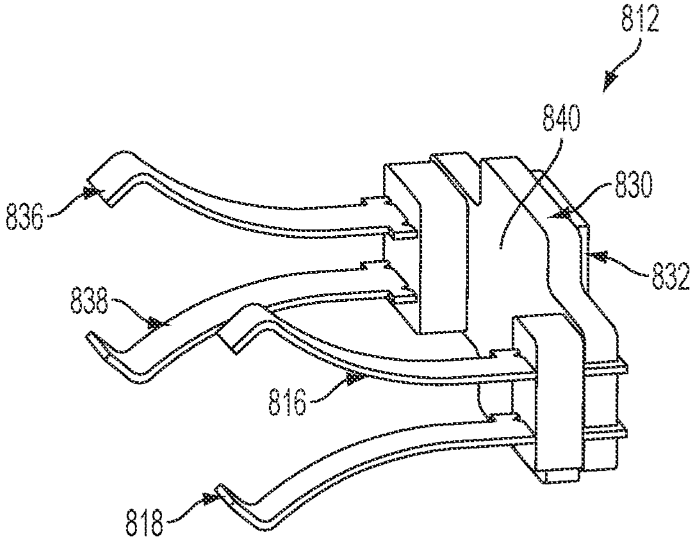

FIG. 43 is a perspective view of one embodiment of the translatable drain of FIGS. 37 and 38.

Figure 44:
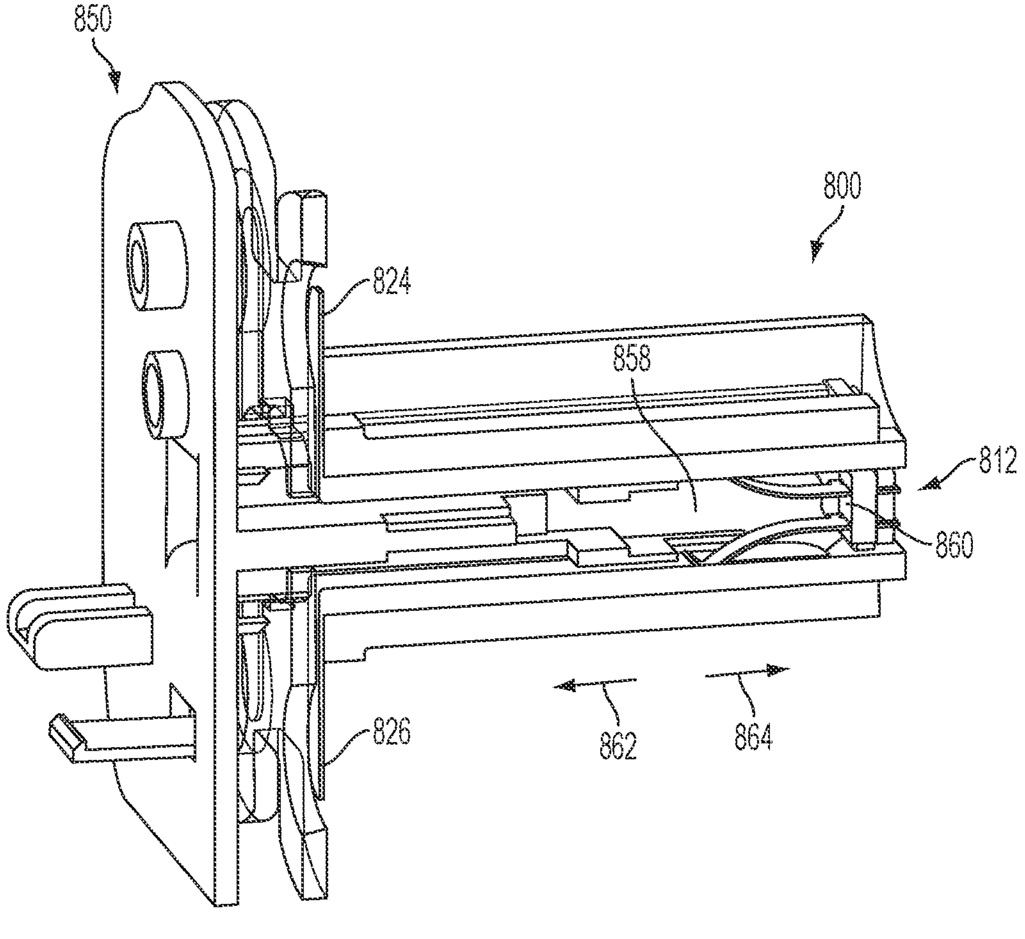

FIG. 44 illustrates one embodiment of the battery unit of FIGS. 33-36 attached to a battery dock with various components omitted for clarity.

Figure 45:
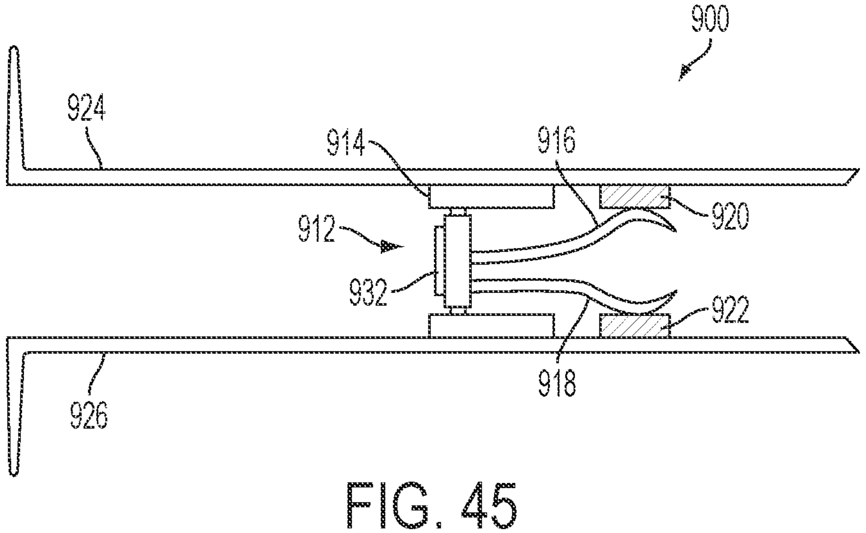
Figure 46:
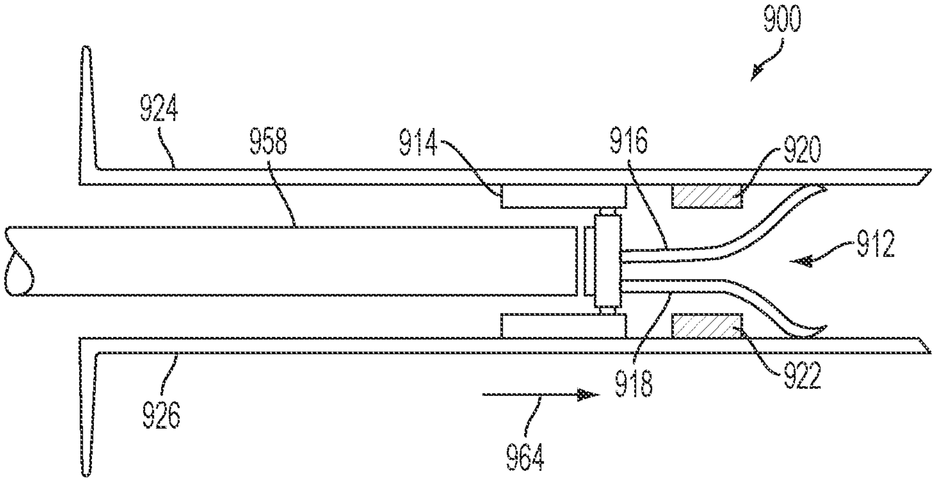

FIGS. 45 and 46 illustrate one embodiment of a battery unit with various components omitted for clarity.

Figure 47:
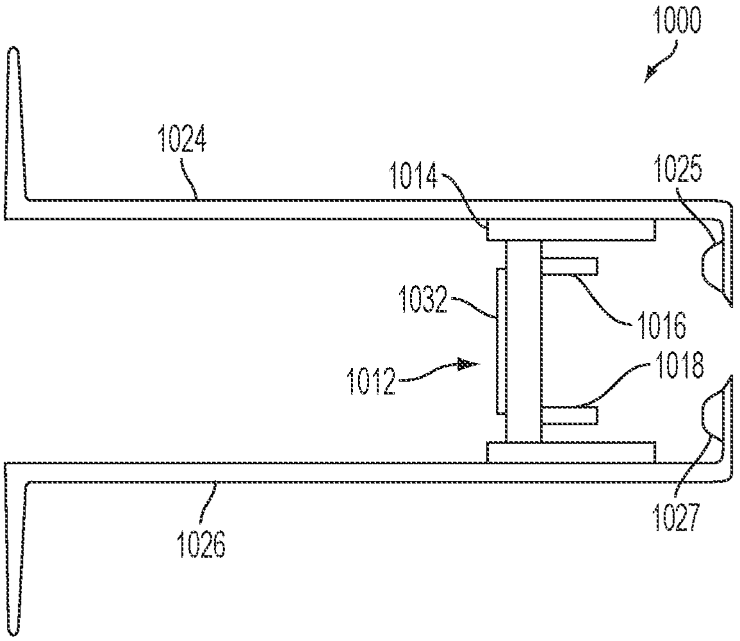
Figure 48:
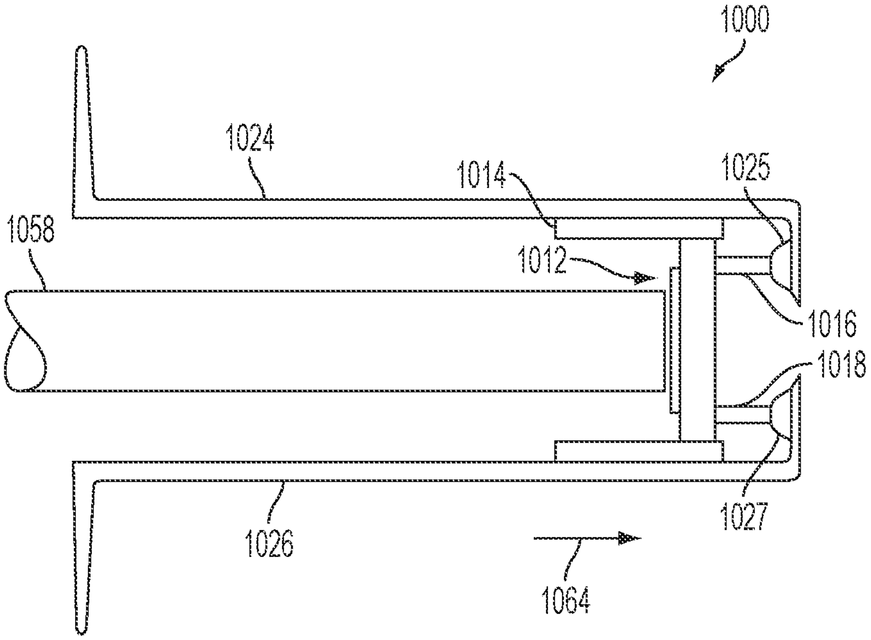

FIGS. 47 and 48 illustrate one embodiment of a battery unit with various components omitted for clarity.

Figure 49:
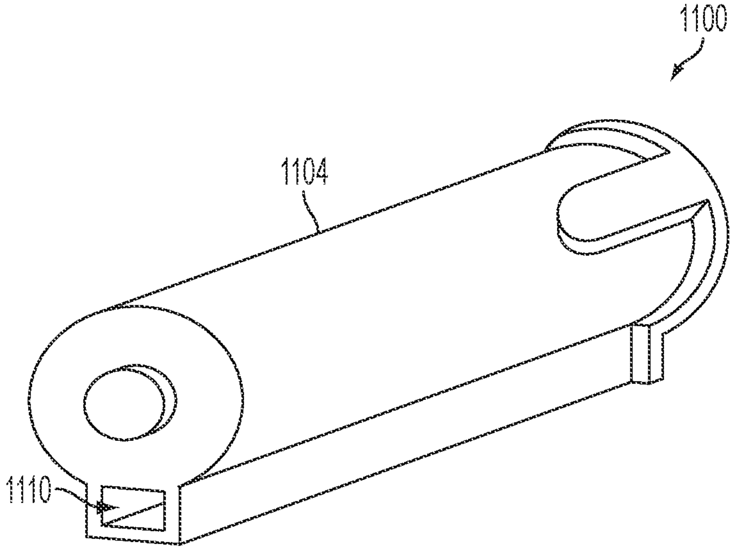

FIG. 49 is a perspective view of one embodiment of single cell battery unit.

Figure 50:
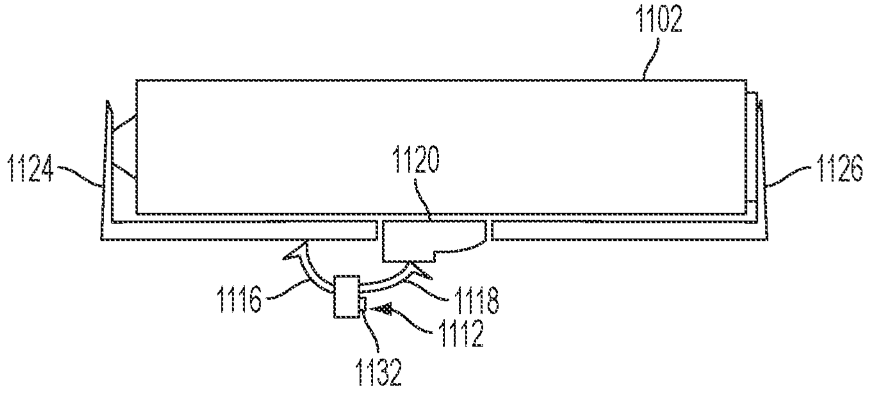
Figure 51:
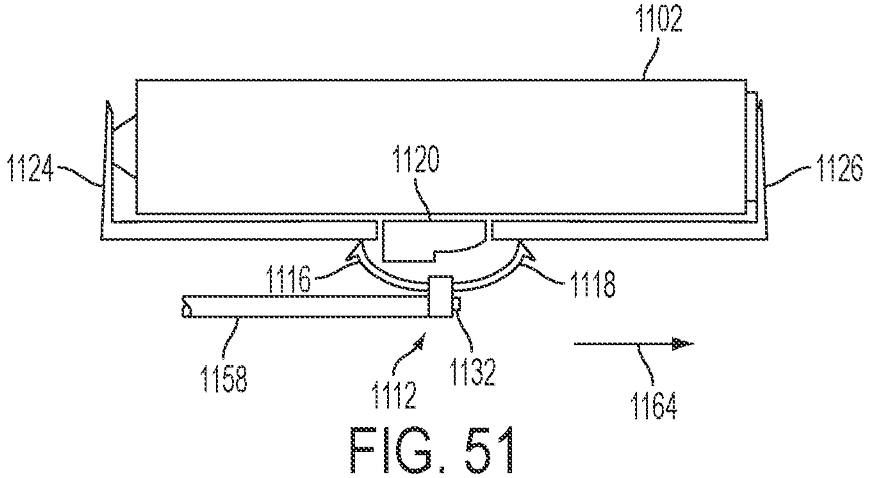

FIGS. 50 and 51 show internal views of the battery unit of FIG. 49 during various stages of operation with various components omitted for clarity.

Figure 52:
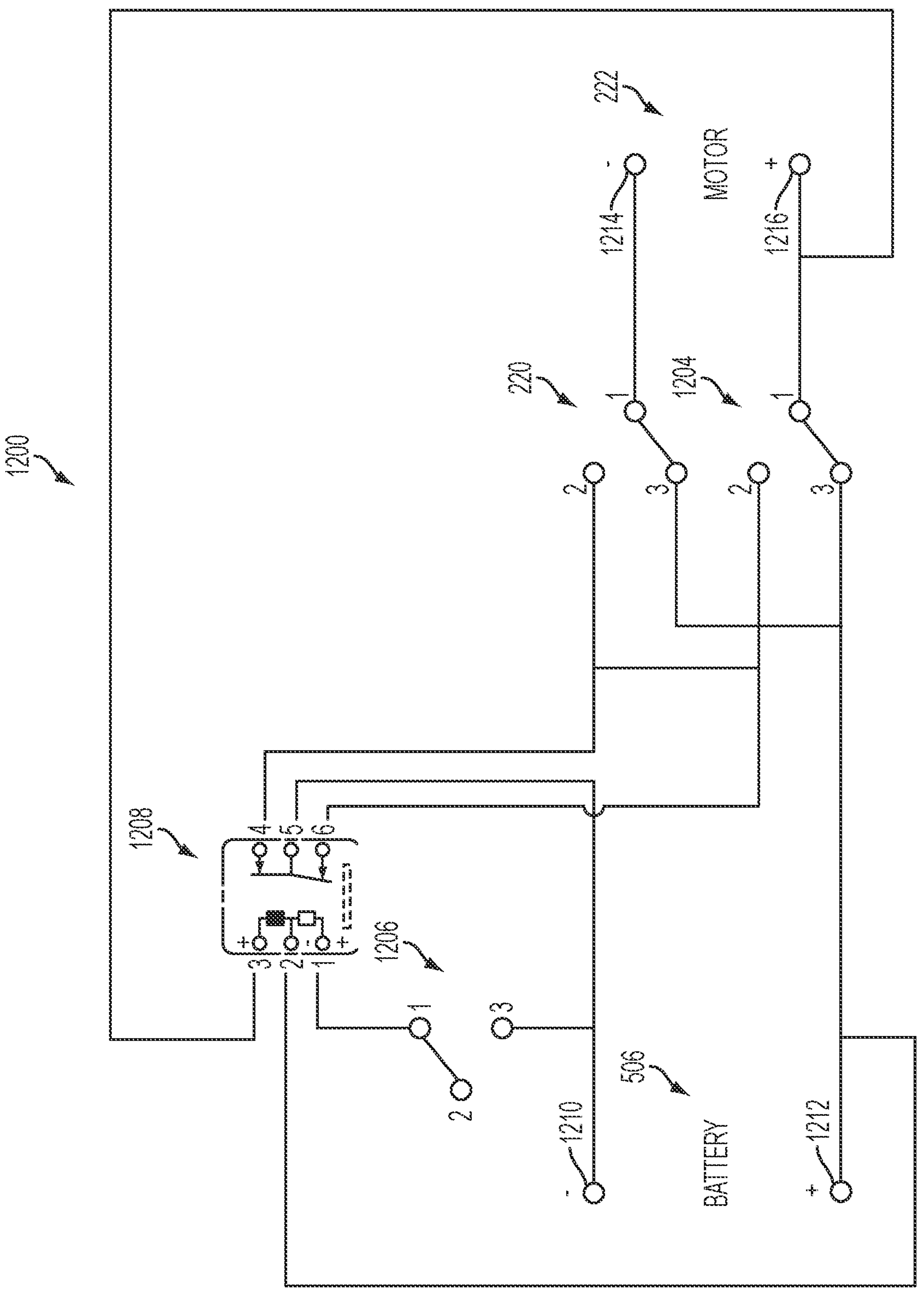

FIG. 52 illustrates one embodiment of a control circuit that may control a connection between the battery unit or other power supply and the motor or other drive device for firing the instrument of FIG. 1.

Figure 53:
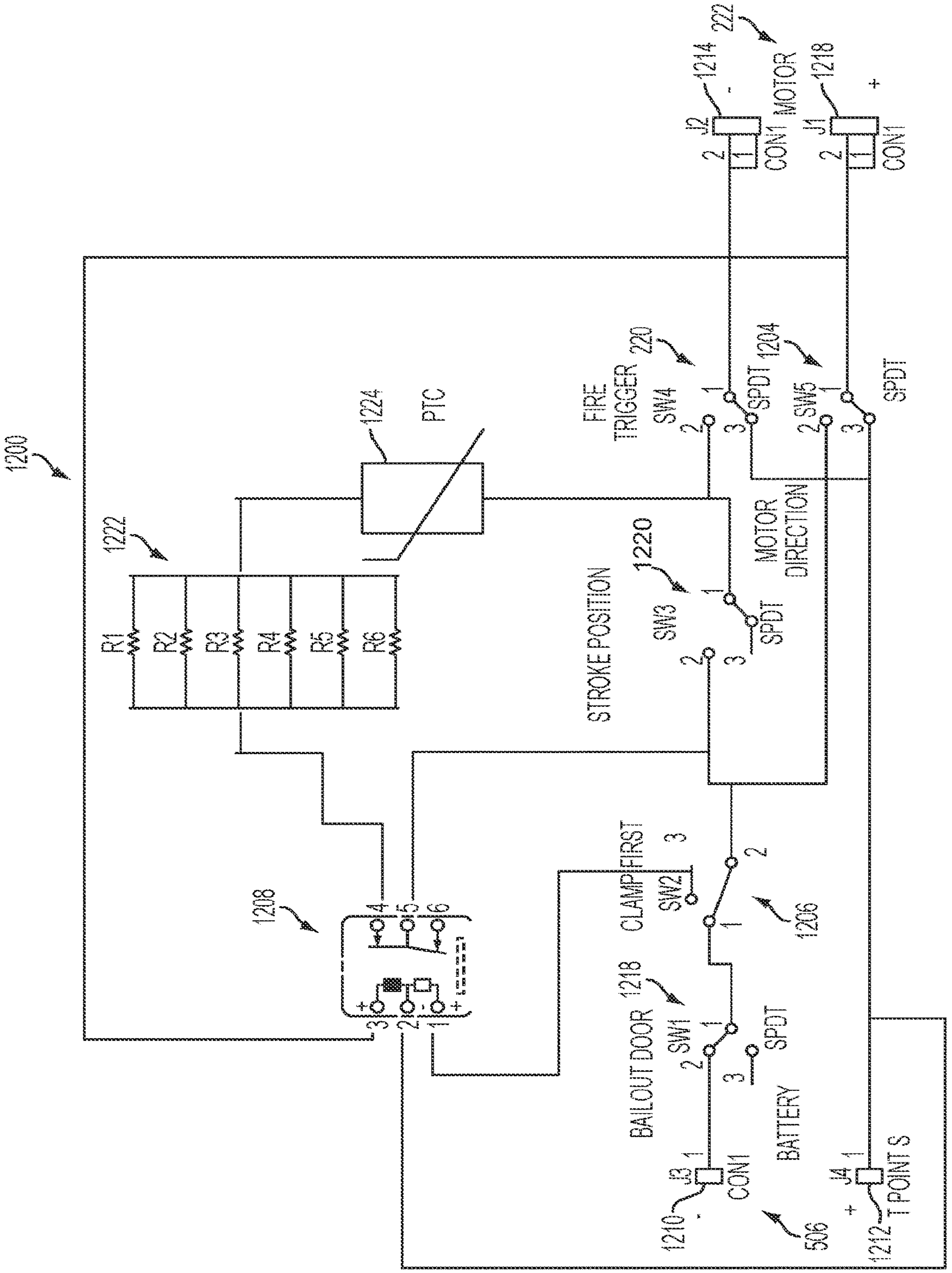

FIG. 53 illustrates one embodiment of the control circuit of FIG. 52 with additional switches and features.

Figure 54:
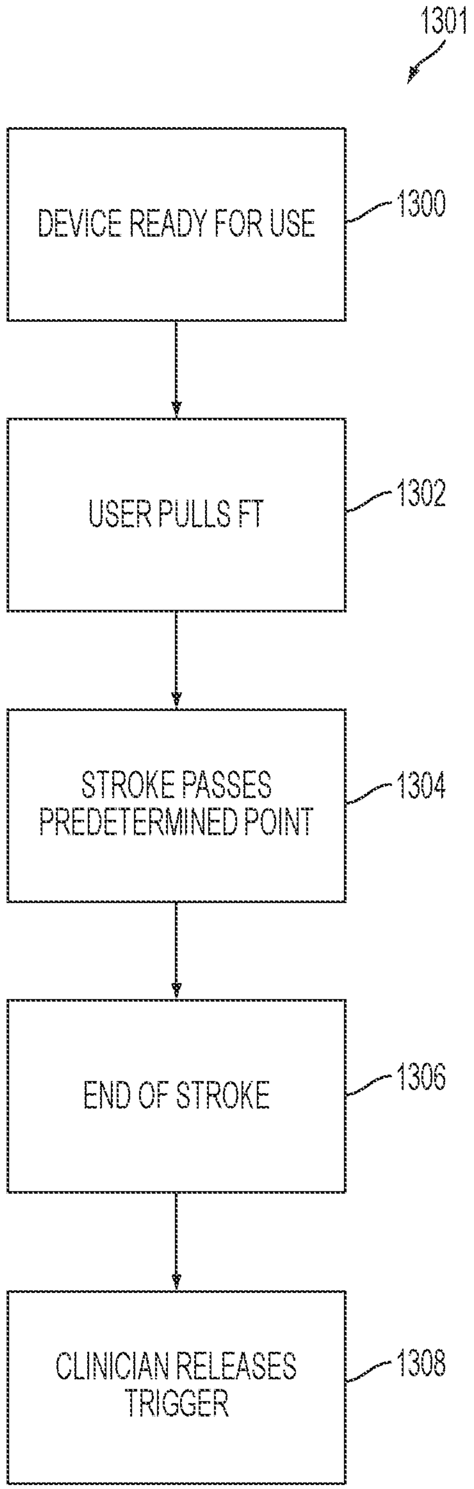

FIG. 54 is a flowchart showing one embodiment of a process flow showing the firing of the instrument of FIG. 1 utilizing the control circuit as illustrated in FIG. 53.

Figure 55:
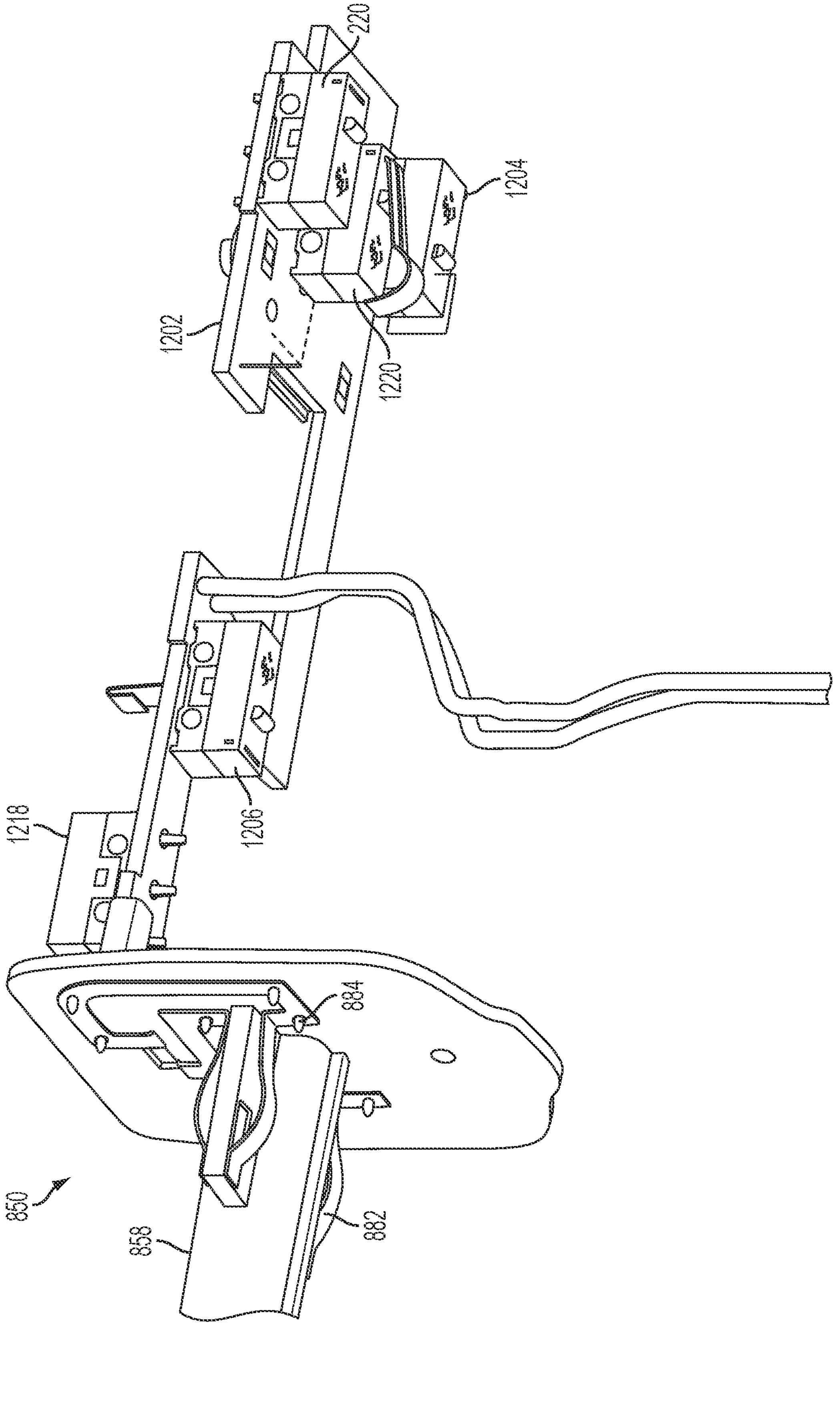

FIG. 55 illustrates a perspective view of one embodiment of circuit board for implementing the control circuit of FIG. 52 or 53, coupled to the battery dock of FIG. 36.

Figure 56:
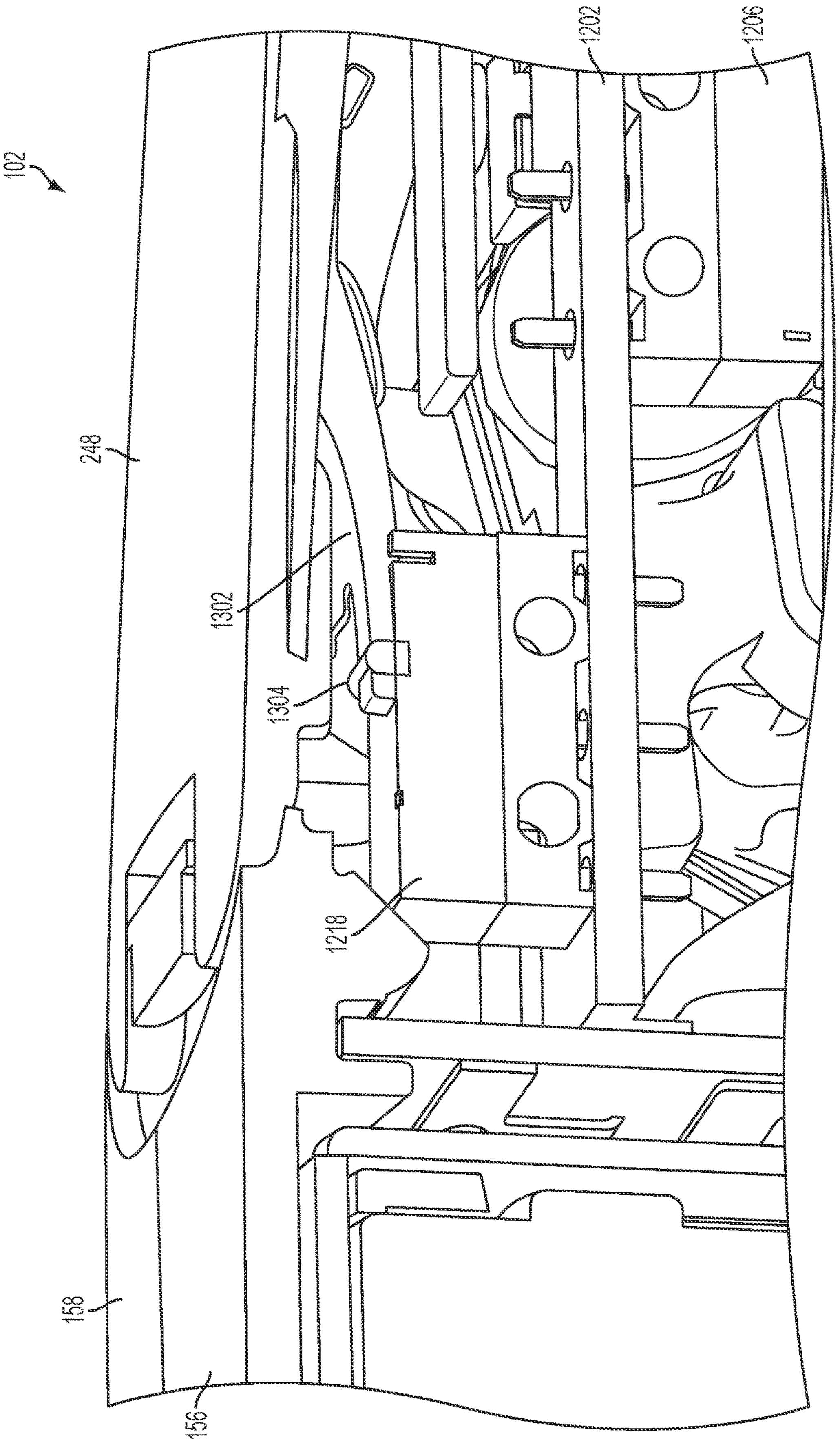

FIG. 56 illustrates a cut away view of one embodiment of the instrument of FIG. 1 showing the emergency access door switch.

Figure 57:
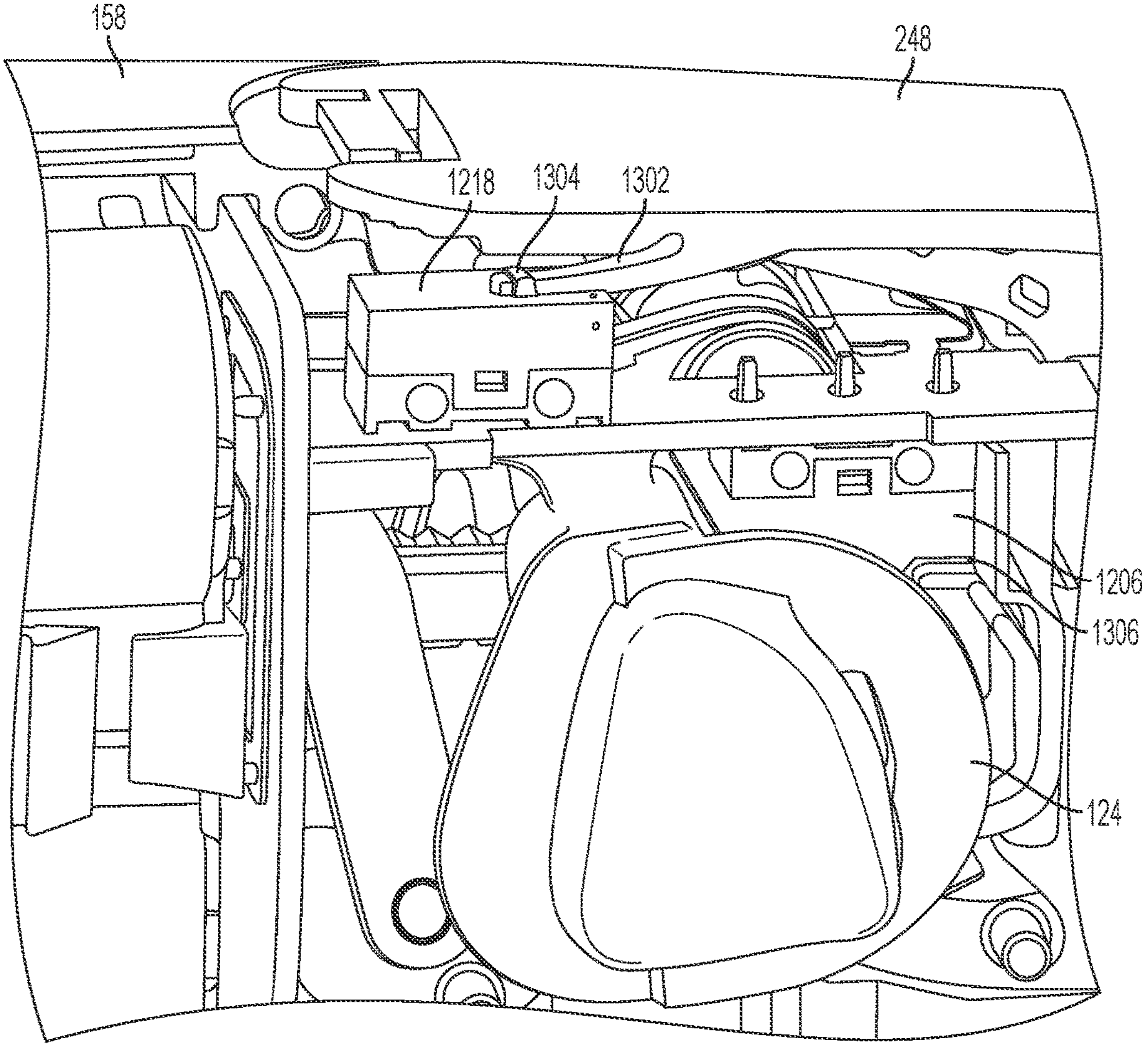

FIG. 57 illustrates another cut away view of one embodiment of the instrument of FIG. 1 showing the clamp switch.

Figure 58:
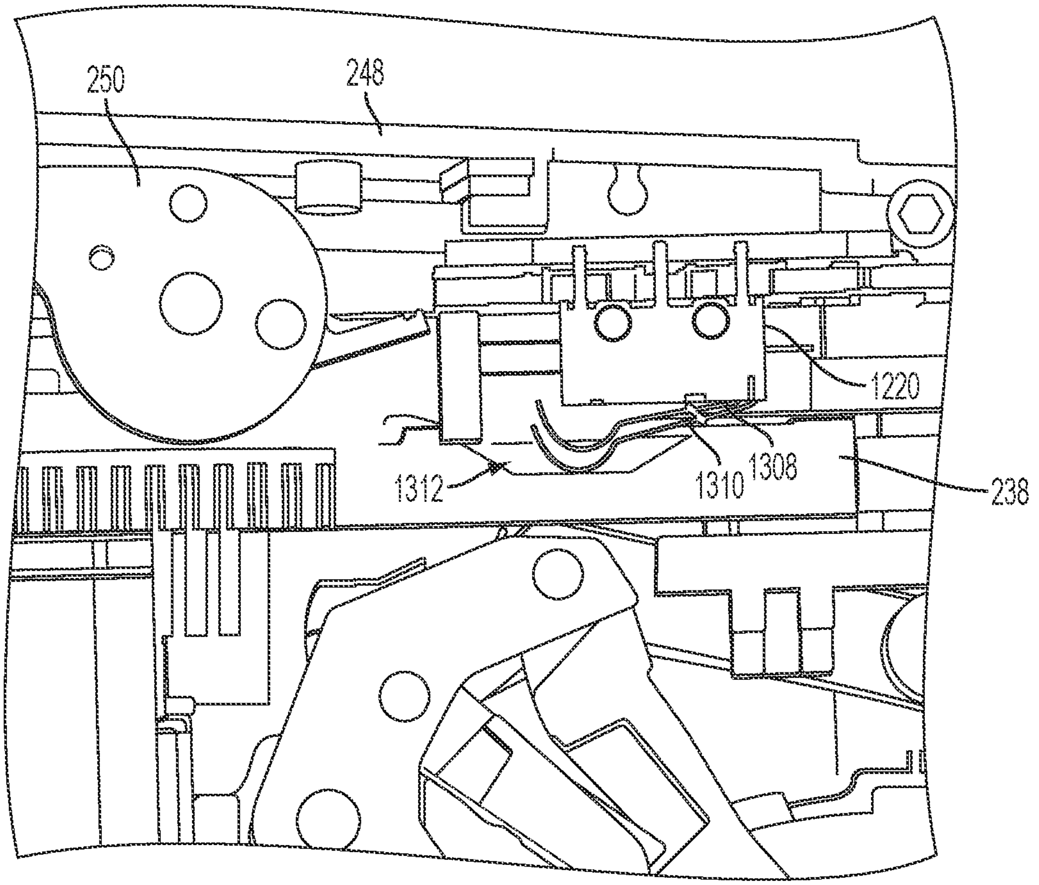

FIG. 58 illustrates another cut away view of one embodiment of the instrument of FIG. 1 showing the stroke position switch.

Figure 59:
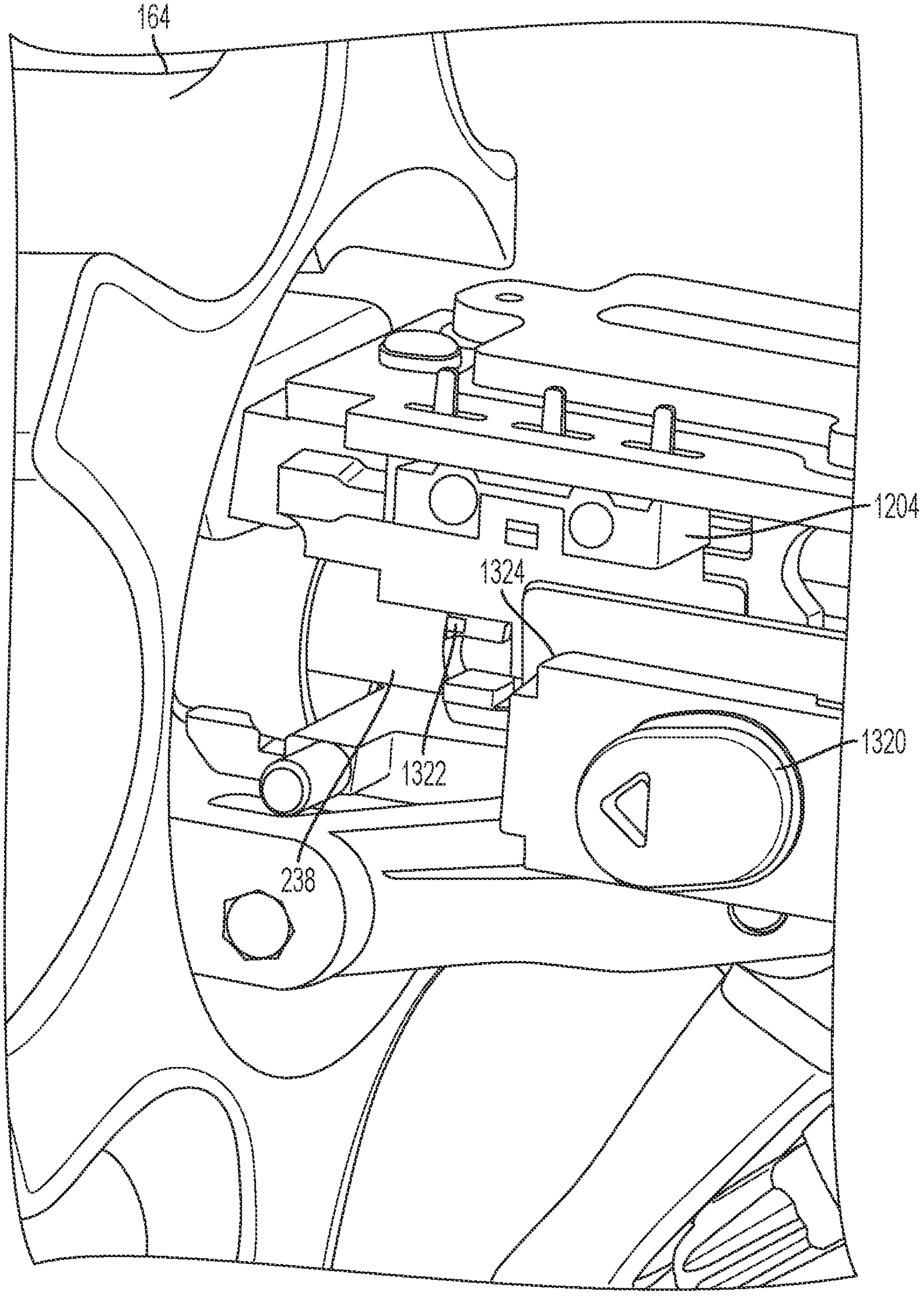

FIG. 59 illustrates another cut away view of one embodiment of the instrument of FIG. 1 showing the end-of-stroke/motor reverse switch.

DESCRIPTION

Various embodiments are directed to surgical instruments having control circuits for implementing an electronic lockout. For example, the control circuit may comprise one or more latching devices such as, for example, a latching relay, a transistor, etc. The surgical devices may comprise an end effector having first and second jaw members, where at least one of the jaw members is translatable (e.g., pivotally or otherwise) towards the other. The surgical instruments may also have a firing bar that is translatable through the end effector when the jaw members are closed (e.g., pivoted towards one another). The jaw members of the end effector may serve to clamp tissue. Once tissue is clamped, the firing bar may act upon the tissue. In various embodiments, distal motion of the firing bar may cause cutting and/or fastening of tissue. For example, the firing bar may define a cutting edge or knife to cut tissue clamped between the jaw members. Also, for example, the firing bar may drive a wedge or other mechanism to drive staples through the tissue clamped between the jaw members. According to various embodiments, the firing bar may be driven by a drive device such as, for example, an electric motor, a pneumatic or hydraulic device, etc. The drive device may be powered by a power supply such as, for example, a battery and/or a connection to an external source of electrical power, such as a wall outlet.

Figure 2:
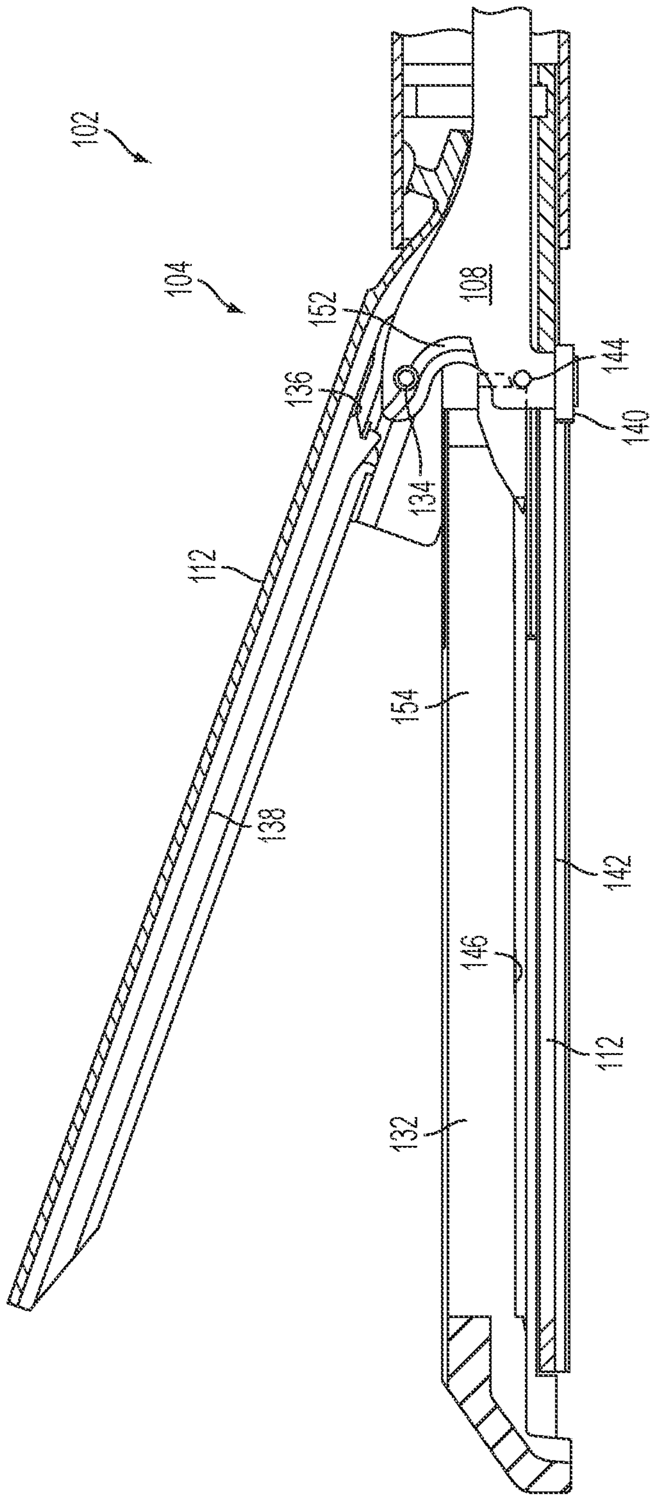
FIG. 2 shows one embodiment of an end effector of the instrument of FIG. 1.

FIG. 1 shows one embodiment of a surgical stapling and cutting instrument 102 with an electrically powered firing feature. The illustrated embodiment is an endoscopic instrument and, in general, the embodiments of the instrument 102 described herein are endoscopic surgical cutting and fastening instruments. It should be noted, however, that according to other embodiments, the instrument may be a non-endoscopic surgical cutting and fastening instrument, such as a laparoscopic or open surgical instrument. The instrument 102 may comprise an end effector 104 that may be operative to staple and cut tissue in response to control operations executed by a clinician grasping a handle portion 106. FIG. 2 shows one embodiment of the end effector 104 of the instrument 102. According to various embodiments, the instrument 102 may utilize an E-beam firing mechanism or firing bar 108 that may control the spacing of the end effector 104. For example, a first jaw member, or elongate channel 110 and a pivotally translatable second jaw member or anvil 112 may be maintained at a spacing that assures effective stapling and severing.

The instrument 102 may comprise the handle portion 106 and an implement portion 114. The implement portion 114 may be connected to the handle portion 106 and may comprise a shaft 116 distally terminating in the end effector 104. The handle portion 106 may comprise a pistol grip 118. A closure trigger 120 may be positioned such that a clinician may pivotally draw the closure trigger 120 towards the pistol grip 118 to cause clamping, or closing, of the anvil 112 toward the elongate channel 110 of the end effector 104. A firing trigger 122 may be positioned farther outboard of the closure trigger 120 and may be pivotally drawn by the clinician to cause the stapling and severing of clamped tissue in the end effector 104. As described below, the stapling and severing of the clamped tissue by the end effector 104 may be powered by an electric motor.

It will be appreciated that the terms “proximal” and “distal” are used herein with reference to a clinician gripping a handle of an instrument. Thus, the end effector 104 is distal with respect to the more proximal handle portion 106. It will be further appreciated that for convenience and clarity, spatial terms such as “vertical” and “horizontal” are used herein with respect to the drawings. However, surgical instruments are used in many orientations and positions, and these terms are not intended to be limiting and absolute.

In use, the clinician may actuate the closure trigger 120 first. For example, once the clinician is satisfied with the positioning of the end effector 104, the clinician may draw back the closure trigger 120 to its fully closed, locked position proximate to the pistol grip 118. Then, the clinician may actuate the firing trigger 122 to initiate powered cutting and stapling of tissue held between the anvil 112 and elongate channel 110. For example, the firing bar 108 may be powered forward to cut tissue and drive staples, for example, as described herein below. When the clinician removes pressure from the firing trigger 122, the firing bar 108 may be returned to the pre-firing position shown in FIG. 2. The clinician may actuate a release button 124 on the handle portion 106 to release the closure trigger 120. The clinician may then release the closure trigger, in turn releasing the anvil 112 and elongate channel 110 to pivot away from one another back to the position shown in FIG. 2.

Referring again to FIG. 1, the shaft 116 may comprise a frame 126 enclosed by a closure sleeve 128. A firing drive member 130 may be positioned within the frame 126 and may extend from the handle portion 106 to the firing bar 108. The drive member 130 may comprise a single component, or may be made up of multiple components. The frame 126 may connect the handle portion 106 to the end effector 104. With the closure sleeve 128 withdrawn proximally by the closure trigger 120 as depicted in FIGS. 1 and 2, the anvil 112 may springedly open, pivoting away from the elongate channel 110 and translating proximally with the closure sleeve 128.

The elongate channel 110 may receive a staple cartridge 132 that may be responsive to the firing bar 108 to drive staples into forming contact with the anvil 112. It will appreciated that although a readily replaceable staple cartridge 132 is advantageously described herein, a staple cartridge 132 consistent with various embodiments may be permanently affixed or integral to the elongate channel 110, for instance when a larger portion of the end effector 104 is replaced after each firing.

Figure 3:
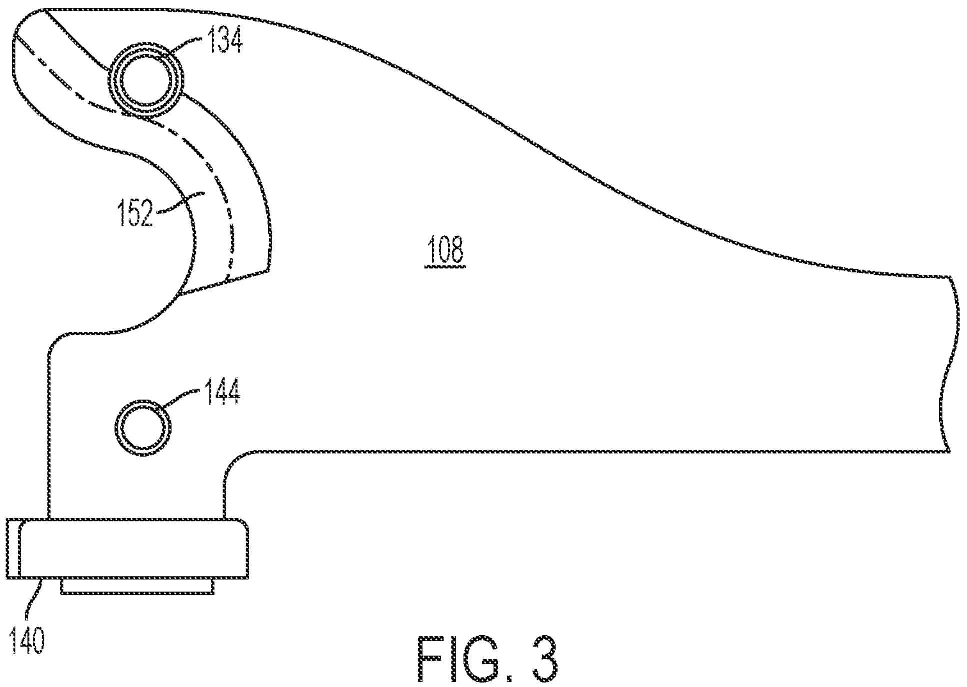
FIGS. 3 and 4 show additional views of one embodiment of a firing bar of the instrument of FIG. 1.
Figure 4:
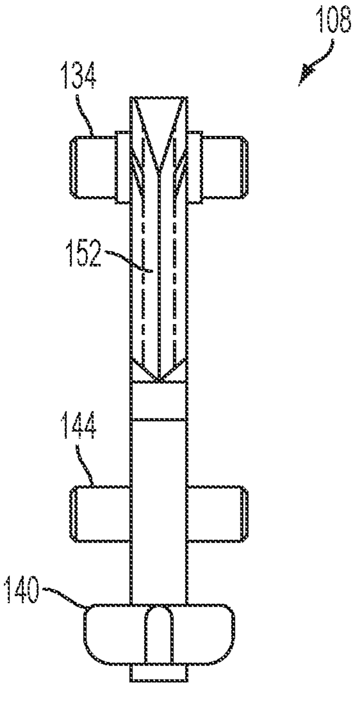

FIGS. 3 and 4 show additional views of one embodiment of the firing bar 108. As illustrated in FIGS. 2-4, the firing bar 108 may include three vertically spaced pins that control the spacing of the end effector 104 during firing. An upper pin 134 may be staged to enter an anvil pocket 136 near the pivot between the anvil 112 and elongate channel 110. When fired with the anvil 112 closed, the upper pin 134 may advance distally within a longitudinal anvil slot 138 extending distally through anvil 112. According to various embodiments, minor upward deflections of the anvil 112 may be overcome by a downward force imparted on the anvil 112 by the upper pin 134. The firing bar 108 may also include a lower pin, or firing bar cap, 140 that may upwardly engage a channel slot 142 in the elongate channel 110, thereby cooperating with the upper pin 134 to draw the anvil 112 and the elongate channel 110 together in the event of excess tissue clamped therebetween.

Figure 5:
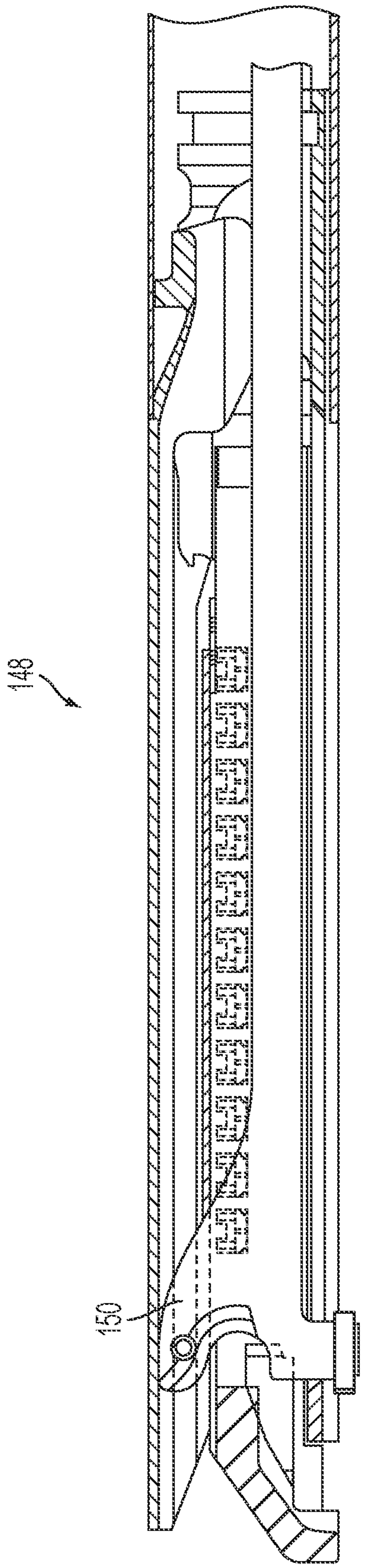
FIG. 5 illustrates an alternative embodiment of an end effector having a firing bar lacking a middle pin.

The firing bar 108 may also comprise a middle pin 144 that may pass through a firing drive slot 146 formed in a lower surface of the cartridge 132 and an upward surface of the elongate channel 110. In this way, the middle pin 144 may initiate the driving of the staples, as described below. The middle pin 144, by sliding against the elongate channel 110, may resist a tendency for the end effector 104 to be pinched shut at its distal end. To illustrate an advantage of the middle pin 144, FIG. 5 illustrates an alternative embodiment of an end effector 148 having a firing bar 150 lacking a middle pin. As shown in FIG. 5, the end effector 148 is allowed to pinch shut at its distal end, which may tend to impair desired staple formation.

Returning to FIGS. 2-4, the firing bar 108 may comprise a distally presented cutting edge 152 between the upper and middle pins 134, 144. When the end effector 104 is fired, the cutting edge 152 may traverse through a proximally presented, vertical slot 154 in the cartridge 132 to sever clamped tissue present between the anvil 112 and the elongate channel 110. The affirmative positioning of the firing bar 108 with regard to the elongate channel 110 and anvil 112 may make it more likely that an effective cut is performed.

The affirmative vertical spacing provided by the E-Beam firing bar 108 may be suitable for the limited size available for endoscopic devices. Moreover, the E-Beam firing bar 108 may enable fabrication of an anvil 112 with a camber imparting a vertical deflection at its distal end, similar to the position depicted in FIG. 5. This cambered anvil 112 may assist in achieving a desirable gap in the end effector 104 even with an anvil 112 having reduced thickness, which may be thus more suited to the size limitations of an endoscopic device. The E-Beam firing bar 108 may further enable increased applications, especially in combination with a range of configurations of staple cartridges. For instance, a clinician may select a gray staple cartridge yielding a 0.02 mm tissue gap, a white staple cartridge yielding a 0.04 mm tissue gap, a blue cartridge yielding a 0.06 mm tissue gap, or a green cartridge yielding a 0.102 mm tissue gap. The vertical height of each respective staple cartridge in combination with the length of staples and an integral wedge sled (described in more detail below) may predetermine this desired tissue thickness with the anvil 112 appropriately vertically spaced by the E-Beam firing bar 108.

Figure 6:
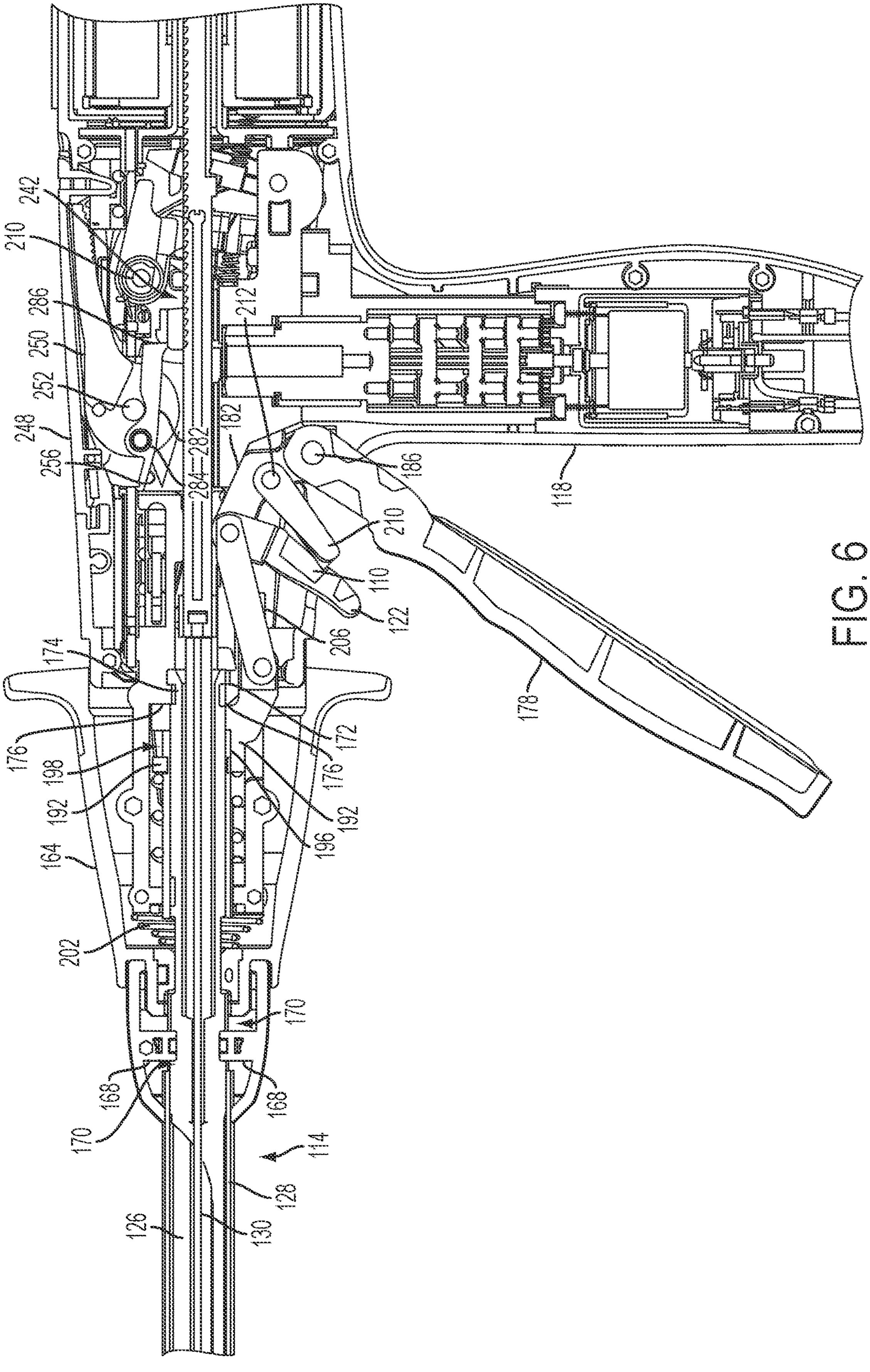
FIG. 6 illustrates a cut-away side view of one embodiment of the surgical instrument of FIG. 1.
Figure 7:
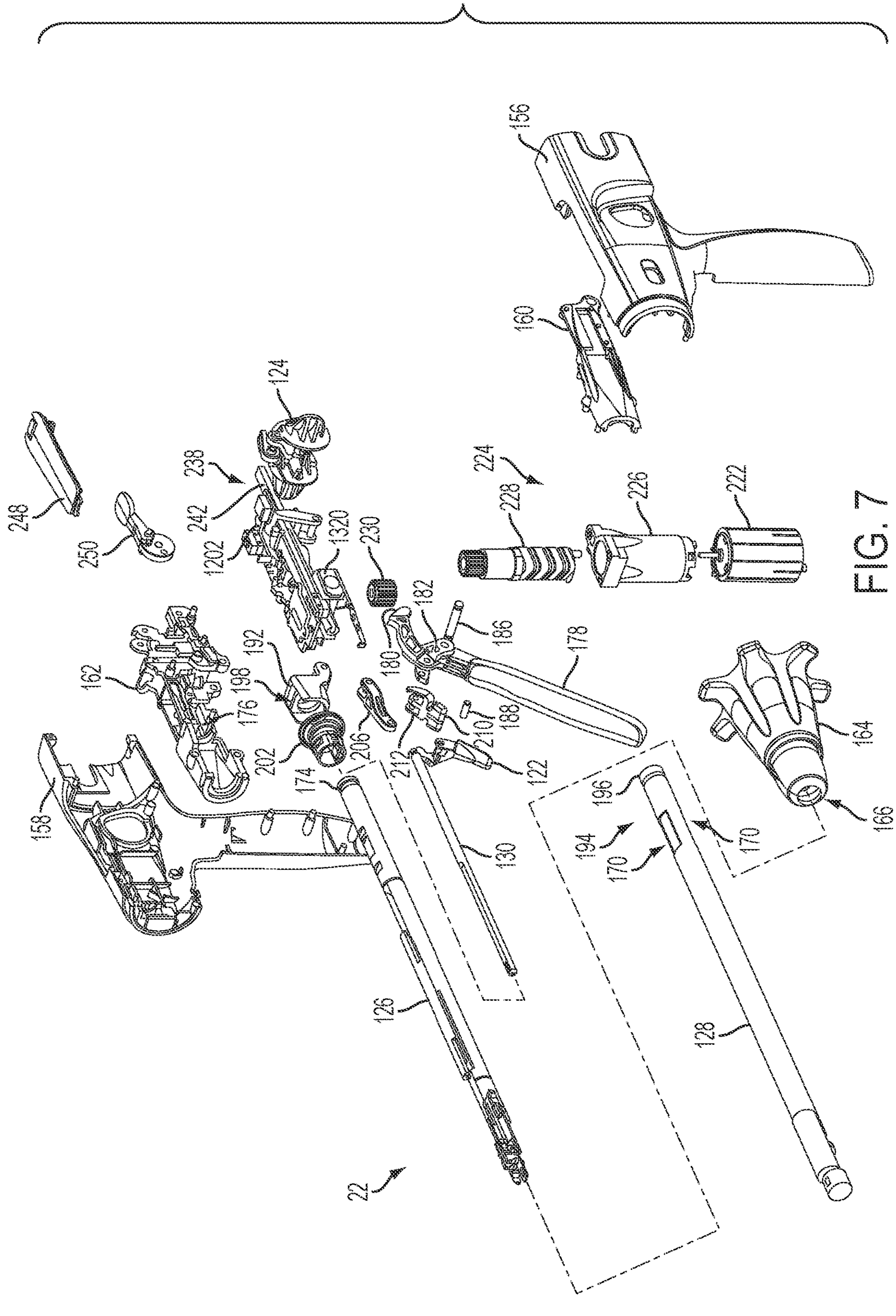
FIG. 7 illustrates an exploded view of one embodiment of the surgical instrument showing various components thereof.
Figure 8:
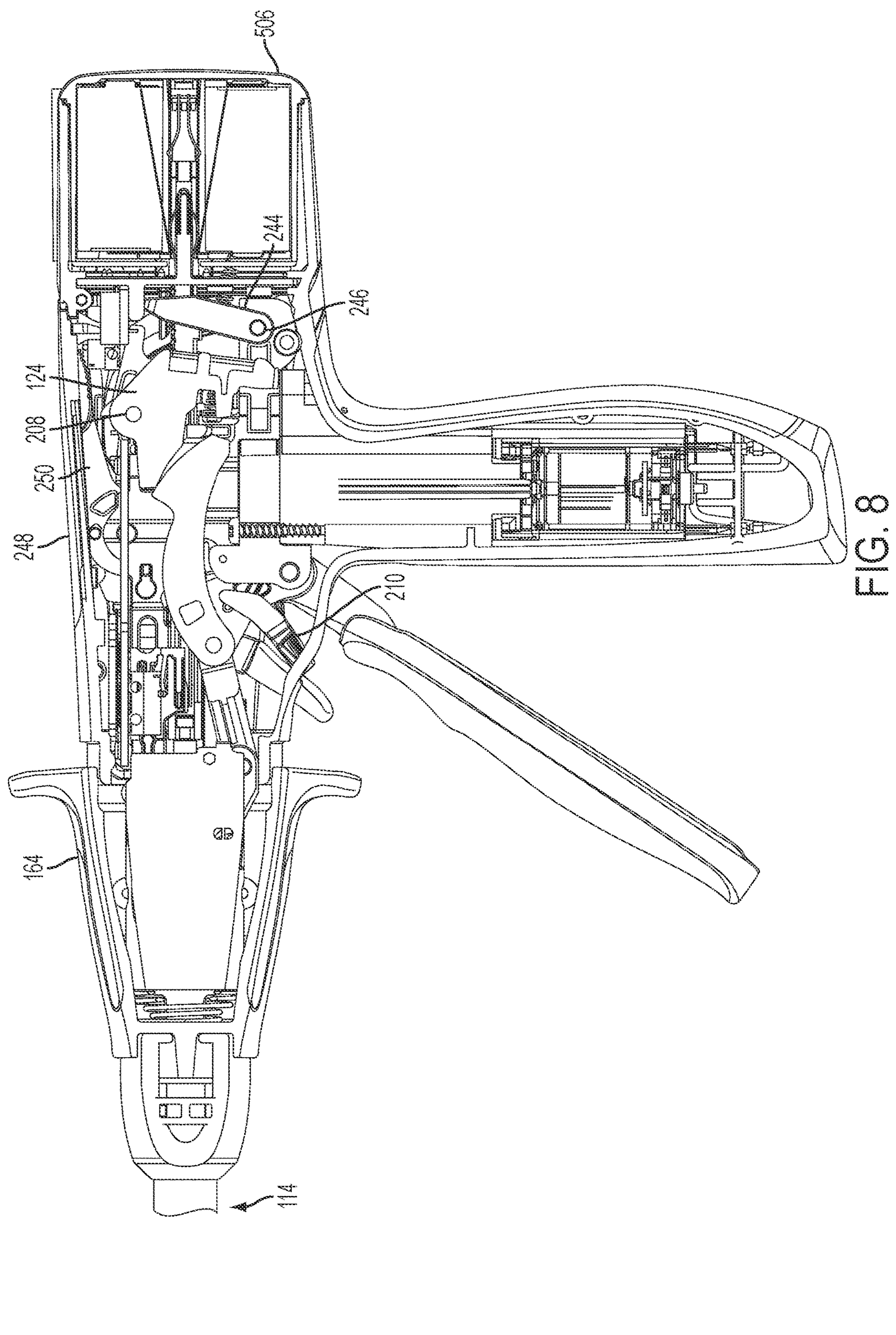
FIG. 8 illustrates a shallower cut-away side view of one embodiment of the surgical instrument of FIG. 1 to show component features not shown in the cut-away side view of FIG. 6.
Figure 9:
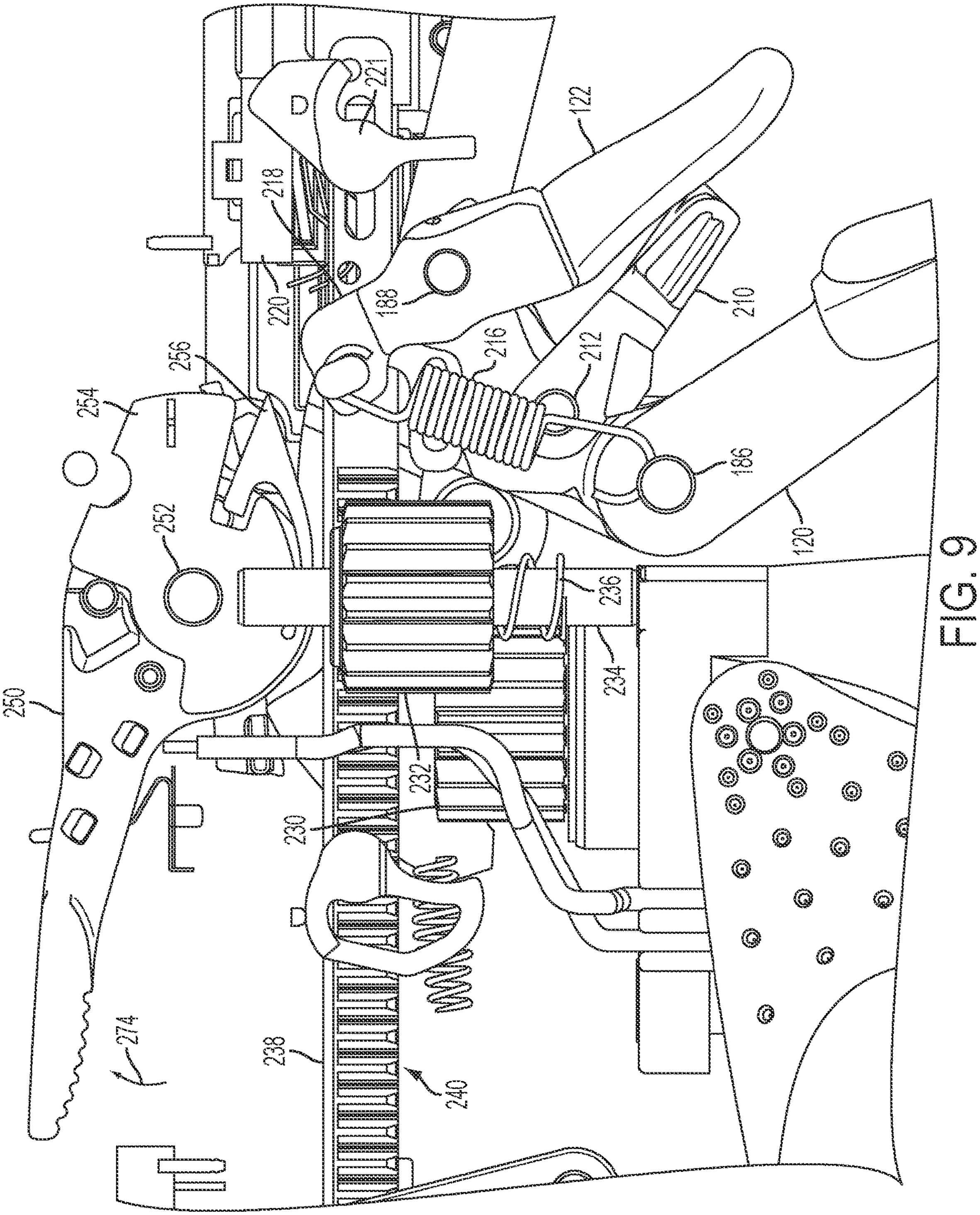
FIG. 9 illustrates an internal view of one embodiment of the surgical instrument of FIG. 1.

FIGS. 6-9 illustrate various internal components of the handle portion 106 of one embodiment of the surgical instrument 102. For example, FIG. 6 illustrates a cut-away side view of one embodiment of the surgical instrument 102. FIG. 7 illustrates an exploded view of one embodiment of the surgical instrument 102 showing a portion of the components thereof. FIG. 8 illustrates a cut-away side view of one embodiment of the surgical instrument of 102 that is shallower than the cut-away of FIG. 6 in order to show component features not shown in the cut-away side view of FIG. 6. FIG. 9 illustrates an internal view of one embodiment of the surgical instrument 102.

With reference to FIGS. 6-9, the handle portion 106 may be comprised of first and second base sections 156 and 158, which may be molded from a polymeric material such as a glass-filled polycarbonate. Within the first and second base sections 156, 158 may be first and second frame sections 160, 162. A rotating knob 164 may have a bore 166 extending completely through it for engaging and rotating the implement portion 114 about its longitudinal axis. The rotating knob 164 may includes an inwardly protruding boss 168 extending along at least a portion of the bore 166. The protruding boss 168 is received within a longitudinal slot 170 formed at a proximal portion of the closure sleeve 128 such that rotation of the rotating knob 164 effects rotation of the closure sleeve 128. It will be appreciated that the boss 168 may further extend through frame 126 and into contact with a portion of the firing drive member 130 to effect its rotation as well. Thus, the end effector 104 may rotate with the rotating knob 164.

A proximal end 172 of the frame 126 may pass proximally through the rotating knob 164 and may be provided with a circumferential notch 174 that is engaged by opposing channel securement members 176 extending respectively from the frame sections 160 and 162. The channel securement members 176 extending from the frame sections 160, 162 may serve to secure the frame 126 to the handle portion 106 such that the frame 126 does not move longitudinally relative to the handle portion 106.

The closure trigger 120 may have a handle section 178, a lever section 180, and an intermediate section 182. A bore 184 may extend through the intermediate section 182. A cylindrical support member 186 may pass through the bore 184 for pivotably mounting the closure trigger 120 on the handle portion 106 (e.g., via the frame sections 160, 162). A second cylindrical support member 188 may pass through a bore 190 of firing trigger 122 for pivotally mounting the firing trigger 122 on the handle portion 106.

A closure yoke 192 may be housed within the handle portion 106 for reciprocating movement therein and serves to transfer motion from the closure trigger 120 to the closure sleeve 128. The closure yoke 192 may be coupled to the handle portion 106 via the respective frame portions 160, 162. A proximal end 194 of the closure sleeve 128 is provided with a flange 196 that is snap-fitted into a receiving recess 198 formed in the yoke 192. A distal end of the yoke 192 may be coupled to a secondary yoke 200 via a biasing member such as a spring 202. A proximal end of the yoke 192 may define a bore 204 for receiving a linkage 206. A proximal end of the linkage 206 may be coupled to the closure trigger 120. For example, the linkage 206 may comprise a bore for receiving the pin 188. In this way, when the clinician moves the handle section 178 of the closure trigger 120 proximally toward the pistol grip 118, the linkage 206 may be pushed distally, causing corresponding distal motion of the secondary yoke 200, compressing the spring 202 biases the yoke proximally and, in turn, pushing the yoke 192 and closure sleeve 128 distally. Distal movement of the closure sleeve 128 may cause pivotal translation movement of the anvil 112 distally and toward the elongate channel 110 of the end effector 104 and proximal movement effects closing, as described below.

As the closure trigger 120 is pulled towards the pistol grip 118, the lever portion 180 of the trigger 120 may translate distally. When the closure trigger 120 is fully pulled against the pistol grip 118, a clamp lock switch 124 may pivot about a clamp lock pin 208 to lock the closure trigger 120 into the clamped position. For example, the clamp lock switch 124 may be biased by a spring (not shown) to pivot about the pin 208. The clinician may unlock the closure trigger 120, for example, by actuating the clamp lock switch 124, causing it to pivot about the clamp lock pin 208 (clockwise as shown in FIGS. 6 and 8). This may allow the closure trigger 120 to return to the open position, causing proximal motion of the closure sleeve and pivoting the anvil 112 proximally and away from the elongate channel 110 of the end effector 104, as described below.

As the closure trigger 120 is moved toward the pistol grip 118, its intermediate section 182 may be pulled proximally, causing the firing trigger 122 to also move proximally to its "firing" position. When in its firing position, the firing trigger 122 may be located at an angle of approximately 45° to the pistol grip 118. To fire the instrument 102, the clinician may first deactivate a firing trigger safety 210. For example, the safety 210 may be pivotally coupled to the closure trigger 120 about a pin 212. A distal portion of the safety 210 may be received into a cavity 214 of the firing trigger 122, preventing the firing trigger 122 from being actuated. The clinician may deactivate the safety 210 by removing it from the cavity 214 and pivoting the safety 210 proximally. This may allow the clinician to actuate the firing trigger 122.

The firing trigger 122 may be biased to an "off" position by a biasing member such as a spring 216 (FIG. 9). When actuated (e.g., against the force of the spring 216), the firing trigger 122 may be rotated clockwise, as shown in FIG. 9. A contactor portion 218 of the trigger may activate a trigger switch 220, e.g., via an actuator 221, which may initiate firing of the instrument 102. Actuation of the trigger switch 220 may activate a motor 222. The motor 222 may be coupled to a gearbox 224 comprising an enclosure 226 and gear cluster 228. The gearbox 224 may gear down the motor 222. In one example embodiment, the motor 222 may rotate at 106,000 RPM, while the gearbox 224 may have a ratio of 509-to-1.

An intermediate gear 230 may be coupled to the output of the gearbox 224. The intermediate gear 230 may be in mechanical communication with a drive gear 232. The drive gear 232 may be rotatable about a drive shaft 234. A biasing member such as a spring 236 may bias the drive gear 232 and/or drive shaft 234 such that the drive gear 232 is in mechanical communication with a geared face 240 of a rack 238. The rack 238 may be coupled to the firing drive member 130 which may, ultimately, be in mechanical communication with the firing bar 108. Accordingly, rotation of the motor 222 may cause rotation of the gearbox 224, leading to rotation of the intermediate 230 and drive 232 gears. Rotation of the drive gear 232 may result in distal or proximal motion of the rack 238, drive member 130, and drive bar 108. Distal and proximal motion of the drive bar 108 may cause the instrument 102 to fire, for example, as described herein below.

When the instrument is fired, the rack 238 may translate distally. A top geared face 242 of the rack 238 may coupled to a clamp lock 244, causing the clamp lock 244 to translate distally about a pivot pin 246. In its distal position, the clamp lock 244 may contact the clamp switch 124, preventing it from disengaging as described above. In this way, the clinician may be mechanically prevented from releasing the clamp switch 124 while the instrument 102 is in a fired position (e.g., the drive bar 108 is extended distally).

According to various embodiments, the surgical instrument 102 may comprise mechanisms allowing a clinician to disable the motor 222 and manually disengage the firing bar 108. For example, the instrument 102 may comprise an emergency access door 248. The access door 248 may be coupled to a switch, as described below, such that when the clinician opens the access door 248, electric power to the motor 222 may be cut. Below the access door 248, the device 102 may comprise a manual retraction lever 250. The retraction lever 250 may be rotatable about a pivot a pin 252. A locking cam 254 may also be pivotable about the pin 252. After the clinician has opened and/or removed the access door 248, the clinician may pull up on the retraction lever 250. This may cause the lever 250 to rotate about the pin 252 (clockwise as shown in FIG. 9 and counter clockwise as shown in FIG. 6). Initially, the locking cam 254 may rotate with the retraction lever 250. As the locking cam 254 rotates, a locking arm 256 of the cam 254 may contact a top surface 258 the drive gear 232, working against the bias of the spring 236 to push the drive gear 232 down and out of contact with the geared face 240 of the rack 238. This may disengage the motor 222 from the rack 238, drive member 130 and drive bar 108. When the locking cam 254 is rotated by a predetermined amount, the locking arm 256 may lock against the drive gear 232, preventing reverse rotation of the locking cam 254.

Figure 10:
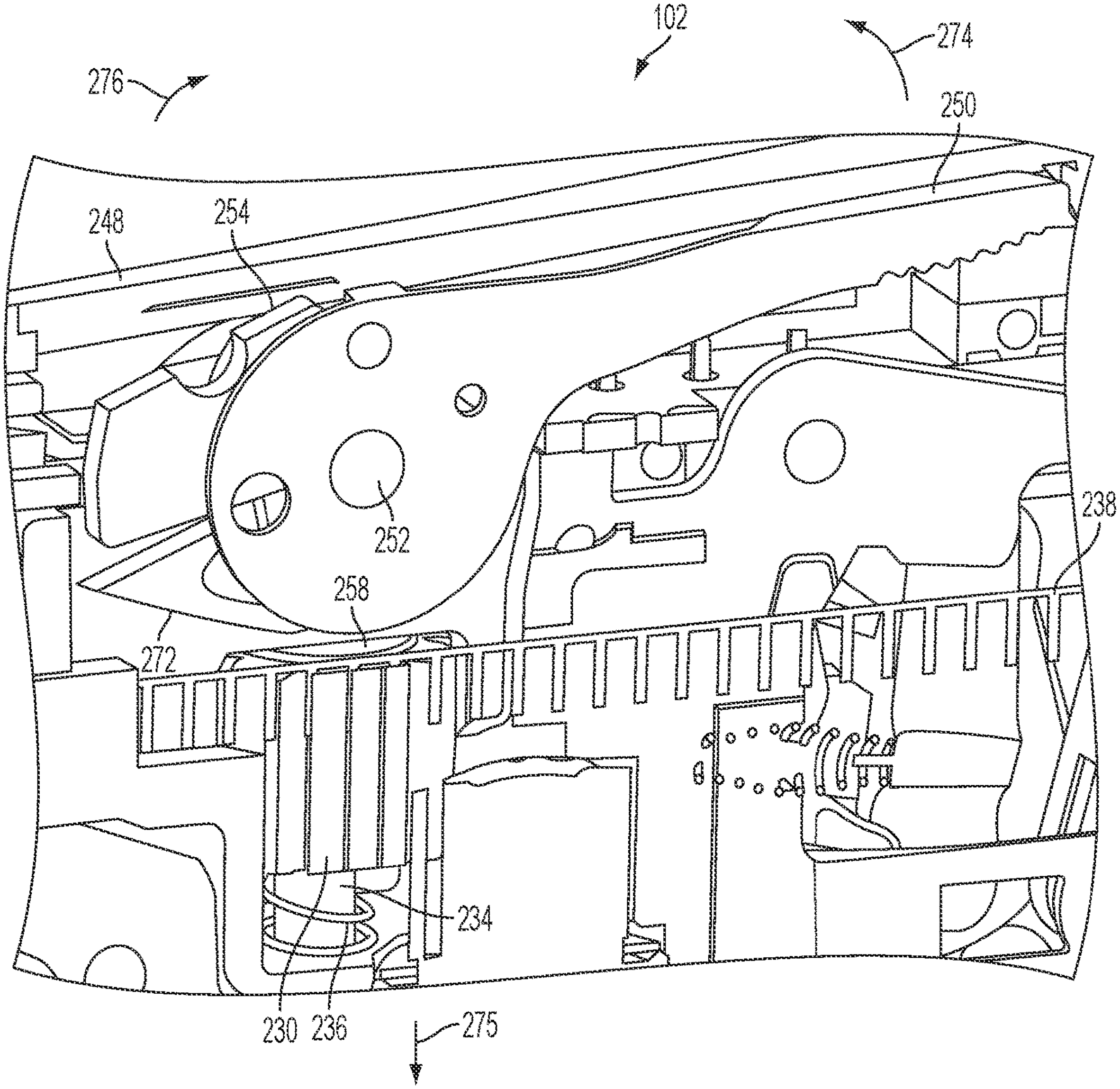
FIG. 10 illustrates a partial cross-sectional view of one embodiment of the surgical instrument of FIG. 1 with various components removed for clarity showing the operation of the retraction lever.
Figure 11:
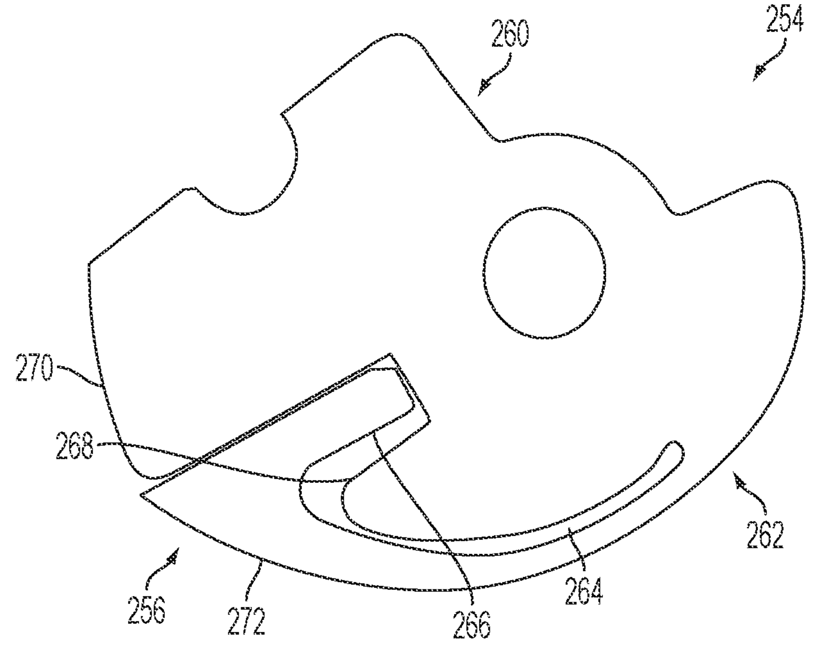
FIGS. 11 and 12 illustrate one embodiment of a locking cam of the surgical instrument of FIG. 1 during various states of operation.
Figure 12:
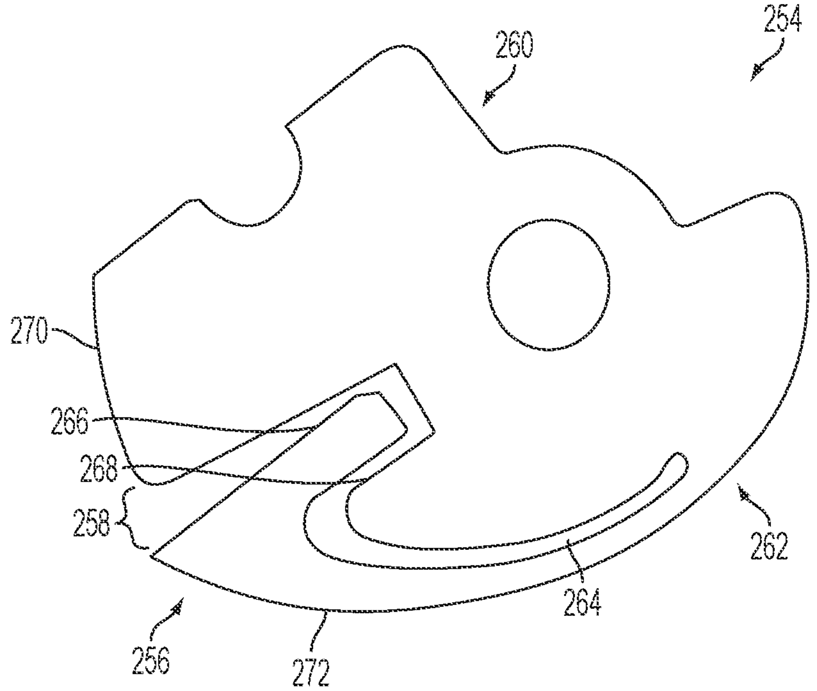

FIGS. 10-15 illustrate additional details of the operation of the locking cam 254. FIG. 10 illustrates a partial cross-sectional view of one embodiment of the surgical instrument 102 with various components removed for clarity showing the operation of the retraction lever 250. In FIG. 10, the rack 238 is shown in cross-section. FIGS. 11 and 12 illustrate one embodiment of the locking cam 254 during various states of operation. The locking cam 254 may comprise a body portion 260. The locking arm 256 that may pivot, or otherwise flex, with respect to the body portion 260 about a hinge portion 262. The hinge portion 262 may comprise, for example, a living hinge. In one embodiment, the body portion 260 and the locking arm 256 may be unitary and formed from a single piece of material. The locking cam 254 may define a clearance 264 that allows the locking arm 256 to pivot toward the body portion 260. The locking arm 256 may have a tooth 266 that is received by a notch 268 in the body portion 260. On their respective outer peripheries, the body portion 260 may have a first contacting surface 270 and the locking arm 256 may have a second contacting surface 272. In the closed position (FIG. 11), the first contacting surface 270 may be generally aligned with the second contacting surface 272 such that the outer periphery of the locking cam 254 has a generally continuous cammed surface. In the open position (FIG. 12), the locking arm 256 pivots away from the body portion 260 to increase the clearance 264. A gap 258 is created between the first contacting surface 270 and the second contacting surface 272.

Referring now to FIGS. 10, 11, and 12, upon rotation of the lever 250 in the direction indicated by arrow 274, the locking cam 254 is rotated and the second outer surface 272 of the locking arm 256 first contacts a top surface 258 of the intermediate gear 230. As a result of this contact, the locking arm 256 may be pivoted toward the body portion 260 to create a generally continuous periphery. As the locking cam 254 continues to rotate, the second contacting surface 272 and then the first contacting surface 270 exerts force on the intermediate gear 230 to overcome the biasing force applied by the spring 236. As a result, the intermediate gear 230 is pushed in the direction indicated by arrow 275 as the lever 250 is rotated in the direction indicated by arrow 274. The movement of the intermediate gear 230 may decouple it from the geared face 240 of the rack 260 allowing the rack 260 to translate freely. Once the locking arm 256 clears the top surface 258 of the intermediate gear 230, it may pivot to the open position (FIG. 12) to lock the locking cam 254 into place. Once in the open position, the locking cam 254 may be impeded from rotating in the direction indicated by arrow 276 (FIG. 10) due to the engagement of the locking arm 256 with the intermediate gear 230.

Figure 15:
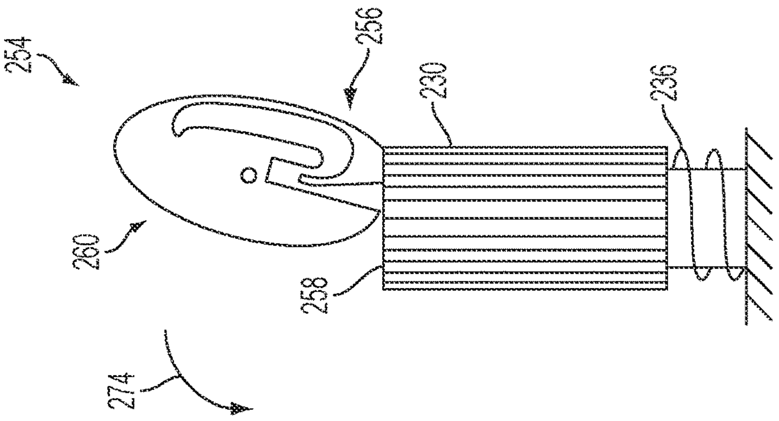
FIGS. 13-15 show various embodiments of the locking cam of FIGS. 11 and 2 and an intermediate gear during three stages of operation.
Figure 14:
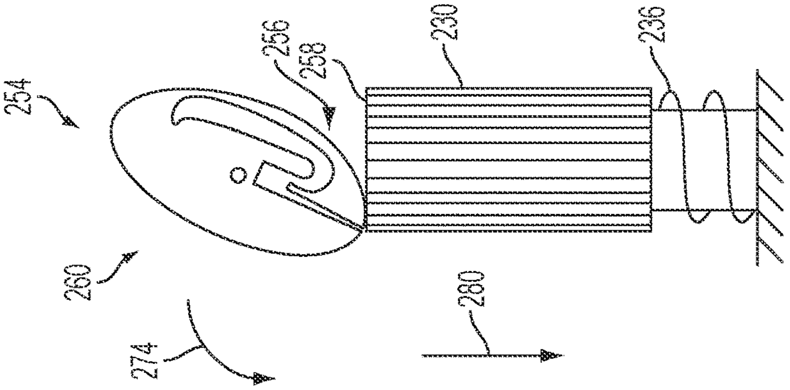
Figure 13:
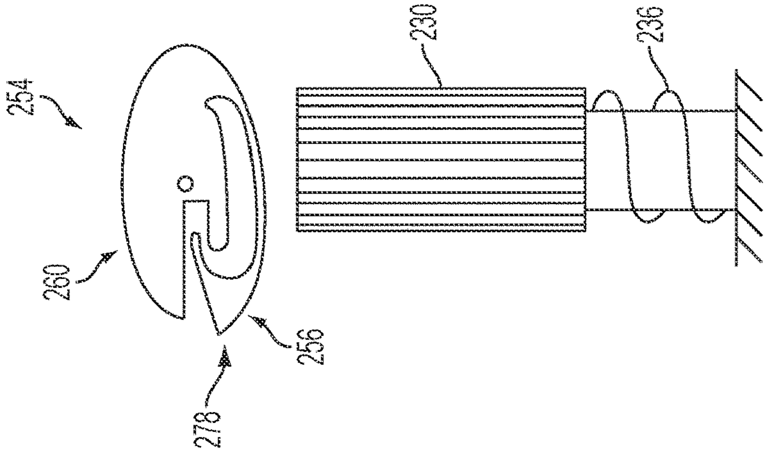
Figure 16:
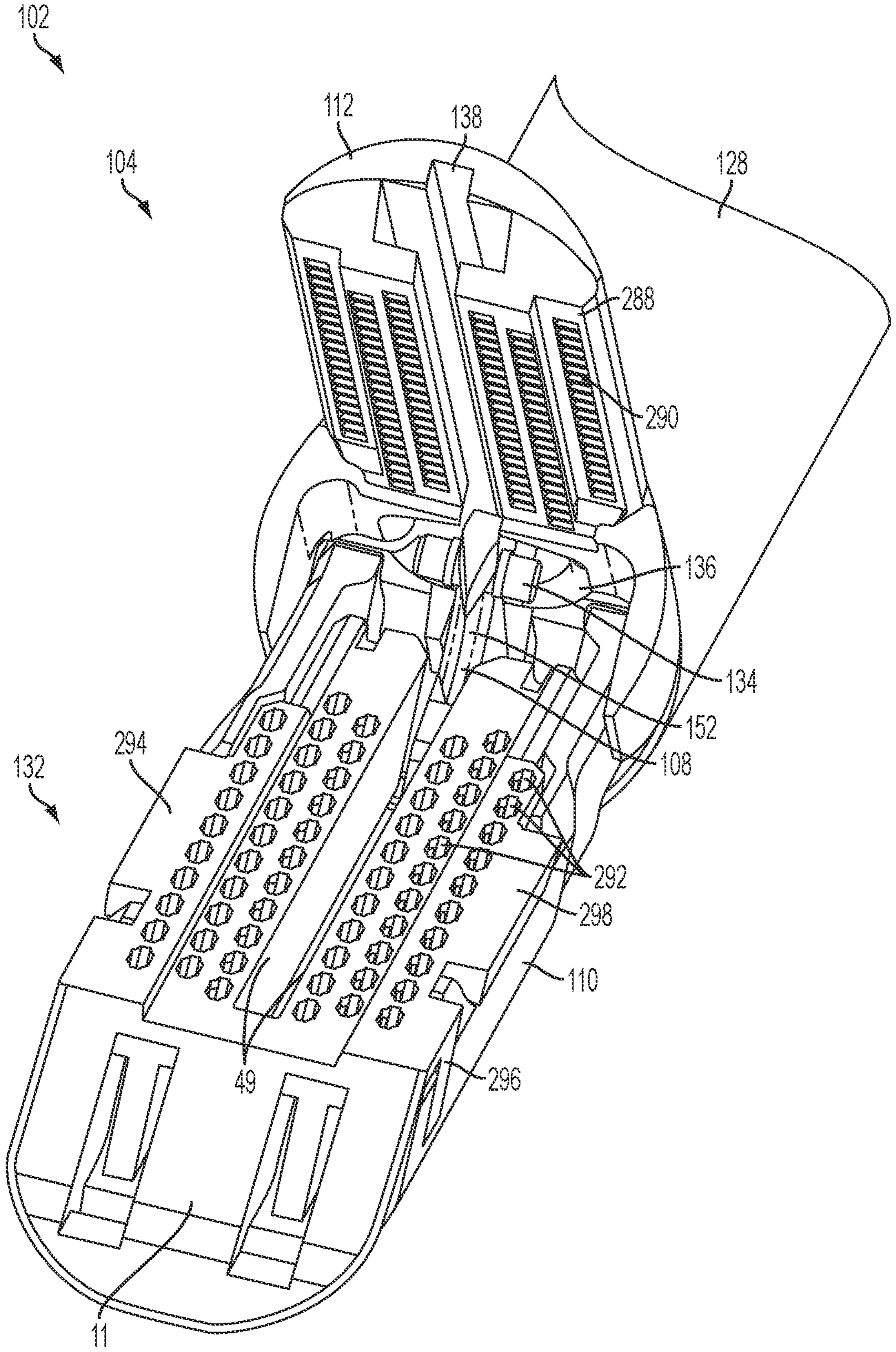
FIG. 16 depicts one embodiment of the end effector of the instrument of FIG. 1 in an open position, as a result of a retracted closure sleeve, with a staple cartridge installed in the elongate channel.

FIGS. 13-15 show various embodiments of the locking cam 254 and a intermediate gear 230 during three stages of operation. Various components have been removed and/or simplified for clarity. As illustrated, the locking cam 254 may be manufactured from a single piece of material. The locking cam 254 comprises a locking arm 256 that is pivotable with respect to a body portion 260. FIG. 13 shows one embodiment of the locking cam 254 in a non-engaged position. In this position, a distal portion 278 of the locking arm 256 is separated from the body portion 260. As illustrated in FIG. 14, when the locking cam 254 is rotated in the direction indicated by arrow 274, the locking arm 256 is drawn toward the body portion 260 to create a generally continuous periphery spanning the locking arm 256 and the body portion 260. As the locking cam 254 contacts a top face 258 of the intermediate gear 230, the gear 230 may move in the direction indicated by arrow 280. As the locking cam 254 continues to rotate in the direction indicated by arrow 274, eventually the locking arm 256 passes over the drive shaft 234. As shown in FIG. 15, when the distal portion 278 of the locking arm 256 separates from the body portion 260, it engages the teeth of the intermediate gear 230 to lock the locking cam 254 into an engaged position. Accordingly, in various embodiments, while the locking cam 254 may be made from a single piece of material, it may function as two parts (e.g., a cam and a locking mechanism).

Referring now to FIG. 6, the retraction lever 250 may also comprise a ratchet arm 282 rotatable about a ratchet pin 284. As the retraction lever 250 is pulled up, a tooth portion 286 of the ratchet arm 282 may come into contact with the top geared face 242 of the rack 238. Further rotation of the ratchet lever 250 may cause the tooth 286 to exert a proximally directed force on the rack 238, causing the drive member 130 and drive bar 108 to translate proximally. Further lifting of the retraction lever 250 may disengage the tooth portion 286 from the top geared face 242, allowing the clinician to replace the retraction lever 250 towards its original position without causing corresponding distal motion of the rack 238. Additional proximal motion of the rack 126, drive member 130 and drive bar 108 may be achieved by additional lifting of the retraction lever 250, repeating the process described above.

Figure 17:
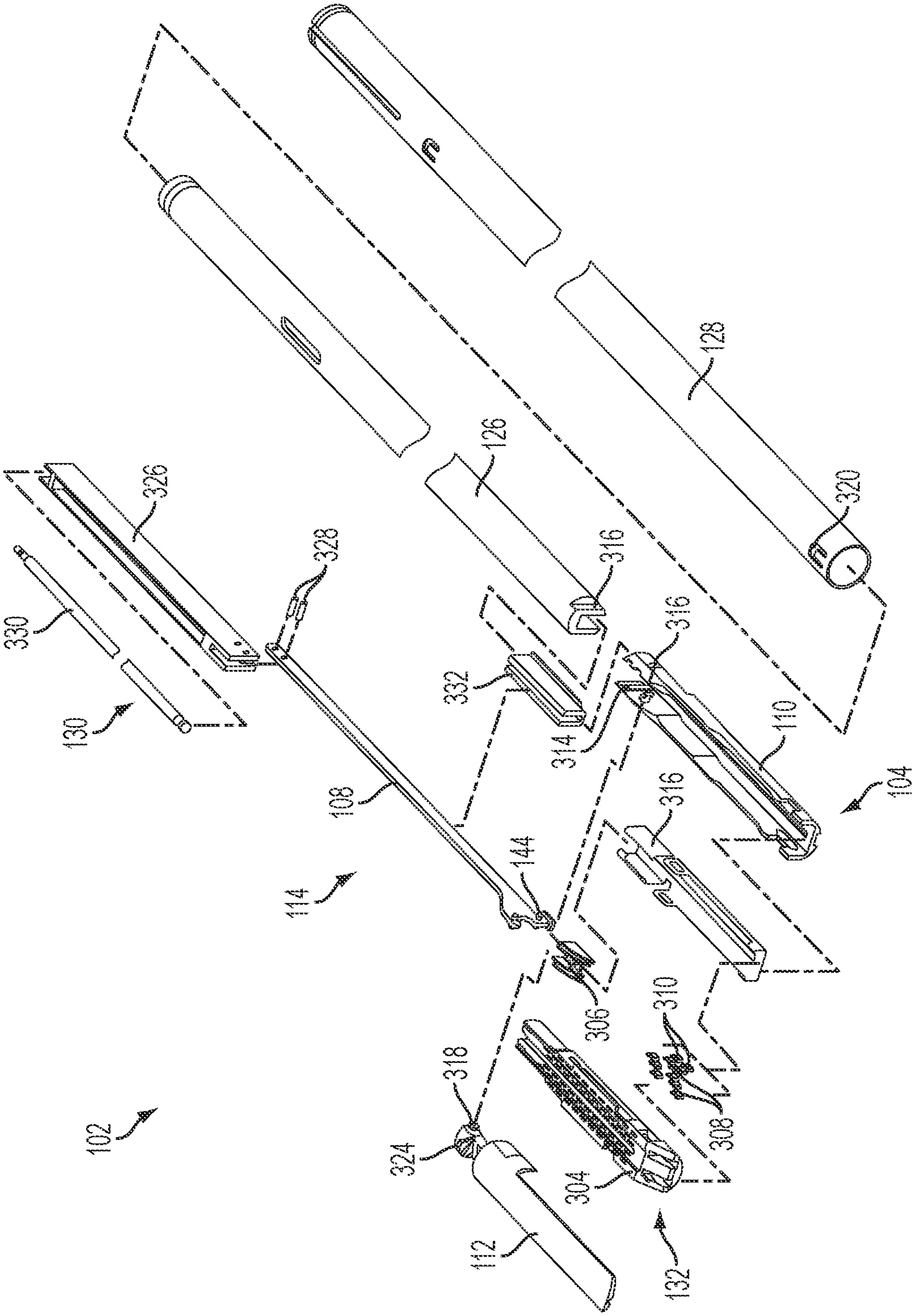
FIG. 17 shows one embodiment of the implement portion of the surgical stapling and severing instrument of FIG. 1 in disassembled form.

FIG. 17 shows one embodiment of the implement portion 114 of the surgical stapling and severing instrument 102 in disassembled form. The staple cartridge 132 is shown as being comprised of a cartridge body 304, a wedge sled 306, single and double drivers 308, staples 310, and a cartridge tray 312. When assembled, the cartridge tray 312 holds the wedge sled 306, single and double drivers 308, and staples 310 inside the cartridge body 304.

The elongate channel 110 may have a proximally placed attachment cavity 314 that receives a channel anchoring member 316 on the distal end of the frame 126 for attaching the end effector 104 to the handle portion 106. The elongate channel 110 may also have an anvil cam slot 316 that pivotally receives an anvil pivot 318 of the anvil 112. The closure sleeve 128 that encompasses the frame 126 may include a distally presented tab 320 that engages an anvil feature 324 proximate but distal to the anvil pivot 318 on the anvil 112 to thereby effect opening and closing of the anvil 112. The firing drive member 130 is shown as being assembled from the firing bar 108 attached to a firing connector 326 by pins 328, which in turn is rotatingly and proximally attached to the metal drive rod 330. The firing bar 108 is guided at a distal end of the frame by a slotted guide 332 inserted therein.

Figure 18:
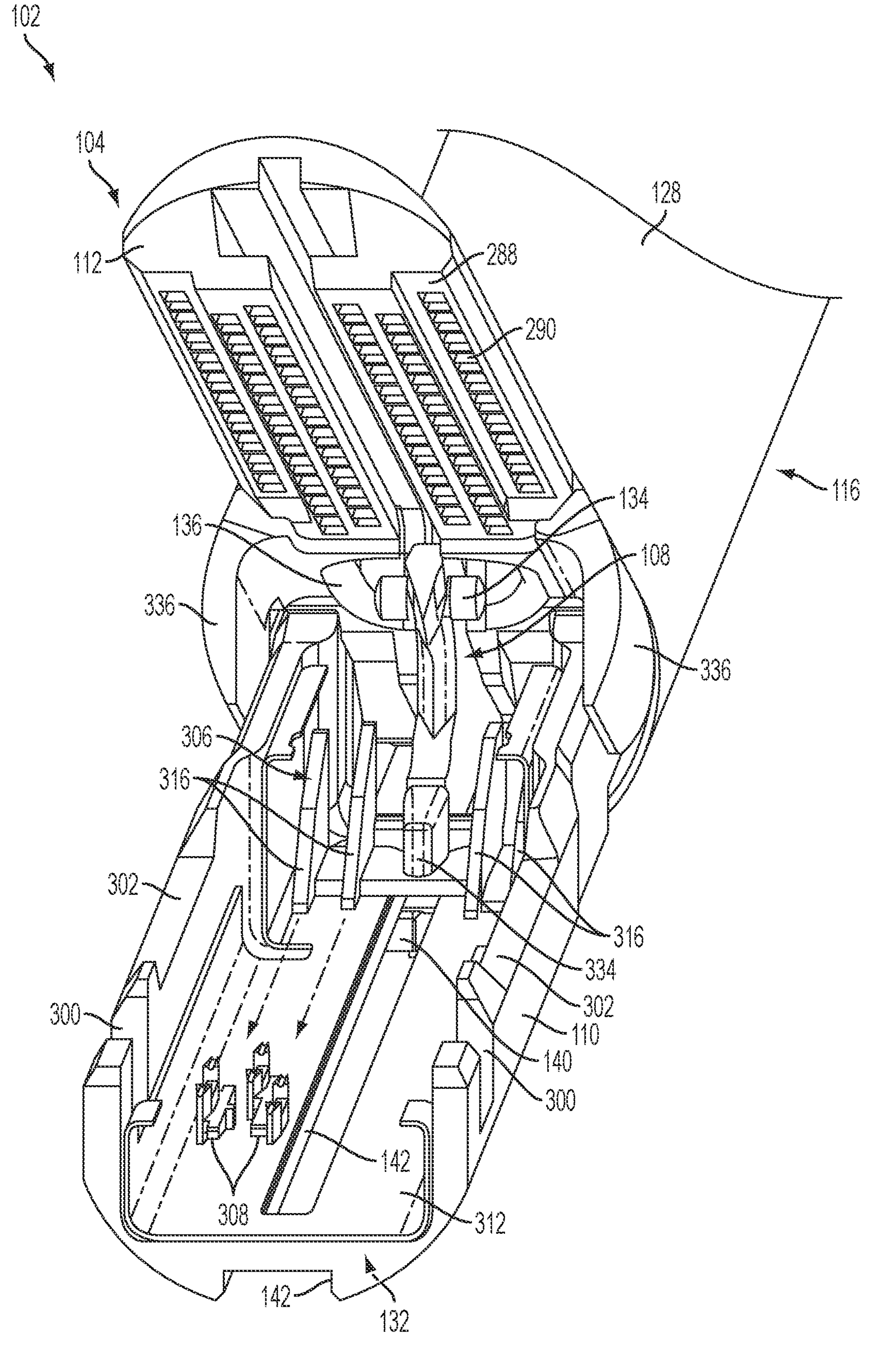
FIG. 18 shows one embodiment of the end effector of the instrument of FIG. 1 with a portion of the staple cartridge removed.

With particular reference to FIG. 18, a portion of the staple cartridge 132 is removed to expose portions of the elongate channel 110, such as recesses 300, 302 and to expose some components of the staple cartridge 132 in their unfired position. In particular, the cartridge body 304 (shown in FIG. 17) has been removed. The wedge sled 306 is shown at its proximal, unfired position with a pusher block 334 contacting the middle pin 144 (not shown in FIG. 18) of the firing bar 108. The wedge sled 306 is in longitudinal sliding contact upon the cartridge tray 312 and includes wedges 308 that force upward the single and double drivers 308 as the wedge sled 306 moves distally. Staples 310 (not shown in FIG. 18) resting upon the drivers 308 are thus also forced upward into contact with the anvil forming pockets 290 on the anvil 112 to form closed staples. Also depicted is the channel slot 142 in the elongate channel 110 that is aligned with the vertical slot 154 in the staple cartridge 132.

Figure 19:
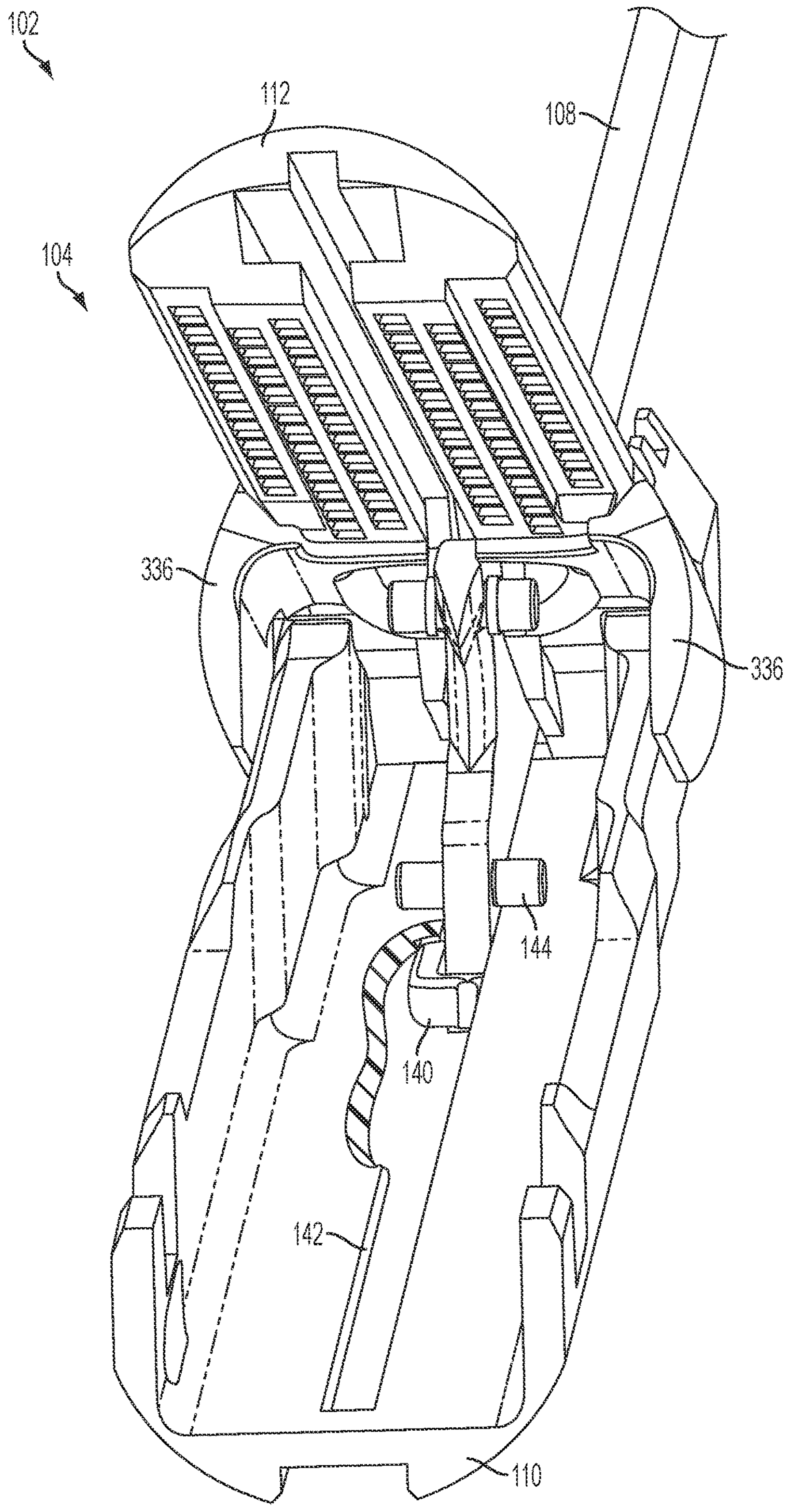
FIG. 19 depicts the end effector of FIG. 18 with all of the staple cartridge removed.

FIG. 19 depicts the end effector 104 of FIG. 18 with all of the staple cartridge 132 removed to show the middle pin 144 of the firing bar 108 as well as portion of the elongate channel 110 removed adjacent to the channel slot 142 to expose the firing bar cap 140. In addition, portions of the shaft 116 are removed to expose a proximal portion of the firing bar 108. Projecting downward from the anvil 112 near the pivot, a pair of opposing tissue stops 346 may prevent tissue being positioned too far up into the end effector 104 during clamping.

Figure 20:
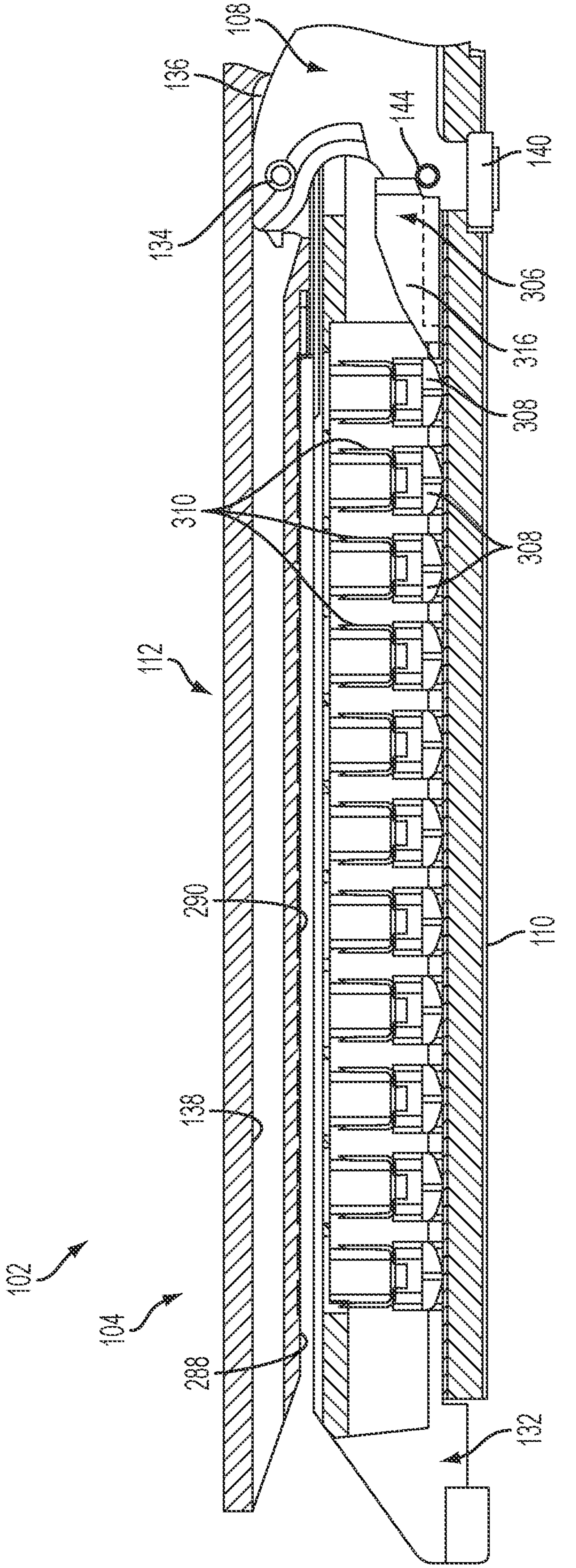
FIG. 20 depicts one embodiment of the end effector of the instrument of FIG. 1 closed in a tissue clamping position with the firing bar unfired.

FIG. 20 depicts one embodiment of the end effector 104 closed in a tissue clamping position with the firing bar 108 unfired. The upper pin 134 is shown in the anvil pocket 136, vertically aligned with the anvil slot 138 for distal longitudinal movement of the firing bar 108 during firing. The middle pin 144 may be positioned to push the wedge sled 306 distally so that wedge 308 sequentially contacts and lifts double drivers 308 and the respective staples 310 into forming contact with staple forming pockets 290 in the lower surface 288 of the anvil 112. According to various embodiments, the end effector 104 may implement a mechanical lock-out mechanism. The mechanical lock-out mechanism may prevent the instrument 102 from being fired twice without reloading a new staple cartridge 132. For example, it will be appreciated that firing the instrument 102 without a loaded staple cartridge present may cause tissue to be cut, but not fastened. The lock-out may be implemented in any suitable manner. For example, the firing bar 108, upon retraction in the proximal direction, may be shifted by the elongate channel 110, or other component, such that the upper pin 134 is no longer in alignment with the anvil slot 138, preventing the firing bar 108 from moving distally (e.g., re-firing). Installation of a new staple cartridge 132 to the elongate channel 110 may snap the firing bar 108 back, aligning the upper pin 134 with the anvil slot 138 and allowing re-firing. It will be appreciated that any suitable mechanism in the end effector or the handle 106 may be utilized to implement a mechanical lock-out.

Figure 21:
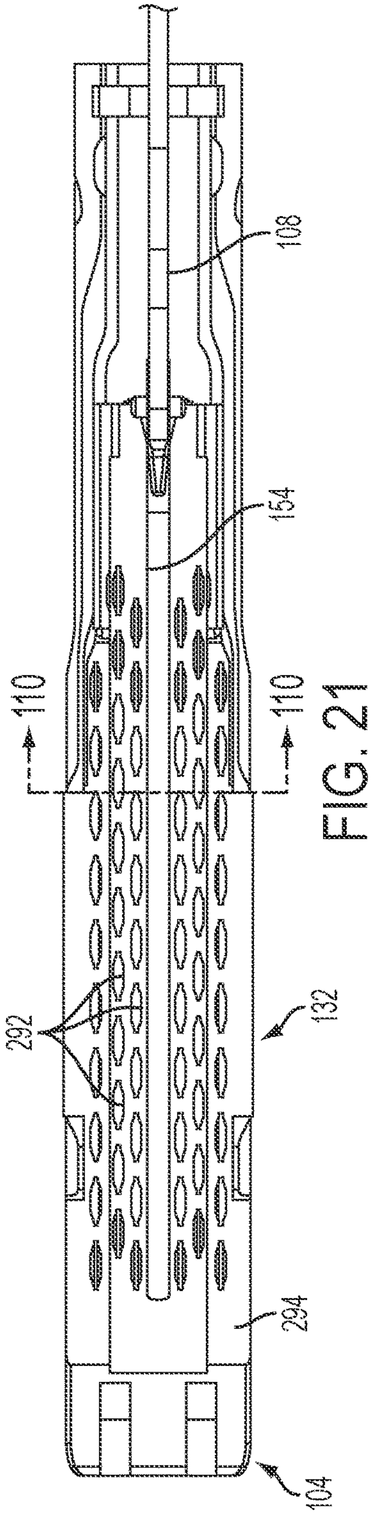
FIG. 21 depicts one embodiment of the upper surface of the staple cartridge shown in FIG. 16 with the firing bar in its unfired, proximal position.
Figure 22:
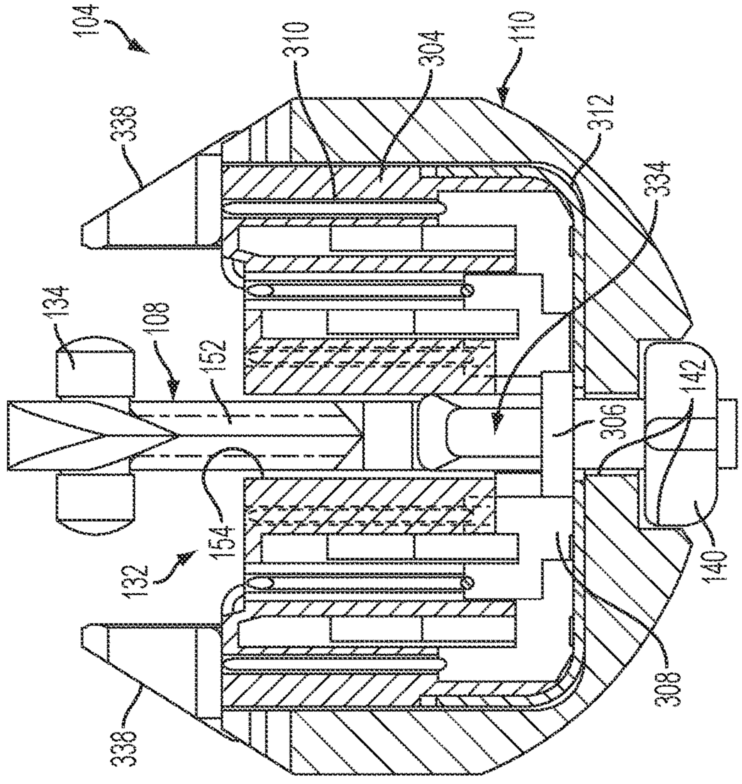
FIG. 22 depicts one embodiment of the end effector of the instrument of FIG. 1 near the pivot showing that the elongate channel has opposing ramp portions to thereby cooperate with the anvil to prevent tissue from jamming the end effector.

FIG. 21 depicts one embodiment of the upper surface 294 of the staple cartridge 132 with the firing bar 108 in its unfired, proximal position. The stapler apertures 292 are arrayed on each side of the vertical slot 154 in the staple cartridge 132. FIG. 22 depicts one embodiment of the end effector 104 near the pivot showing that the elongate channel 110 has opposing ramp portions 348 to thereby cooperate with the tissue stops 346 of the anvil 112 to prevent tissue from jamming the end effector 104. Also depicted in greater detail are the double drivers 308 and their relation to the staples 310.

Figure 23:
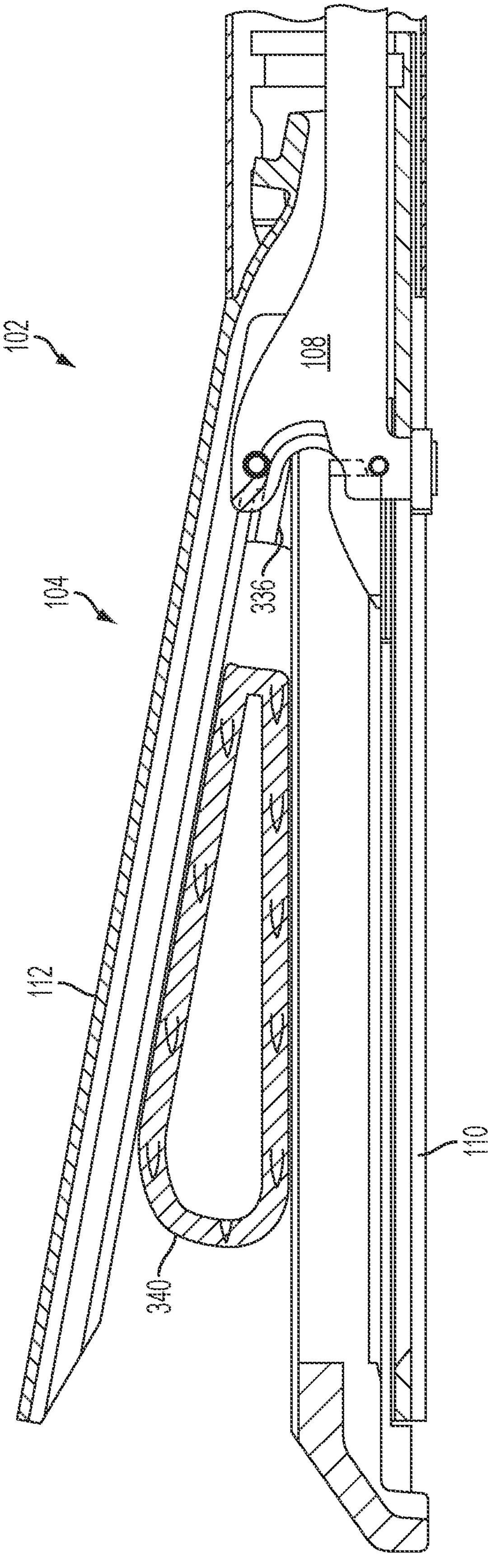
FIG. 23 illustrates one embodiment of the end effector of the instrument of FIG. 1 with tissue present between the staple cartridge and the anvil.
Figure 24:
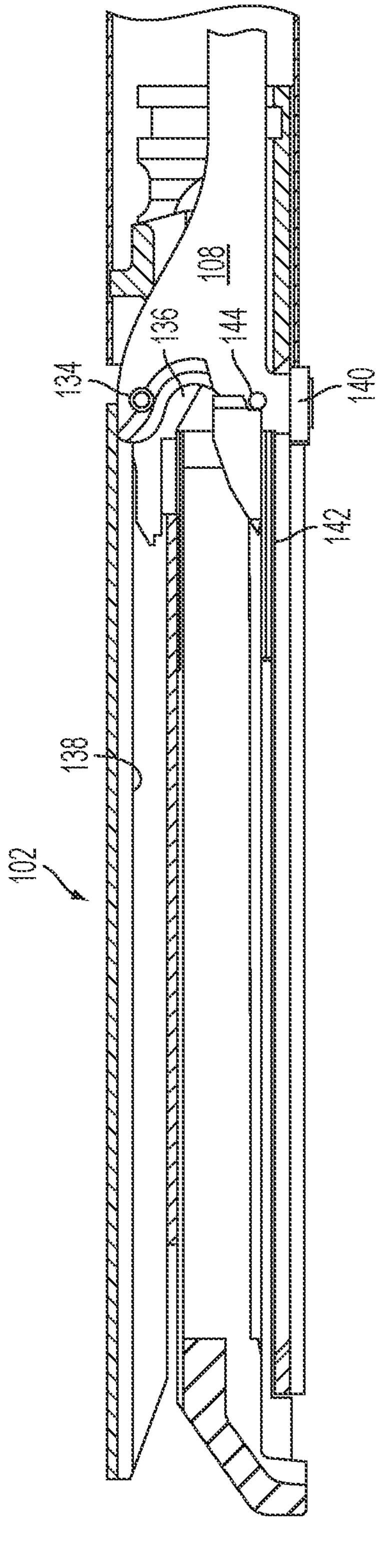
FIGS. 24-26 illustrate one embodiment of the end effector of the instrument of FIG. 1 at various stages of firing.
Figure 25:
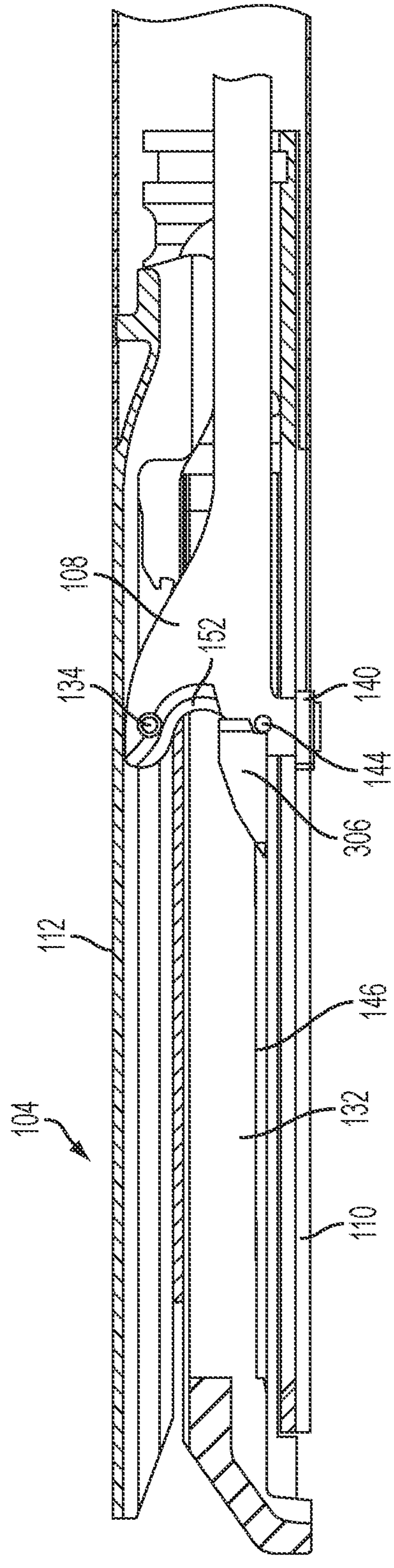
Figure 26:
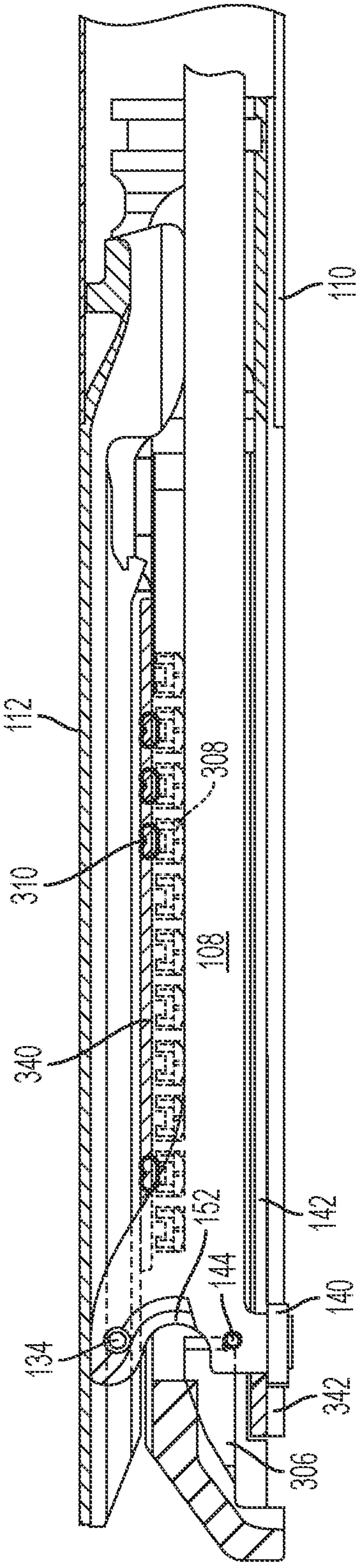

FIGS. 24-26 illustrate one embodiment of the end effector 104 at various stages of firing. In use, the surgical stapling and severing instrument 102 may be used to cut and staple tissue. In FIGS. 1-2, the instrument 102 is shown in its start position, having had an unfired, fully loaded staple cartridge 132 snap-fitted into the distal end of the elongate channel 110. Both triggers 120, 122 are forward and the end effector 104 is open, such as would be typical after inserting the end effector 104 through a trocar or other opening into a body cavity. The instrument 102 may then be manipulated by the clinician such that tissue 340 to be stapled and severed is positioned between the staple cartridge 132 and the anvil 112. FIG. 23 illustrates the end effector 104, according to one embodiment, with tissue 340 present between the staple cartridge 132 and the anvil 112.

Next, the clinician moves the closure trigger 120 proximally until positioned directly adjacent to the pistol grip 118, locking the handle portion 106 into the closed and clamped position. The retracted firing bar 108, shown in FIG. 24 in the end effector 104 may not impede the selective opening and closing of the end effector 104, but rather may reside within the anvil pocket 136. With the anvil 112 closed and clamped, the firing bar 108 may be aligned for firing through the end effector 104. In particular, the upper pin 134 may be aligned with the anvil slot 138 and the elongate channel 110 may be affirmatively engaged about the channel slot 142 by the middle pin 144 and the firing bar cap 140.

After tissue clamping has occurred, the clinician may move the firing trigger 122 proximally causing the firing bar 108 to move distally into the end effector 104, shown in FIG. 25. In particular, the middle pin 144 enters the staple cartridge 132 through the firing drive slot 146 to cause the firing of the staples 310 via wedge sled 306 toward the anvil 112. The lower most pin, or firing bar cap 140, cooperates with the middle pin 144 to slidingly position cutting edge 152 of the firing bar 108 to sever tissue. The two pins 140, 144 also position the upper pin 134 of the firing bar 108 within longitudinal anvil slot 138 of the anvil 112, affirmatively maintaining the spacing between the anvil 112 and the elongate channel 110 throughout its distal firing movement.

The clinician may continue moving the firing trigger 122 until brought proximal to the closure trigger 120 and pistol grip 118. Thereby, all of the ends of the staples 310 may be bent over as a result of their engagement with the anvil 112, as shown in FIG. 26. The firing bar cap 140 may be arrested against a firing bar stop 342 projecting toward the distal end of the channel slot 142. The cutting edge 152 may have traversed completely through the tissue. The process is complete by releasing the firing trigger 122. Releasing the firing trigger 122 may, as described herein below, cause the motor 222 to reverse its rotation, causing retraction of the firing bar 108. Upon retraction of the firing bar 108, the clinician may depress the clamp switch 124. (e.g., while simultaneously squeezing the closure trigger 120) This may open the end effector 104.

Referring back to FIG. 1, the handle 106 of the instrument 102 may house at least one battery unit 506. The battery unit 506 may comprise a single battery or a plurality of batteries arranged in a series and/or parallel configuration. The handle 502 may comprise a battery dock 508 to which the battery unit 506 may be attached. The battery dock 508 may be any suitable structure for coupling the battery unit 506 to the instrument 102. For example, the battery dock 508 may be or comprise a cavity in the handle 106 configured to receive at least a portion of the battery unit 506, as illustrated. In other embodiments, the battery dock 508 may be implemented using a variety of other structures. In one embodiment, the battery dock 508 may comprise a post that is received by the battery unit 506. In one embodiment, the pistol grip 120 may comprise the battery dock 508. In any event, as discussed in more detail below, the battery dock 508 may comprise a protruding portion to interact with the battery unit 506 upon attachment of the battery unit 506 to the handle 502. Once attached, the battery unit 506 may be electrically connected to and may provide power to the motor 222 of the instrument 102.

FIGS. 27-29 schematically illustrate one embodiment of the battery unit 506 and a portion of the instrument 102 showing the attachment and detachment of the battery unit 506 to the instrument 102. The battery unit 506 may comprise a drain 512 that automatically completes a circuit within the battery unit 506 upon attachment to the instrument 102. The drain may serve to slowly reduce the charge of the battery unit 506 over time. Once the battery unit 506 has been sufficiently drained it may be disposed as non-hazardous waste, for example. The battery unit 506 may comprise a voltage source 510. In one embodiment, the voltage source 510 is a lithium battery and comprises at least one cell selected from the group consisting of a CR123 cell and a CR2 cell. As is to be appreciated, any suitable voltage source may be used. The battery unit 506 may also comprise a drain 512 that may be electrically coupled to the voltage source 510 when a switch 516 is closed. The battery unit 506 and the instrument 102 each comprise electrically conductive contacts 518, 520, respectively, that are placed into contact upon attachment of the battery unit 506 to the instrument 102. FIG. 27 illustrates the battery in a non-attached position. The switch 516 is in an open position and the voltage source 510 may be in a fully charged condition. FIG. 28 illustrates that battery unit 506 in an attached position. The conductive contacts 518 of the battery unit 506 are in electrical communication with the contacts 520 of the instrument thereby allowing the battery unit 506 to supply energy to the circuit 514 (FIG. 46). In the attached position, the switch 516 may transition to the closed position to electrically couple the voltage source 510 to the drain 512. Energy will flow from the voltage source 510 through the drain 512 during operation of the instrument. In other words, the drain 512 will be draining the charge from the voltage source 510 concurrently as the battery unit 506 is supplying operational power to the instrument 102. As discussed in more detail below, a portion of the instrument 102 may physically interact with the drain 512 during attachment of the battery unit 506 to the instrument 102 to transition the switch 516 from the open to the closed state. FIG. 29 illustrates the battery unit 506 in a non-attached position. In one embodiment, the switch 516 remains in the closed position to continue to drain the voltage source 510 even after the battery unit 506 has been detached from the instrument 102.

FIG. 30 illustrates a graph 600 of the voltage level of one embodiment of the battery unit 506 over time, as measured from the time of attachment to the instrument 102. The graph 600 includes three example discharge curves 602, 604, 606. As illustrated by the first discharge curve 602, the voltage of the power source 510 may drop below 2.0 volts after around 28 hours. As illustrated by the second discharge curve 604, the voltage of the power source 510 may drop below 2.0 volts after around 30 hours. As illustrated by the third discharge curve 606, the voltage of the power source 510 may drop below 2.0 volts after around 33 hours. The overall shape of the discharge curve may depend upon, for example, the level of activity of the instrument 102 during the surgical procedure. For example, the instrument associated with the first discharge curve 602 was more heavily used during the surgical procedure than the instrument associated with discharge curve 606. In any event, the drain 512 may maintain the voltage level of the battery unit 506 at a satisfactory level for a certain time period to ensure that the instrument can be used for its intended purpose during the course of the surgical procedure. For example, in one embodiment, the voltage level of the battery unit 506 may be maintained around 6 volts for approximately 12 hours. After 12 hours, the voltage level gradually decreases to a non-hazardous level. As is to be appreciated, the drain 512 may be calibrated to deplete the voltage source faster or slower.

In one embodiment, a resistive element may be used to reduce the energy level of the voltage source. FIG. 31 shows a simplified circuit diagram of one embodiment of a battery unit 616 comprising a drain 612. The battery unit 616 may be attached to an instrument 102, for example, via its contacts 618. In this embodiment, the battery unit 616 may comprise a first grouping of cells 610 and a second grouping of cells 611. In one embodiment, the first and second grouping of cells 610, 611 may be lithium batteries. The first and second grouping of cells 610, 611 may each have a plurality of separate cells 610*a*, 610*b*, 611*a*, 611*b* arranged in a parallel formation. For example, the first and second grouping of cells 610, 611 may each be 6 VDC and arranged in a series configuration to produce 12 VDC at the contacts 618 of the battery unit 616 when fully charged. The cells 610*a*, 610*b*, 611*a*, 611*b*, however, may be electrically connected to one another in series or parallel or any other combination thereof. The number of cells 610*a*, 610*b*, 611*a*, 611*b* may be chosen to reduce the fire hazard resulting from the battery unit 616. For example, the number of connected cells may be selected such that the cumulative energy available to an arc or short is less than the energy required to ignite common shipping and/or packing materials. According to various embodiments, this value may be defined by appropriate government regulations.

In one embodiment, the drain 612 may comprise a first resistive element 622 and a second resistive element 624. As is to be appreciated, in some embodiments, the battery unit 616 may comprise, for example, multiple drains 612 each having more or less than two resistive elements or other circuitry. In the illustrated embodiment, the first resistive element 622 is coupled across a first anode 626 and a first cathode 628 of the first grouping of cells 610 through a first switch 630. The first resistive element 624 may be coupled across a second anode 632 and a second cathode 634 of the second grouping of cells 611 through a second switch 636. The first and second switches 630, 636 may be closed upon attachment of the battery unit 616 to the surgical instrument 102 in order to initiate the draining of the first and second grouping of cells 610, 611.

The value of the resistive elements utilized by the drain 612 may vary based on implementation. In one embodiment, the first resistive element 622 has a resistance in the range of about 90 ohms to about 110 ohms. In one embodiment, the first resistive element 622 has a resistance in the range of about 97 ohms to about 104 ohms. In one embodiment, the resistive element 622 is 102.9 ohms and has a power rating of 1 watt. The determination of the necessary resistance is based at least partially on the capacity of the voltage source, the voltage level of the voltage source, and the desired temporal length of the drainage curve. For example, in one embodiment the battery capacity of the first grouping of cells 610 is 1400 mAh, the voltage level is 6 VDC, and the target drain time is 24 hours. Diving 1400 mAh by 24 hours yields a current of 0.0582 A. Using Ohm's law, 6 V divided by 0.582 A yields a resistance of 102.9 ohms. With a current of 0.583 and a resistance of 102.9 ohms, the power dissipated by the resistor is 350 W. As is to be appreciated, different voltage levels, battery capacities, and desired time of discharge will result in different resistance values.

FIG. 32 is a simplified circuit diagram of one embodiment of a battery unit 716 comprising a first drain 712 and a second drain 713. The battery unit 716 may be attached to an instrument 102, for example, via its contacts 718. In this embodiment, the battery unit 716 comprises a first grouping of cells 710, a second grouping of cells 711, and a third cell 714. The first drain 712 comprises a first resistive element 722 and a second resistive element 724. The second drain 713 comprises a third resistive element 726. The resistive elements 722, 724, 726 are coupled to respective cells through switches 730, 736, and 738. The switches 730, 736, and 738 may be closed upon attachment of the battery unit 716 to the surgical instrument 102 in order to initiate the draining of the first and second grouping of cells 610, 611 and the third cell 716. The resistance of the third resistive element 726 may be similar or different from the resistances of the first and second resistive element 722, 724. As described above, the resistance of the third resistive element 726 may at least partially depend on the voltage of the third cell 714 and the desired characteristics of the drainage curve.

Figure 34:
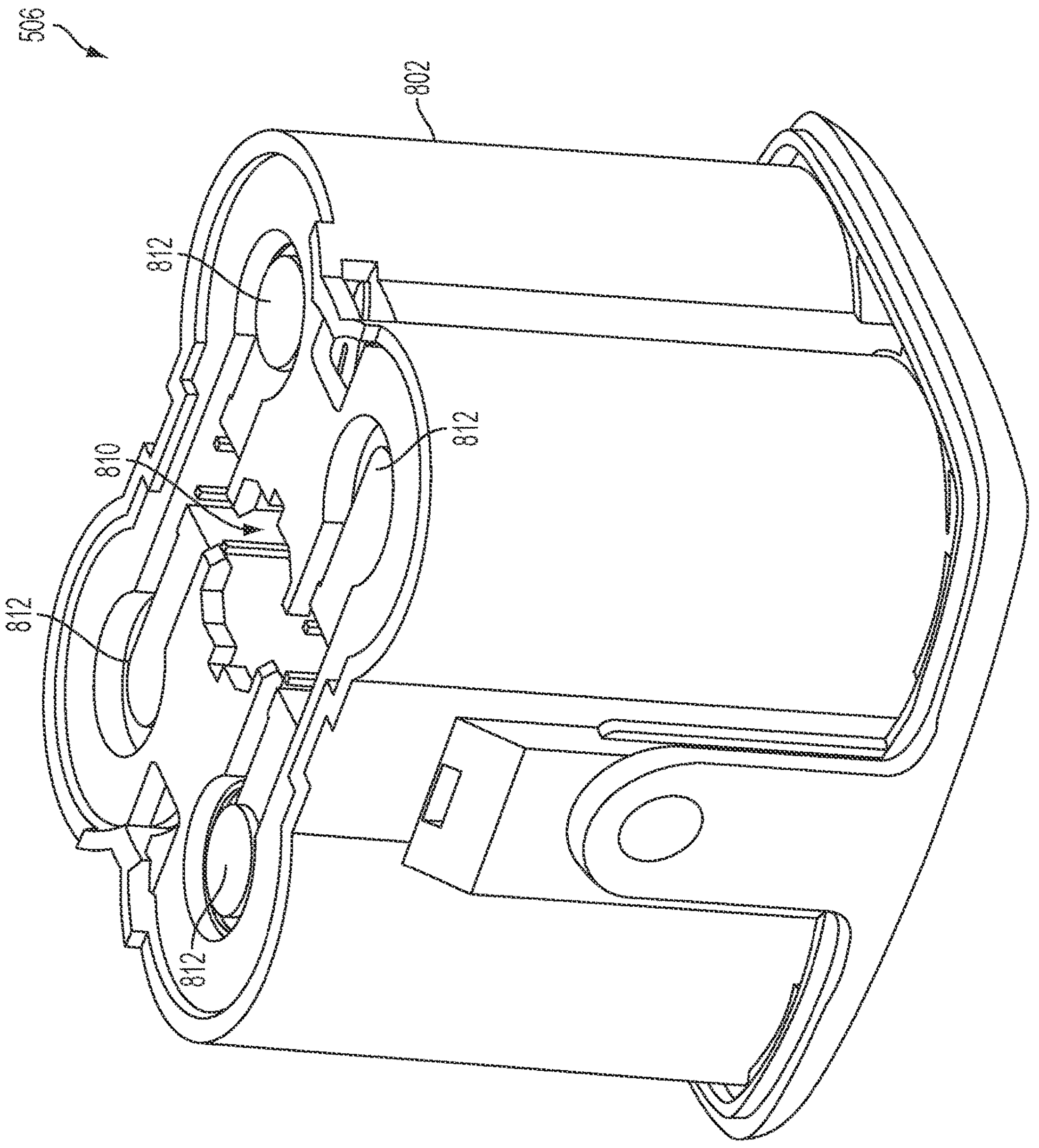

FIGS. 33-36 are perspective views of one embodiment of a battery unit 506 implementing the schematic of the battery unit 616 shown in FIG. 31. The battery unit 506 may comprise a casing 802 defining an interior cavity 810. While the interior cavity 810 is illustrated in a central portion of the casing 802, it is to be appreciated that the internal cavity 810 may be positioned in any suitable location. The casing 802 may be covered by a cap 804 that may be secured to the casing 802 utilizing one or more mechanical latches 806, 808. FIG. 34 illustrates one embodiment of the battery unit 506 with the cap 804 removed to show a plurality of cells 812 within. Any suitable number and/or type of cells 812 may be used. For example, CR123 and/or CR2 cells may be used. FIG. 35 illustrates one embodiment of the battery unit 506 with a portion of the casing 802 removed to reveal the cells 812. FIG. 36 illustrates one embodiment of the battery unit, with a portion of the casing 802 missing as in FIG. 35. FIG. 36 shows the battery pack 506 from a side 890 positioned to face distally when the battery pack 506 is installed on the surgical device 102. The interior cavity 810 is visible as well as a pair of contacts 886, 888 in electrical communication with the various cells 812.

FIGS. 37 and 38 illustrate cross-sectional views of one embodiment of the battery unit 506 including a translatable drain 812. The drain 812 may be positioned within the interior cavity 810 and may be translatable within the interior cavity 810 in the directions of arrow 815. FIG. 37 shows the drain 812 in an open position and FIG. 38 shows the drain 812 in a closed position. The drain 812 may comprise at least two contacts 816, 818. When the drain 812 is in the open position, a portion of the contacts 816, 818 may touch a non-conductive portion of the casing 802, such as fingers 820, 822. According to various embodiments, the contacts 816, 818 may be biased to exert a force against the fingers 820, 822 in order to resist movement of the drain 812 in the direction of the arrows 815. Also, in some embodiments, the fingers 820, 822 may define one or more protrusions or stepped down portions, as shown in FIGS. 37 and 38. The battery unit 506 may also comprise one or more electrodes, such as first electrode 824 and second electrode 826. The first and second electrodes 824 and 826 may each be electrically coupled to a cathode or an anode of cells contained within the battery unit 506. In the closed position (FIG. 38), the contacts 816, 818 are in electrical connection with the electrodes 824, 826, thereby allowing the voltage source to discharge through the drain 812. As discussed in more detail below, the drain 812 may be translated from the open position to the closed position upon attachment of the battery unit 506 to a surgical instrument.

FIG. 43 is a perspective view of one embodiment of the drain 812 in accordance with one non-limiting embodiment. The contacts 816, 818 of the drain 812 may be coupled to a base portion 830 of the drain 812. Similarly contacts 836, 838 of the drain 812 may be coupled to the base portion 830 of the drain 812. According to various embodiments, the contacts 816, 818 may be electrically connected to one another via a resistive element (not shown) mounted to a circuit board 832. Similarly, the contacts 836, 838 may be electrically connected to one another via a resistive element mounted to the circuit board 832. As illustrated, the contacts 816, 818, 836, 838 may have a bend or curvature to bias the contacts towards an outward position when they are inwardly compressed. Additionally, in one embodiment, the distal end of each of the contacts 816, 818, 836, 838 may have an inwardly turned section. The base portion 830 may comprise a contacting surface 840 that engages the instrument when the battery unit 506 is attached to the instrument. Through this engagement, the drain 812 may be translated relative to the casing 802.

FIGS. 39-42 illustrate multiple views of a one embodiment of a battery dock 850. The battery dock 850 may be positioned within the handle 106 of the instrument 102 and may receive the battery unit 506. For example, the battery dock 850 may comprise a protruding member or bulkhead 858. The battery dock 850 may be positioned within the base sections 156, 158 and, in some embodiments, may be coupled to the frame sections 160, 162 such that the protruding member 858 extends proximally. The battery unit 506 may be installed into the device 102 by pushing it distally against the battery dock 850. The protruding member 858 of the battery dock 850 may extend into the exterior cavity 810 of the battery unit 506. Contacts 882, 884 of the battery dock 850 may also extend into the interior cavity 810 of the battery unit 506. Within the cavity, the contacts 882, 884 of the battery dock 850 may be in electrical communication with the contact 886, 888 of the battery unit 506 (FIG. 36). When the contacts 886, 888 of the battery unit 506 come into contact with the contacts 882, 884 of the battery dock 850, the battery unit 506 may be in electrical communication with the instrument 102.

FIG. 44 illustrates one embodiment of the battery unit 506 attached to the battery dock 850. For clarity, various components have been removed. Referring now to FIGS. 37, 38, 43 and 44 as well as to FIGS. 39-42, the battery dock 850 is shown with its protruding member 858 sized to be received by the cavity 810 (FIG. 33) of the battery unit 506. Prior to attachment, the drain 812 may be in the open position (FIG. 37). During attachment of the battery unit 506 to the battery dock 850, the protruding member 858 is inserted into the cavity 810 and the battery unit 506 is moved relative to the battery dock 850 in the direction indicated by arrow 862. Eventually the distal end 860 of the protruding member 858 contacts the contacting surface 840 of the drain 812. As the user continues to attach the battery unit 506, the drain 812 is translated relative to the casing 802 in the direction indicated by arrow 864 and moves into the closed position (FIG. 38). In this position, the battery unit 506 commences to slowly drain. When the battery unit 506 is removed from the battery dock 850, the drain 812 may remain in the position shown in FIG. 38. In this way, the cells (not shown) of the battery unit 506 may drain any remaining charge across a resistive element either before or during disposal.

As is to be appreciated, the translatable discharge drain of the battery unit is not limited to the implementation illustrated in FIG. 44. FIGS. 45 and 46, for example, illustrate one embodiment of a battery unit 900 and drain 912 with various components removed for clarity. The drain 912 that is translatable between an open position (FIG. 45) and a closed position (FIG. 46). In the open position, contacts 916, 918 are engaged with non-conductive portions of a casing 920, 922, respectively. The drain 912 may ride in a track 914 when translating between the open position and the closed position. FIG. 46 shows the battery unit 900 in a closed position after a ram 958 has translated the drain 912 in the direction indicated by arrow 964. The ram 958 may be a component of a battery dock of a surgical instrument, for example. In one embodiment, the battery dock comprises a cavity that is dimensioned to receive the battery unit 900, and the ram 958 is positioned within the cavity. In the closed position, the contacts 916, 918 are in electrical contact with electrodes 924, 926. The drain 912 may comprise a printed circuit board 932 to which at least one resistive element is mounted using a surface mount or a through-hole connection, for example.

FIGS. 47 and 48 illustrate a battery unit 1000 in accordance with another non-limiting embodiment. Various components have been omitted for clarity. The battery unit 1000 may comprise a drain 1012 that may be translatable between an open position (FIG. 47) and a closed position (FIG. 48). The battery unit 1000 may also comprise a first electrode 1024 with a contact 1025 and a second electrode 1026 with a contact 1027. The electrodes 1024, 1026 may be in contact with cells (not shown) of the battery unit 1000. In the open position, contacts 1016, 1018 of the drain 1012 are not engaged with contacts 1025, 1027 of the electrodes 1024, 1026. The drain 1012 may ride in a track 1014 when translating between the open position and the closed position. FIG. 48 shows the battery unit 1000 in a closed position after a ram 1058 has translated the drain 1012 in the direction indicated by arrow 1064. The ram 1058 may be a component of a battery dock of a surgical instrument, for example. In the closed position, the contacts 1016, 1018 of the drain 1012 are in electrical contact with the contacts 1025, 1027 of the electrodes 1024, 1026. The drain 1012 may comprise a printed circuit board 1032 that includes at least one resistive element. In some embodiments, the contacts 1016, 1018 themselves may comprise the resistive elements. In fact, the resistive elements may be elements of any suitable resistance value and any suitable mechanical configuration.

FIG. 49 is a perspective view of one embodiment of a battery unit 1100. FIGS. 50 and 51 show internal views of the battery unit 1100 during various stages of operation with various components removed for clarity. The battery unit 1100 has one cell 1102 and an outer casing 1104 that defines a cavity 1110. The outer casing 1104 may be non-conductive and have conductive contacts for supplying energy to circuitry of a surgical instrument when the battery unit 1100 is attached to a surgical instrument. In one embodiment, the battery unit 1100 is received by a cavity in a pistol grip portion of a surgical instrument. The battery unit 1100 comprises a drain 1112 that is translatable between an open position (FIG. 50) and a closed position (FIG. 51). In one embodiment the drain 1112 has first and second contacts 1116, 1118 that are coupled to a circuit board 1132. The circuit board 1132 may include, for example, at least one resistive element. In some embodiments, the circuit board 1132 includes additional circuitry. The battery unit 1100 comprises a first electrode 1124 coupled to an anode of the cell 1102 and a second electrode coupled to a cathode of the cell 1102. Before the battery unit 1100 is attached to an instrument, the drain 1112 is in the open position (FIG. 50). In the illustrated embodiment, the first contact 1116 is electrically coupled to the first electrode 1124 and the second contact 1118 is resting on, or otherwise contacting, a non-conductive finger 1120. As the battery unit 1100 is attached to an instrument, a protruding portion 1158 of the instrument may be received by the cavity 1110 and contact the drain 1112 to drive the drain 1112 in the direction indicated by the arrow 1164. In the closed position (FIG. 51) the first contact 1116 is electrically coupled to the first electrode 1124 and the second contact 1118 is electrically coupled to the second electrode 1126. In this position, a closed circuit is created that allows the cell 1102 to discharge energy through the drain 1112. Additional embodiments of battery units are disclosed in commonly-owned U.S. patent application Ser. No. 12/884,995 entitled, POWER CONTROL ARRANGEMENTS FOR SURGICAL INSTRUMENTS AND BATTERIES, filed on Sep. 17, 2010, now U.S. Pat. No. 8,632,525 and incorporated herein by reference in its entirety. Still other embodiments of battery units are disclosed in commonly-owned U.S. patent application Ser. No. 12/884,838, entitled SURGICAL INSTRUMENTS AND BATTERIES FOR SURGICAL INSTRUMENTS, filed on Sep. 17, 2010, now U.S. Pat. No. 9,289,212 and also incorporated herein by reference in its entirety.

According to various embodiments, electrical connection of the battery unit 506 or other power supply to the motor 222 may initiate a firing of the instrument 102. FIG. 52 illustrates one embodiment of a control circuit 1200 that may control a connection between the battery unit 506 or other power supply and the motor 222 or other drive device for firing the instrument 102. According to various embodiments, the control circuit 1200 may be implemented with components on a PC board 1202 shown in FIG. 7. The control circuit 1200 may comprise various switches and other components for controlling the connection between the battery unit 506 and the motor 222. The battery unit 506 is shown with a positive electrode 1212 and a negative electrode 1210. Similarly, the motor 222 is shown with a positive terminal 1216 and a negative terminal 1214. It will be appreciated that the polarity of the circuit 1200 could be reversed, for example, based on other design considerations.

The control circuit 1200 may comprise a firing switch 220 (also shown in FIG. 9), which may be in mechanical communication with the firing trigger 120 (e.g., via a actuator 221). The control circuit 1200 may also comprise an end-of-stroke/reverse motor switch 1204 and a clamp switch 1206. The end-of-stroke/reverse motor switch 1204 may be actuated when the firing bar 108 reaches the end of its stroke (e.g., at or near its distal-most position). Also, according to various embodiments, the end-of-stroke/reverse motor switch 1204 may be actuated manually by the clinician prior to the end of the stroke of the firing bar 108 to abort and/or reverse the firing of the instrument 102. A clamp switch 1206 may be actuated when the end effector 104 is closed (e.g., the anvil 112 and elongate channel 110 are brought into contact with one another) and also when the end effector 104 is opened. A clamping relay 1208 may also be a component of the circuit 1200. According to various embodiments, the relay 1208 may be a non-solid state relay (e.g., a mechanical relay, an electromagnetic relay, etc.). This may allow the instrument 102 to be subjected to gamma sterilization as well as other sterilization techniques that have the potential to damage solid state components. It will be appreciated, however, that the clamping relay 1208 may, in various embodiments, be replaced with any sort of switching device including, for example, a field effect transistor (FET), bipolar junction transistor (BJT), etc. Also, in some embodiments, the relay 1208 may be replaced with a microprocessor.

When the instrument is ready for use (e.g., a staple cartridge 132 is loaded to the elongate channel 110), the control circuit 1200 may be configured as shown in FIG. 52. The end-of-stroke/reverse motor switch 1204 may be connected between 1 and 3, creating an electrical connection between the positive electrode 1212 of the battery and the positive terminal 1216 of the motor 222. The relay 1208 may be in a closed state. For example, an electrical connection may be made between pins 4 and 5 of the relay 1208. The firing switch 220 may be connected between points 1 and 3, creating an electrical connection between the positive electrode 1212 of the battery 506 and the negative terminal 1214 of the motor 222. Because both terminals 1214, 1216 of the motor 222 are connected to a single electrode 1212 of the battery 506, the motor 222 may not operate.

The clinician may initiate a firing operation by actuating the firing trigger 122, which, via the actuator 221, may cause the firing switch 220 to transition to a second state where the points 1 and 3 are connected. This may create an electrical connection between the negative terminal 1214 of the motor 222 and the negative electrode 1210 of the battery 506 (e.g., via pints 1 and 2 of the firing switch 220 and pins 4 and 5 of the relay 1208. This may cause the motor 222 to rotate in a forward direction. For example, the motor may rotate the gearbox 224, intermediate gear 230, drive gear 232 and rack 238 to ultimately push the firing bar 108 distally.

When the firing bar 108 reaches the end of its stroke, the end-of-stroke switch 1204 may transition from the position shown in FIG. 52 to a position where the points 1 and 2 of the switch 1204 are connected. This may connect pin 3 of the relay 1208 to the negative electrode 1210 of the battery 506 (e.g., via the pin 4-5 connection of the relay 1208). In turn, this may energize the relay 1208 causing removal of the electrical connection between pins 4 and 5 and generation of an electrical connection between pins 5 and 6. When the clinician releases the firing trigger 122, the firing switch may revert to the state shown in FIG. 52. This may cause the motor 222 to be connected to the battery 506 with a reverse polarity. For example, the positive terminal 1216 of the motor 222 may be connected to the negative electrode 1210 of the battery 506 via the switch 1204 and the relay 1208 (e.g., via pins 5 and 6). The negative terminal 1214 of the motor 222 may be connected to the positive electrode 1212 of the battery 506 via the firing switch 220. As a result, the motor 222 may rotate in reverse, pulling the firing bar 108 proximally, via the gearbox 224, intermediate gear 230, drive gear 232 and rack 238.

At the conclusion of the firing operation, the relay 1208 may be in a state where there is no electrical connection between pins 4 and 5. In this state, the instrument 102 may not be re-fired (e.g., the motor 222 may not be connected to the batter 506 with the correct polarity to cause forward rotation). According to various embodiments, a clamp switch 1206 may be positioned to energize the relay 1208 (e.g., pulling pin 1 low) in order to transition the relay 1208 back to the initial state having an electrical connection between pins 4 and 5. This may allow the instrument 102 to fire again. The clamp switch 1206 may be in mechanical communication with a portion of the drive train actuated by the closure trigger 120 to close the anvil 114 against the elongate channel 110. For example, the clamp switch 1206 may be in mechanical communication with the clamp lock 244 described herein above. When the anvil 114 is closed against the elongate channel 110 (e.g., when the clamp lock 244 is engaged), the switch 1206 may be in the position shown in FIG. 52, resulting in an electrical connection between points 1 and 3 of the switch 1206. When the clamp lock 244 is disengaged, the clamp switch 1206 may be configured to create an electrical connection between points 1 and 2, energizing the relay 1208 as described. Accordingly, after the instrument 102 is fired, the circuit 1200 may be configured to prevent the motor 222 from operating in the forward direction until the end effector 104 is re-opened. This may prevent the clinician from accidentally re-firing the instrument 102 before the end effector 104 is opened to install a new staple cartridge 132. According to various embodiments, the instrument 102 may comprise a mechanical lock-out device in addition to the relay lock-out implemented by the circuit 1200. The circuit 1200, as described herein, however, may prevent the clinician from driving the instrument 102 into the mechanical lock-out. This may save wear and tear on the instrument 102 and may also prevent clinician confusion that may occur when the device is in a mechanical lock-out state.

FIG. 53 illustrates one embodiment of the control circuit 1200 with additional switches and features. For example, the circuit 1200, as shown in FIG. 53, may additionally comprise an emergency access or bailout door switch 1218. The emergency access door switch 1218 may be in mechanical communication with the emergency access door 248. For example, when the emergency access door 248 is in place, the switch 1204 may be closed, as shown in FIG. 53. When the emergency access door 248 is removed, the switch 1204 may be opened, creating an open circuit relative to the negative terminal of the battery 506. A stroke position switch 1220 may be connected to switch a resistive element 1222 into and out of the circuit 1200 based on the position of the firing bar 108. The resistive element may be a single resistor and/or a resistor network connected in series, parallel (as shown) or any other suitable configuration. When the resistive element 1222 is switched into the circuit 1200, the current provided to the motor 222 may be reduced. This may reduce the speed and torque provided by the motor 222. Additionally, the control circuit 1200, as illustrated in FIG. 53 may comprise a PTC or other thermal fuse element 1224 to break a connection between the motor 222 and the battery 506 in the event that too much heat is generated (e.g., by the resistive element 1222).

FIG. 54 is a flowchart showing one embodiment of a process flow 1301 showing the firing of the instrument 102 utilizing the control circuit 1200 as illustrated in FIG. 53. At 1300, the instrument 102 may be ready to fire. For example, the switches 1218, 1206, 1220, 220, 1204 and relay 1208 may be configured as illustrated in Table 1 below:

TABLE 1

| Switch | Pin/Point Connection |
|---|---|
| Emergency Access Door (1218) | 1-2 |
| Clamp (1206) | 1-2 |
| Stroke Position (1220) | 1-2 |
| Fire (220) | 1-3 |
| End-of-stroke/Motor Direction (1204) | 1-3 |
| Relay (1208) | 4-5 |

At 1302, the clinician may actuate the firing trigger 122. This may cause the fire switch 220 to close, creating a connection between points 1 and 2 of the switch 220. Accordingly, the positive terminal of the motor 222 may be connected to the positive electrode 1212 of the battery 506 via the end-of-stroke/motor direction switch 1204. The negative terminal 1214 of the motor 222 may be connected to the negative electrode 1210 of the battery 506 via the thermal fuse element 1224, the resistive element 1222, and the connection between pins 4 and 5 of the relay. This may cause rotation of the motor 222 resulting in distal movement of the firing bar 108 (e.g., via the gearbox 224, intermediate gear 230, drive gear 232 and rack 238). Because the resistive element 1222 is electrically connected between the motor 222 and the battery 506, the current provided to the motor 222 may be reduced. This may, in turn, reduce the speed and/or torque provided by the motor 222 while the resistive element 1222 is active.

At 1304, the firing bar 108 may pass a predetermined position in its firing stroke. This may cause the stroke position switch 1220 to be opened, causing a connection between points 1 and 2 of the switch 1220. This may, in turn, switch the resistive element 1222, thermal fuse 1224, and relay 1208 out of circuit, allowing full current to be provided to the motor 222. The predetermined position in the firing stoke, in various embodiments, may be a point past which a mechanical lockout is no longer possible and/or likely. For example, the resistive element 1222 may be utilized to limit the current to the motor 222 during the portion of the firing stroke where the firing bar 108 or other drive train element may encounter a mechanical lock-out. This may limit damage to the drive train or other component of the device 102 if the mechanical lock-out is encountered. When the possibility of encountering a mechanical lock-out has passed, the stroke position switch 1220 may be actuated to switch out the resistive element 1222, allowing full power to be provided to the motor 222 (e.g., for cutting tissue).

The firing bar 108 may reach the end of its stroke (e.g., at or near its distal-most position) at 1306. At this point, the end-of-stroke/motor direction switch 1204 may be actuated, causing it to be connected between points 1 and 2. In this way, the positive terminal 1216 of the motor 222 may be electrically connected to the negative electrode 1210 of the battery 506. The pin 3 of the relay 1208 may also be electrically connected to the negative electrode 1210 of the battery 506, energizing the relay 1208 and breaking the connection between relay pins 4 and 5. When the clinician releases the trigger 122 at 1308, the firing switch 220 may also be actuated, causing it to be connected between points 1 and 2. This may cause the negative terminal 1214 of the motor to be electrically connected to the positive electrode 1212 of the battery 506. In this way, the rotation direction of the motor 222 may be reversed, causing the motor 222 to return the firing bar to its initial, proximal position (e.g., via the via the gearbox 224, drive gear 232 and rack 238).

Similar to embodiment described above, when the relay 1208 is opened (e.g., the connection between pins 4 and 5 is broken), it may not be possible to rotate the motor 222 in a forward direction to fire the firing bar 108 until the clamp switch 1206 is actuated (e.g., by opening the end effector 104). In this way, the clinician may be prevented from re-firing the instrument 102 prior to opening the end effector 104, for example, to load a new staple cartridge 132. Also, similar to the embodiment described above, the clinician may abort a firing stroke by manually switching the end-of-stroke/motor direction switch 1204 to the state where points 1 and 2 are connected, causing the circuit 1200 and instrument 102 to behave as described above with respect to 1306 and 1308.

FIGS. 55-59 show the orientation and operation of various embodiments of the switches 1218, 1206, 1220, 220, and 1204 described above. FIG. 55 illustrates a perspective view of one embodiment of the circuit board 1202 coupled to the battery dock 850. The circuit board 1202 and battery dock 850, as shown, may be positioned within the handle 106 of the instrument 102, for example, as illustrated in FIG. 7. FIG. 55 shows, on the circuit board 1202, the emergency access door switch 1218, the clamp switch 1206, the stroke position switch 1220, the trigger switch 220 and the end-of-stroke/motor direction switch 1204. FIG. 56 illustrates a cut away view of one embodiment of the instrument 102 showing the emergency access door switch 1218. The switch 1218 may comprise an actuator 1304, which may be spring biased. The emergency access door 248, as shown, may comprise an arm 1302. The arm 1302 may be positioned under the actuator 1304 of the switch 1218. When the emergency access door 248 is removed, the arm 1302 may be removed from under the actuator 1304, changing the state of the switch 1218.

FIG. 57 illustrates another cut away view of one embodiment of the instrument 102 showing the clamp switch 1206. The clamp switch 1206 may comprise an actuator 1306. The actuator 1306 may be positioned such that the state of the switch 1206 is changed when the clamp release button 124 is actuated to unclamp the end effector 104.

FIG. 58 shows another cut away view of one embodiment of the instrument 102 showing the stroke position switch 1220. The stroke position switch 1220 may comprise an actuator 1308 and an actuator lever 1310. The actuator lever 1310 may ride along a top surface of the rack 238. According to various embodiments, the rack 238 may define an indentation 1312 along its top surface. The indentation 1312 may be positioned longitudinally on the rack such that the actuator lever 1310 of the switch 1220 falls into the indentation 1312 at the predetermined position of the firing stroke referred to with respect to FIG. 54. Alternatively, it will be appreciated that the rack 238 may comprise a protrusion positioned to contact the actuator at the predetermined part of the firing stroke.

FIG. 59 illustrates another cut away view of one embodiment of the instrument 102 showing the end-of-stroke/motor reverse switch 1204. The switch 1204 may comprise an actuator 1322. The actuator 1322 may be activated by an external reverse motor button 1320 or by the rack 238 as it reaches the distal end of its travel (e.g., indicating an end of the stroke of the firing bar 108). For example, the rack 238 may comprise a protrusion 1324 that contacts the actuator 1322 of the switch 1204. Also, for example, the rack 238 may comprise an indentation or cavity (not shown) positioned to contact the actuator 1322 at the distal end of the travel of the track 238.

Although the device described herein shows the rotational movement of the motor 222 being translated into longitudinal motion in the handle 106 (e.g., via the rack 238 and firing bar 108), it will be appreciated that instruments according to various embodiments may perform this translation outside of the handle, for example, in the shaft, or at the end effector itself. For example, in some embodiments, a rotating drive shaft (not shown) may extend some or all of the way through the shaft 114 from the handle 106 to the end effector 104. The various switches described herein may be utilized in such an embodiment. For example, the various switches described herein may be positioned to be actuated in the same relationship to the position of the firing bar 108 as described herein.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. For another example, although the E-beam firing beam 108 has advantages for an endoscopically employed surgical severing and stapling instrument 102, a similar E-Beam may be used in other clinical procedures. It is generally accepted that endoscopic procedures are more common than laparoscopic procedures. Accordingly, the present invention has been discussed in terms of endoscopic procedures and apparatus. However, use herein of terms such as "endoscopic", should not be construed to limit the present invention to a surgical stapling and severing instrument for use only in conjunction with an endoscopic tube (i.e., trocar). On the contrary, it is believed that the present invention may find use in any procedure where access is limited to a small incision, including but not limited to laparoscopic procedures, as well as open procedures. For yet another example, although an illustrative handle portion 106 described herein is manually operated by a clinician, it is consistent with aspects of the invention for some or all of the functions of a handle portion to be powered (e.g., pneumatic, hydraulic, electromechanical, ultrasonic, etc.). Furthermore, controls of each of these functions may be manually presented on a handle portion or be remotely controlled (e.g., wireless remote, automated remote console, etc.).

It is to be understood that at least some of the figures and descriptions herein have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein.

While several embodiments have been described, it should be apparent, however, that various modifications, alterations and adaptations to those embodiments may occur to persons skilled in the art with the attainment of some or all of the advantages of the disclosure. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosure as defined by the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument comprising:

(a) an end effector comprising:
  (i) a first jaw,
  (ii) a second jaw movable relative to the first jaw from an open position to a closed position,
  (iii) a firing bar movable through a firing stroke from a stroke start position to a stroke end position when the first and second jaws are in the closed position, and
  (iv) a motor operatively coupled with the firing bar; and (b) a circuit assembly, wherein the circuit assembly comprises:
  (i) a power source,
  (ii) a first circuit configured to establish electrical communication between the power source and the motor, wherein the first circuit includes a resistor configured to provide a reduced current to the motor,
  (iii) a second circuit configured to establish electrical communication between the power source and the motor and provide a full current to the motor, and
  (iv) a stroke position switch electrically connected to both the first circuit and the second circuit, wherein the stroke position switch is configured to transition from a first position to a second position when the firing bar advances from the stroke start position to a predetermined position that precedes the stroke end position, wherein the stroke position switch in the first position is configured to provide electrical communication between the power source and the motor via the first circuit, and the stroke position switch in the second position is configured to provide electrical communication between the power source and the motor via the second circuit.

2. The surgical instrument of claim 1, wherein the end effector includes a mechanical lockout configured to mechanically block advancement of the firing bar toward the stroke end position during a first stroke portion of the firing stroke, wherein the mechanical lockout is incapable of blocking advancement of the firing bar toward the stroke end position during a second stroke portion of the firing stroke, wherein the predetermined position coincides with a transition from the first stroke portion to the second stroke portion.

3. The surgical instrument of claim 1, wherein the stroke position switch includes an actuator and an actuator lever.

4. The surgical instrument of claim 3, further comprising a gearbox in mechanical communication with the motor, wherein the gearbox is mechanically connected with a rack, and the rack is mechanically connected with a driver rod, wherein the motor is configured to drive the gearbox, the gearbox is configured to drive the rack, and the rack is configured to drive the driver rod.

5. The surgical instrument of claim 4, wherein the rack is configured to engage the actuator lever in the predetermined position, wherein the actuator lever is configured to engage the actuator and thereby transition the stroke position switch from the first position to the second position.

6. The surgical instrument of claim 5, wherein the rack includes one of an indentation or a protrusion configured to engage the actuator lever in the predetermined position.

7. The surgical instrument of claim 5, wherein the rack is configured to translate distally when the motor rotates in a first direction, and wherein the rack is configured to translate proximally when the motor rotates in a second direction.

8. The surgical instrument of claim 1, further comprising a third circuit including a relay in electrical communication with the power source, wherein the relay is configured to supply power to the first circuit.

9. The surgical instrument of claim 8, further comprising an emergency access door, wherein the third circuit further includes an emergency access door switch operatively coupled with the emergency access door and positioned in series with the relay and the power source, wherein the emergency access door switch is configured to break electrical communication between the power source and the relay when the emergency access door is in an open configuration.

10. The surgical instrument of claim 9, wherein the third circuit includes a clamp switch positioned in series with the relay, the power source, and the emergency access door switch, wherein the clamp switch is configured to break electrical communication between the power source and the relay when the first and second jaws are in the open position.

11. The surgical instrument of claim 1, wherein the first circuit includes a thermal fuse configured to break electrical connection between the power source and the motor when too much heat is generated by the resistor.

12. The surgical instrument of claim 1, wherein the power source is a battery.

13. The surgical instrument of claim 1, wherein the resistor comprises a first resistor, wherein the first circuit further includes a second resistor arranged in parallel with the first resistor.

14. The surgical instrument of claim 1, wherein the firing bar is movable distally from the stroke start position to the stroke end position, wherein the predetermined position is distal to the stroke start position and proximal to the stroke end position.

15. A surgical instrument comprising:

(a) an end effector comprising:
  (i) a first jaw,
  (ii) a second jaw movable relative to the first jaw from an open position to a closed position, (iii) a firing bar movable through a firing stroke from a stroke start position to a stroke end position when the first and second jaws are in the closed position, and (iv) an actuator operatively coupled with the firing bar; and (b) a circuit, wherein the circuit comprises:

(i) a battery, (ii) a resistor in electrical communication with the battery and the actuator, wherein the resistor is configured to reduce at least one of a speed or a torque of the actuator as the firing bar advances from the stroke start position to a predetermined position in a direction toward the stroke end position, and (iii) a stroke position switch configured to deactivate the resistor in the circuit when the firing bar reaches the predetermined position, wherein the stroke position switch is configured to maintain the resistor in a deactivated state as the firing bar continues to advance in the direction from the predetermined position to the stroke end position.

16. The surgical instrument of claim 15, wherein when the resistor is in the deactivated state the circuit is configured to provide full power to the actuator.

17. The surgical instrument of claim 15, wherein the circuit further includes a relay, wherein the relay is configured to provide electrical communication to the actuator via the resistor.

18. The surgical instrument of claim 15, wherein the firing bar is movable distally from the stroke start position to the stroke end position, wherein the predetermined position is distal to the stroke start position and proximal to the stroke end position.

19. A surgical instrument comprising:

(a) an end effector comprising:

(i) a first jaw, (ii) a second jaw movable relative to the first jaw from an open position to a closed position, (iii) a firing bar translatable distally within the end effector from a stroke start position to a stroke end position when the first and second jaws are in the closed position, and (iv) a motor operatively coupled with the firing bar; and (b) a control circuit, wherein the control circuit comprises:

(i) a battery, (ii) a stroke position switch positioned to be actuated when the firing bar advances distally from the stroke start position to a predetermined position proximal of the stroke end position, and (iii) a resistor in electrical communication with the battery and the motor, wherein the resistor is configured to reduce a current between the battery and the motor, wherein in response to actuation of the stroke position switch, the control circuit is configured to electrically isolate the resistor from the battery and the motor.

20. The surgical instrument of claim 19, wherein the control circuit further comprises a relay circuit including a relay in electrical communication with the battery, wherein the relay circuit is configured to provide electrical communication between the battery and the motor via the resistor.

21. The surgical instrument of claim 20, wherein the relay circuit further comprises a clamp switch configured to break electrical communication between the relay and the battery and thereby break electrical communication between the battery and the motor when the first and second jaws are in the open position.

* * * * *